US012457899B2

(12) United States Patent
Ahn et al.

(10) Patent No.: US 12,457,899 B2
(45) Date of Patent: Oct. 28, 2025

(54) MULTI-COMPONENT HOST MATERIAL AND AN ORGANIC ELECTROLUMINESCENCE DEVICE COMPRISING THE SAME

(71) Applicant: ROHM AND HAAS ELECTRONIC MATERIALS KOREA LTD., Chungcheongnam-do (KR)

(72) Inventors: Hee-Choon Ahn, Gyeonggi-do (KR); Young-Kwang Kim, Gyeonggi-do (KR); Su-Hyun Lee, Gyeonggi-do (KR); Ji-Song Jun, Gyeonggi-do (KR); Seon-Woo Lee, Gyeonggi-do (KR); Chi-Sik Kim, Gyeonggi-do (KR); Kyoung-Jin Park, Gyeonggi-do (KR); Nam-Kyun Kim, Gyeonggi-do (KR); Kyung-Hoon Choi, Gyeonggi-do (KR); Jae-Hoon Shim, Seoul (KR); Young-Jun Cho, Gyeonggi-do (KR); Kyung-Joo Lee, Seoul (KR)

(73) Assignee: DuPont Specialty Materials Korea Ltd. (KR)

( * ) Notice: Subject to any disclaimer, the term of this patent is extended or adjusted under 35 U.S.C. 154(b) by 0 days.

(21) Appl. No.: 18/495,274

(22) Filed: Oct. 26, 2023

(65) Prior Publication Data

US 2024/0090328 A1 Mar. 14, 2024

Related U.S. Application Data

(63) Continuation of application No. 17/689,438, filed on Mar. 8, 2022, now abandoned, and a continuation of (Continued)

(30) Foreign Application Priority Data

Apr. 18, 2014 (KR) ........................ 10-2014-0046857
Jul. 11, 2014 (KR) ........................ 10-2014-0087769

(51) Int. Cl.

| | |
|---|---|
| ***H01L 51/54*** | (2006.01) |
| ***C07D 209/86*** | (2006.01) |
| ***C07F 15/00*** | (2006.01) |
| ***C09K 11/02*** | (2006.01) |
| ***C09K 11/06*** | (2006.01) |
| ***H10K 85/30*** | (2023.01) |
| ***H10K 85/40*** | (2023.01) |
| ***H10K 85/60*** | (2023.01) |
| *C07D 209/88* | (2006.01) |
| *C07D 401/04* | (2006.01) |
| *C07D 401/10* | (2006.01) |
| *C07D 401/14* | (2006.01) |
| *C07D 405/14* | (2006.01) |
| *C07D 409/14* | (2006.01) |
| *C07D 487/04* | (2006.01) |
| *C07D 491/04* | (2006.01) |
| *C07D 495/04* | (2006.01) |
| *H10K 50/11* | (2023.01) |
| *H10K 50/15* | (2023.01) |
| *H10K 101/00* | (2023.01) |
| *H10K 101/10* | (2023.01) |

(52) U.S. Cl.

CPC ....... *H10K 85/6572* (2023.02); *C07D 209/86* (2013.01); *C07F 15/0033* (2013.01); *C09K 11/025* (2013.01); *C09K 11/06* (2013.01); *H10K 85/342* (2023.02); *H10K 85/40* (2023.02); *H10K 85/615* (2023.02); *H10K 85/654* (2023.02); *H10K 85/657* (2023.02); *H10K 85/6574* (2023.02); *H10K 85/6576* (2023.02); *C07D 209/88* (2013.01); *C07D 401/04* (2013.01); *C07D 401/10* (2013.01); *C07D 401/14* (2013.01); *C07D 405/14* (2013.01); *C07D 409/14* (2013.01); *C07D 487/04* (2013.01); *C07D 491/04* (2013.01); *C07D 495/04* (2013.01); *C09K 2211/1007* (2013.01); *C09K 2211/1029* (2013.01); *C09K 2211/1088* (2013.01); *C09K 2211/185* (2013.01); *H10K 50/11* (2023.02); *H10K 50/156* (2023.02); *H10K 85/636* (2023.02); *H10K 2101/10* (2023.02); *H10K 2101/90* (2023.02)

(58) Field of Classification Search

None

See application file for complete search history.

(56) References Cited

U.S. PATENT DOCUMENTS

2009/0091253 A1* 4/2009 Yasukawa .............. H05B 33/14
313/504
2010/0084966 A1 4/2010 Otsu et al.

(Continued)

FOREIGN PATENT DOCUMENTS

WO WO-2013146942 A1 * 10/2013 ........... C07D 209/86

OTHER PUBLICATIONS

Search Report from China National Intellectual Property Administration for Chinese patent application No. 202210183455.6; Application Date: Apr. 17, 2015.

*Primary Examiner* — Andrew K Bohaty
(74) *Attorney, Agent, or Firm* — G. Creston Campbell

(57) ABSTRACT

The present invention relates to a multi-component host material and an organic electroluminescent device comprising the same. By comprising a specific combination of the multi-component host compounds, the organic electroluminescent device according to the present invention can provide high luminous efficiency and excellent lifespan characteristics.

4 Claims, No Drawings

Related U.S. Application Data application No. 17/689,508, filed on Mar. 8, 2022, now abandoned, which is a continuation of application No. 15/301,975, filed on Oct. 5, 2016, now abandoned, said application No. 17/689,438 is a continuation of application No. 15/301,975, filed as application No. PCT/KR2015/003890 on Apr. 17, 2015, now abandoned.

(56) References Cited

U.S. PATENT DOCUMENTS

| | | | | |
|---|---|---|---|---|
| 2012/0068170 | A1* | 3/2012 | Pflumm | C09B 19/00<br>544/212 |
| 2014/0151647 | A1* | 6/2014 | Mizuki | H05B 33/20<br>257/40 |
| 2014/0217378 | A1 | 8/2014 | Nishimura et al. | |

* cited by examiner

MULTI-COMPONENT HOST MATERIAL AND AN ORGANIC ELECTROLUMINESCENCE DEVICE COMPRISING THE SAME

CROSS-REFERENCE TO RELATED APPLICATIONS

This application is a continuation of U.S. patent application Ser. Nos. 17/689,508 and 17/689,438, filed Mar. 8, 2022, which are continuations of U.S. patent application Ser. No. 15/301,975, filed Oct. 5, 2016, which is the national stage entry, filed under 35 U.S.C. § 371, of International Patent Application No. PCT/KR2015/003890, filed Apr. 17, 2015, each of which is incorporated by reference herein in its entirety.

TECHNICAL FIELD

The present invention relates to a multi-component host material and an organic electroluminescence device comprising the same.

BACKGROUND ART

An electroluminescence device (EL device) is a self-light-emitting device which has advantages in that it provides a wider viewing angle, a greater contrast ratio, and a faster response time. An organic EL device was first developed by Eastman Kodak, by using small aromatic diamine molecules, and aluminum complexes as materials for forming a light-emitting layer [Appl. Phys. Lett. 51, 913, 1987].

An organic EL device (OLED) is a device changing electronic energy to light by applying electricity to an organic electroluminescent material, and generally has a structure comprising an anode, a cathode, and an organic layer between the anode and the cathode. The organic layer of an organic EL device may be comprised of a hole injection layer, a hole transport layer, an electron blocking layer, a light-emitting layer (which comprises host and dopant materials), an electron buffer layer, a hole blocking layer, an electron transport layer, an electron injection layer, etc., and the materials used for the organic layer are categorized by their functions in hole injection material, hole transport material, electron blocking material, light-emitting material, electron buffer material, hole blocking material, electron transport material, electron injection material, etc. In the organic EL device, due to an application of a voltage, holes are injected from the anode to the light-emitting layer, electrons are injected from the cathode to the light-emitting layer, and excitons of high energies are formed by a recombination of the holes and the electrons. By this energy, luminescent organic compounds reach an excited state, and light emission occurs by emitting light from energy due to the excited state of the luminescent organic compounds returning to a ground state.

The most important factor determining luminous efficiency in an organic EL device is the light-emitting material. A light-emitting material must have high quantum efficiency, high electron and hole mobility, and the formed light-emitting material layer must be uniform and stable. Light-emitting materials are categorized into blue, green, and red light-emitting materials dependent on the color of the light emission, additionally yellow or orange light-emitting materials. In addition, Light-emitting materials can also be categorized into host and dopant materials according to their functions. Recently, the development of an organic EL device providing high efficiency and long lifespan is an urgent issue. In particular, considering EL characteristic requirements for a middle or large-sized panel of OLED, materials showing better characteristics than conventional ones must be urgently developed. The host material which acts as a solvent in a solid state and transfers energy needs to have high purity and a molecular weight appropriate for vacuum deposition. Furthermore, the host material needs to have high glass transition temperature and high thermal degradation temperature to achieve thermal stability, high electro-chemical stability to achieve long lifespan, ease of forming amorphous thin film, good adhesion to materials of adjacent layers, and non-migration to other layers.

A light-emitting material can be used as a combination of a host and a dopant to improve color purity, luminous efficiency, and stability. Generally, an EL device having excellent characteristics has a structure comprising a light-emitting layer formed by doping a dopant to a host. Since host materials greatly influence the efficiency and lifespan of the EL device when using a dopant/host material system as a light emitting material, their selection is important.

International Publication Nos. WO 2013/168688 A1 and WO 2009/060757 A1, and Japanese Patent Appln. Laying-Open No. 2013-183036 A1, etc. disclose organic electroluminescent devices using a biscarbazole derivative as a host material. However, the references fail to disclose an organic electroluminescent device using a multi-component host comprising a biscarbazole derivative and a carbazole derivative including a nitrogen-containing heteroaryl.

DISCLOSURE OF THE INVENTION

Problems to be Solved

The objective of the present invention is to provide an organic electroluminescent device having high efficiency and long lifespan.

Solution to Problems

The present inventors found that the above objective can be achieved by an organic electroluminescent device comprising at least one light-emitting layer between an anode and a cathode, wherein the light-emitting layer comprises a host and a phosphorescent dopant, the host consists of multi-component host compounds, at least a first host compound of the multi-component host compounds is represented by the following formula 1, and a second host compound is represented by the following formula 2:

(1)

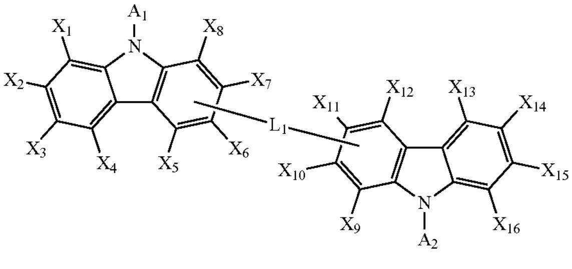

wherein $A_1$ and $A_2$ each independently represent a substituted or unsubstituted (C6-C30)aryl;

$L_1$ represents a substituted or unsubstituted (C6-C30) arylene;

$X_1$ to $X_{16}$ each independently represent hydrogen, deuterium, a halogen, a cyano, a substituted or unsubstituted (C1-C30)alkyl, a substituted or unsubstituted (C2-C30) alkenyl, a substituted or unsubstituted (C2-C30)alkynyl, a substituted or unsubstituted (C3-C30)cycloalkyl, a substituted or unsubstituted (C6-C60)aryl, a substituted or unsubstituted (3- to 30-membered)heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi (C6-C30)arylsilyl, or a substituted or unsubstituted mono- or di-(C6-C30)arylamino; or are linked to an adjacent substituent(s) to form a substituted or unsubstituted, mono- or polycyclic, (C3-C30) alicyclic or aromatic ring, whose carbon atom(s) may be replaced with at least one hetero atom selected from nitrogen, oxygen and sulfur;

(2)

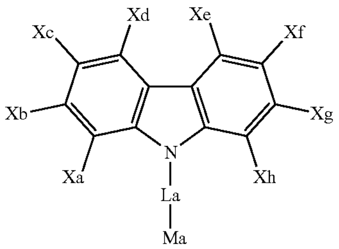

wherein

Ma represents a substituted or unsubstituted nitrogen-containing (5- to 11-membered)heteroaryl;

La represents a single bond, or a substituted or unsubstituted (C6-C30)arylene;

Xa to Xh each independently represent hydrogen, deuterium, a halogen, a cyano, a substituted or unsubstituted (C1-C30)alkyl, a substituted or unsubstituted (C2-C30) alkenyl, a substituted or unsubstituted (C2-C30)alkynyl, a substituted or unsubstituted (C3-C30)cycloalkyl, a substituted or unsubstituted (C6-C60)aryl, a substituted or unsubstituted (3- to 30-membered)heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, or a substituted or unsubstituted mono- or di-(C6-C30)arylamino; or are linked to an adjacent substituent(s) to form a substituted or unsubstituted, mono- or polycyclic, (C3-C30) alicyclic or aromatic ring, whose carbon atom(s) may be replaced with at least one hetero atom selected from nitrogen, oxygen and sulfur; and the heteroaryl contains at least one hetero atom selected from B, N, O, S, P(═O), Si, and P.

Effects of the Invention

According to the present invention, an organic electroluminescent device having high efficiency and long lifespan is provided, and it is possible to manufacture a display device or a lighting device using the organic electroluminescent device.

EMBODIMENTS OF THE INVENTION

Hereinafter, the present invention will be described in detail. However, the following description is intended to explain the invention, and is not meant in any way to restrict the scope of the invention.

Hereinafter, the organic electroluminescent device comprising the organic electroluminescent compounds of formulae 1 and 2 will be described in detail.

The compound represented by formula 1 can be represented by formula 3, 4, 5, or 6:

(3)

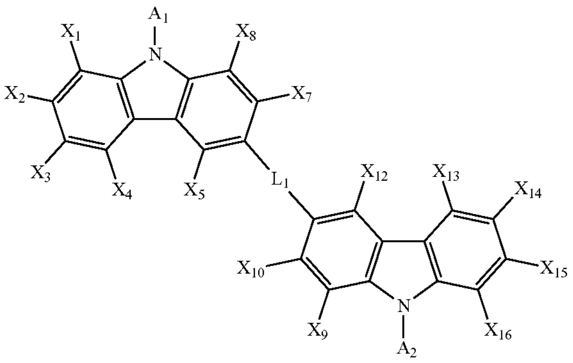

(4)

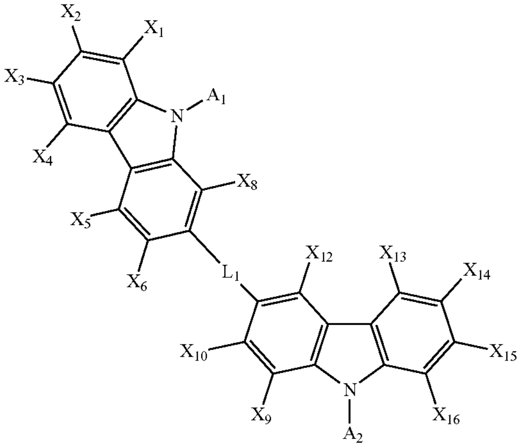

(5)

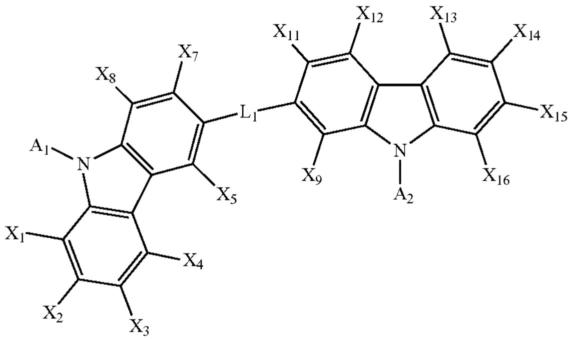

-continued (6)

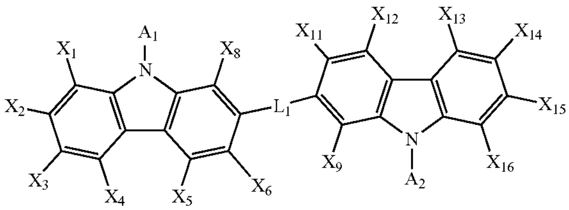

wherein $A_1$, $A_2$, $L_1$, and $X_1$ to $X_{16}$ are as defined in formula 1.

In formula 1 above, $A_1$ and $A_2$ each independently represent a substituted or unsubstituted (C6-C30)aryl, preferably, each independently represent a substituted or unsubstituted (C6-C18)aryl, more preferably, each independently represent a (C6-C18)aryl unsubstituted or substituted with a cyano, a (C1-C6)alkyl, a (C6-C12)aryl, or a tri(C6-C12)arylsilyl, and even more preferably, each independently represent phenyl, biphenyl, terphenyl, naphthyl, fluorenyl, phenanthrenyl, anthracenyl, indenyl, triphenylenyl, pyrenyl, tetracenyl, perylenyl, chrysenyl, or fluoranthenyl.

In formula 1 above, $X_1$ to $X_{16}$ each independently represent hydrogen, deuterium, a halogen, a cyano, a substituted or unsubstituted (C1-C30)alkyl, a substituted or unsubstituted (C2-C30)alkenyl, a substituted or unsubstituted (C2-C30)alkynyl, a substituted or unsubstituted (C3-C30)cycloalkyl, a substituted or unsubstituted (C6-C60)aryl, a substituted or unsubstituted (3- to 30-membered)heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, or a substituted or unsubstituted mono- or di-(C6-C30)arylamino; or are linked to an adjacent substituent(s) to form a substituted or unsubstituted, mono- or polycyclic, (C3-C30) alicyclic or aromatic ring, whose carbon atom(s) may be replaced with at least one hetero atom selected from nitrogen, oxygen and sulfur, preferably, each independently represent hydrogen, a cyano, a substituted or unsubstituted (C6-C20)aryl, a substituted or unsubstituted (5- to 20-membered)heteroaryl, or a substituted or unsubstituted tri(C6-C12)arylsilyl, and more preferably, each independently represent hydrogen, a cyano, a (C6-C20)aryl unsubstituted or substituted with a cyano, an unsubstituted (5- to 20-membered)heteroaryl, or an unsubstituted tri(C6-C12)arylsilyl.

In formula 1 above, $L_1$ represents a substituted or unsubstituted (C6-C30)arylene, preferably, represents a substituted or unsubstituted (C6-C15)arylene, and more preferably, represents a (C6-C15)arylene unsubstituted or substituted with a cyano, a (C1-C6)alkyl, or a tri(C6-C12)arylsilyl.

In addition, $L_1$ can be represented by one of formulae 7 to 19:

(7)

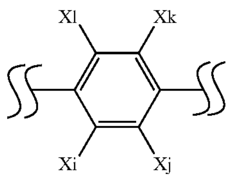

-continued (8)

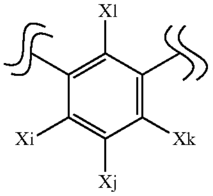

(9)

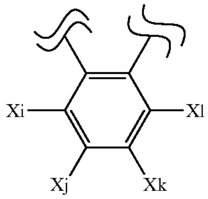

(10)

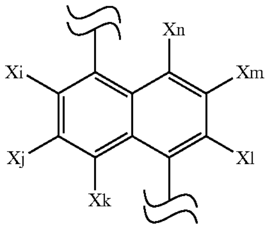

(11)

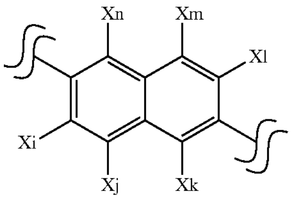

(12)

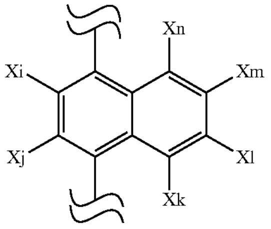

(13)

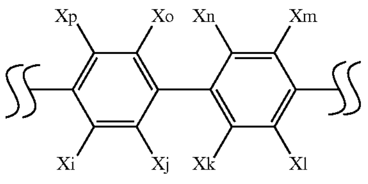

(14)

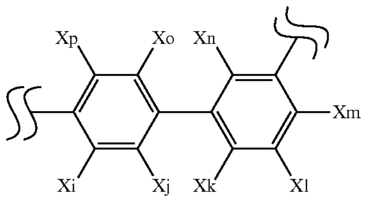

-continued (15)

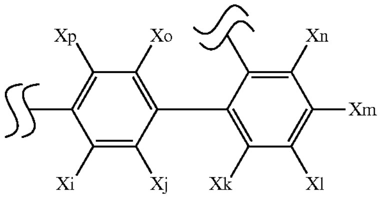

(16)

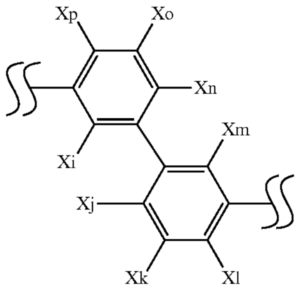

(17)

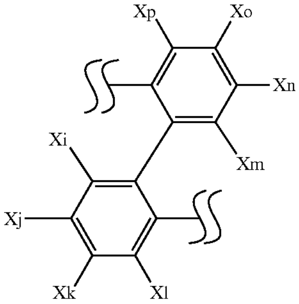

(18)

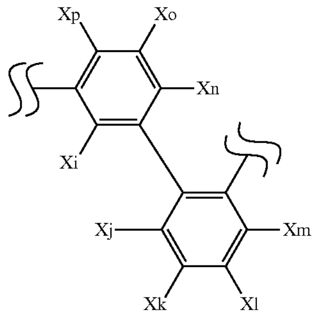

(19)

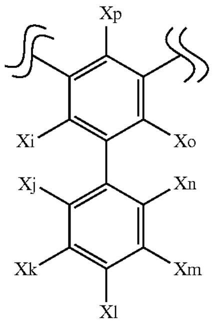

wherein

Xi to Xp each independently represent hydrogen, deuterium, a halogen, a cyano, a substituted or unsubstituted (C1-C30)alkyl, a substituted or unsubstituted (C2-C30) alkenyl, a substituted or unsubstituted (C2-C30)alkynyl, a substituted or unsubstituted (C3-C30)cycloalkyl, a substituted or unsubstituted (C6-C60)aryl, a substituted or unsubstituted (3- to 30-membered)heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi (C6-C30)arylsilyl, or a substituted or unsubstituted mono- or di-(C6-C30)arylamino; or are linked to an adjacent substituent(s) to form a substituted or unsubstituted, mono- or polycyclic, (C3-C30) alicyclic or aromatic ring, whose carbon atom(s) may be replaced with at least one hetero atom selected from nitrogen, oxygen and sulfur.

Preferably, Xi to Xp may each independently represent hydrogen, a halogen, a cyano, a (C1-C10)alkyl, a (C3-C20) cycloalkyl, a (C6-C12)aryl, a (C1-C6)alkyldi(C6-C12)arylsilyl, or a tri(C6-C12)arylsilyl, and more preferably, each independently represent hydrogen, a cyano, a (C1-C6)alkyl, or a tri(C6-C12)arylsilyl.

In formula 2 above, Ma represents a substituted or unsubstituted nitrogen-containing (5- to 11-membered)heteroaryl, preferably, represents a substituted or unsubstituted nitrogen-containing (6- to 10-membered)heteroaryl, and more preferably, represents a nitrogen-containing (6- to 10-membered)heteroaryl substituted with an unsubstituted (C6-C18) aryl, a (C6-C12)aryl substituted with a cyano, a (C6-C12) aryl substituted with a (C1-C6)alkyl, a (C6-C12)aryl substituted with a tri(C6-C12)arylsilyl, or a (6- to 15-membered)heteroaryl.

In addition, Ma may represent a monocyclic heteroaryl selected from the group consisting of pyrrolyl, imidazolyl, pyrazolyl, triazinyl, tetrazinyl, triazolyl, tetrazolyl, pyridyl, pyrazinyl, pyrimidinyl, and pyridazinyl, or a fused heteroaryl selected from the group consisting of benzoimidazolyl, isoindolyl, indolyl, indazolyl, benzothiadiazolyl, quinolyl, isoquinolyl, cinnolinyl, quinazolinyl, naphthyridinyl, and quinoxalinyl, and preferably may represent triazinyl, pyrimidinyl, pyridyl, quinolyl, isoquinolyl, quinazolinyl, naphthyridinyl, or quinoxalinyl.

In formula 2 above, La represents a single bond, or a substituted or unsubstituted (C6-C30)arylene, preferably, represents a single bond, or a substituted or unsubstituted (C6-C12)arylene, and more preferably, represents a single bond, or a (C6-C12)arylene unsubstituted or substituted with a tri(C6-C10)arylsilyl.

In addition, La can represent a single bond, or be represented by one of formulae 7 to 19 as above.

In formula 2 above, Xa to Xh each independently represent hydrogen, deuterium, a halogen, a cyano, a substituted or unsubstituted (C1-C30)alkyl, a substituted or unsubstituted (C2-C30)alkenyl, a substituted or unsubstituted (C2-C30)alkynyl, a substituted or unsubstituted (C3-C30)cycloalkyl, a substituted or unsubstituted (C6-C60)aryl, a substituted or unsubstituted (3- to 30-membered)heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, or a substituted or unsubstituted mono- or di-(C6-C30)arylamino; or are linked to an adjacent substituent(s) to form a substituted or unsubstituted, mono- or polycyclic, (C3-C30) alicyclic or aromatic ring, whose carbon atom(s) may be replaced with at least one hetero atom selected from nitrogen, oxygen and sulfur, preferably, each independently represent hydrogen, a cyano, a substituted or unsubstituted (C6-C15)aryl, a substituted or unsubstituted (10- to 20-membered)heteroaryl, or a substituted or unsubstituted tri(C6-C10)arylsilyl; or are linked to an adjacent substituent (s) to form a substituted or unsubstituted, mono- or polycyclic, (C6-C20) aromatic ring, and more preferably, each independently represent hydrogen; a cyano; a (C6-C15)aryl unsubstituted or substituted with a tri(C6-C10)arylsilyl; a (10- to 20-membered)heteroaryl unsubstituted or substituted with a (C6-C12)aryl or a cyano(C6-C12)aryl; or an unsubstituted tri(C6-C10)arylsilyl; or are linked to an adjacent substituent(s) to form a substituted or unsubstituted benzene, a substituted or unsubstituted indole, a substituted or unsubstituted benzoindole, a substituted or unsubstituted indene, a substituted or unsubstituted benzofuran, or a substituted or unsubstituted benzothiophene.

Herein, "(C1-C30)alkyl" is meant to be a linear or branched alkyl having 1 to 30 carbon atoms, in which the number of carbon atoms is preferably 1 to 20, more preferably 1 to 10, and includes methyl, ethyl, n-propyl, isopropyl, n-butyl, isobutyl, tert-butyl, etc.; "(C2-C30)alkenyl" is meant to be a linear or branched alkenyl having 2 to 30 carbon atoms, in which the number of carbon atoms is preferably 2 to 20, more preferably 2 to 10, and includes vinyl, 1-propenyl, 2-propenyl, 1-butenyl, 2-butenyl, 3-butenyl, 2-methylbut-2-enyl, etc.; "(C2-C30)alkynyl" is meant to be a linear or branched alkynyl having 2 to 30 carbon atoms, in which the number of carbon atoms is preferably 2 to 20, more preferably 2 to 10, and includes ethynyl, 1-propynyl, 2-propynyl, 1-butynyl, 2-butynyl, 3-butynyl, 1-methylpent-2-ynyl, etc.; "(C3-C30)cycloalkyl" is a mono- or polycyclic hydrocarbon having 3 to 30 carbon atoms, in which the number of carbon atoms is preferably 3 to 20, more preferably 3 to 7, and includes cyclopropyl, cyclobutyl, cyclopentyl, cyclohexyl, etc.; "(3- to 7-membered)heterocycloalkyl" is a cycloalkyl having 3 to 7 ring backbone atoms, preferably 5 to 7, including at least one heteroatom selected from B, N, O, S, P(═O), Si and P, preferably O, S and N, and includes tetrahydrofuran, pyrrolidine, thiolan, tetrahydropyran, etc.; "(C6-C30)aryl(ene)" is a monocyclic or fused ring derived from an aromatic hydrocarbon having 6 to 30 carbon atoms, in which the number of carbon atoms is preferably 6 to 20, more preferably 6 to 15, and includes phenyl, biphenyl, terphenyl, naphthyl, binaphthyl, phenylnaphthyl, naphthylphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, etc.; "(3- to 30-membered) heteroaryl" is an aryl having 3 to 30 ring backbone atoms, including at least one, preferably 1 to 4 heteroatoms selected from the group consisting of B, N, O, S, P(═O), Si and P; is a monocyclic ring, or a fused ring condensed with at least one benzene ring; may be partially saturated; may be one formed by linking at least one heteroaryl or aryl group to a heteroaryl group via a single bond(s); and includes a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl including benzofuranyl, benzothiophenyl, isobenzofuranyl, dibenzofuranyl, dibenzothiophenyl, benzoimidazolyl, benzothiazolyl, benzoisothiazolyl, benzoisoxazolyl, benzoxazolyl, isoindolyl, indolyl, benzoindolyl, indazolyl, benzothiadiazolyl, quinolyl, isoquinolyl, cinnolinyl, quinazolinyl, quinoxalinyl, carbazolyl, phenoxazinyl, phenanthridinyl, benzodioxolyl, etc.; "nitrogen-containing (5- to 30-membered)heteroaryl" is an aryl having 5 to 30 ring backbone atoms, preferably 5 to 20, and more preferably 5 to 15, including at least one heteroatom, N; is a monocyclic ring, or a fused ring condensed with at least one benzene ring; may be partially saturated; may be one formed by linking at least one heteroaryl or aryl group to a heteroaryl group via a single bond(s); and includes a monocyclic ring-type heteroaryl including pyrrolyl, imidazolyl, pyrazolyl, triazinyl, tetrazinyl, triazolyl, tetrazolyl, pyridyl, pyrazinyl, pyrimidinyl, pyridazinyl, etc., and a fused ring-type heteroaryl including benzoimidazolyl, isoindolyl, indolyl, indazolyl, benzothiadiazolyl, quinolyl, isoquinolyl, cinnolinyl, quinazolinyl, quinoxalinyl, carbazolyl, phenanthridinyl, etc. Further, "halogen" includes F, Cl, Br, and I.

Herein, "substituted" in the expression "substituted or unsubstituted" means that a hydrogen atom in a certain functional group is replaced with another atom or group, i.e. a substituent. The substituents of the substituted alkyl, the substituted alkenyl, the substituted alkynyl, the substituted cycloalkyl, the substituted aryl(ene), the substituted heteroaryl, the substituted trialkylsilyl, the substituted triarylsilyl, the substituted dialkylarylsilyl, the substituted alkyldiarylsilyl, the substituted mono- or di-arylamino, and the substituted nitrogen-containing heteroaryl in $A_1$, $A_2$, $L_1$, $X_1$ to $X_{16}$, Ma, La, and Xa to Xh in formulae 1 and 2 each independently are at least one selected from the group consisting of deuterium, a halogen, a cyano, a carboxyl, a nitro, a hydroxyl, a (C1-C30)alkyl, a halo(C1-C30)alkyl, a (C2-C30)alkenyl, a (C2-C30)alkynyl, a (C1-C30)alkoxy, a (C1-C30)alkylthio, a (C3-C30)cycloalkyl, a (C3-C30)cycloalkenyl, a (3- to 7-membered)heterocycloalkyl, a (C6-C30)aryloxy, a (C6-C30)arylthio, a (3- to 30-membered) heteroaryl unsubstituted or substituted with a (C6-C30)aryl, a (C6-C30)aryl unsubstituted or substituted with a cyano, a (3- to 30-membered)heteroaryl, or a tri(C6-C30)arylsilyl, a tri(C1-C30)alkylsilyl, a tri(C6-C30)arylsilyl, a di(C1-C30)alkyl(C6-C30)arylsilyl, a (C1-C30)alkyldi(C6-C30)arylsilyl, an amino, a mono- or di-(C1-C30)alkylamino, a mono- or di-(C6-C30)arylamino, a (C1-C30)alkyl(C6-C30)arylamino, a (C1-C30)alkylcarbonyl, a (C1-C30)alkoxycarbonyl, a (C6-C30)arylcarbonyl, a di(C6-C30)arylboronyl, a di(C1-C30)alkylboronyl, a (C1-C30)alkyl(C6-C30)arylboronyl, a (C6-C30)aryl(C1-C30)alkyl, and a (C1-C30)alkyl (C6-C30)aryl, and preferably are at least one selected from the group consisting of a cyano, a (C1-C6)alkyl, a (5- to 15-membered)heteroaryl, a (C6-C18)aryl unsubstituted or substituted with a cyano or a tri(C6-C12)arylsilyl, a tri(C6-C12)arylsilyl, and a (C1-C6)alkyl(C6-C12)aryl.

In formula 1, a triarylsilyl as $X_1$ to $X_{16}$ is preferably a triphenylsilyl.

The first host compound represented by formula 1 includes the following compounds, but is not limited thereto:

H1-1
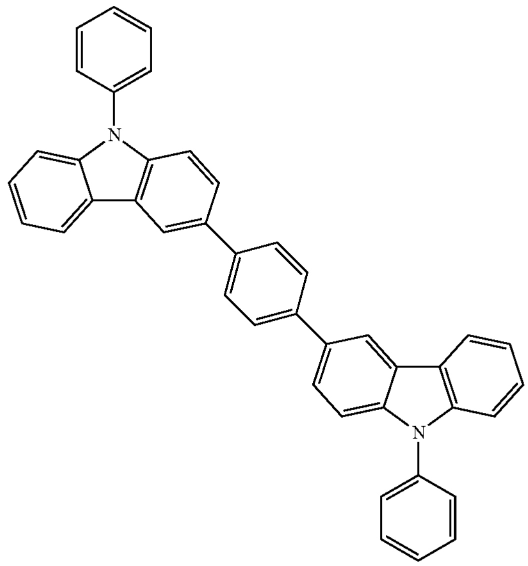
H1-2
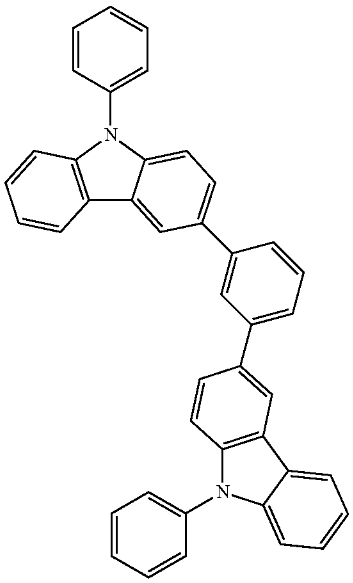
H1-3
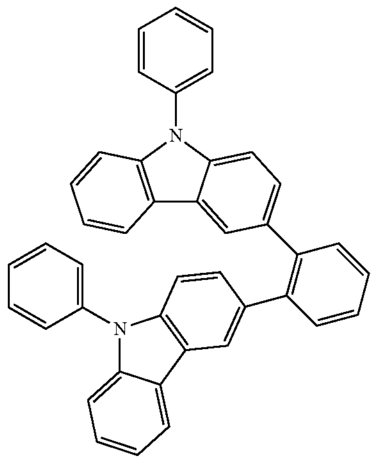
H1-4
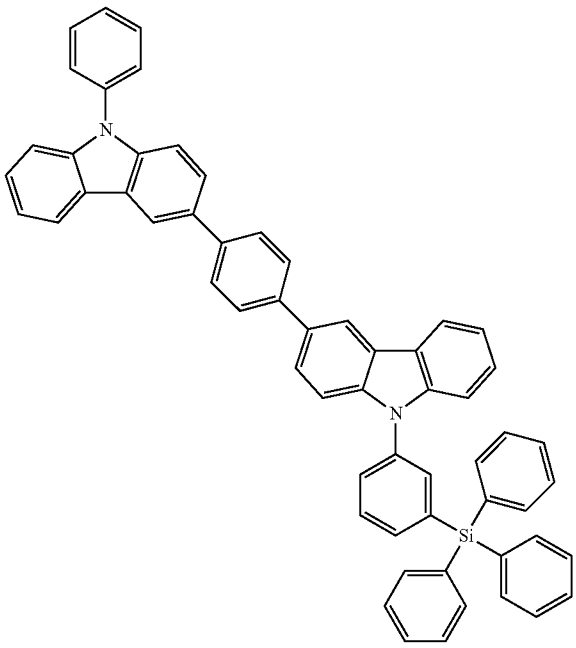

-continued
H1-5
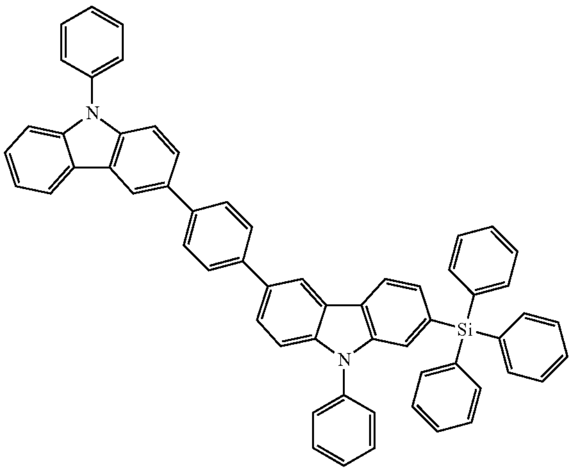
H1-6
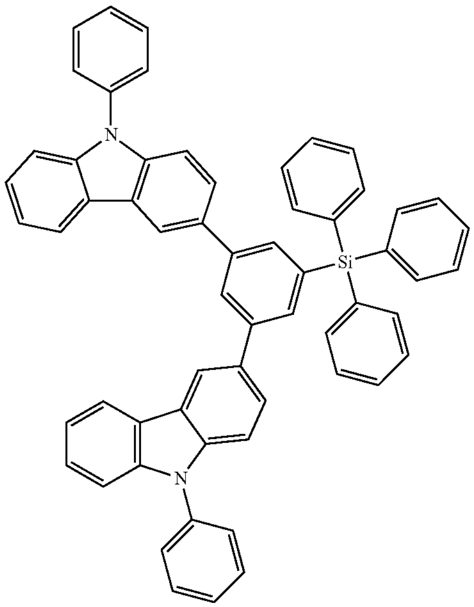
H1-7
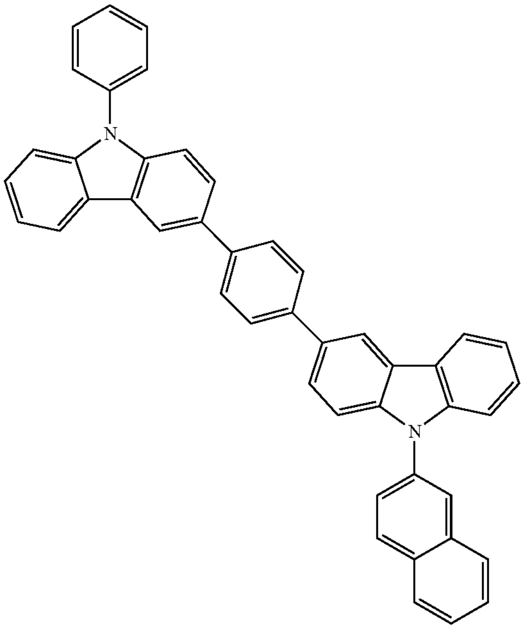
H1-8
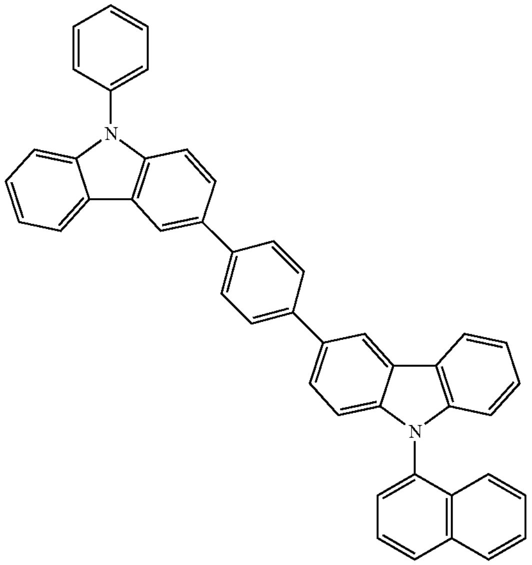

-continued
H1-9
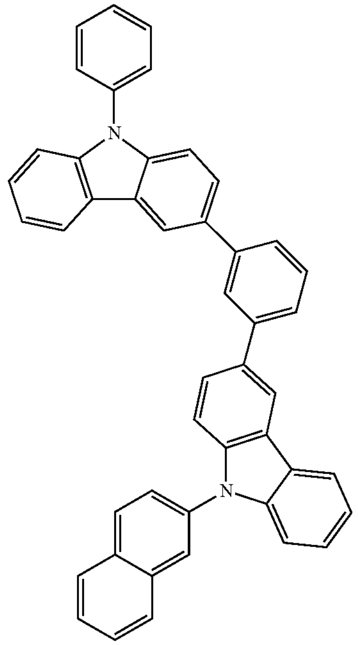
H1-10
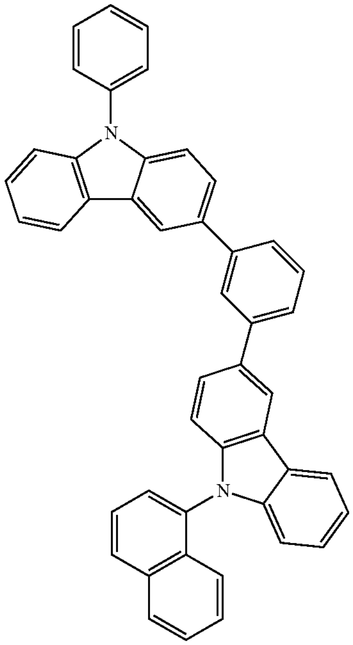
H1-11
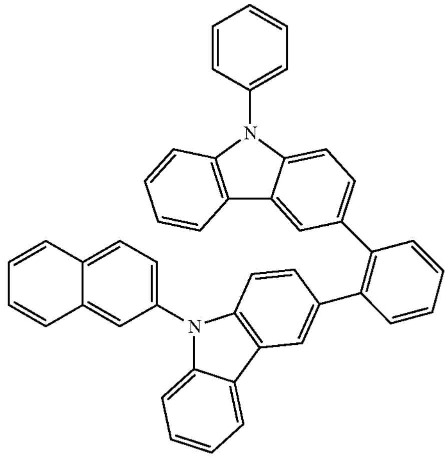
H1-12
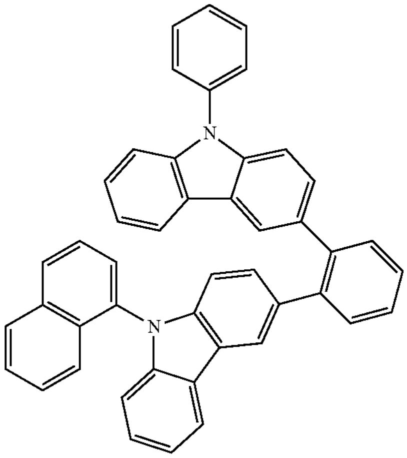

-continued
H1-13
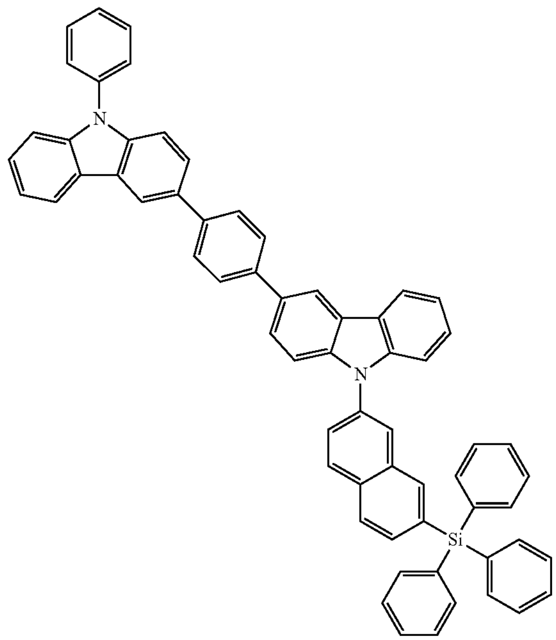
H1-14
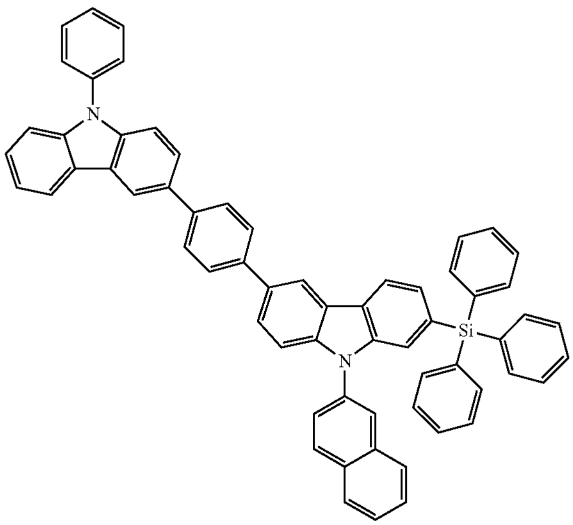
H1-15
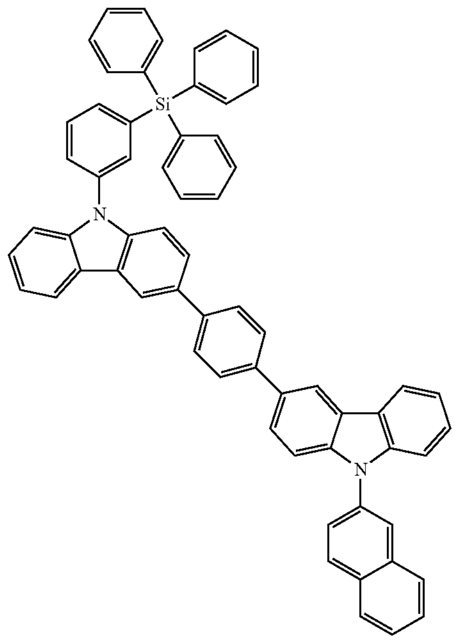
H1-16
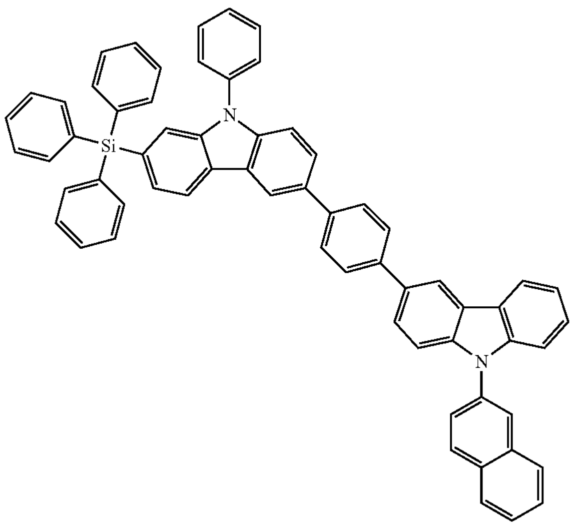

-continued
H1-17
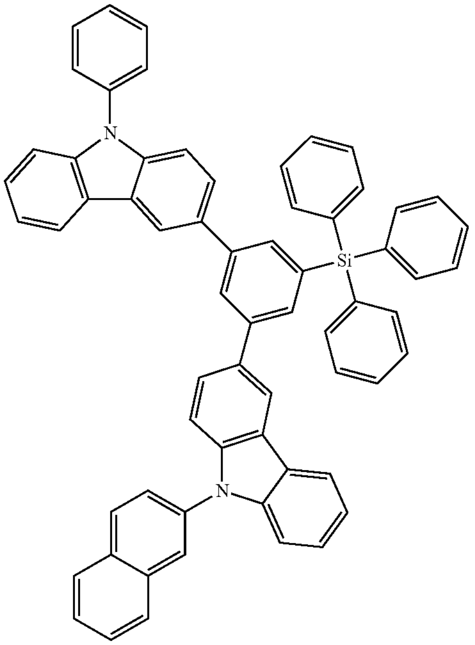
H1-18
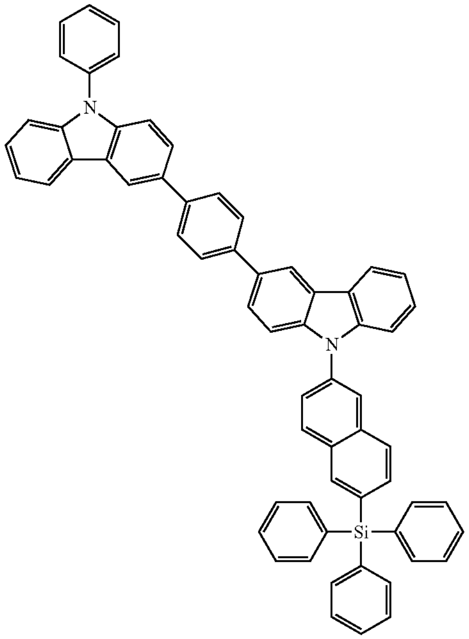
H1-19
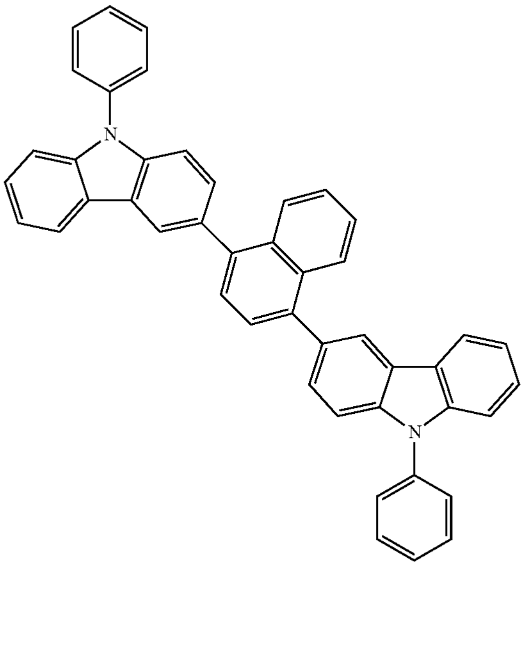
H1-20
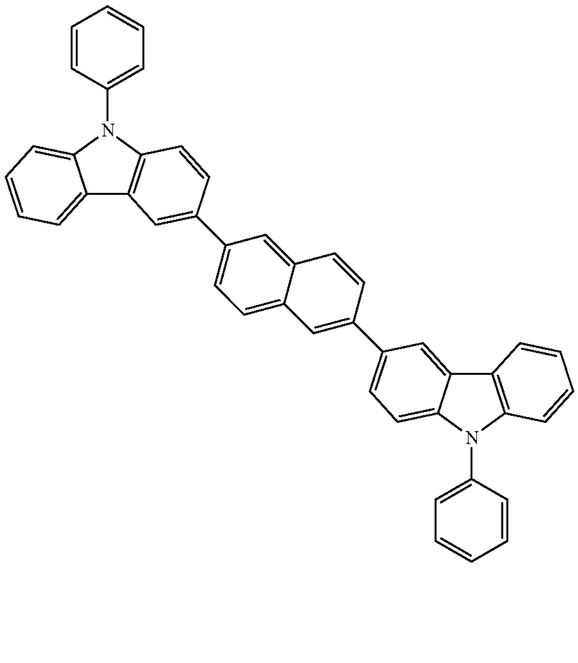

-continued
H1-21
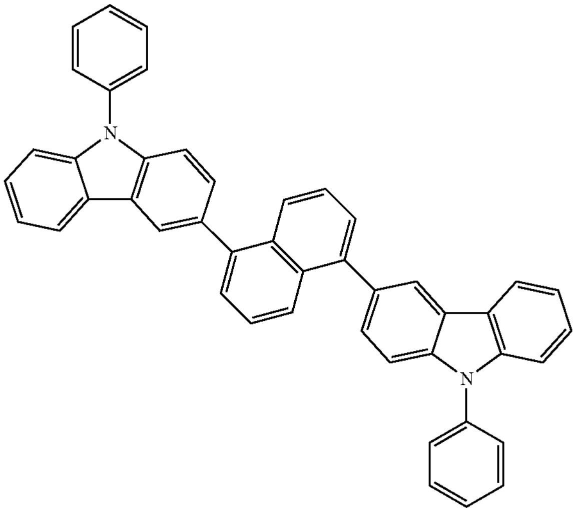
H1-22
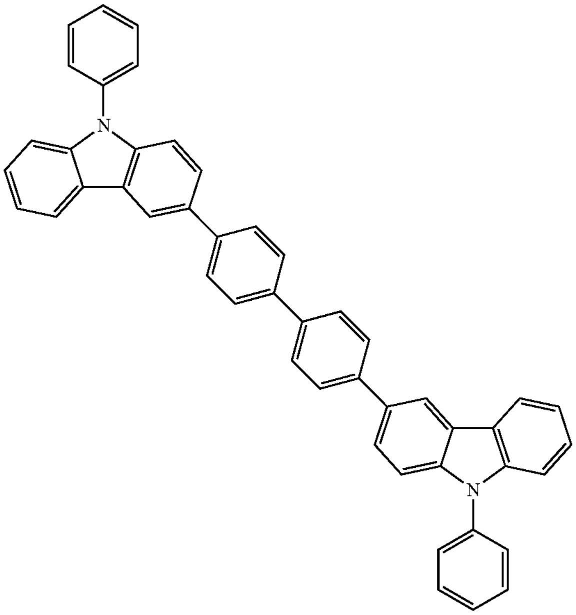
H1-23
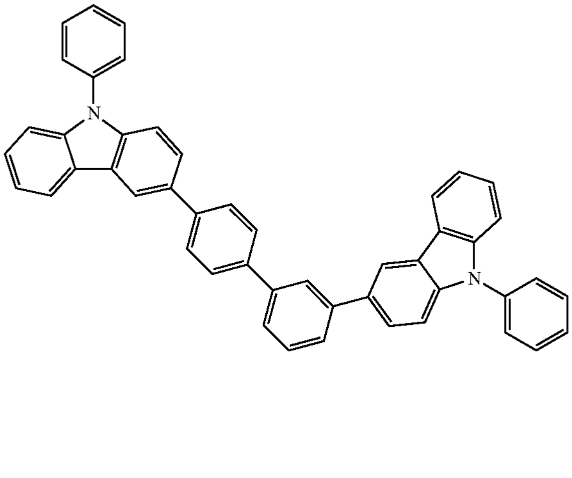
H1-24
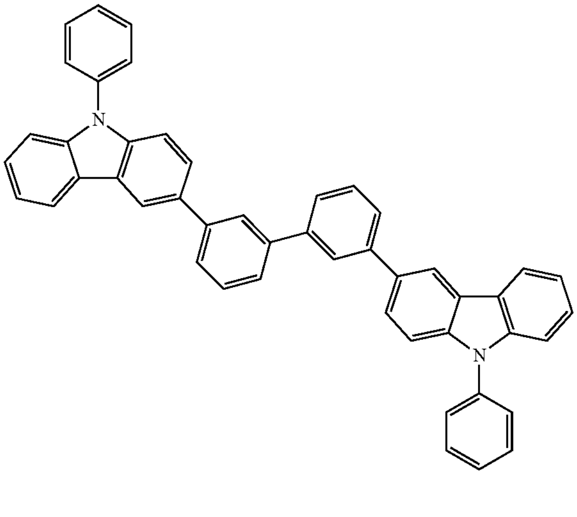

-continued
H1-25
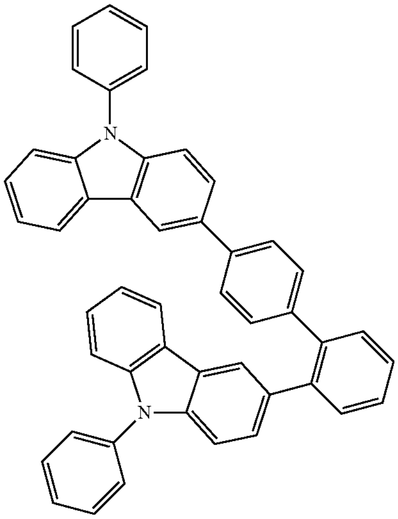
H1-26
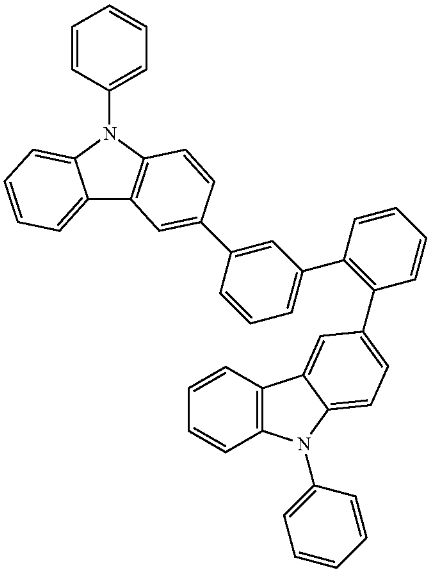
H1-27
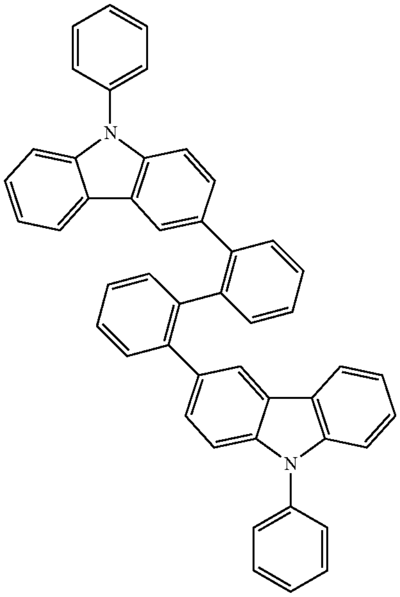
H1-28
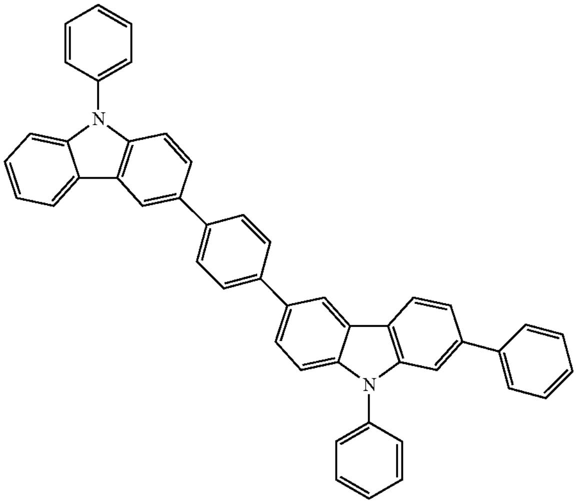

-continued
H1-29
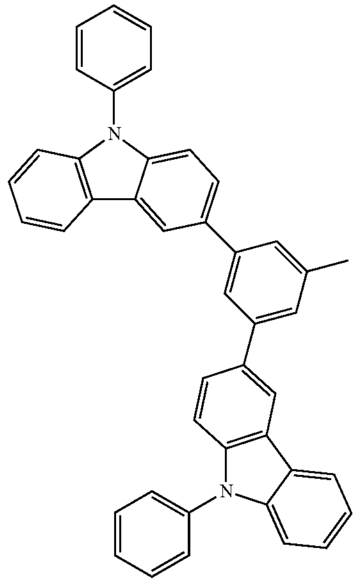
H1-30
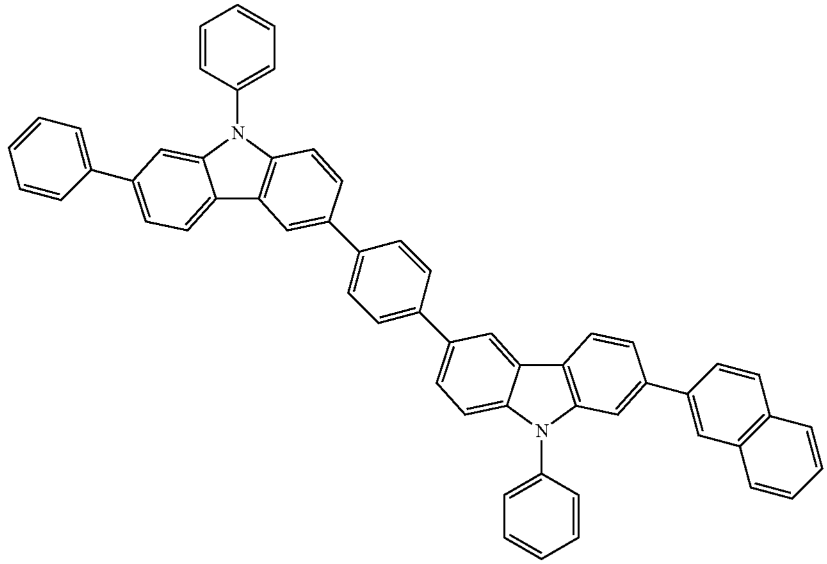
H1-31
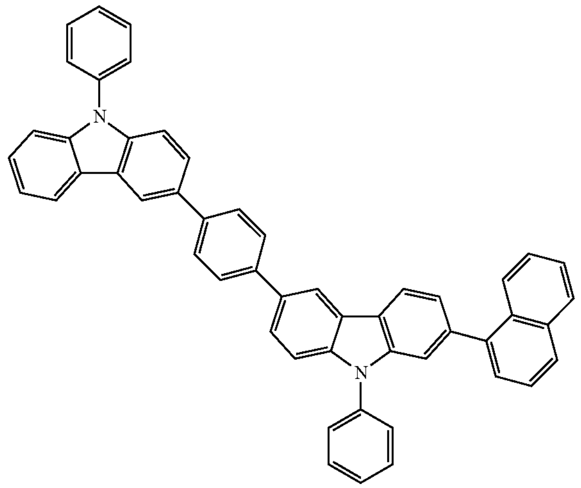
H1-32
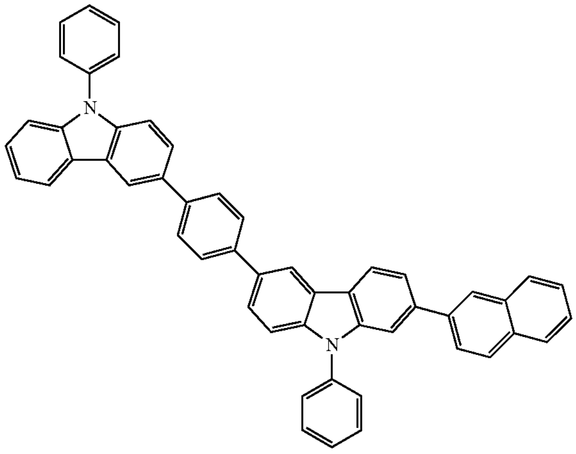

-continued
H1-33
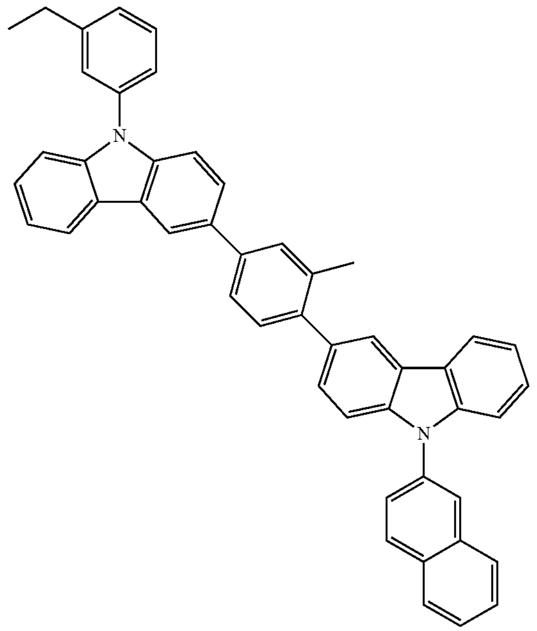
H1-34
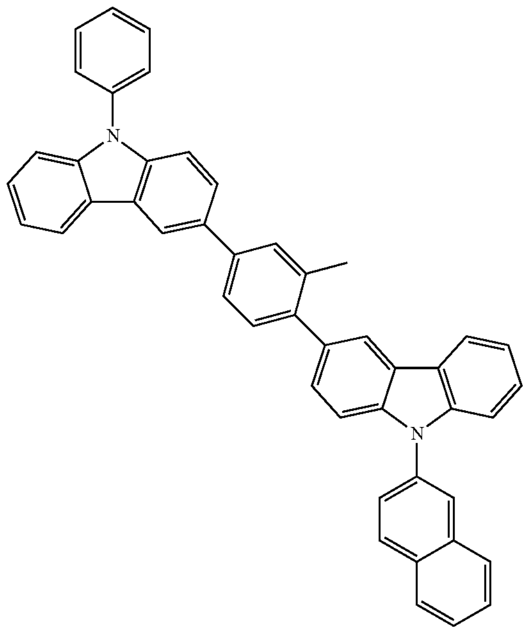
H1-35
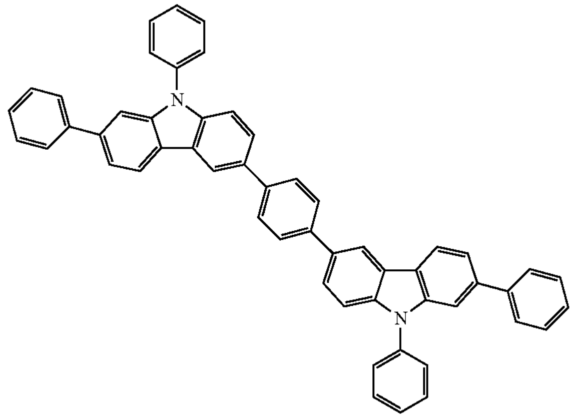
H1-36
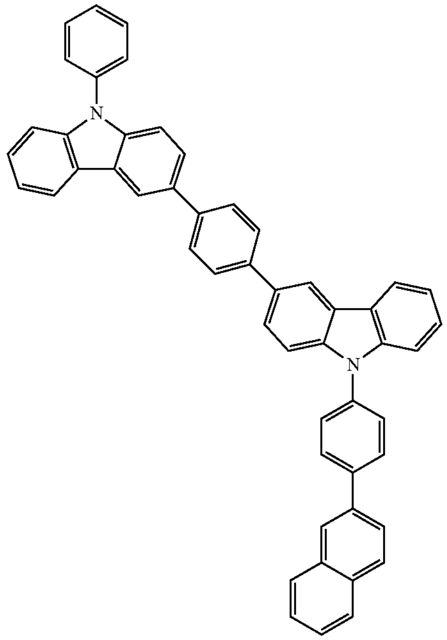

-continued
H1-37
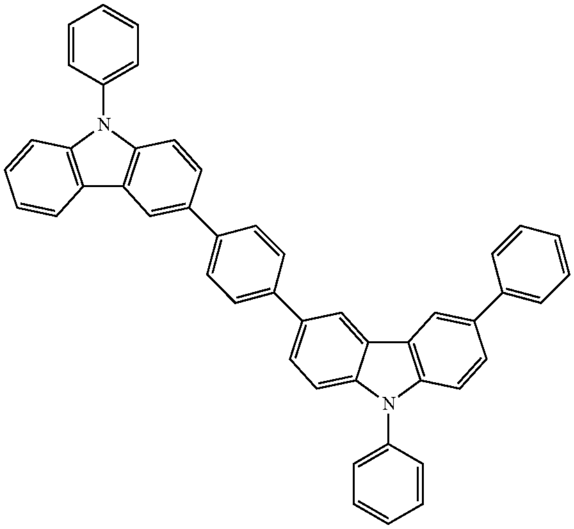
H1-38
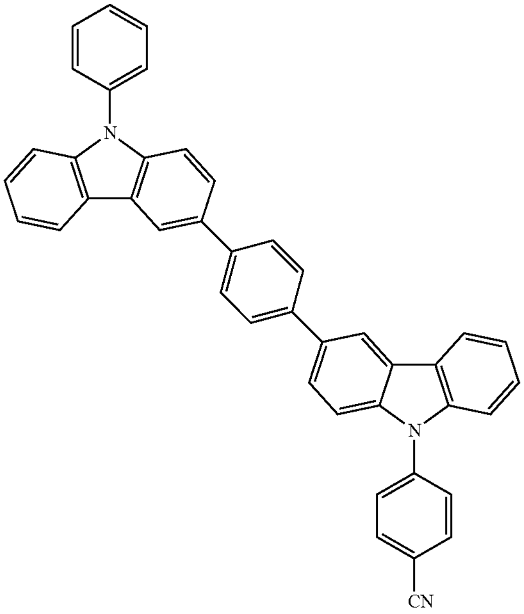
H1-39
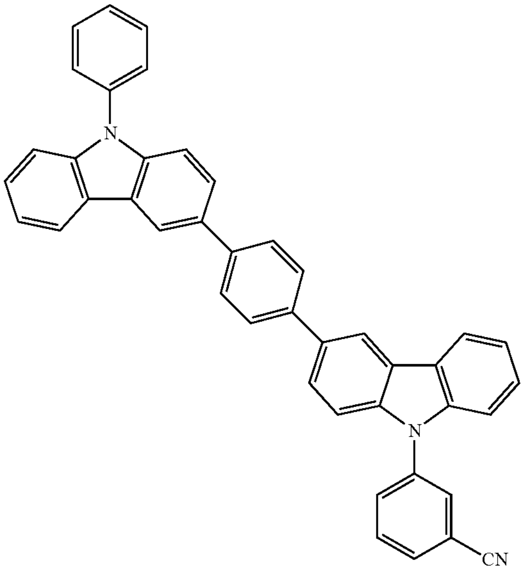
H1-40
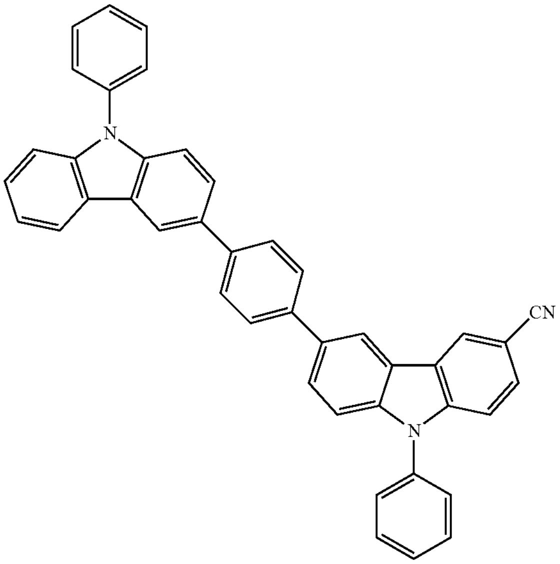

-continued
H1-41
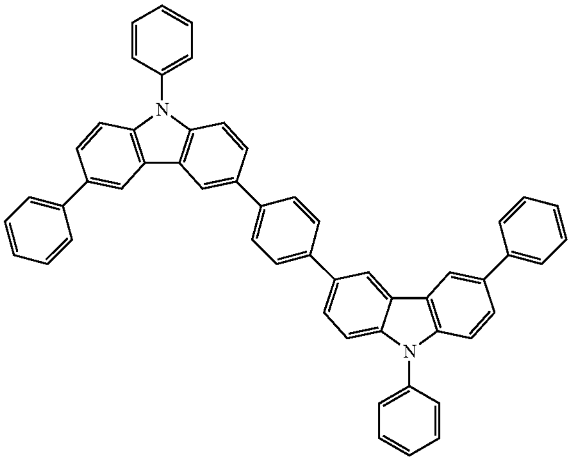
H1-42
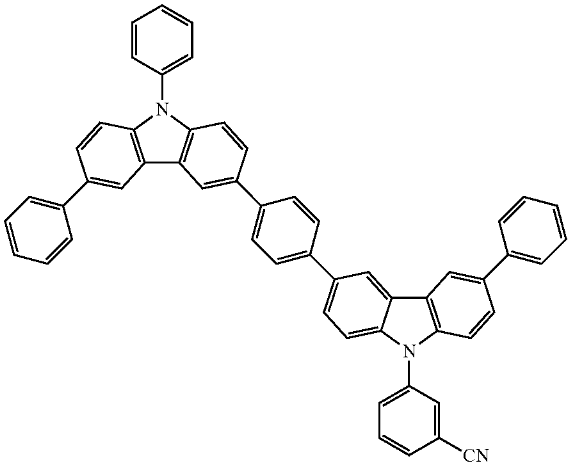
H1-43
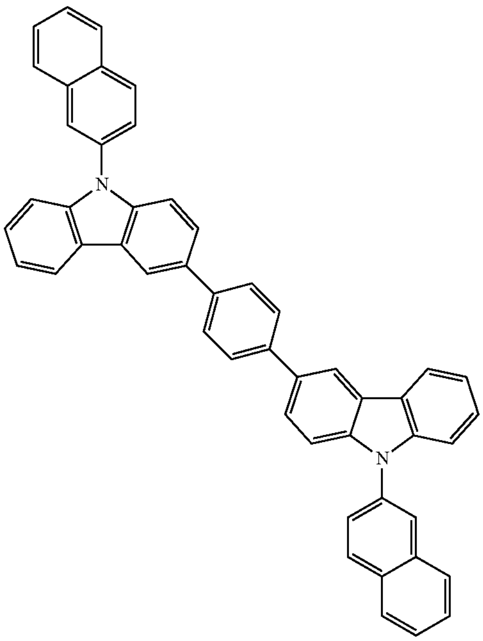
H1-44
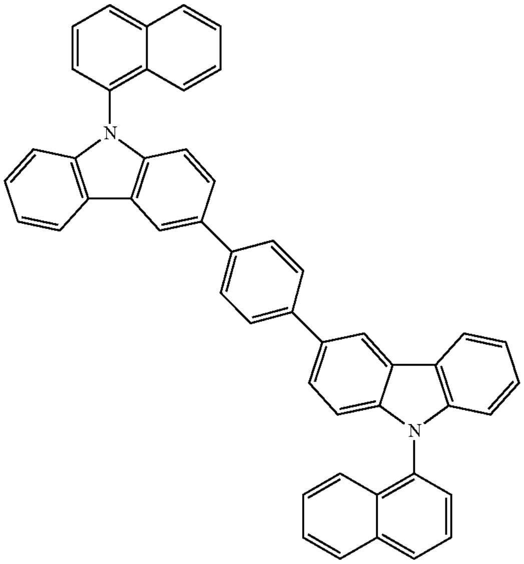

-continued
H1-45
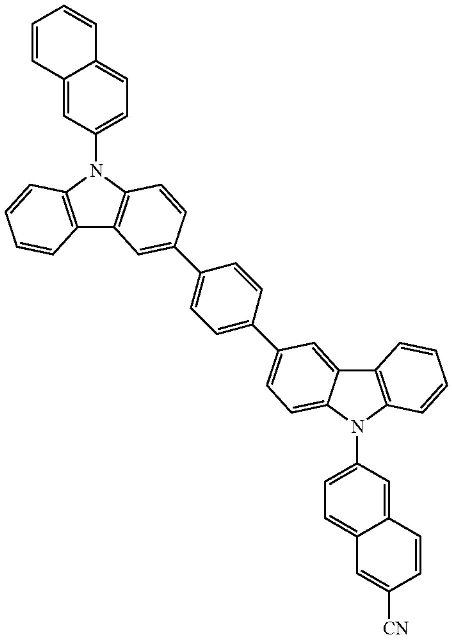
H1-46
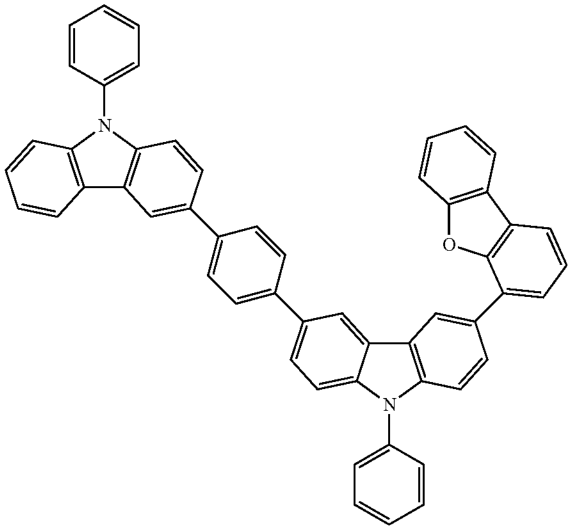
H1-47
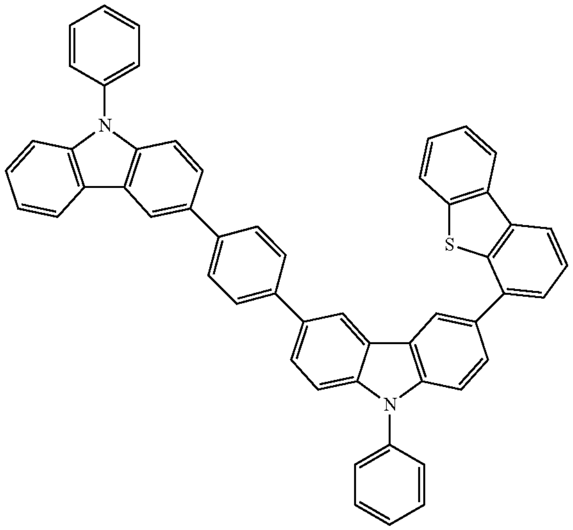
H1-48
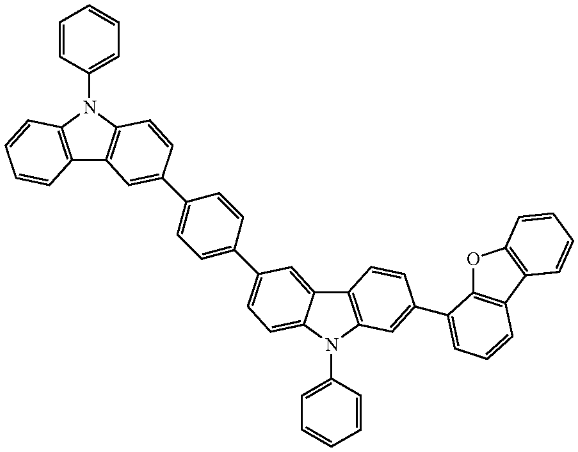

-continued
H1-49
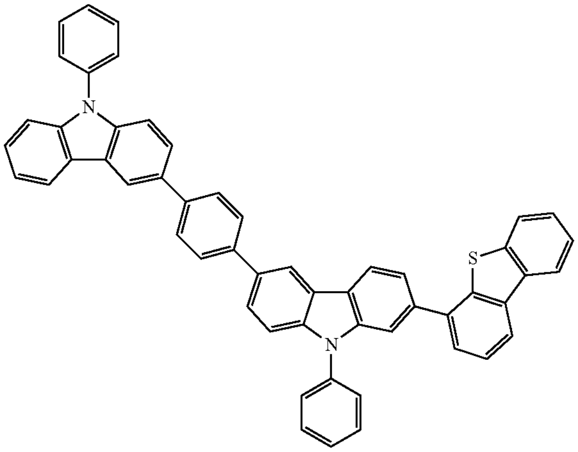
H1-50
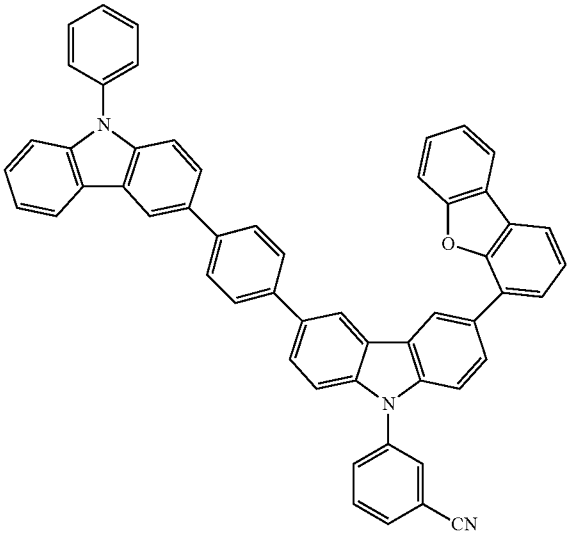
H1-51
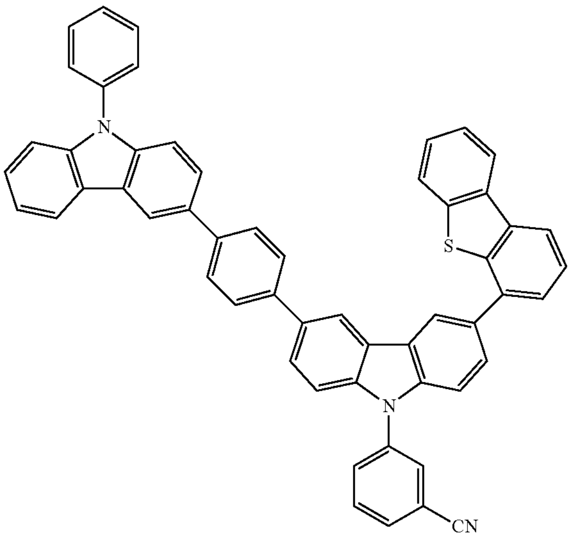
H1-52
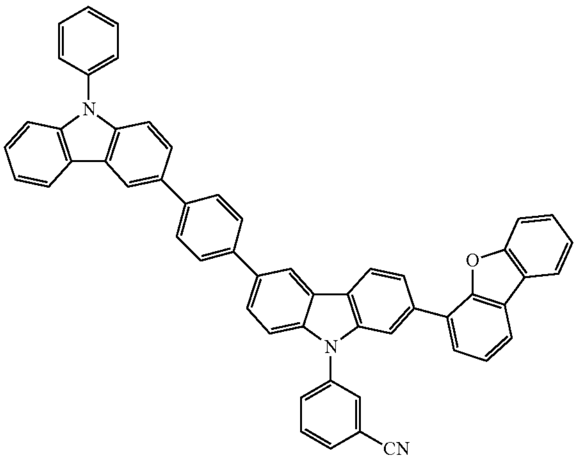

-continued
H1-53
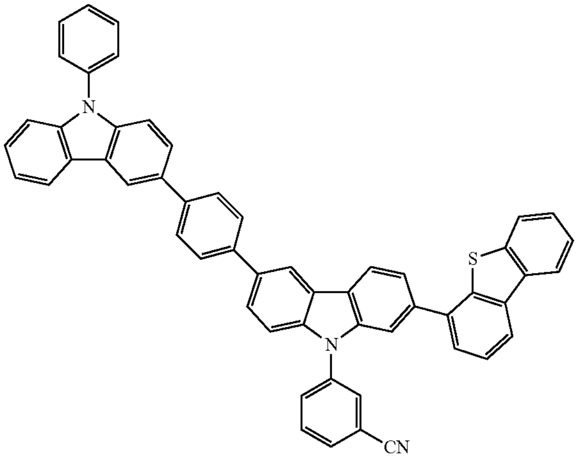
H1-54
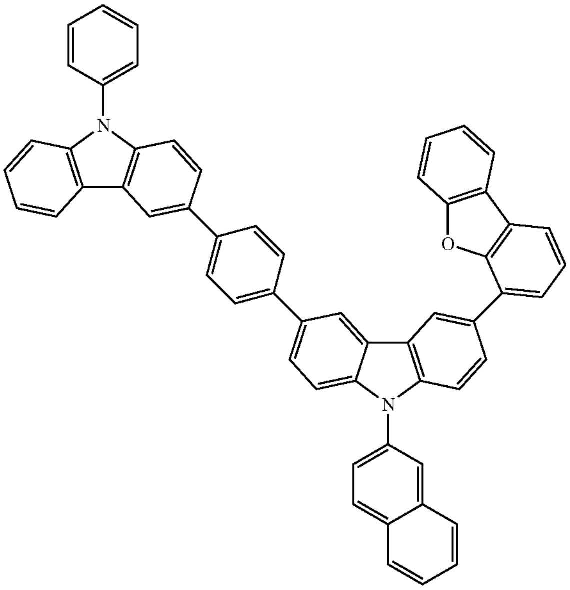
H1-55
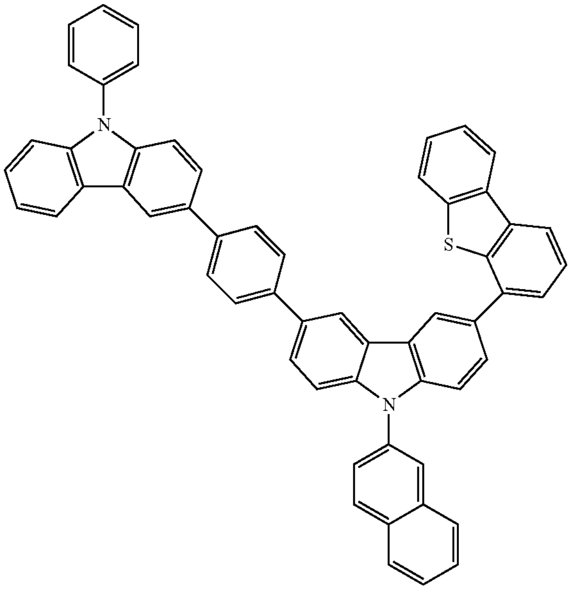
H1-56
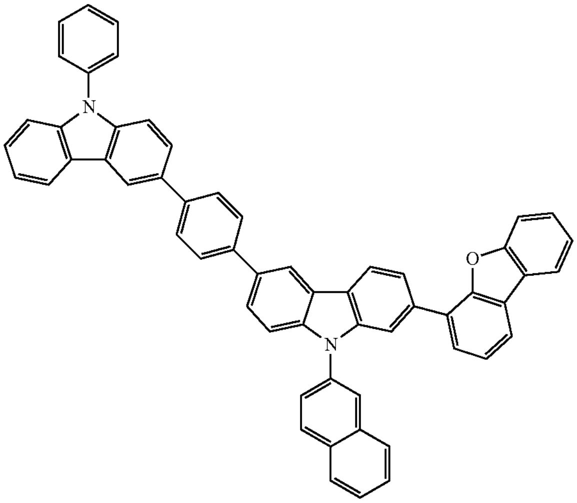

-continued
H1-57
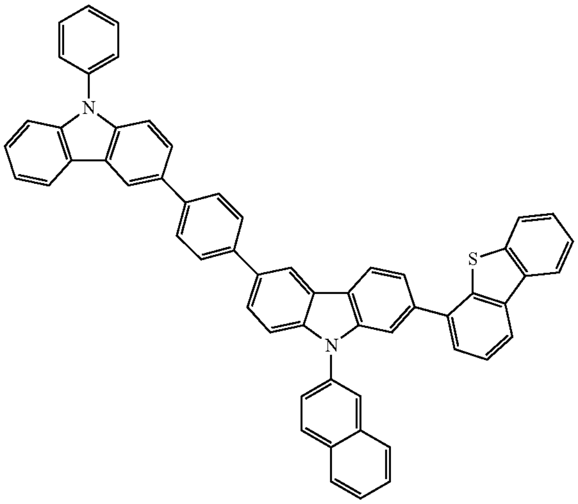
H1-58
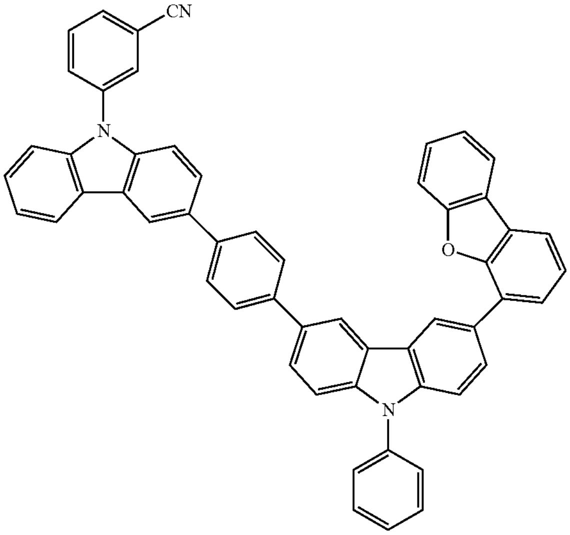
H1-59
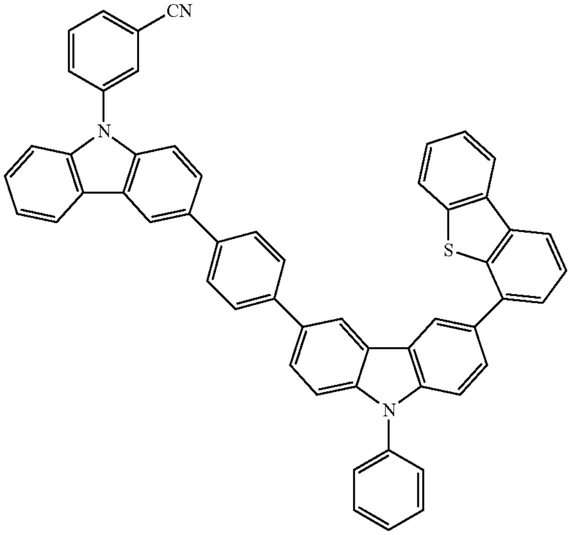
H1-60
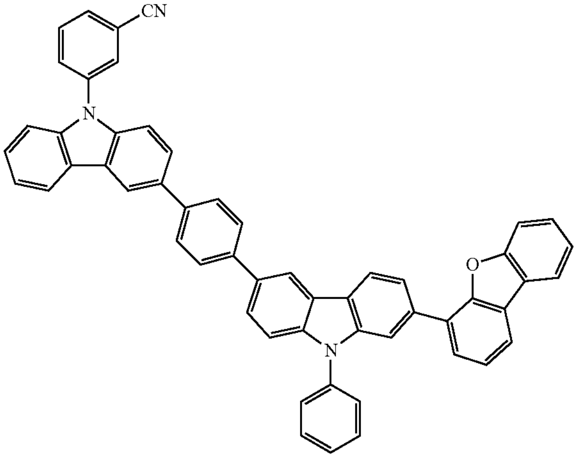

-continued
H1-61
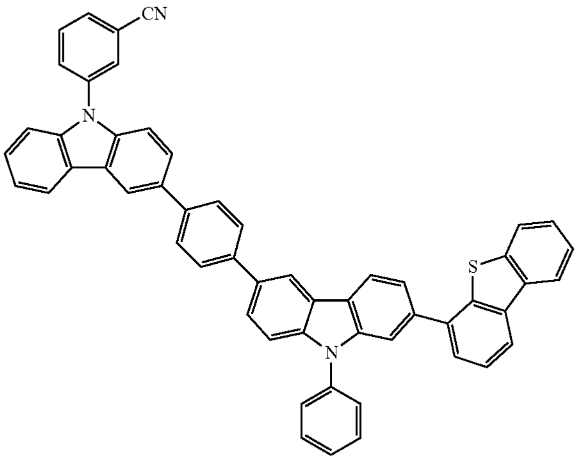
H1-62
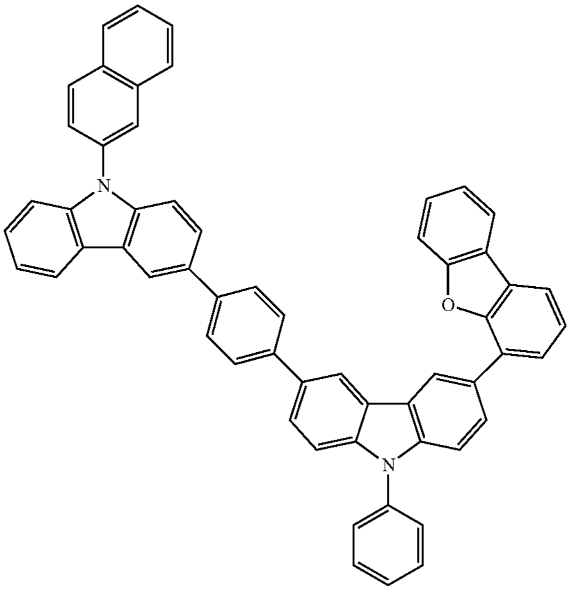
H1-63
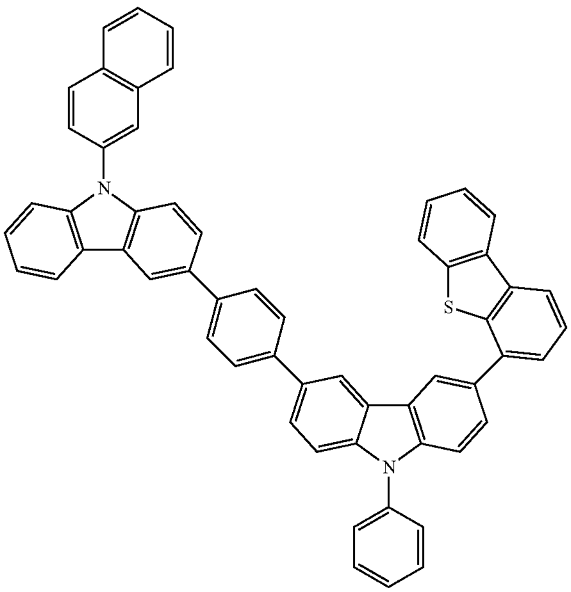
H1-64
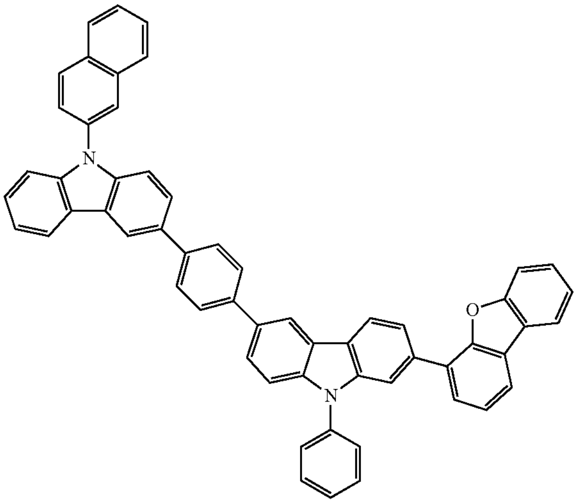

-continued
H1-65
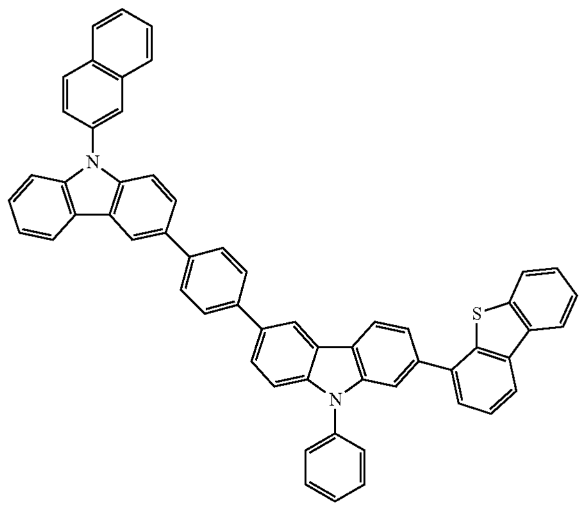
H1-66
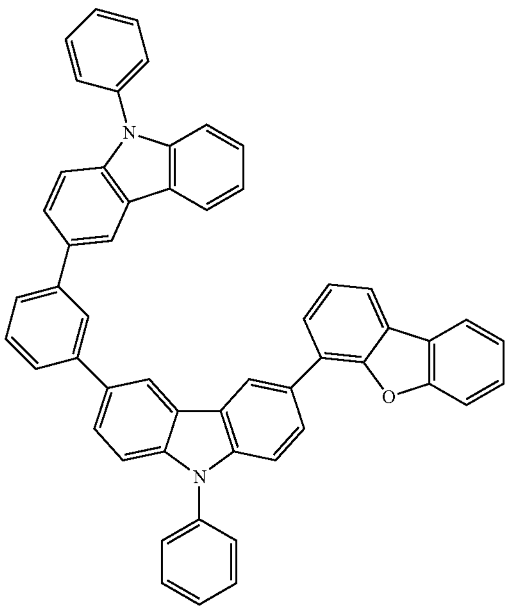
H1-67
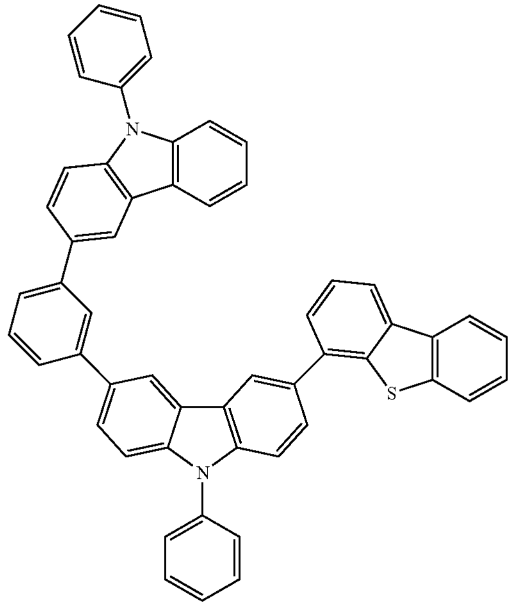
H1-68
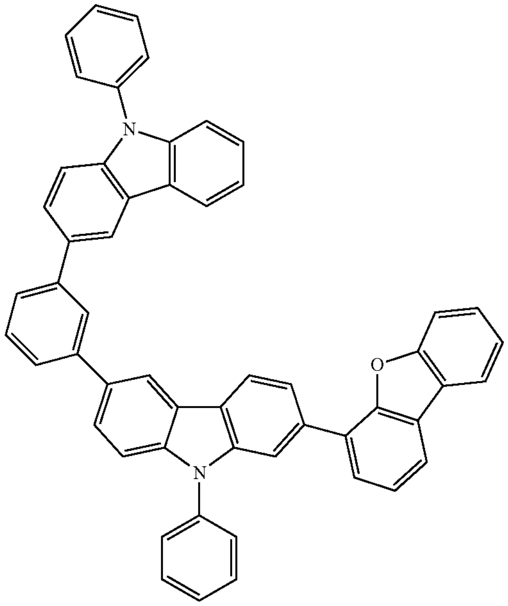

-continued
H1-69
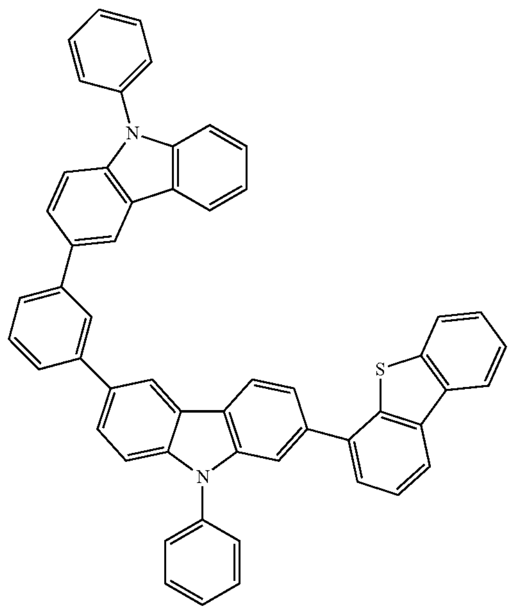
H1-70
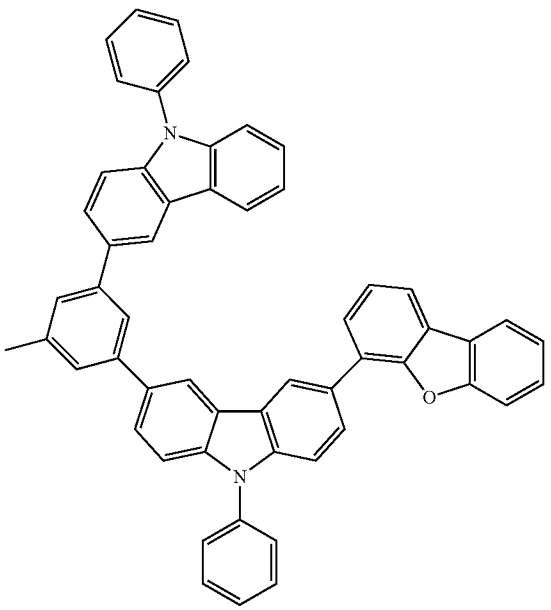
H1-71
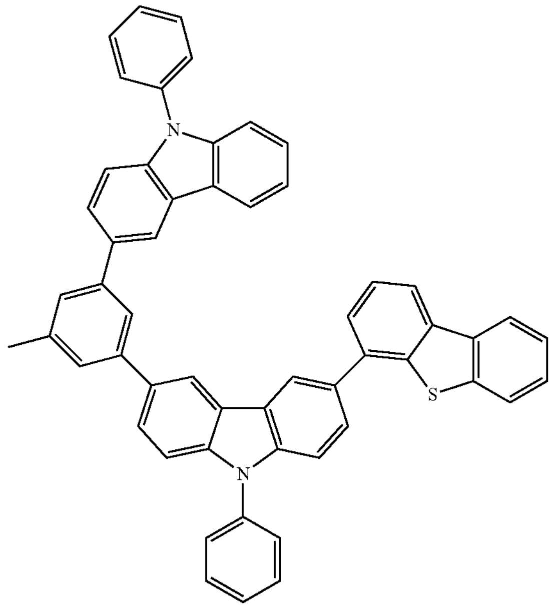
H1-72
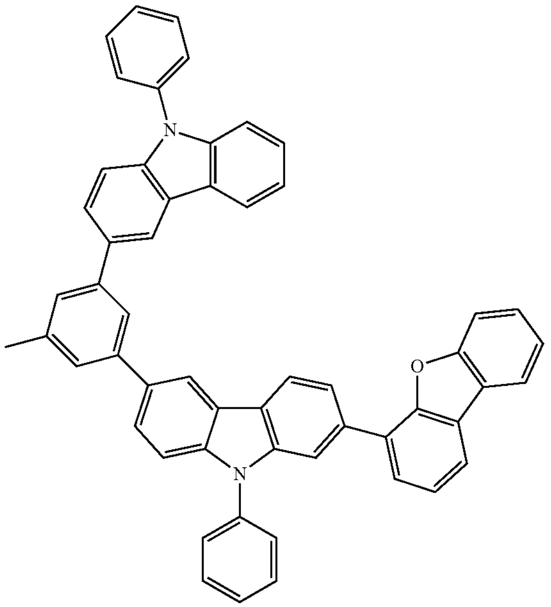

-continued
H1-73
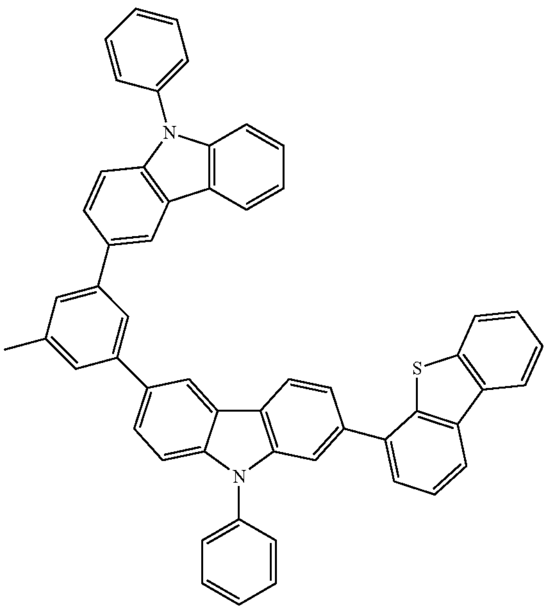
H1-74
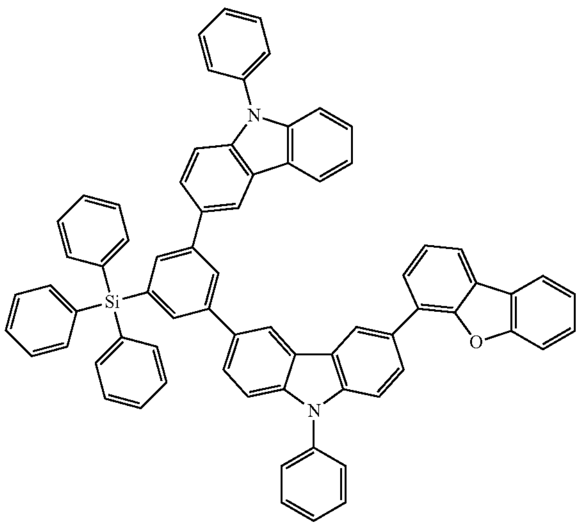
H1-74
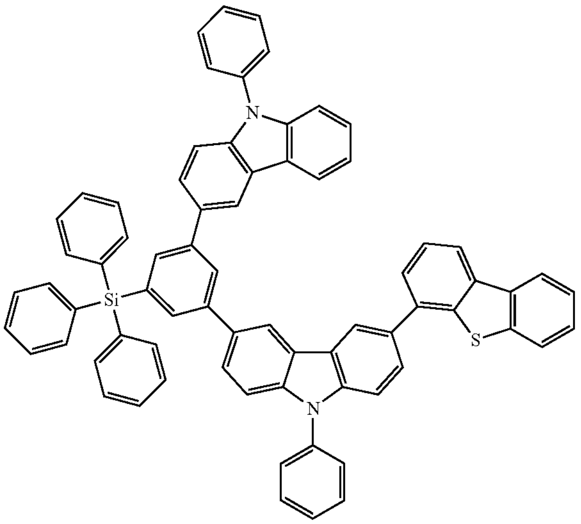
H1-76
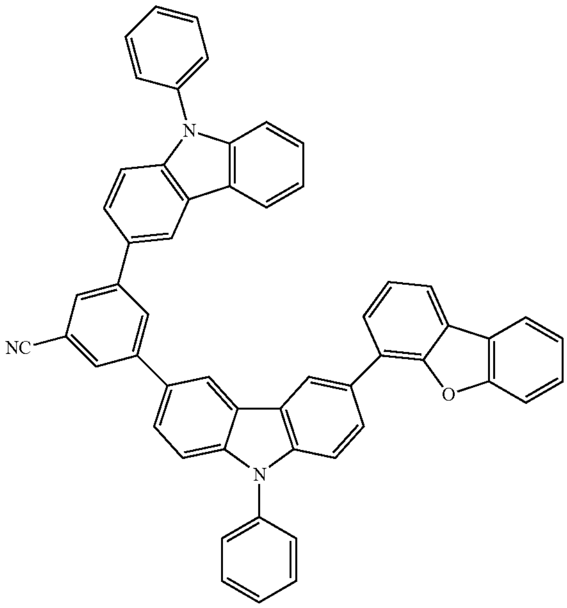

-continued
H1-77
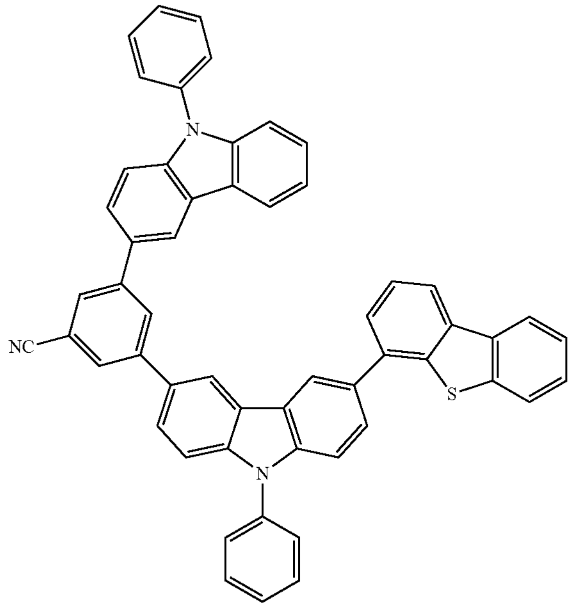
H1-78
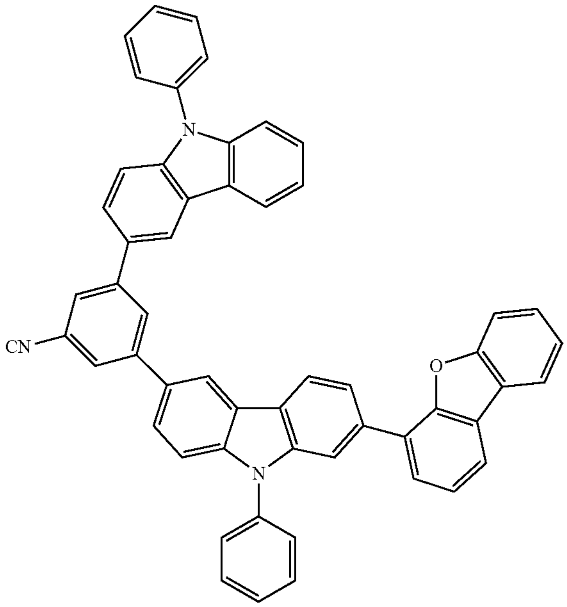
H1-79
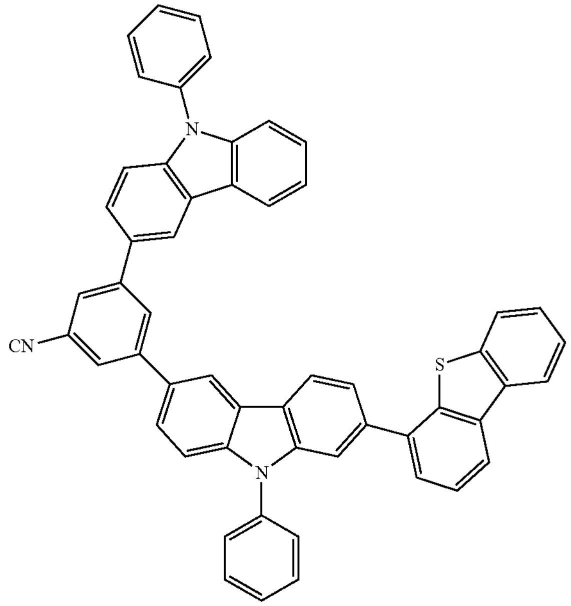
H1-80
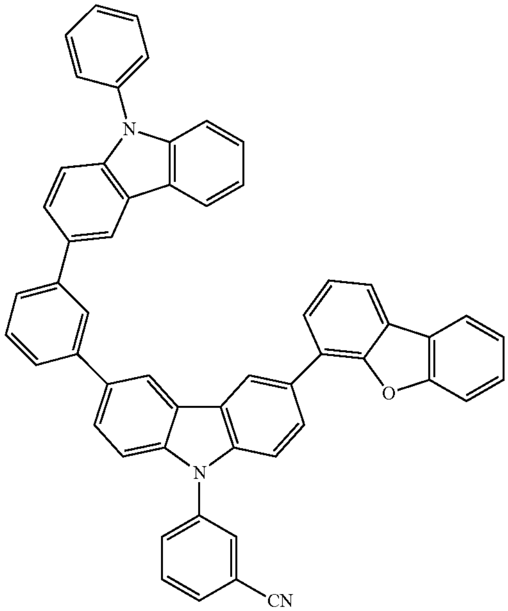

-continued
H1-80
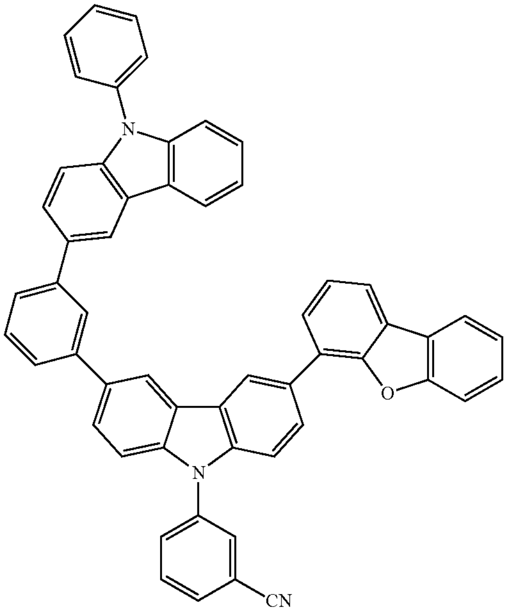
H1-81
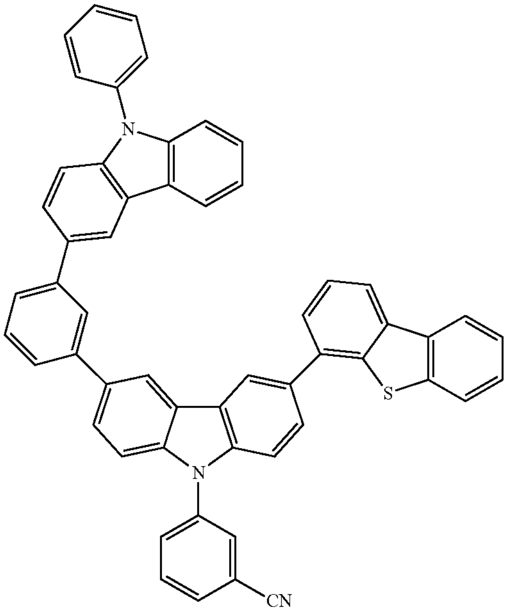
H1-82
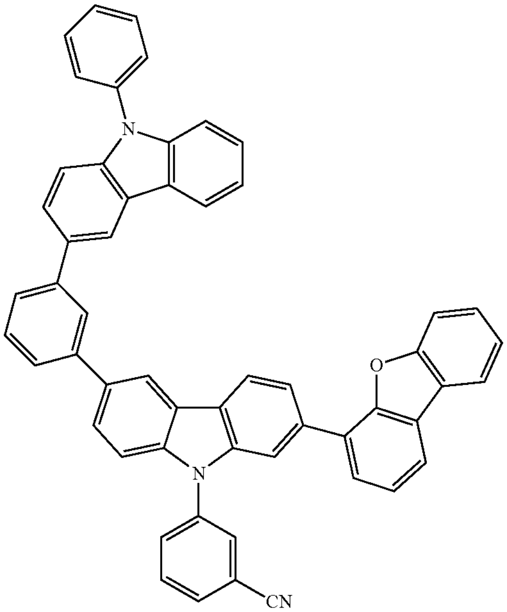
H1-83
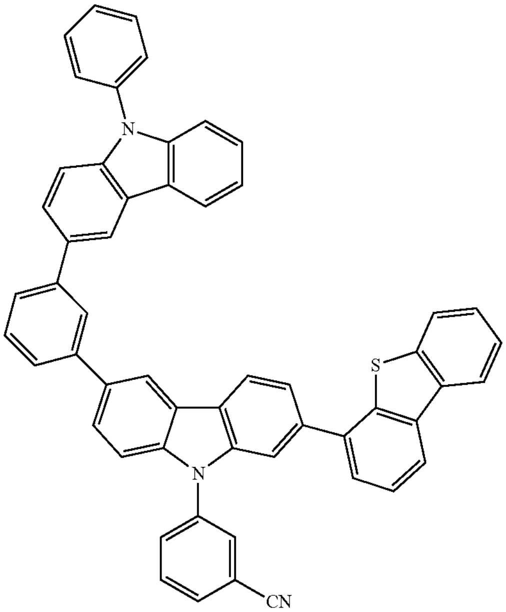

-continued
H1-84
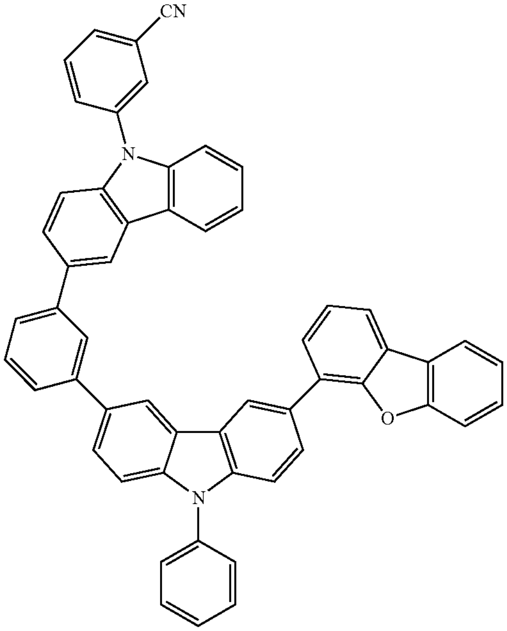
H1-85
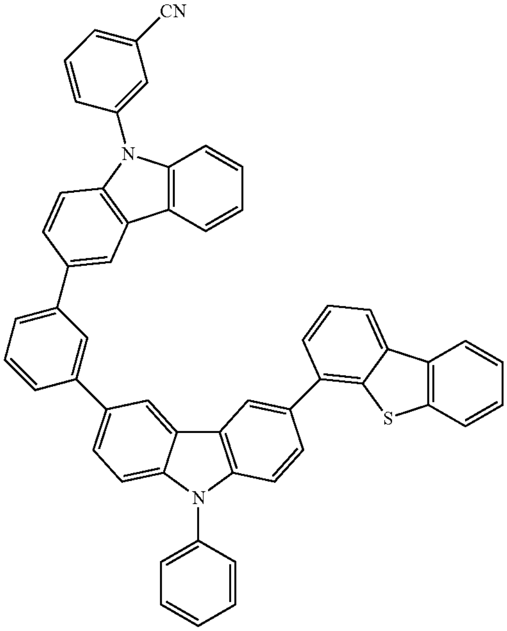
H1-86
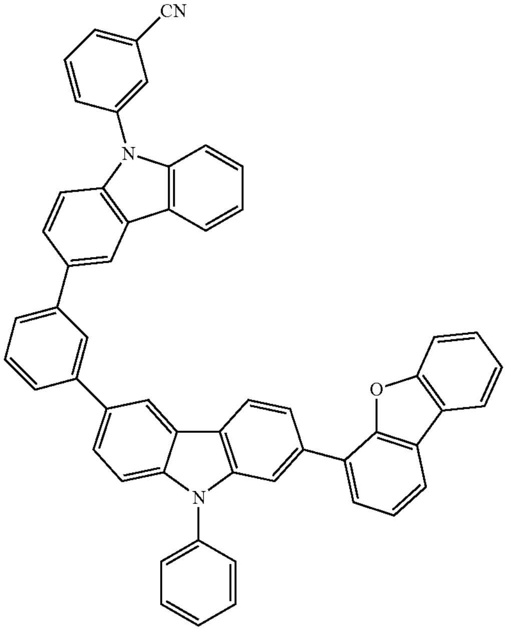
H1-87
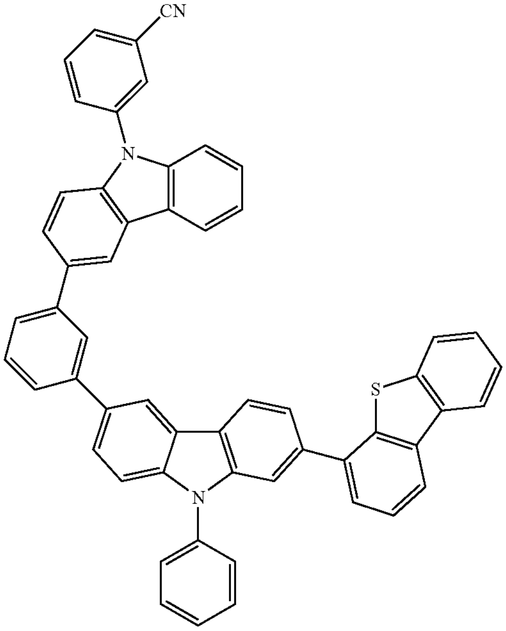

-continued
H1-88
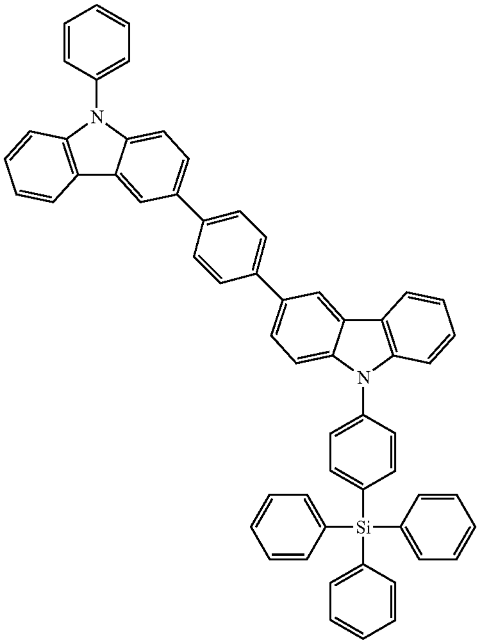
H1-89
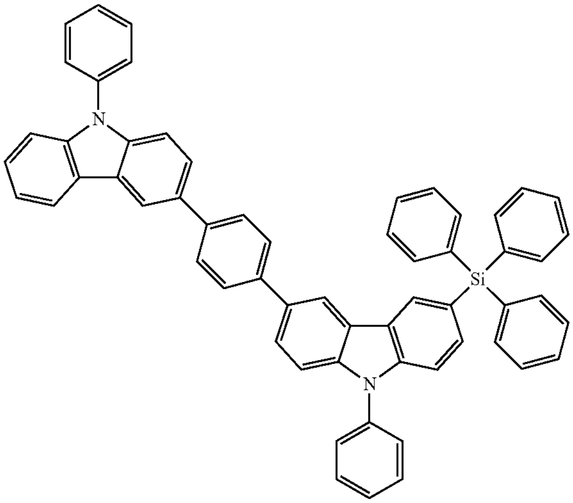
H1-90
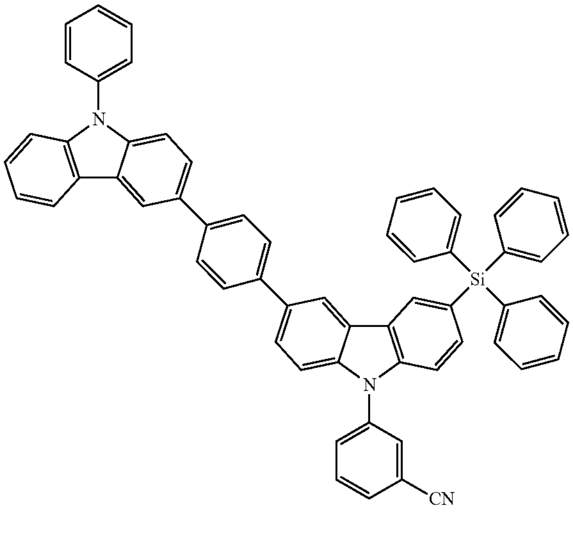
H1-91
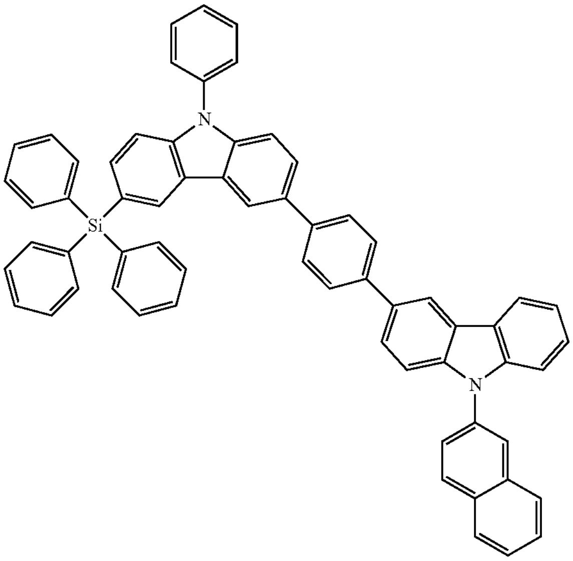

-continued
H1-92
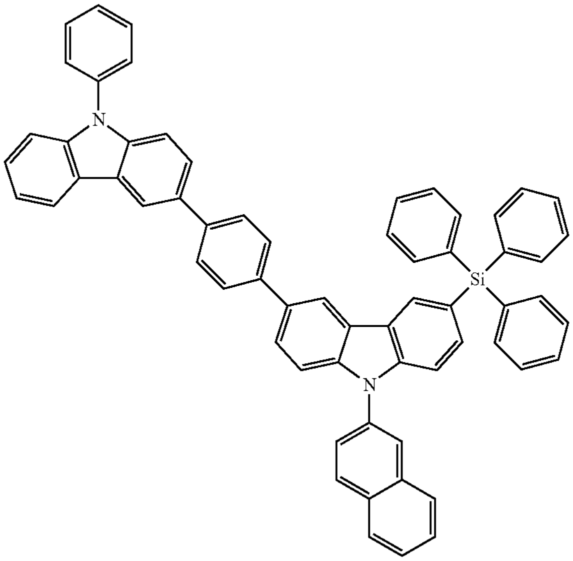
H1-93
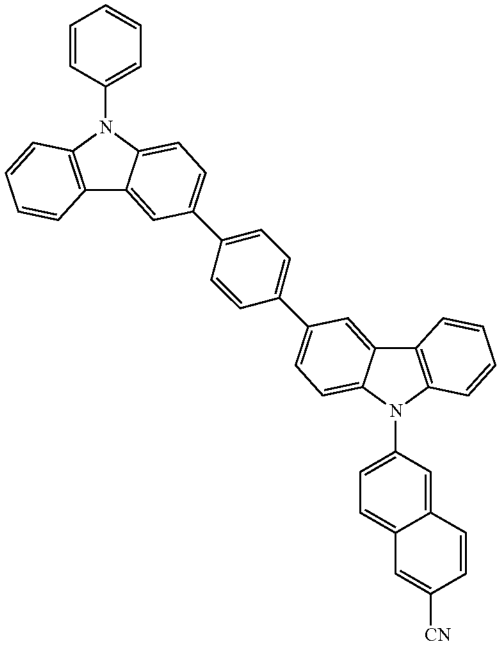
H1-94
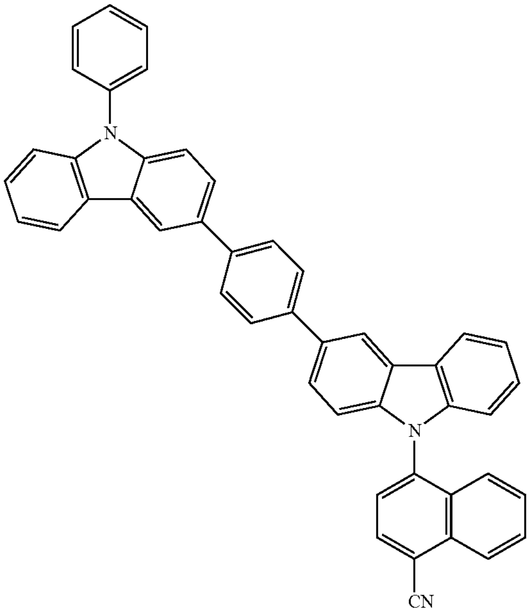
H1-95
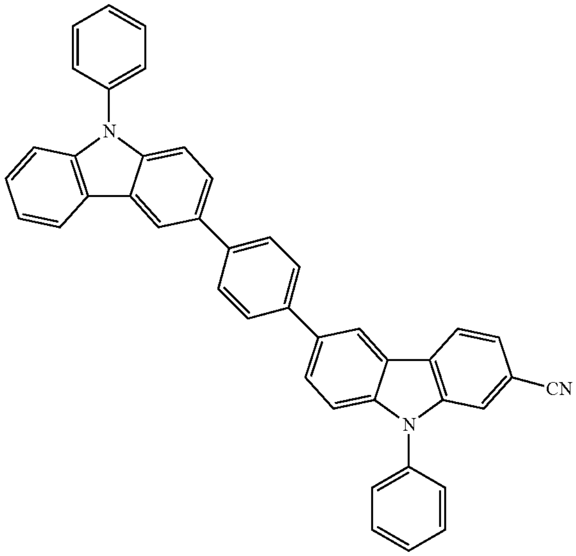

-continued
H1-96
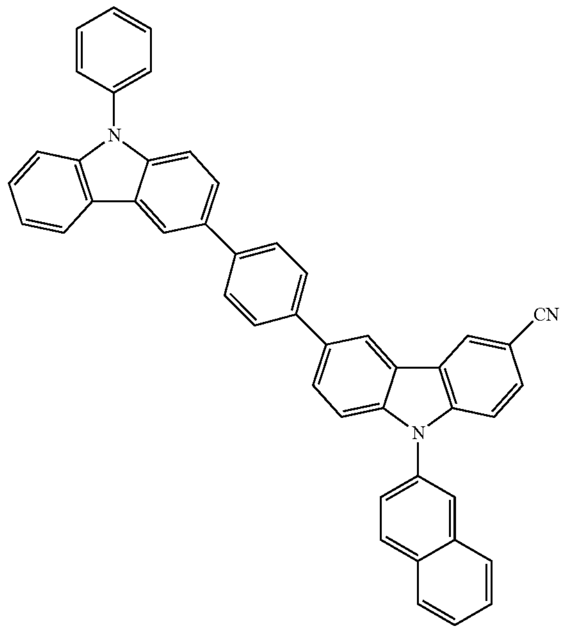
H1-97
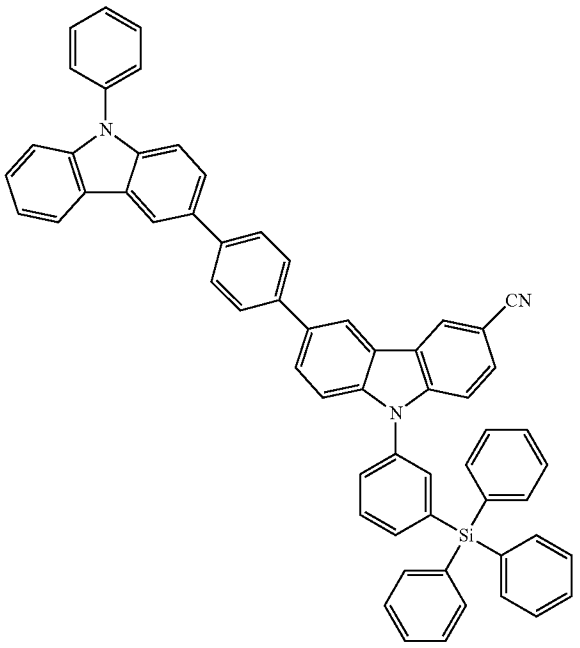
H1-98
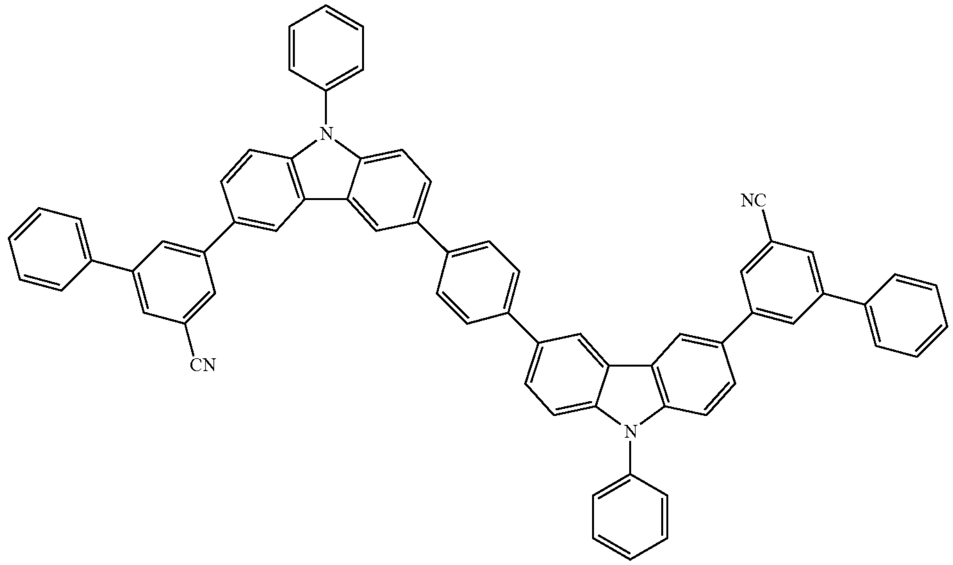

-continued
H1-99
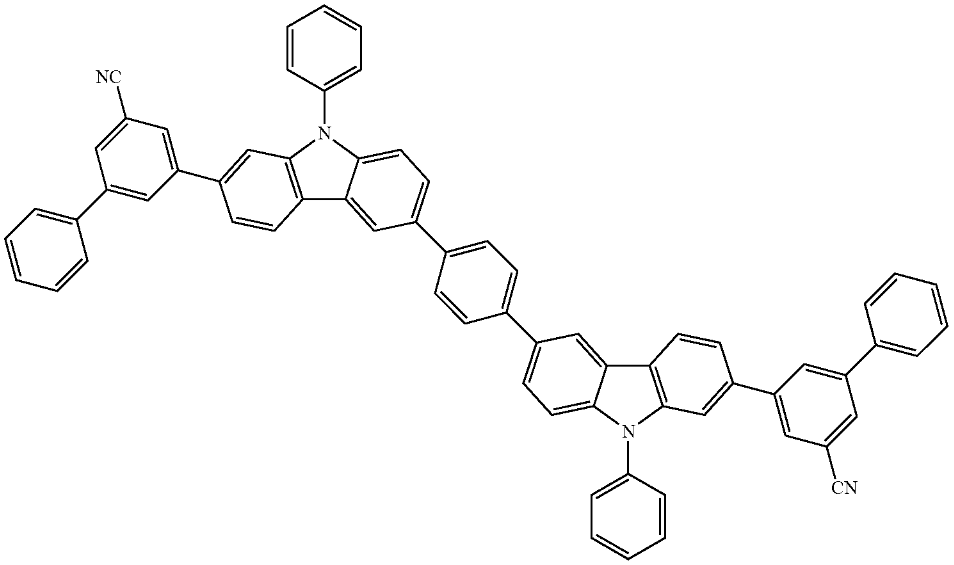
H1-100
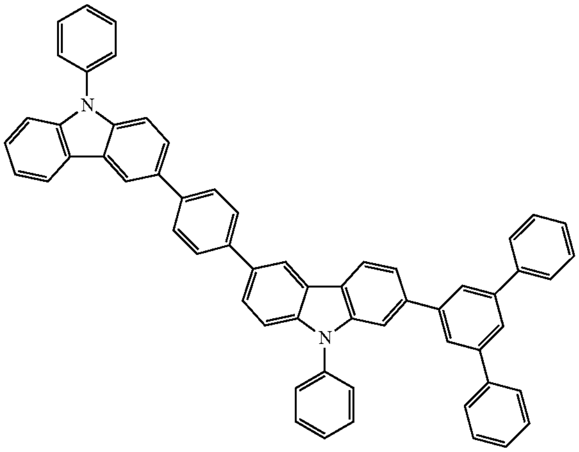
H1-101
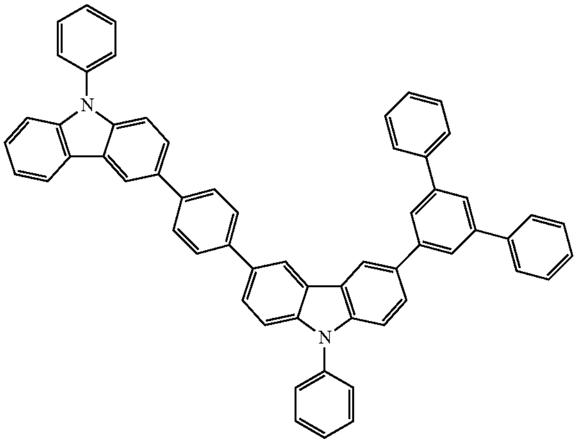
H1-102
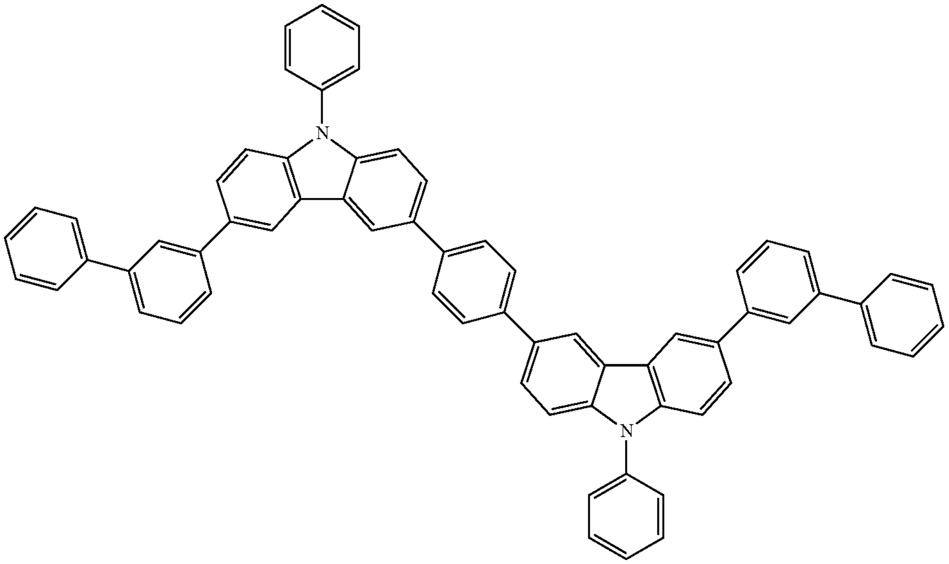

-continued
H1-103
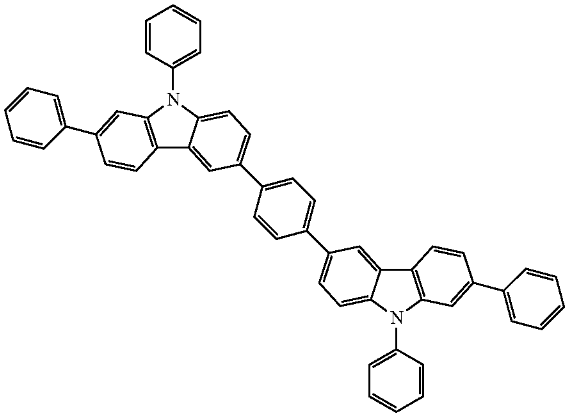
H1-104
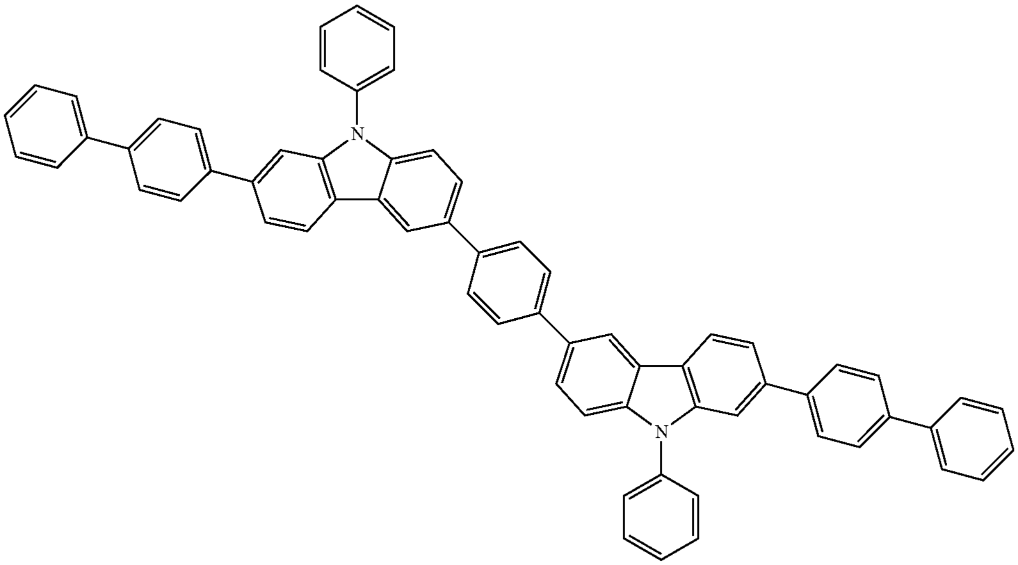
H1-105
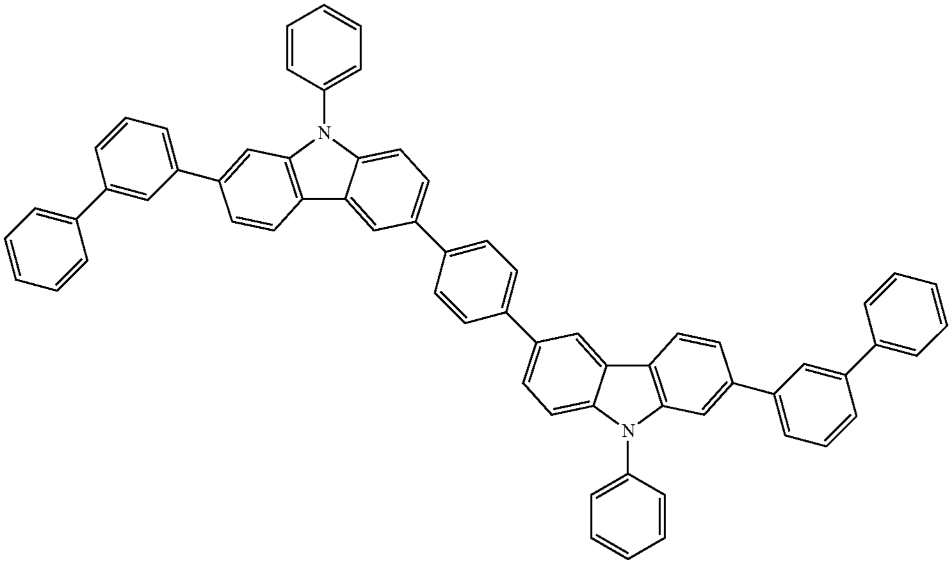

-continued
H1-106
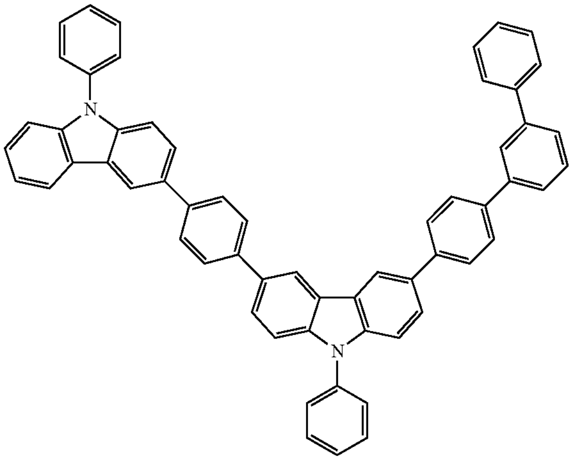
H1-107
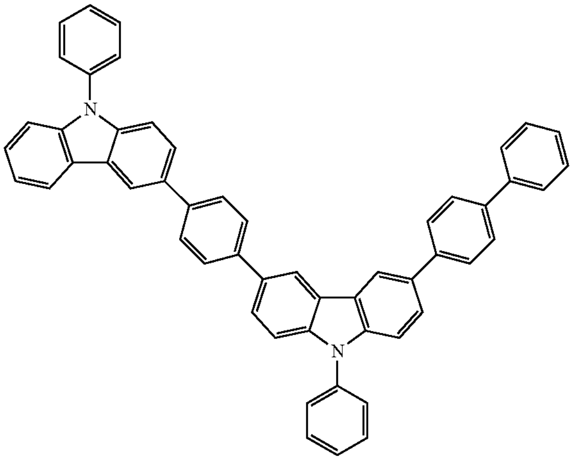
H1-108
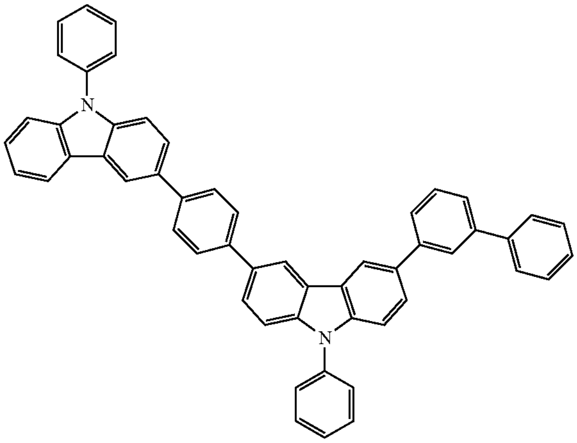
H1-109
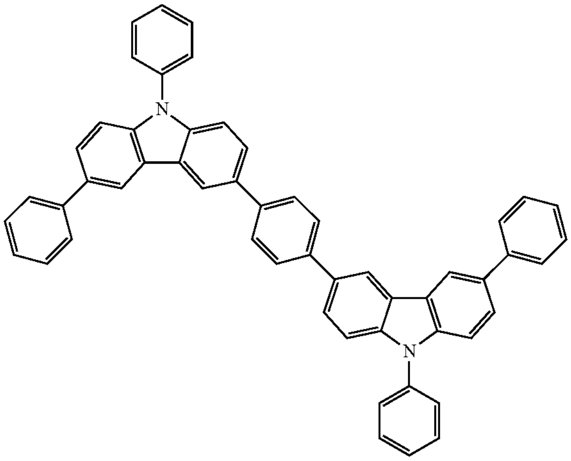
H1-110
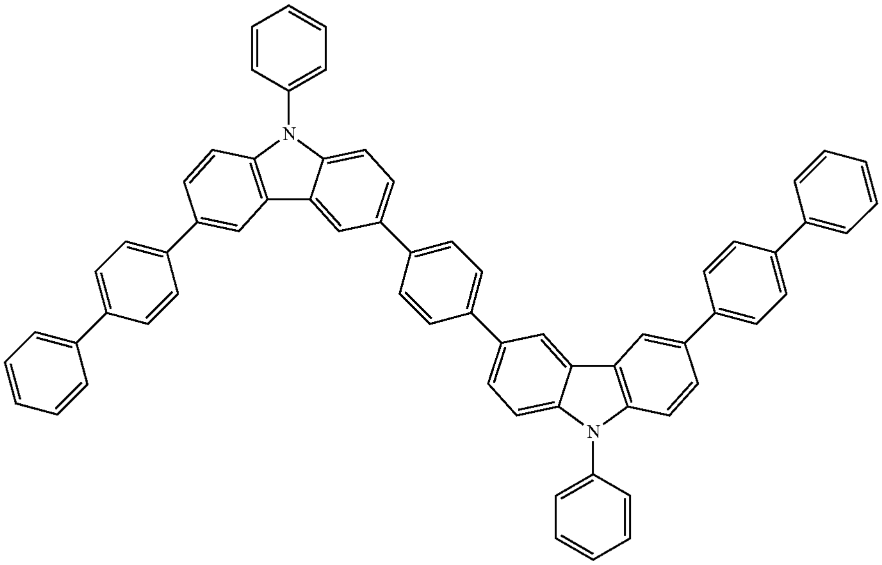

-continued
H1-111
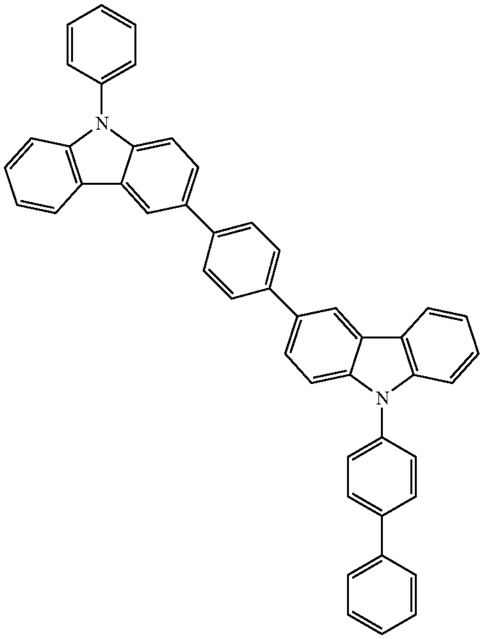
H1-112
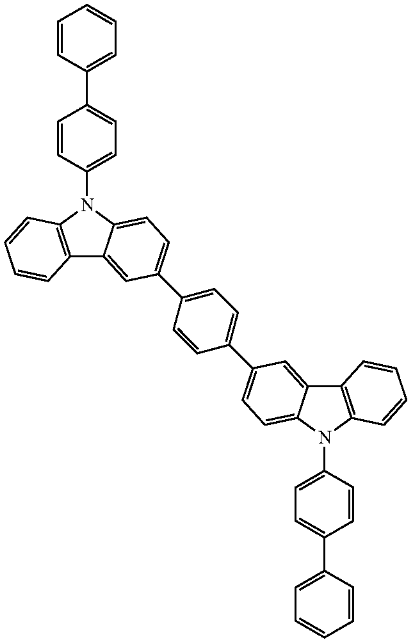
H1-113
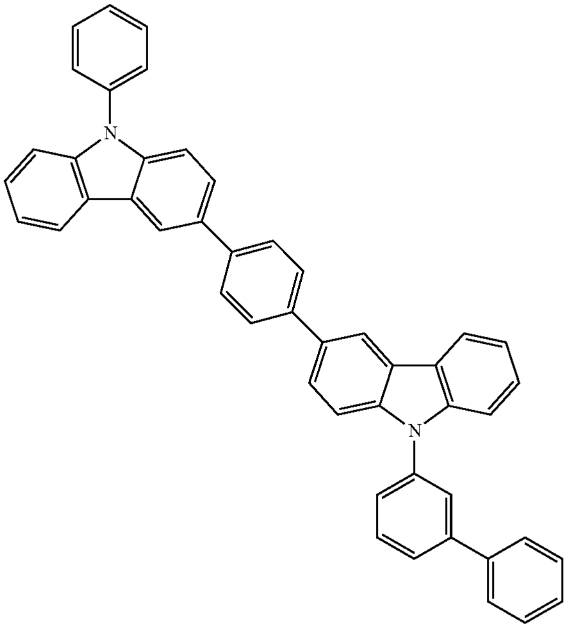
H1-114
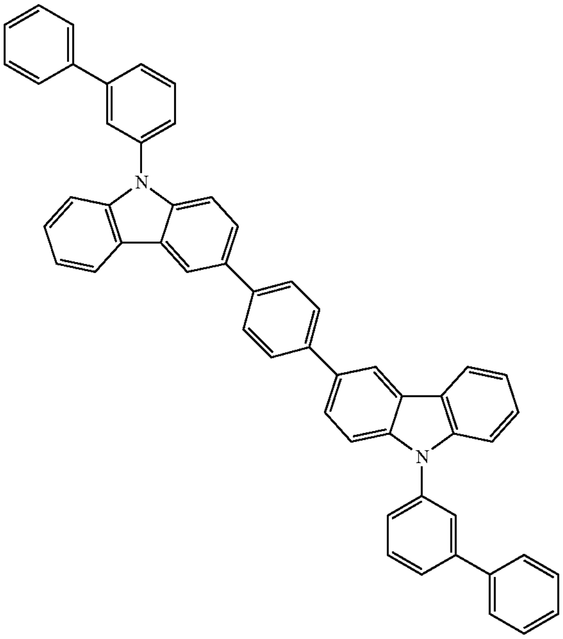

-continued
H1-115
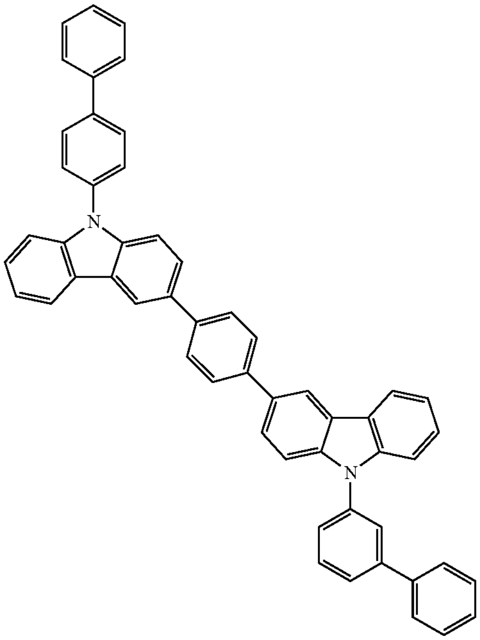
H1-116
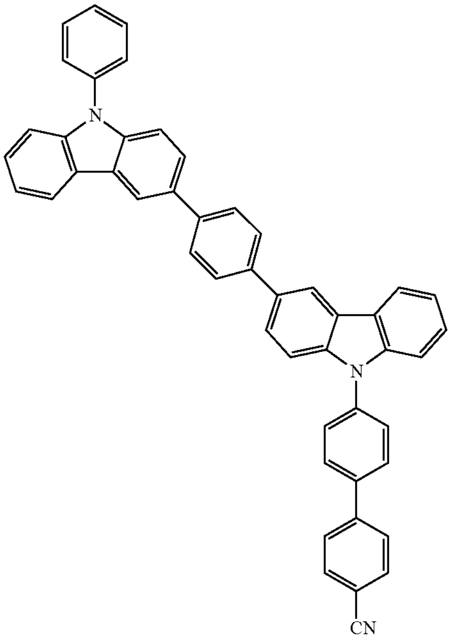
H1-117
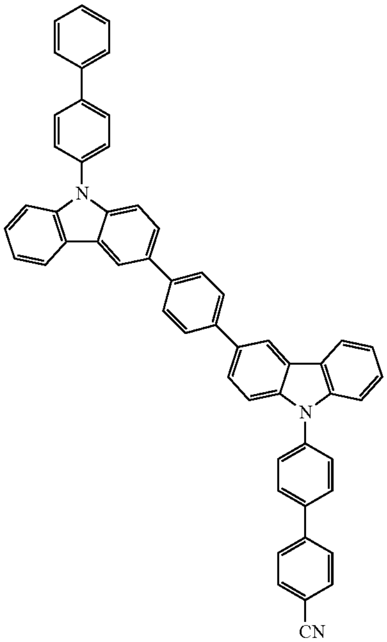
H1-118
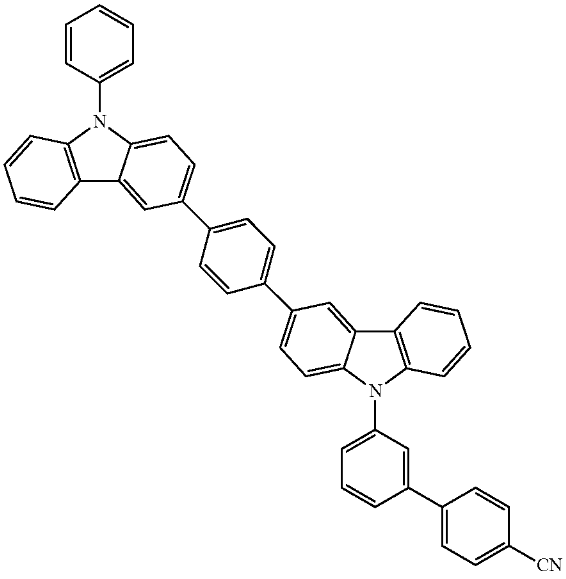

-continued
H1-119
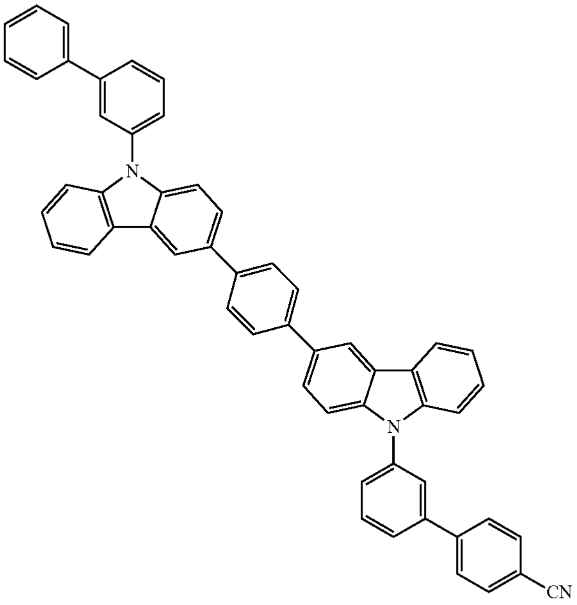
H1-120
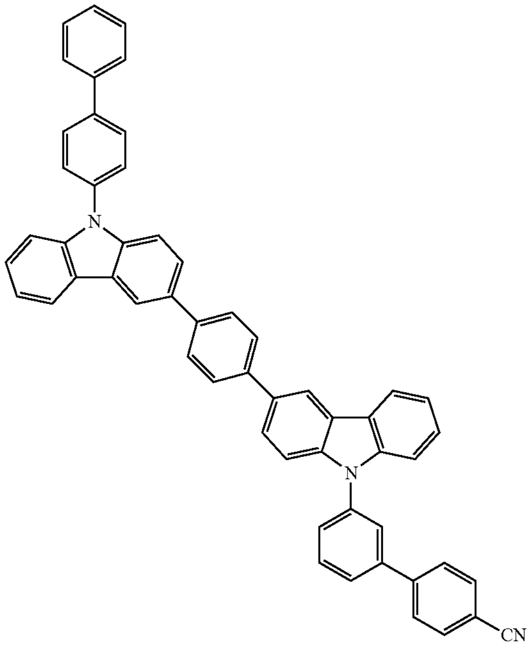
H1-121
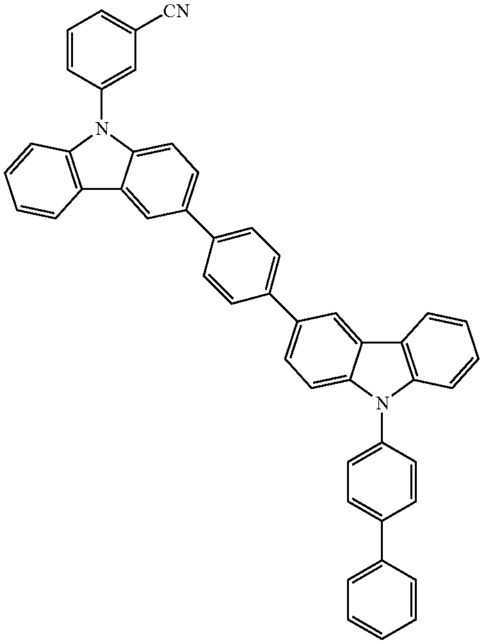
H1-122
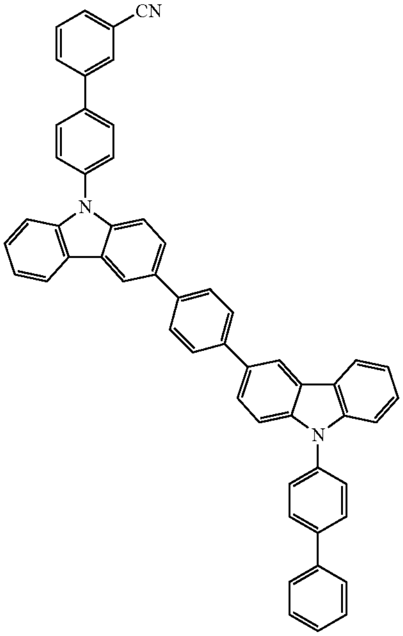

-continued
H1-123
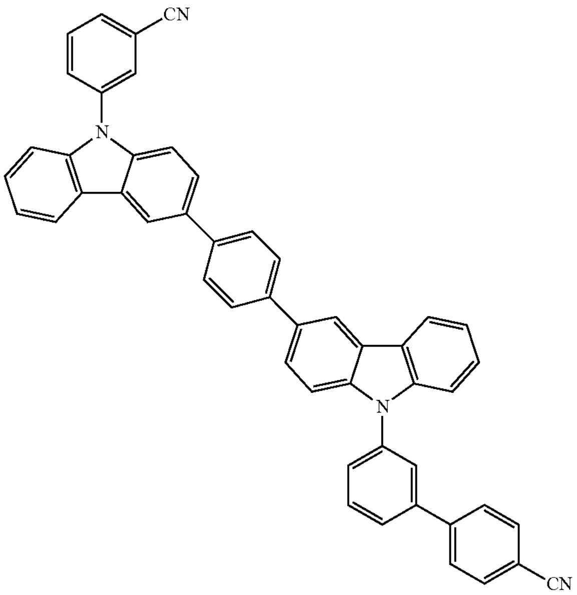
H1-124
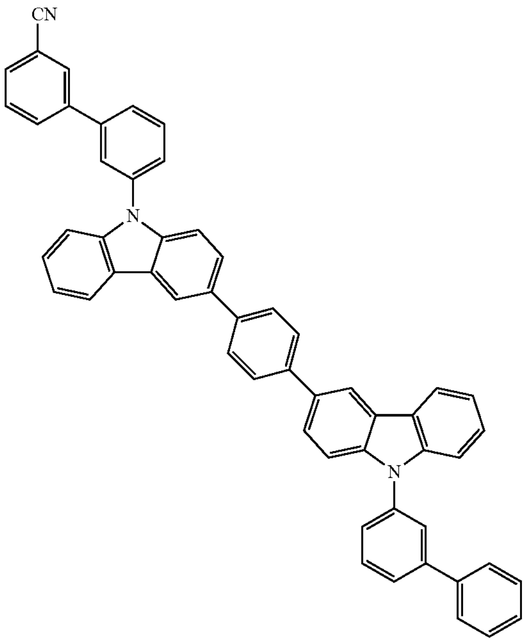
H1-125
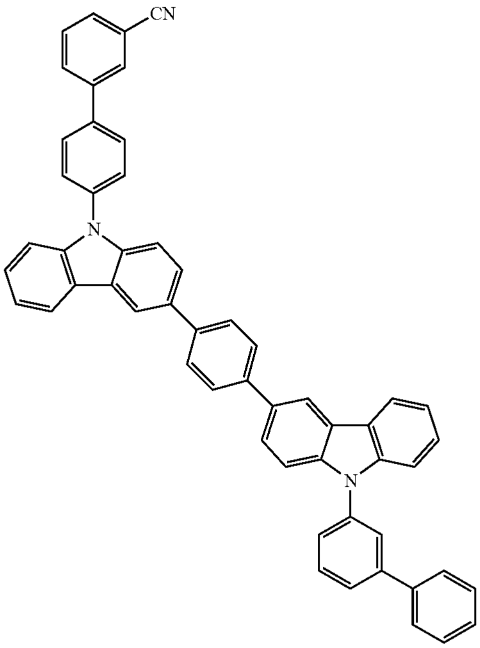
H1-126
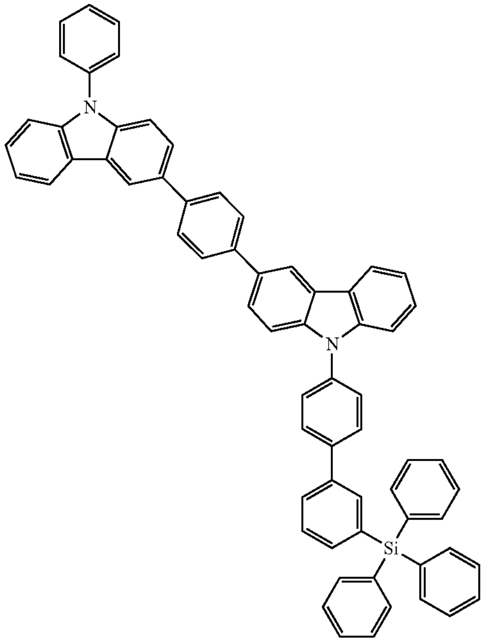

-continued
H1-127
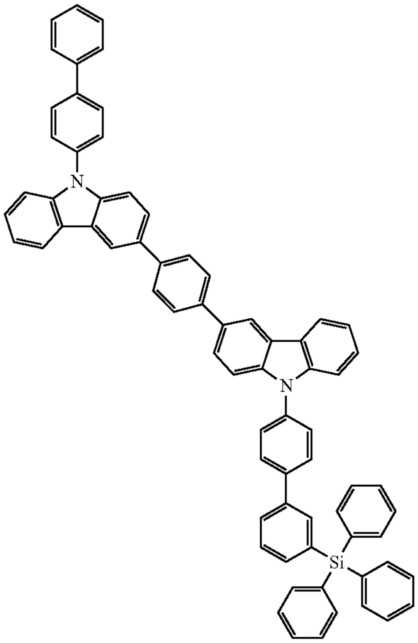
H1-128
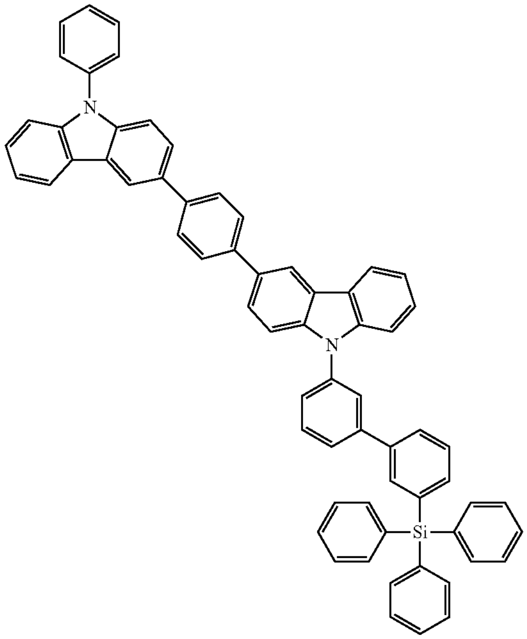
H1-129
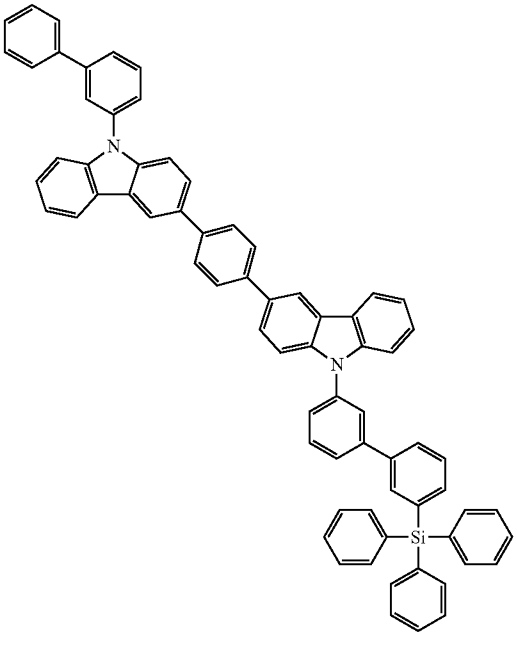
H1-130
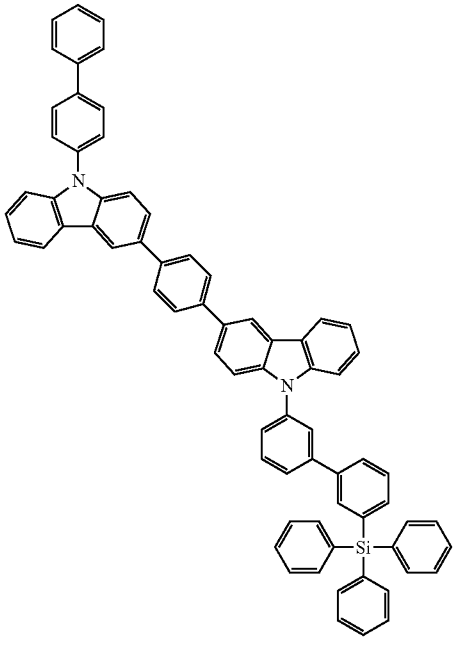

-continued
H1-131
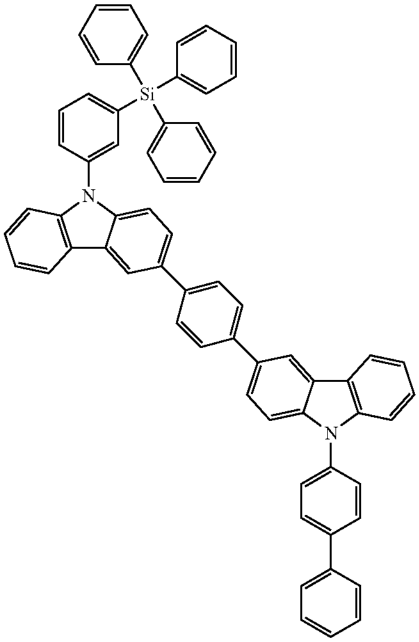
H1-132
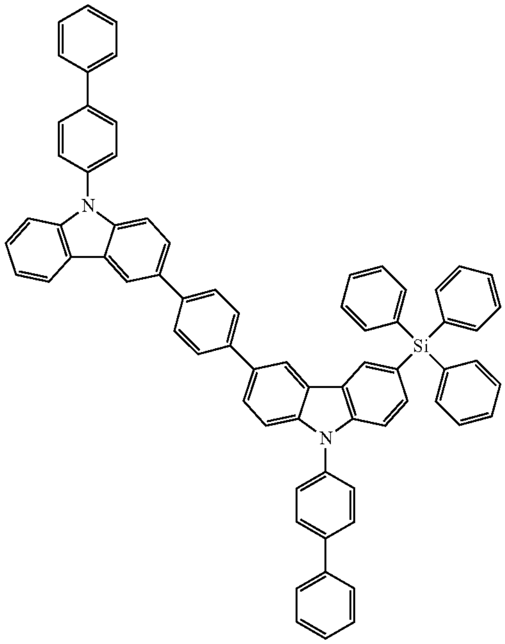
H1-133
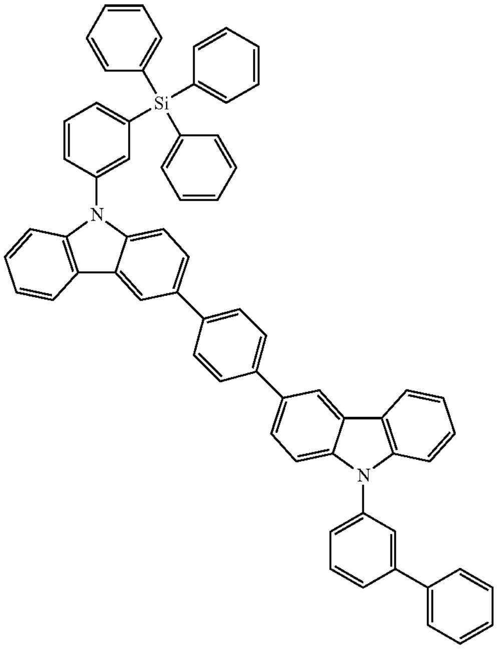
H1-134
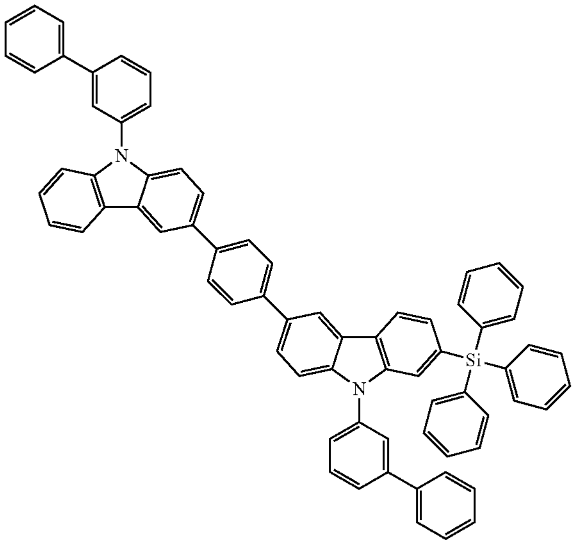

-continued
H1-135
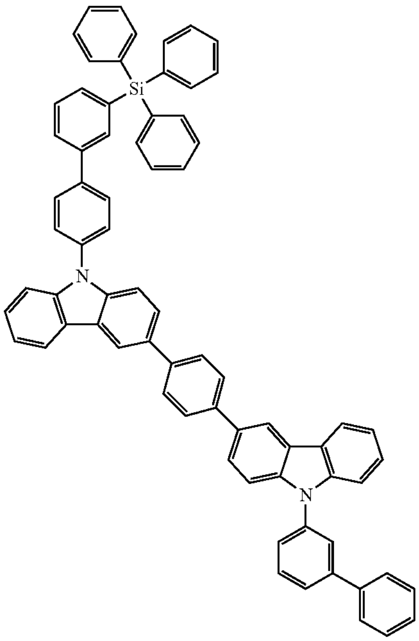
The second host compound represented by formula 2 includes the following compounds, but is not limited thereto:
H2-1
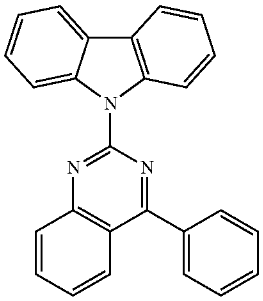
H2-2
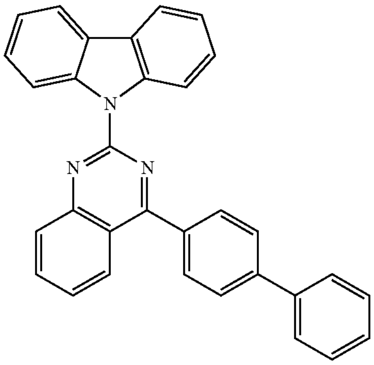
-continued
H2-3
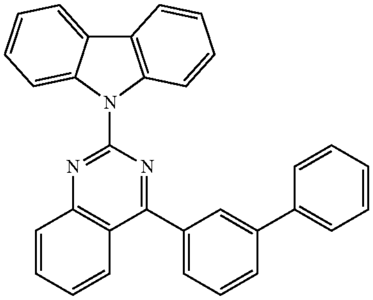
H2-4
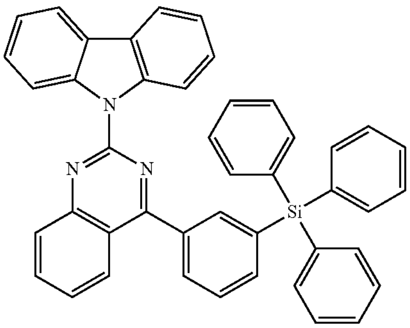

-continued
H2-5
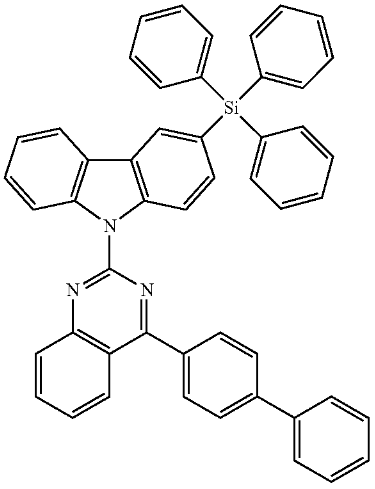
H2-6
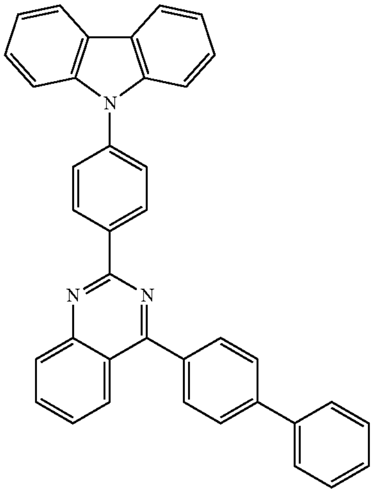
H2-7
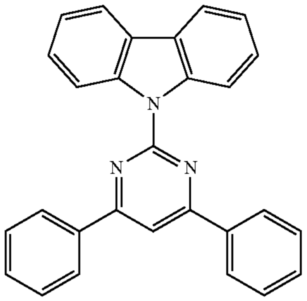
H2-8
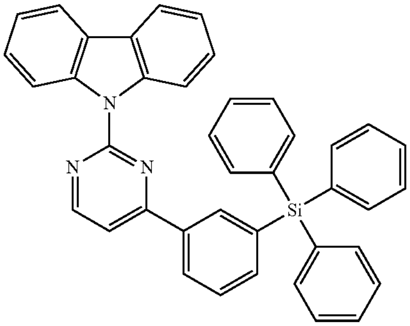
-continued
H2-9
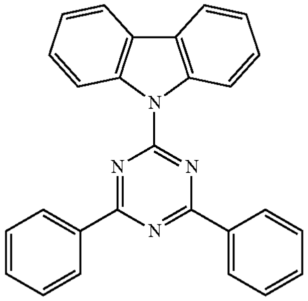
H2-10
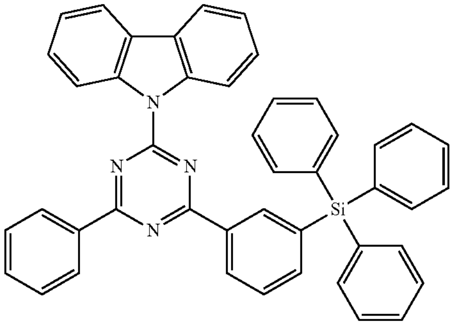
H2-11
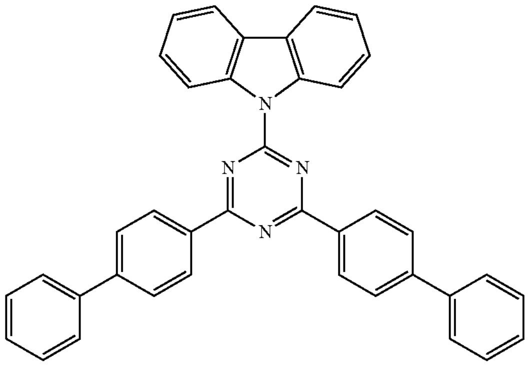
H2-12
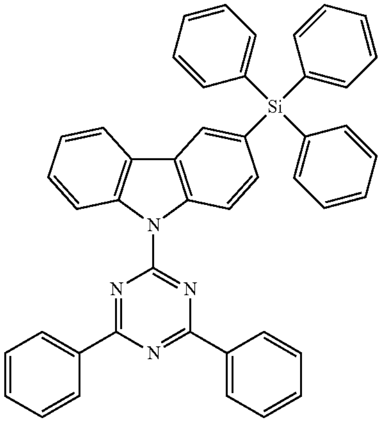

-continued
H2-13
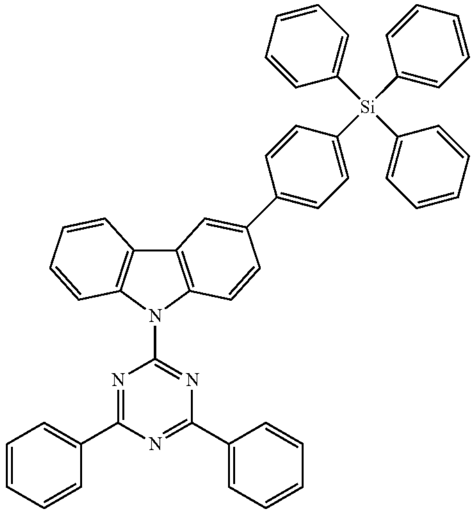
H2-14
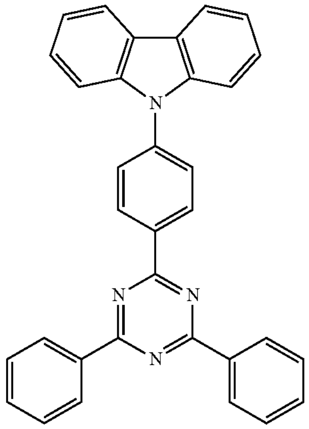
H2-15
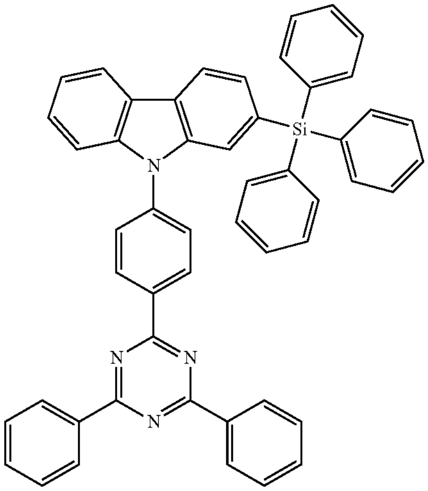
-continued
H2-16
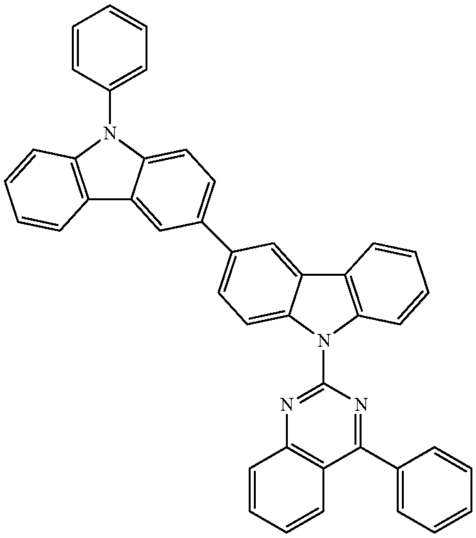
H2-17
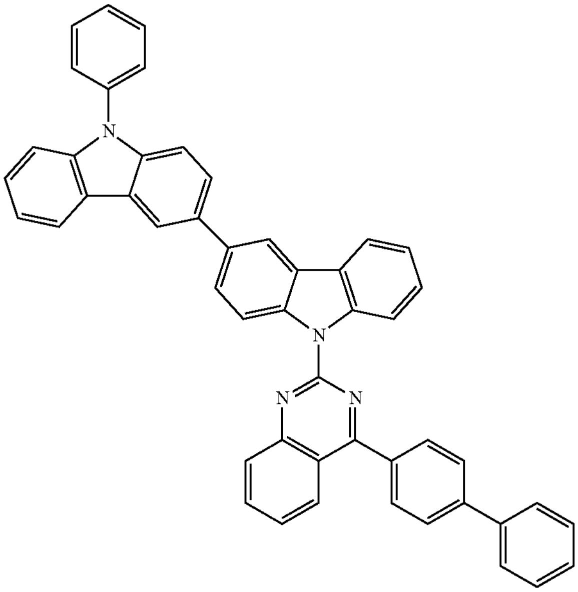

-continued
H2-18
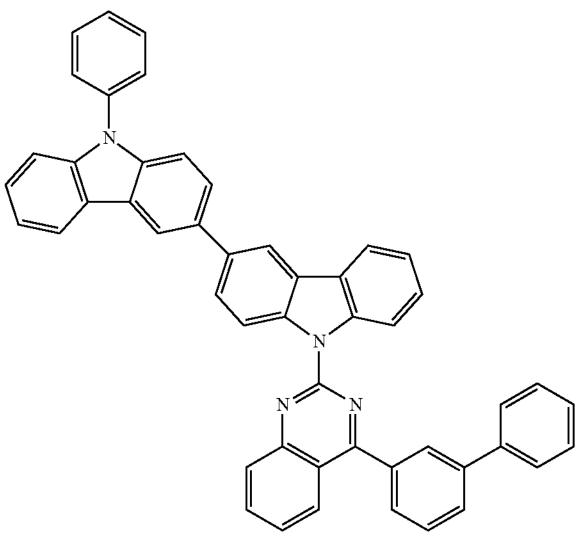
H2-19
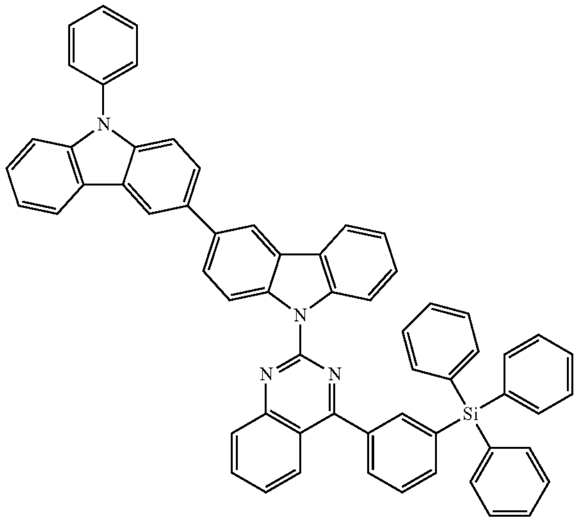
H2-20
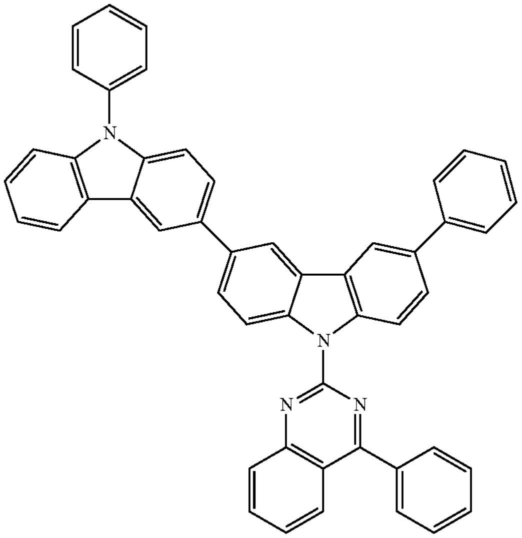
-continued
H2-21
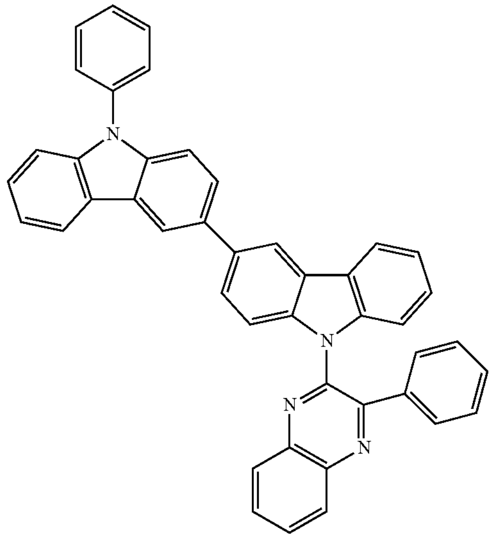
H2-22
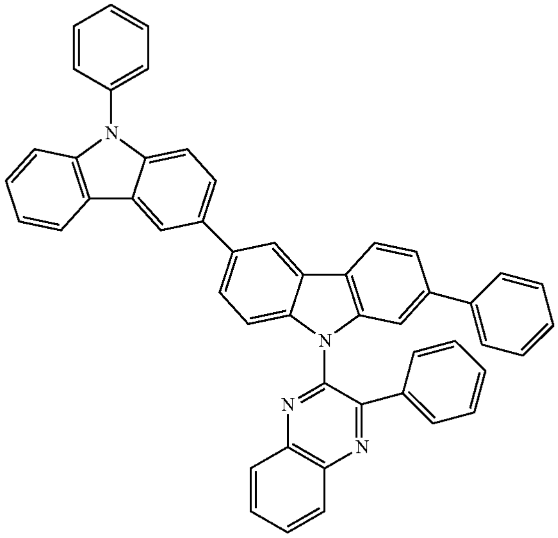
H2-23
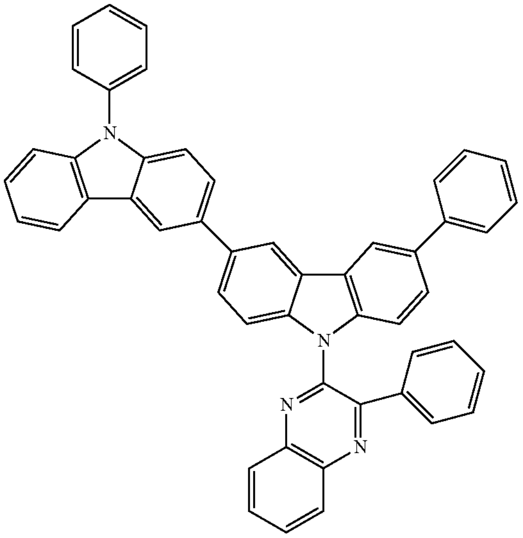

-continued
H2-24
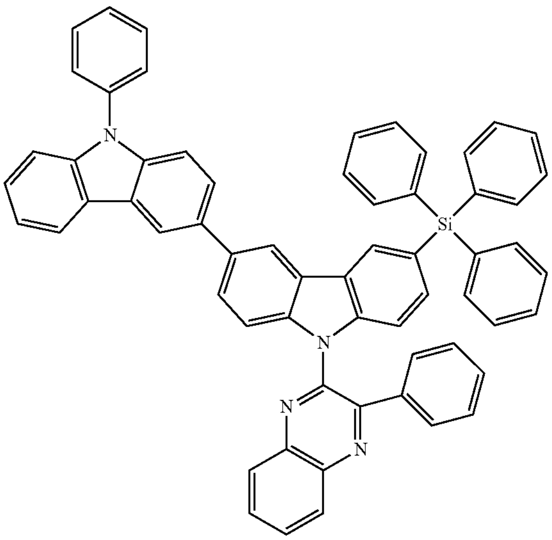
H2-25
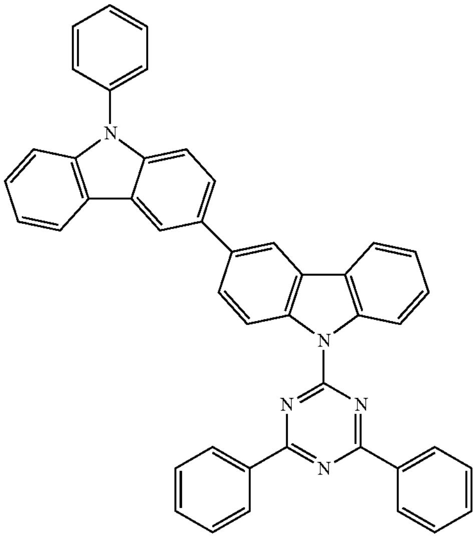
H2-26
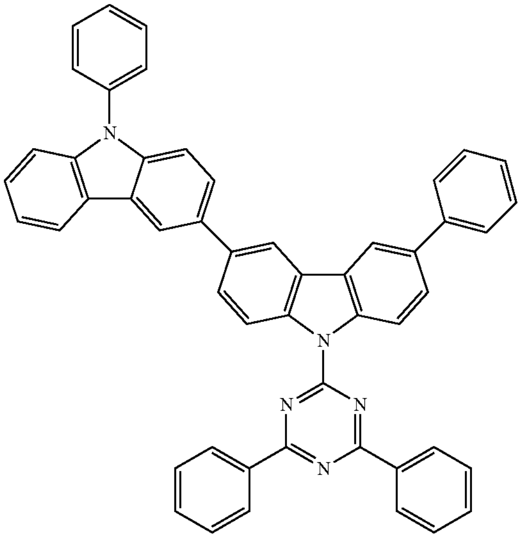
-continued
H2-27
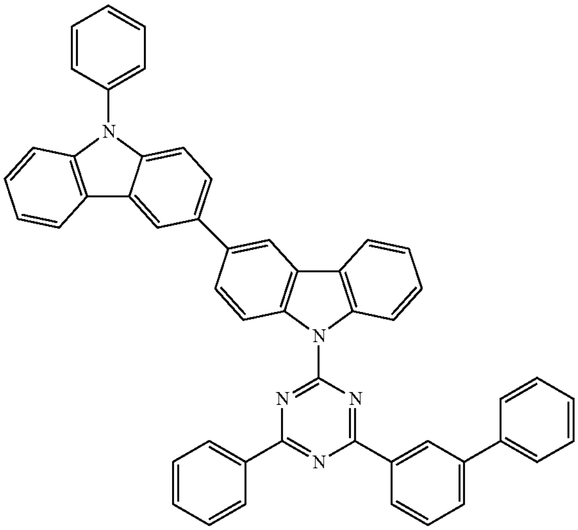
H2-28
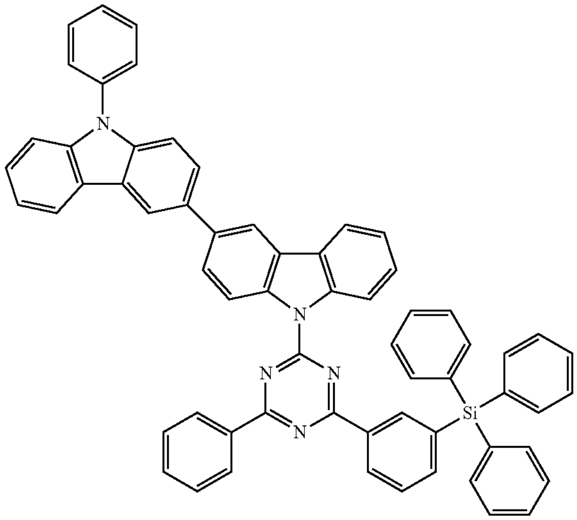

-continued
H2-29
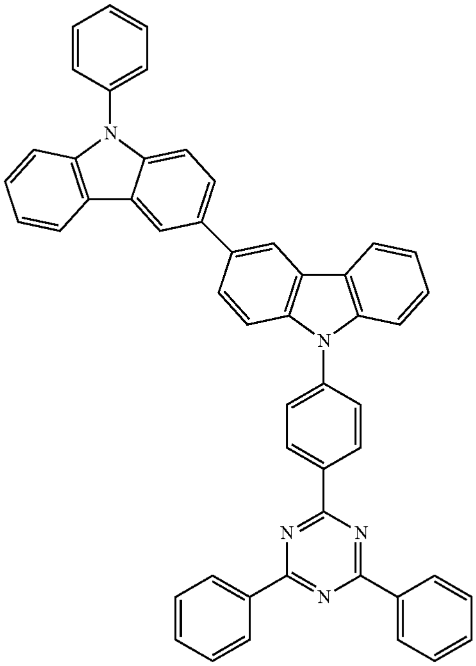
H2-30
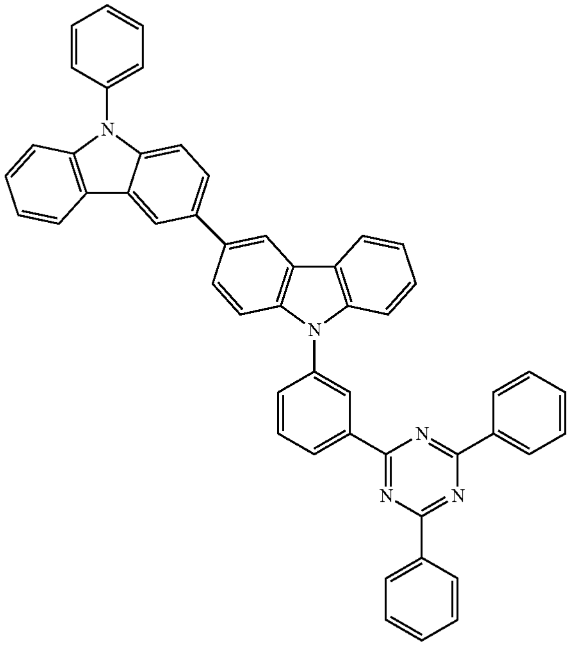
-continued
H2-31
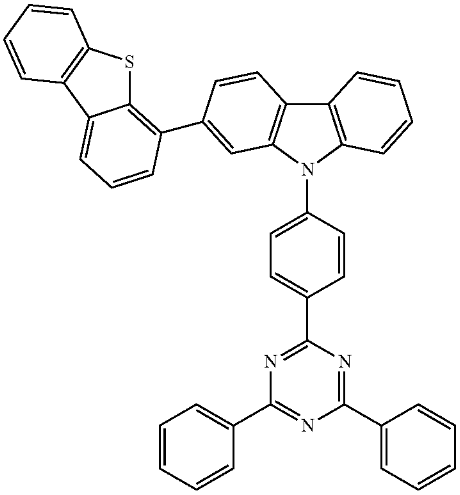
H2-32
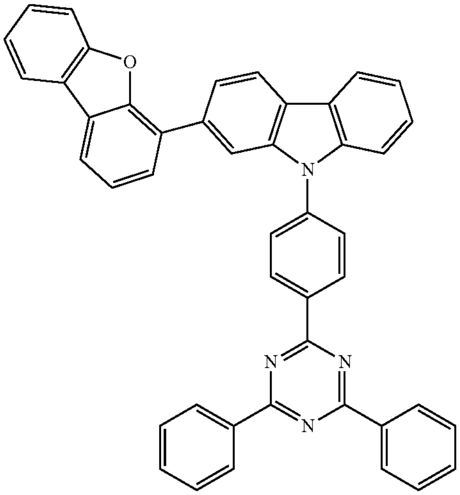
H2-33
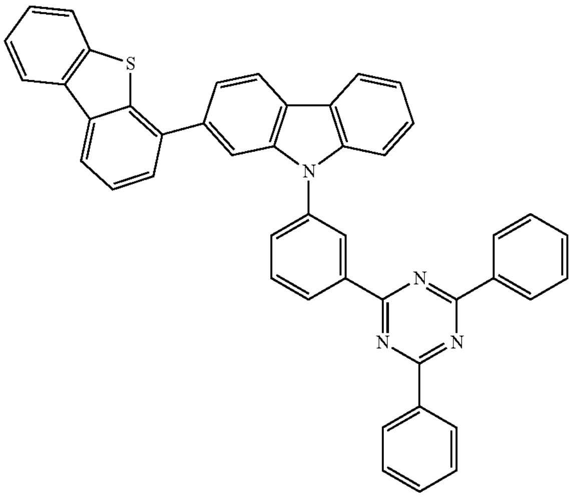

-continued
H2-34
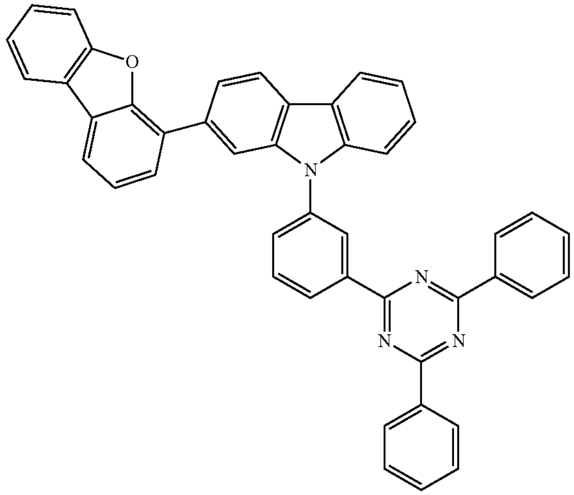
H2-35
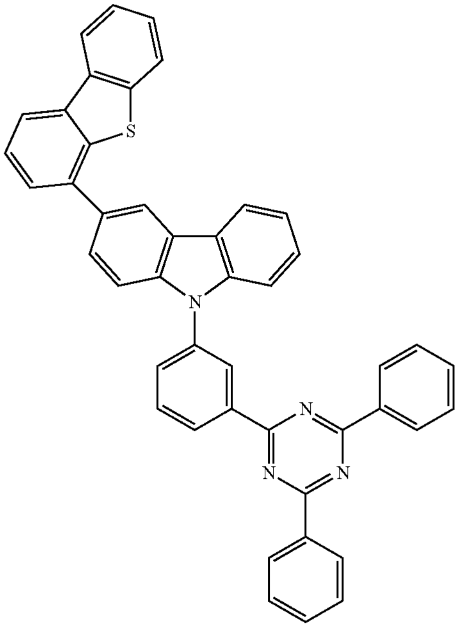
H2-36
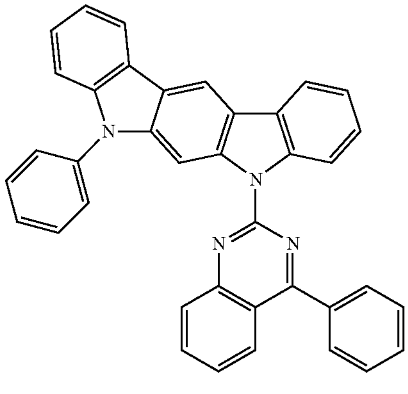
-continued
H2-37
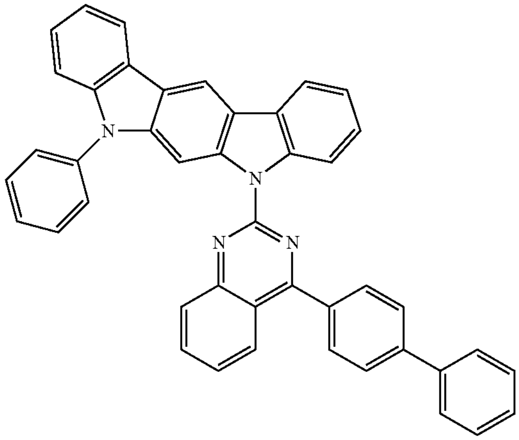
H2-38
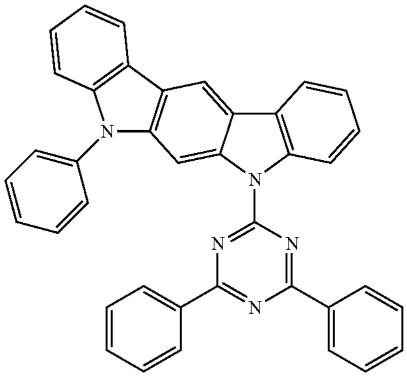
H2-39
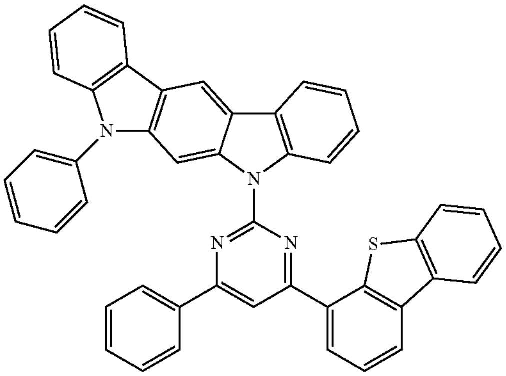

-continued
H2-40
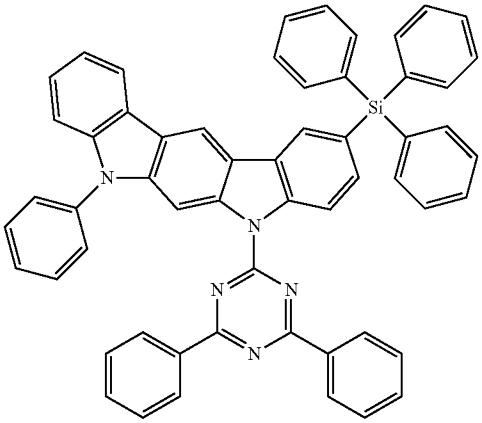
H2-41
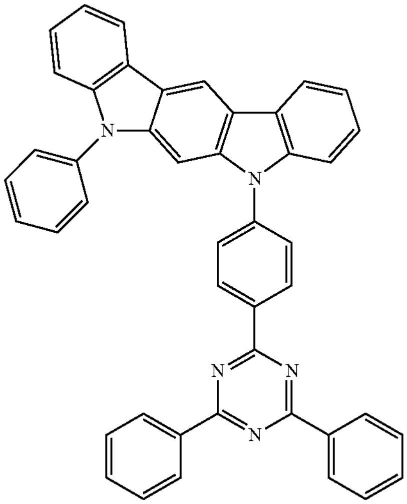
H2-42
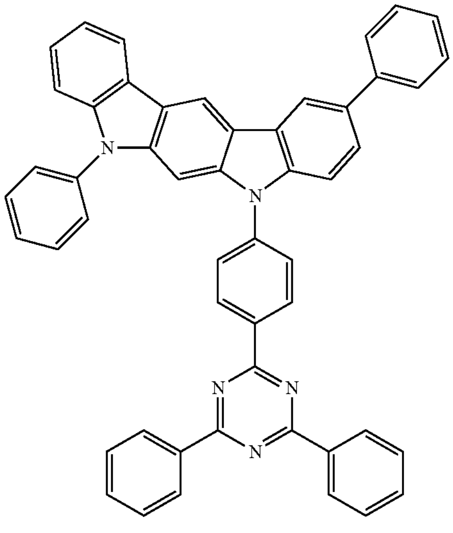
-continued
H2-43
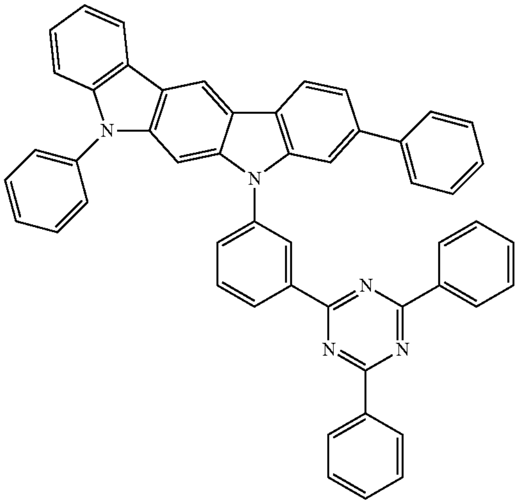
H2-44
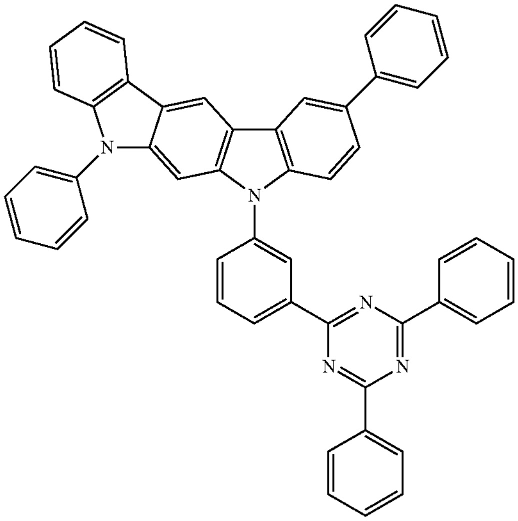
H2-45
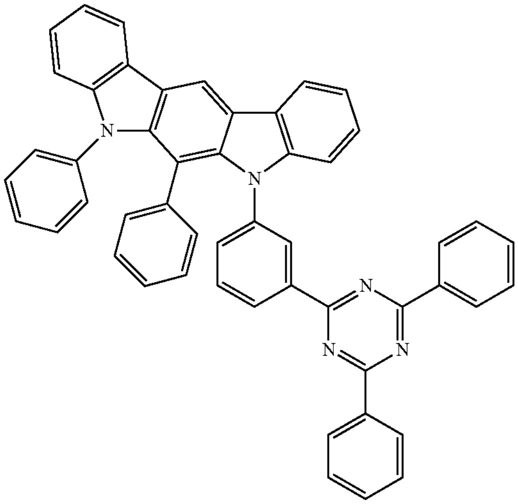

-continued
H2-46
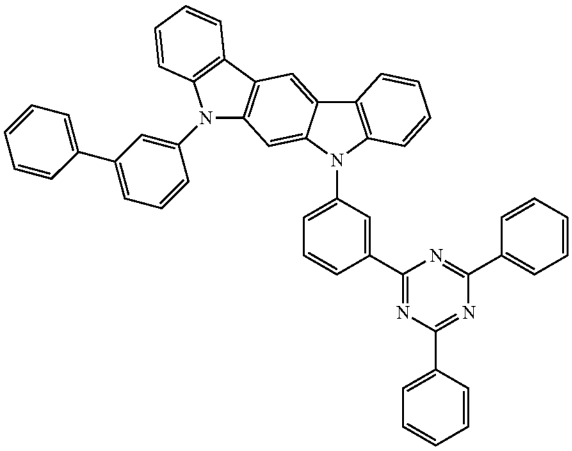
H2-47
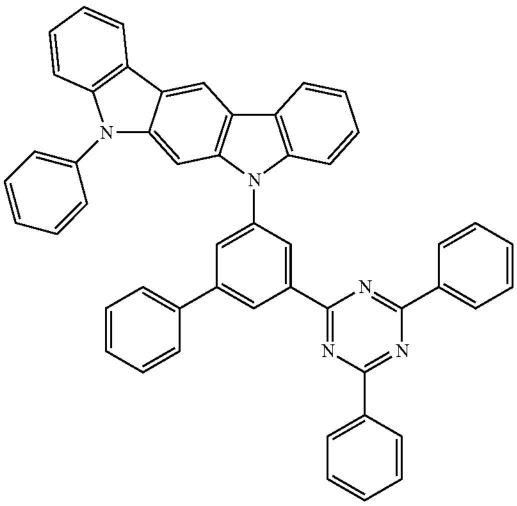
H2-48
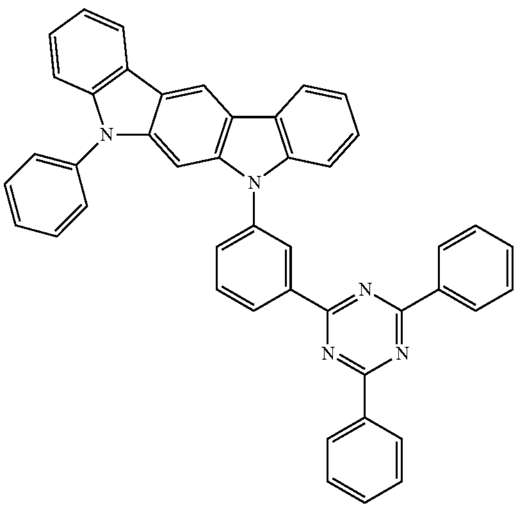
-continued
H2-49
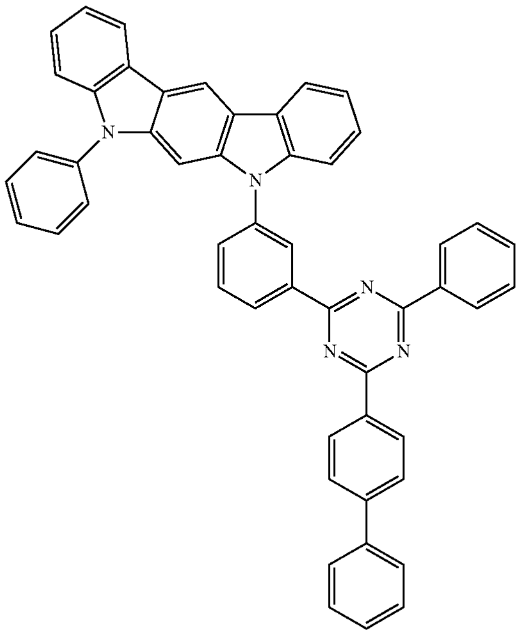
H2-50
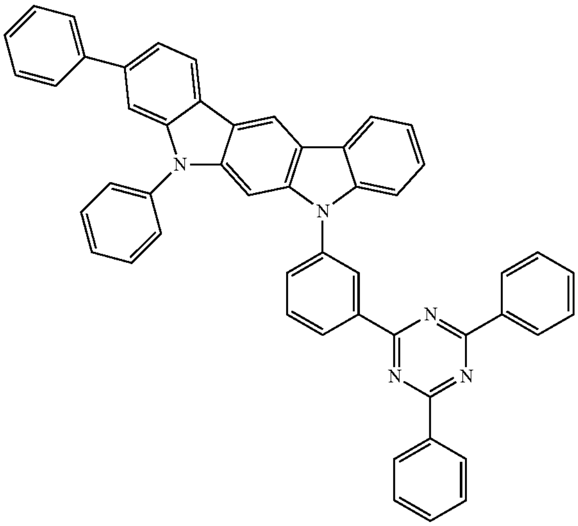

-continued
H2-51
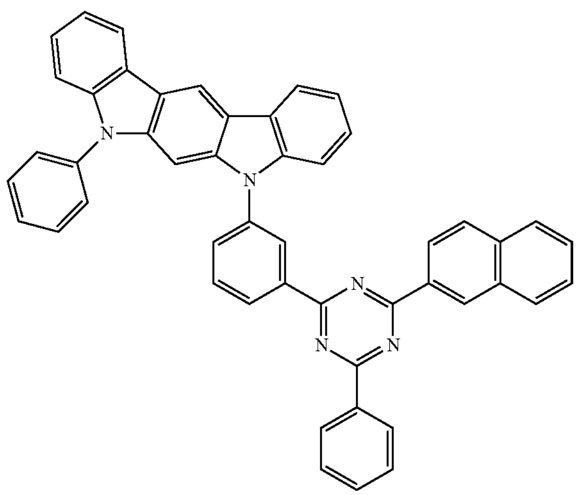
H2-52
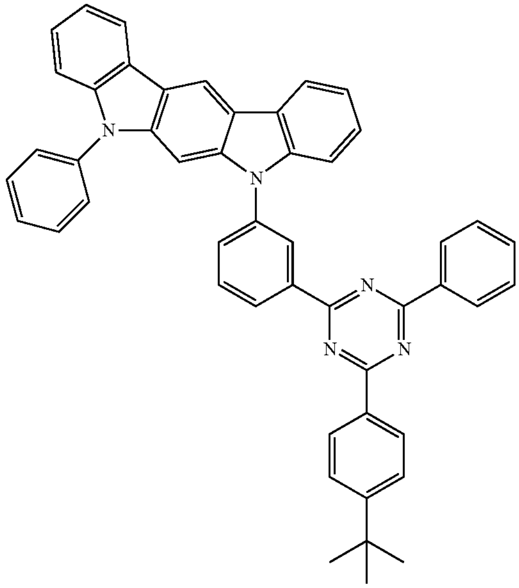
-continued
H2-53
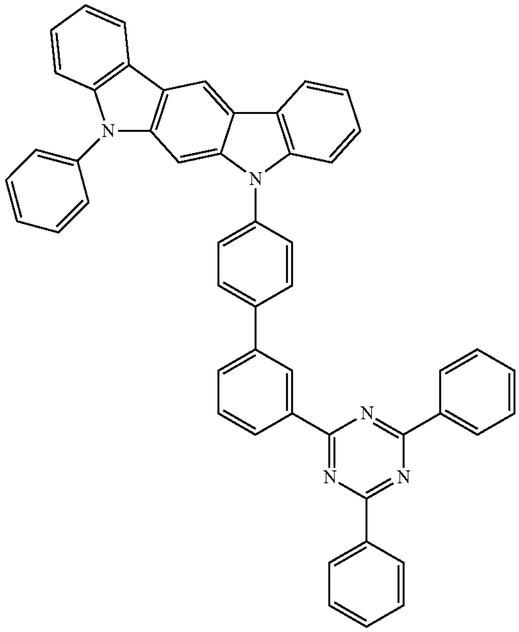
H2-54
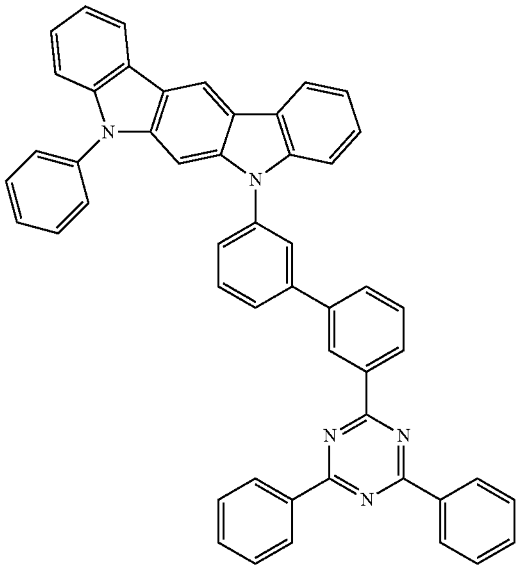

-continued
H2-55
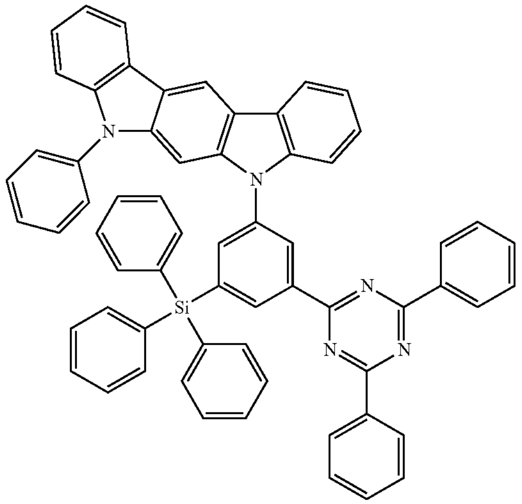
H2-56
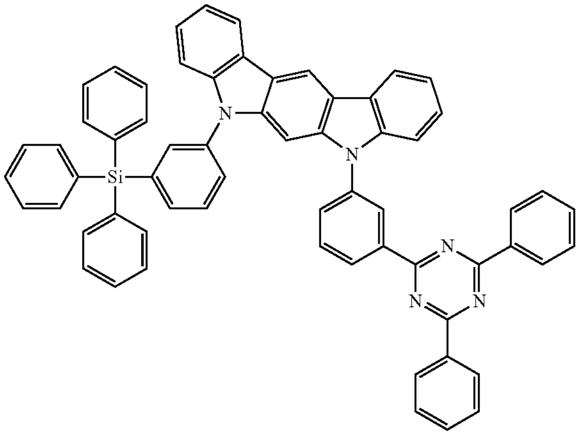
H2-57
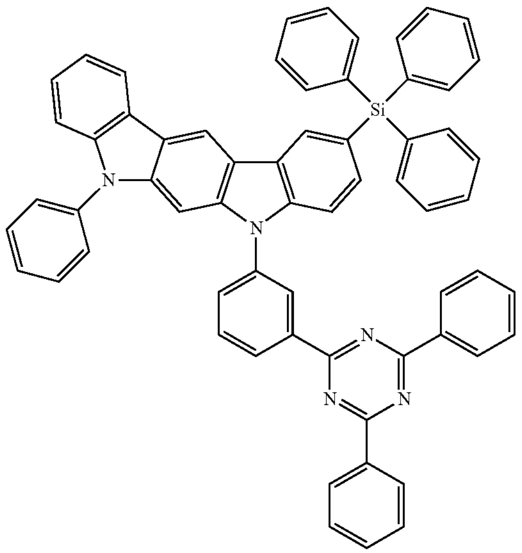
-continued
H2-58
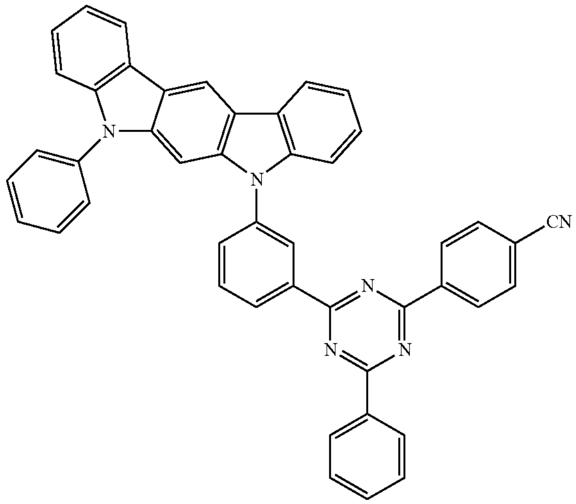
H2-59
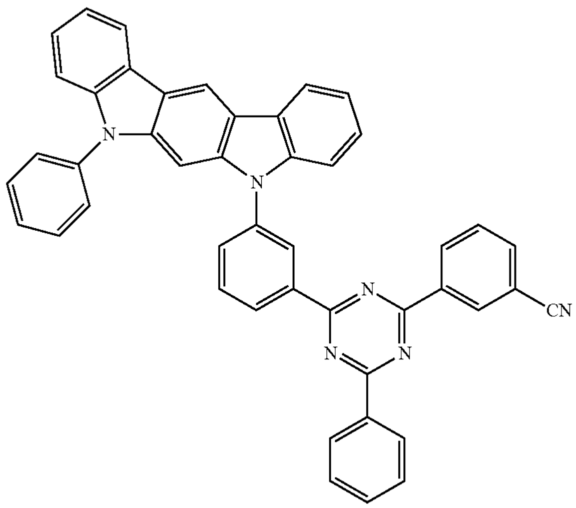
H2-60
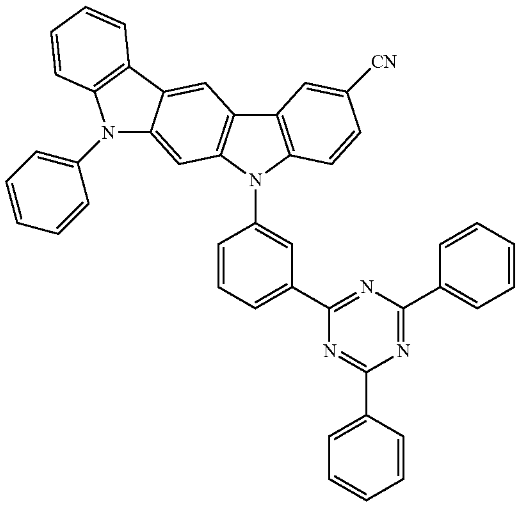

H2-61
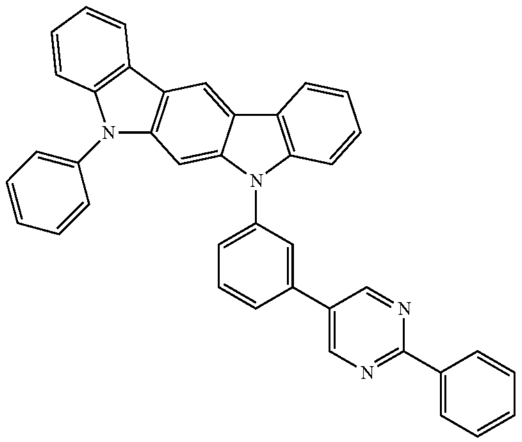
H2-62
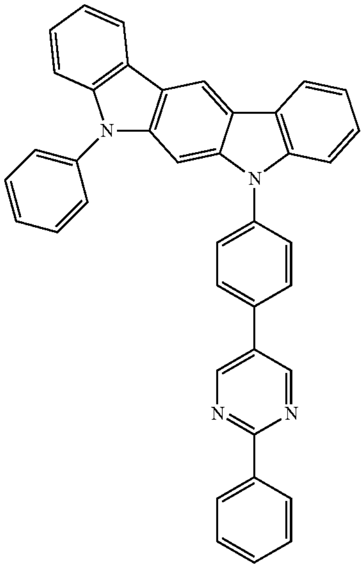
H2-63
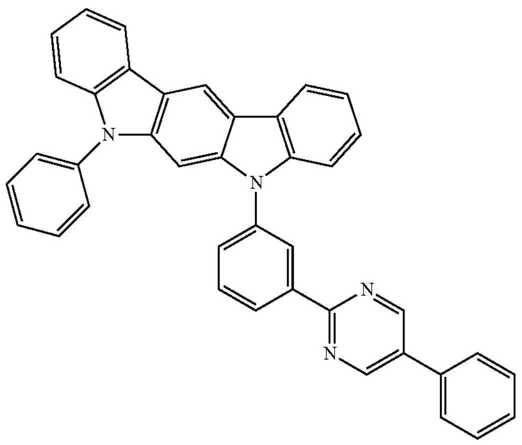
H2-64
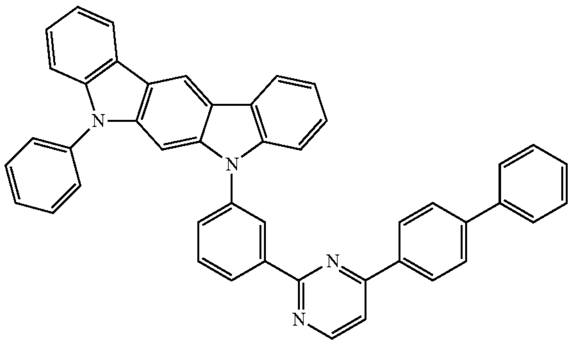
H2-65
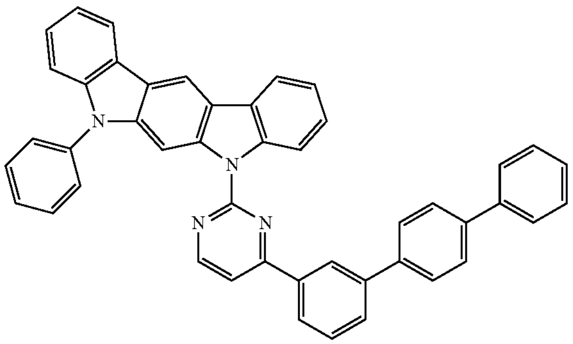
H2-66
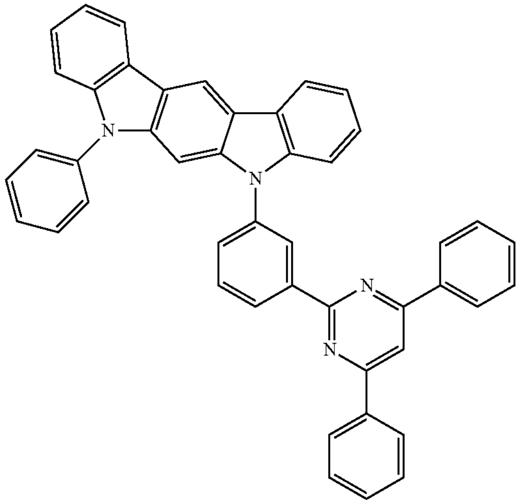

-continued
H2-67
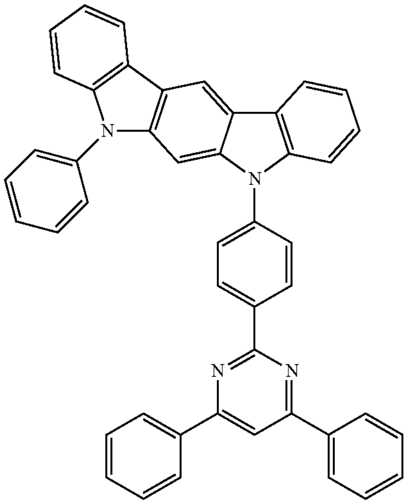
H2-68
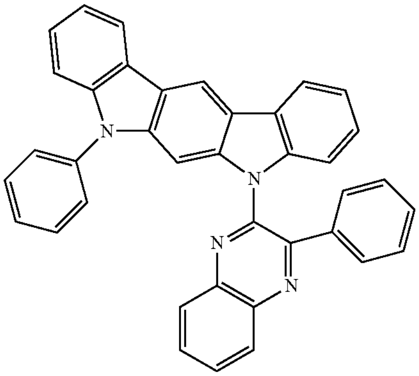
H2-69
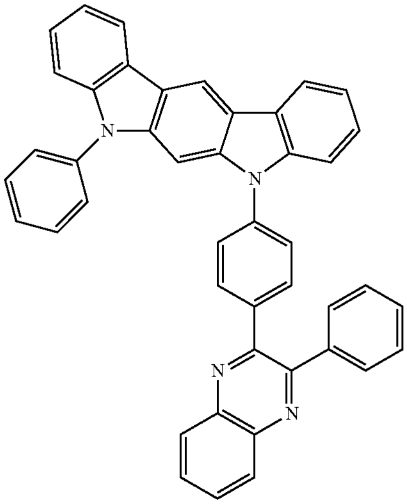
-continued
H2-70
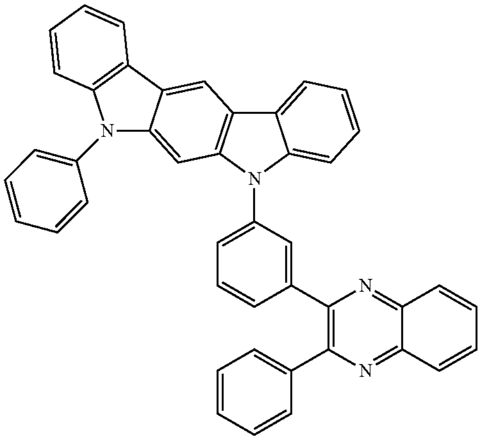
H2-71
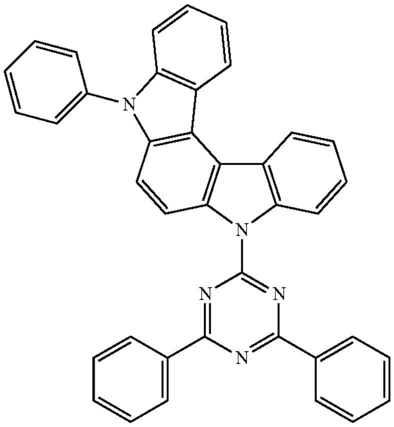
H2-72
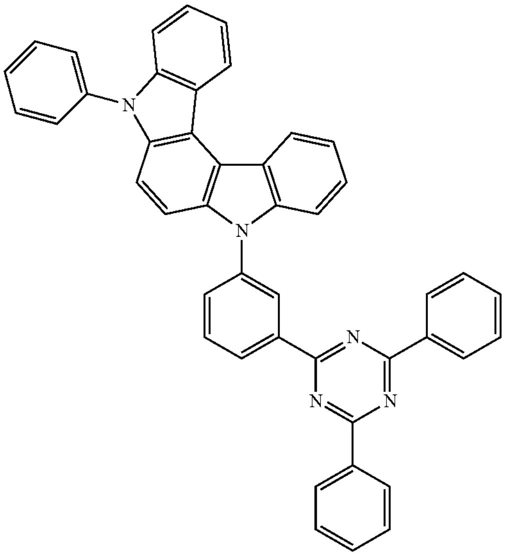

-continued
H2-73
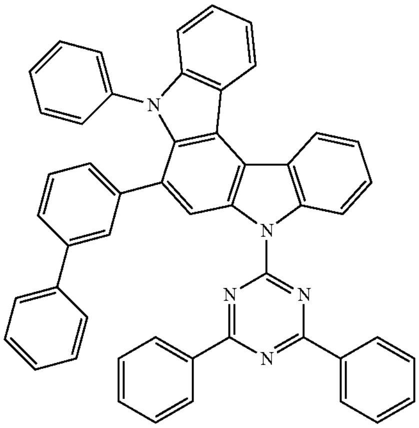
H2-74
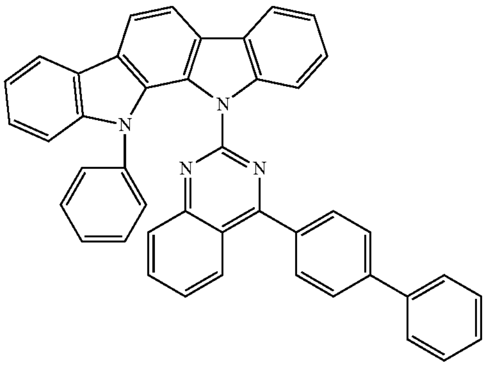
H2-75
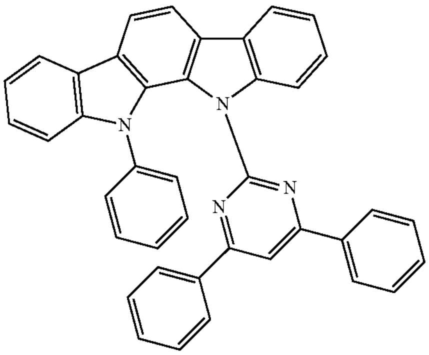
H2-76
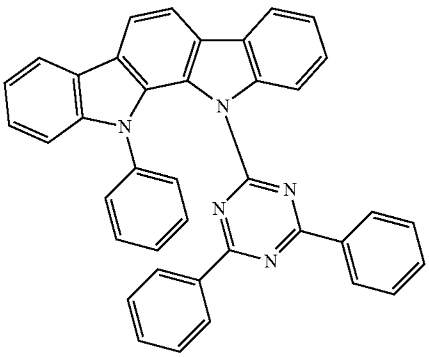
-continued
H2-77
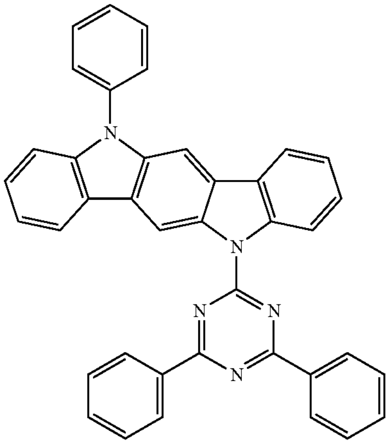
H2-78
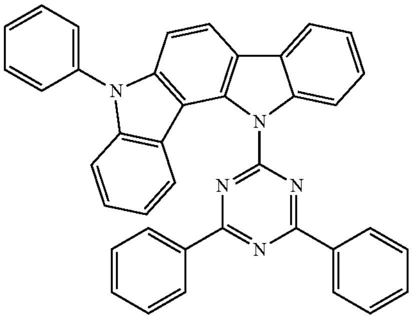
H2-79
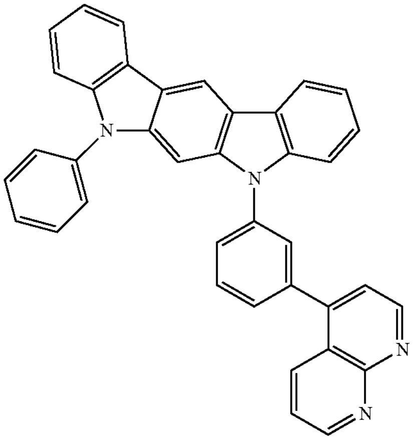
H2-80
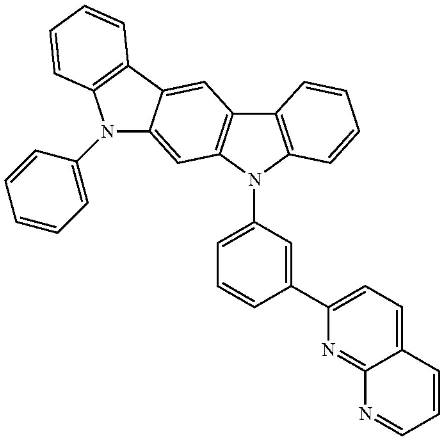

-continued
H2-81
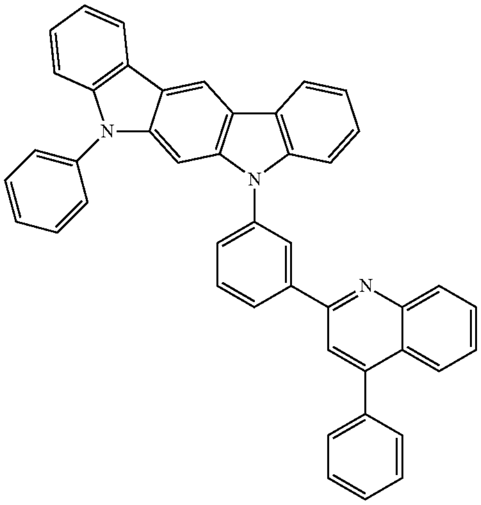
H2-82
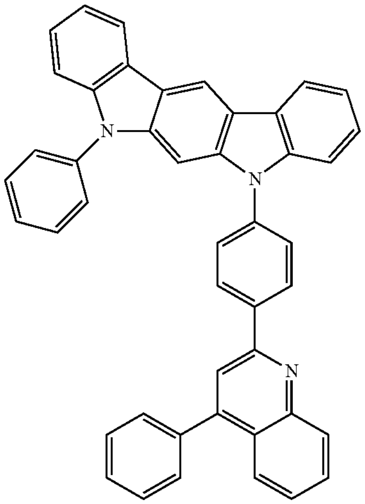
H2-83
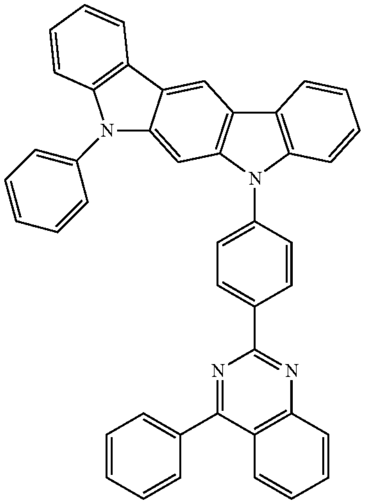
-continued
H2-84
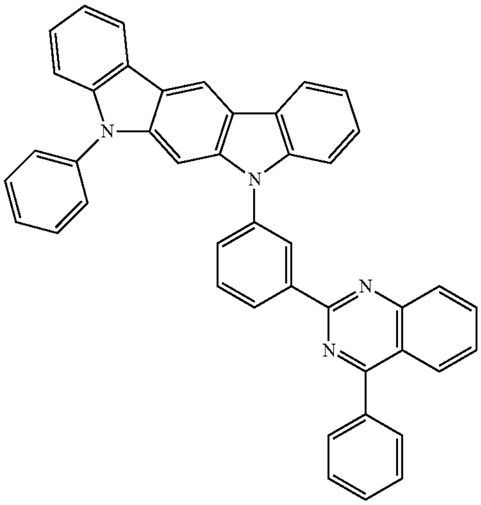
H2-85
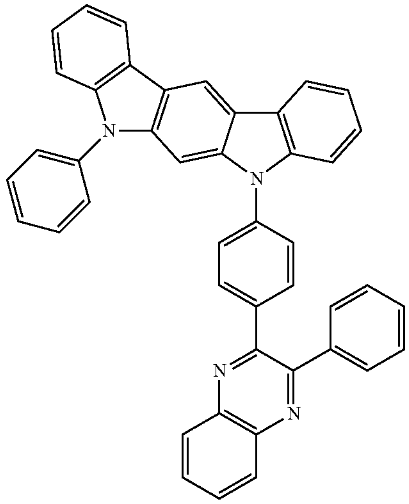
H2-86
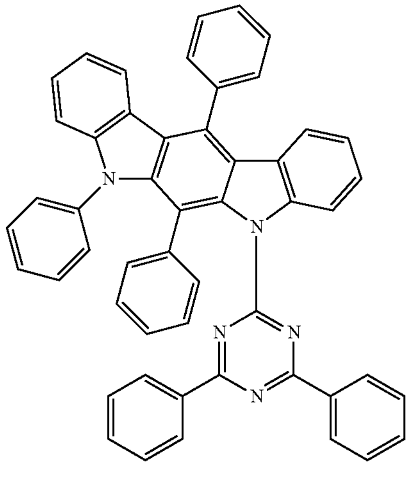

-continued
H2-87
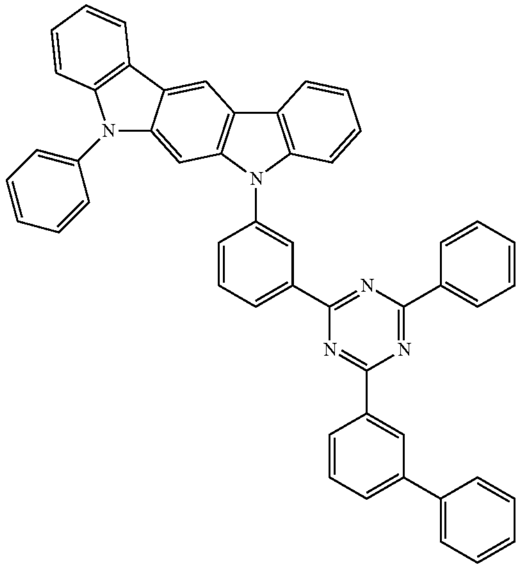
H2-88
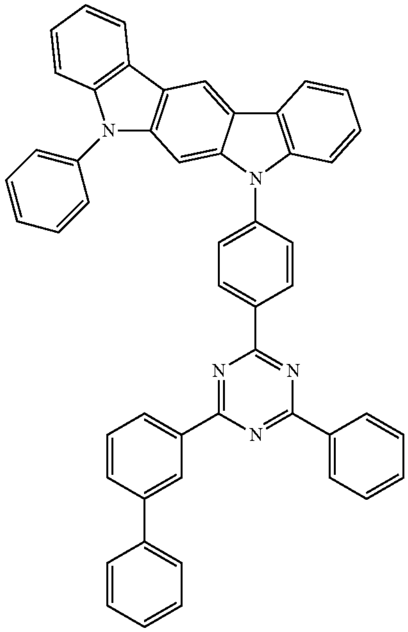
-continued
H2-89
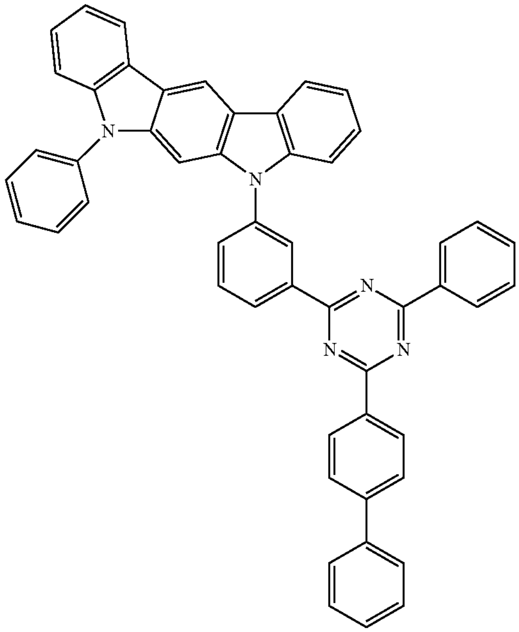
H2-90
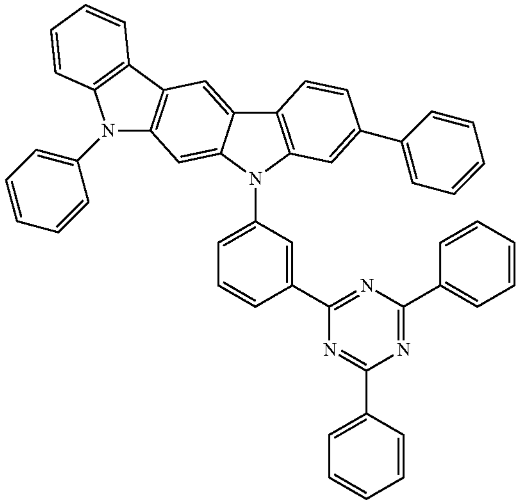

H2-91
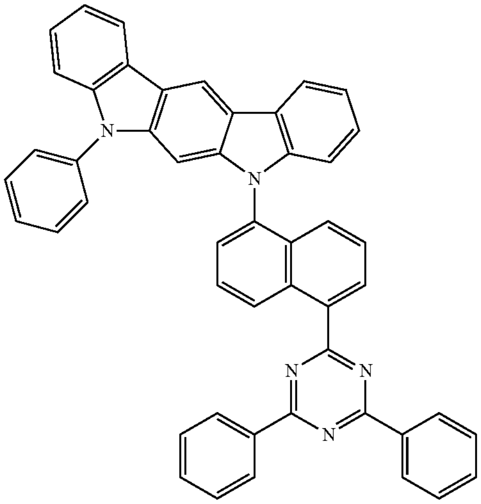
H2-92
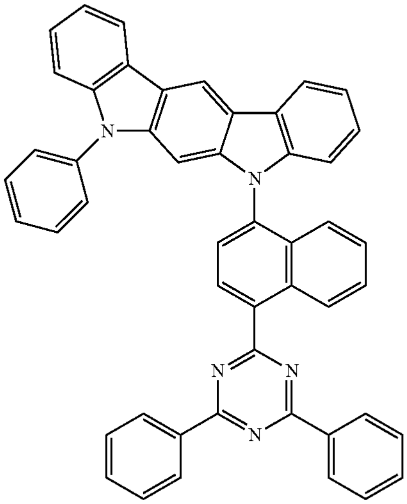
H2-93
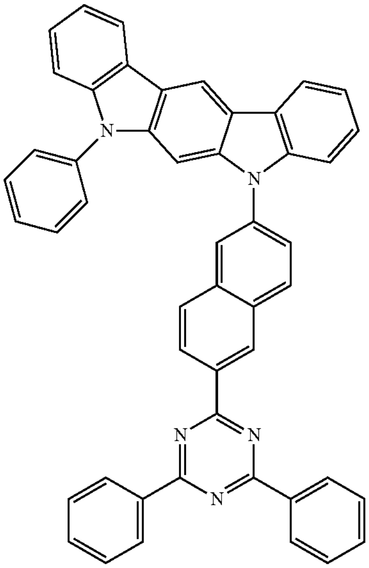
H2-94
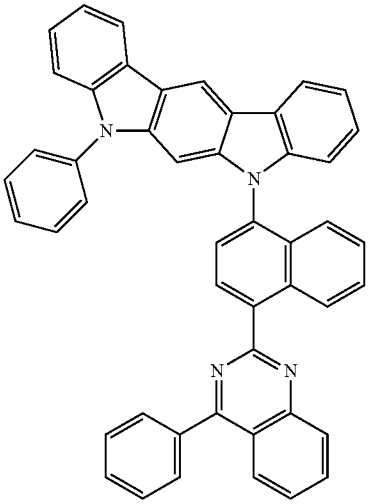
H2-95
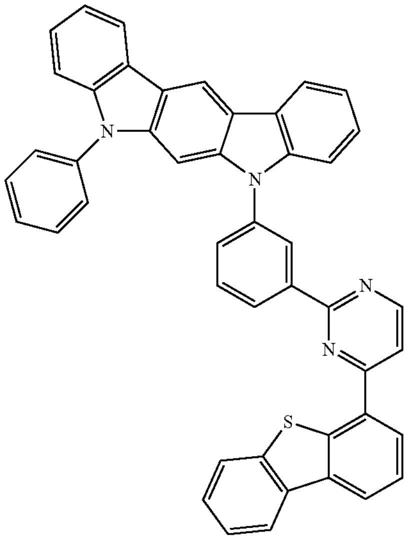
H2-96
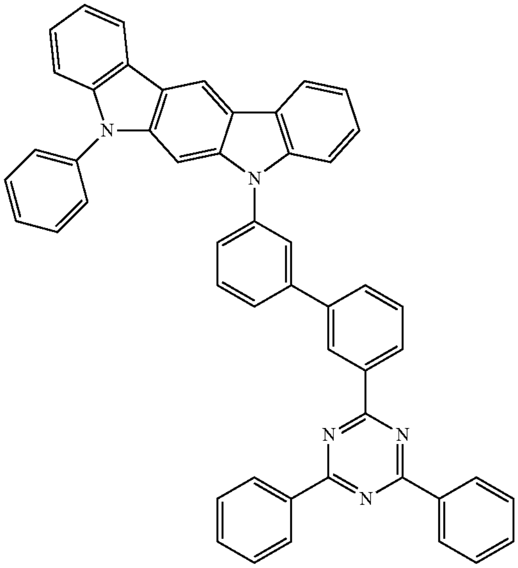

-continued
H2-97
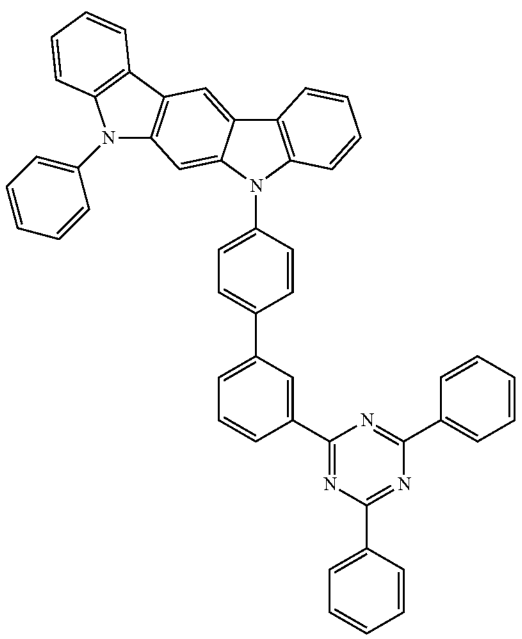
H2-98
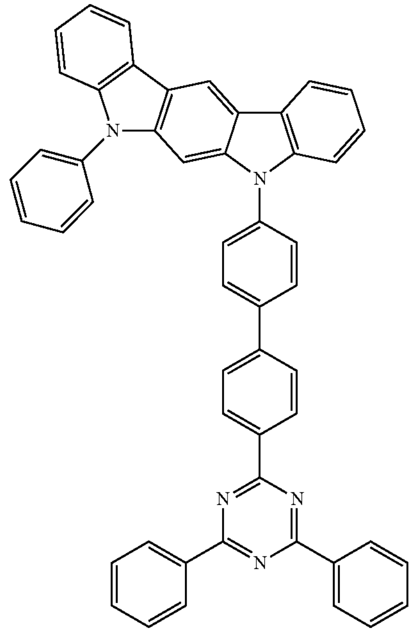
-continued
H2-99
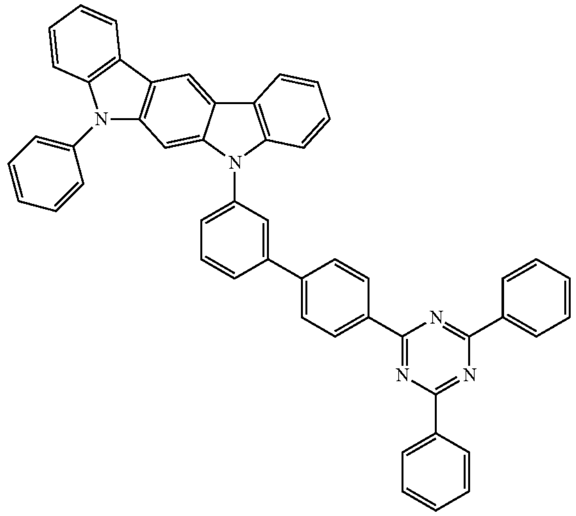
H2-100
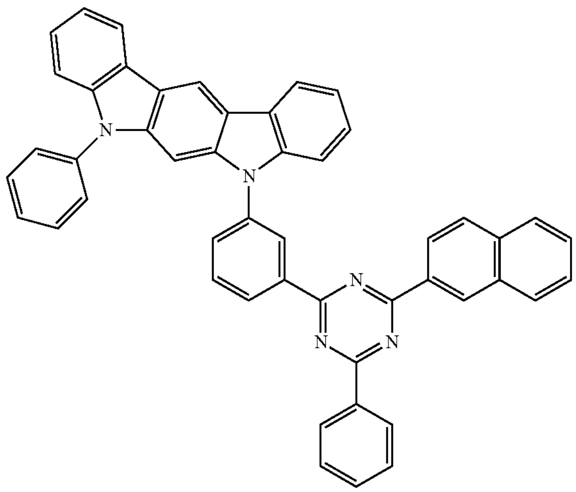
H2-101
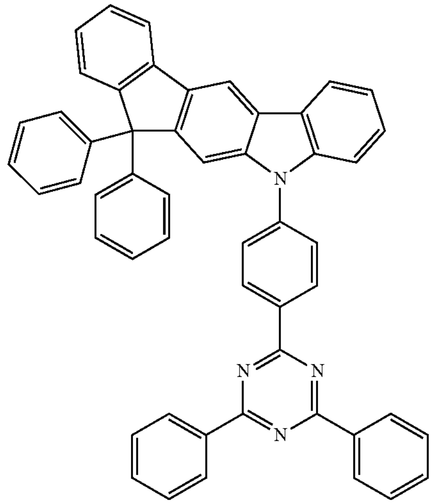

-continued
H2-102
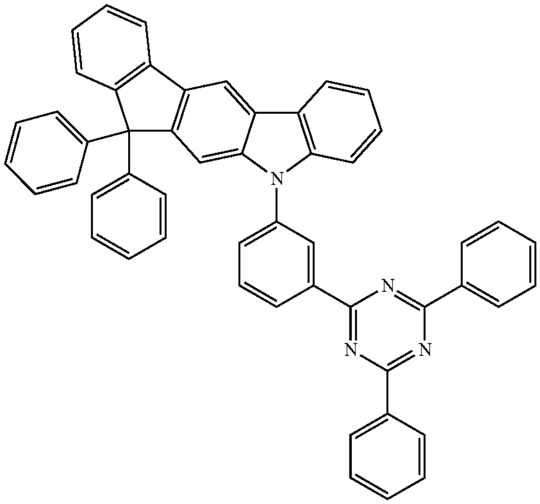
H2-103
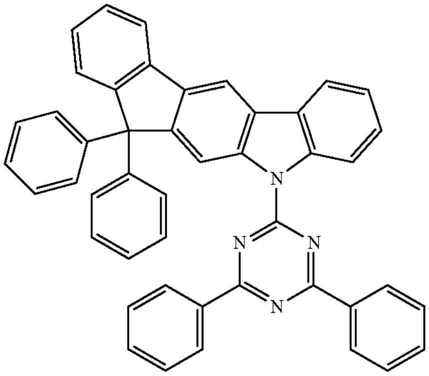
H2-104
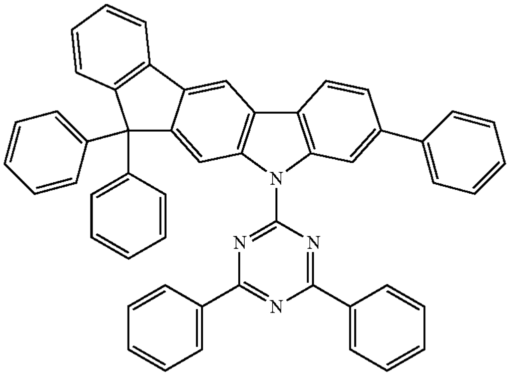
-continued
H2-105
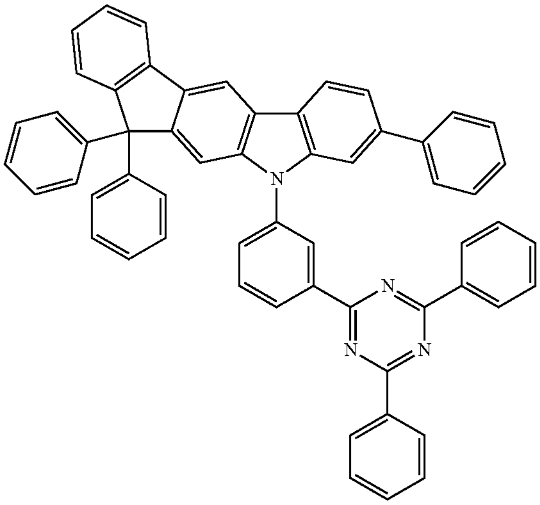
H2-106
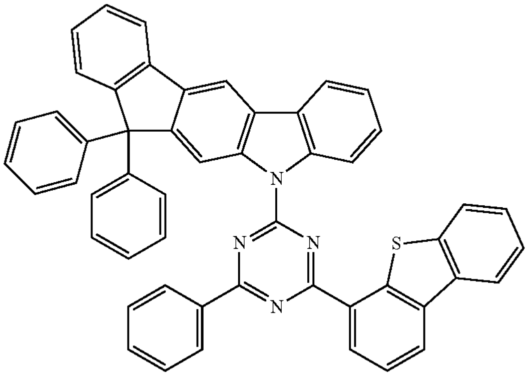
H2-107
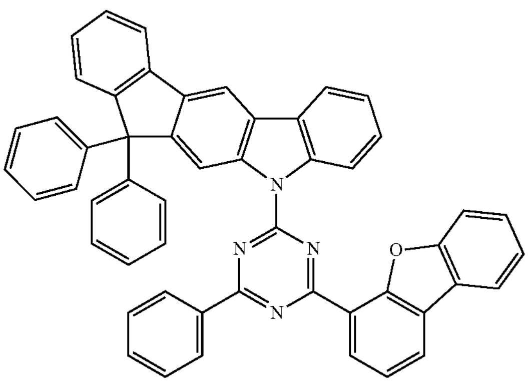

-continued
H2-108
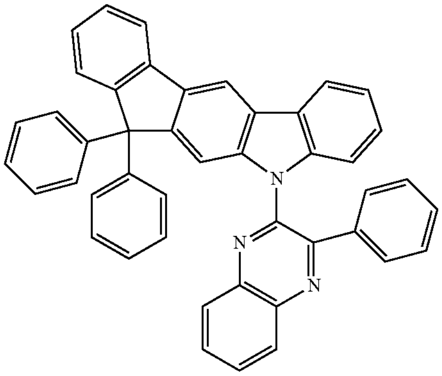
H2-109
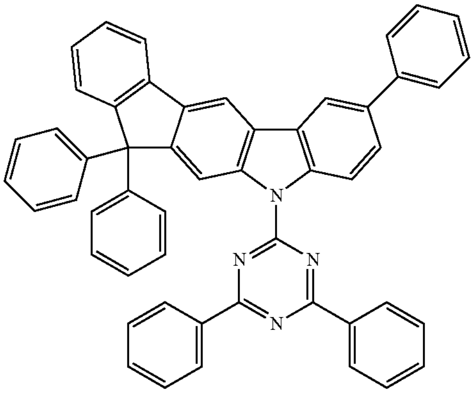
H2-110
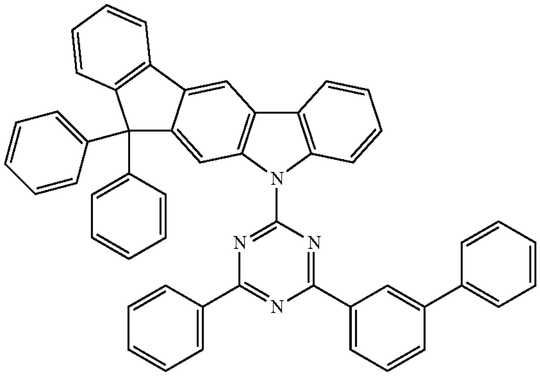
-continued
H2-111
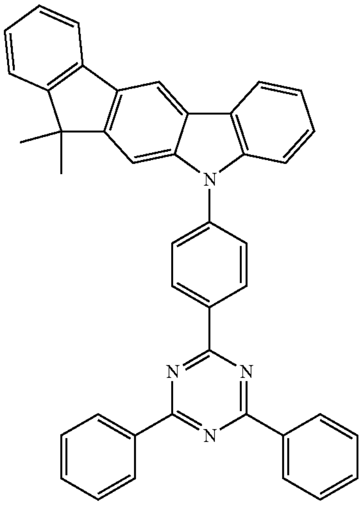
H2-112
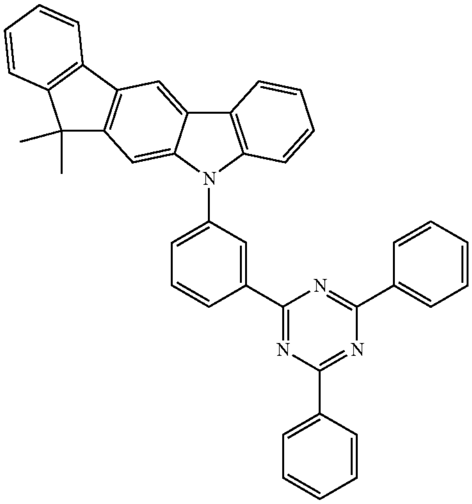
H2-113
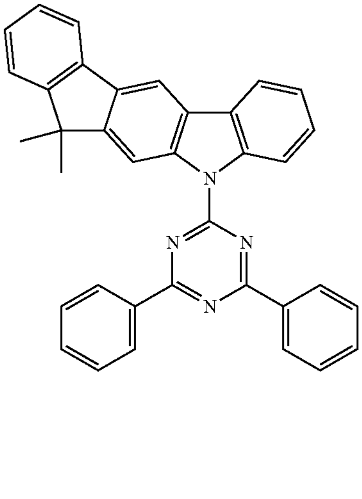

-continued
H2-114
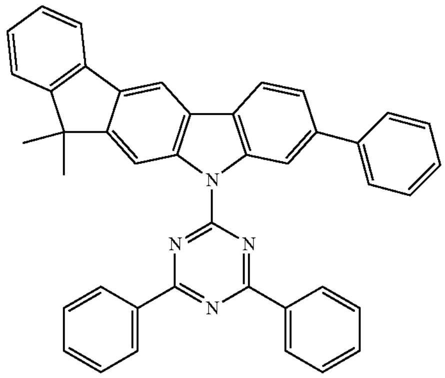
H2-115
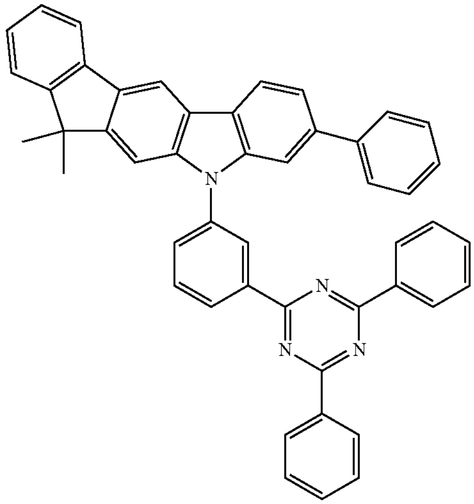
H2-116
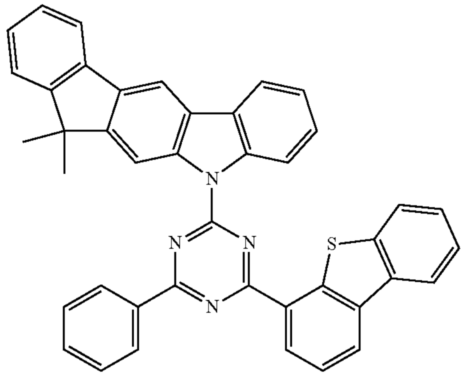
-continued
H2-117
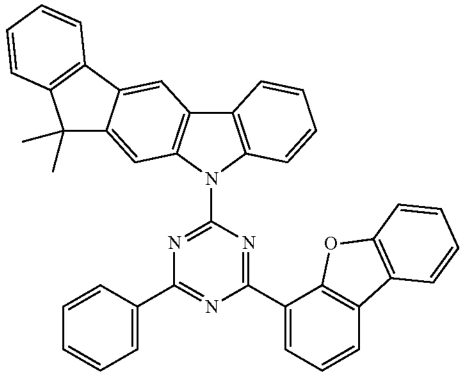
H2-118
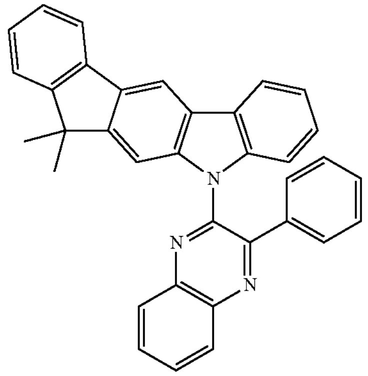
H2-119
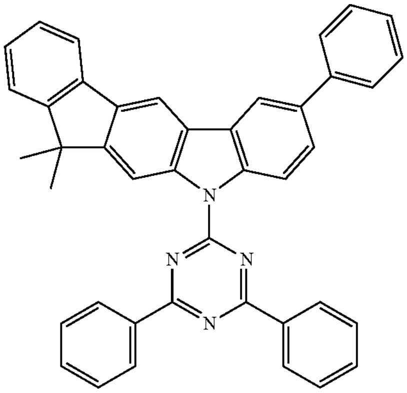
H2-120
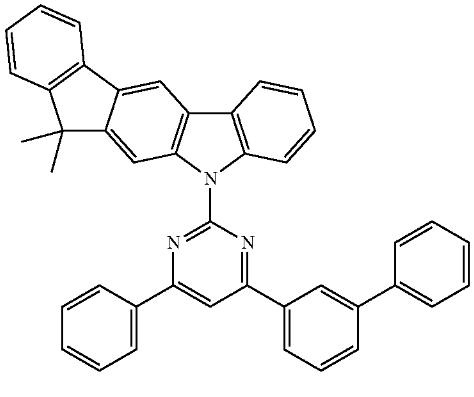

-continued
H2-121
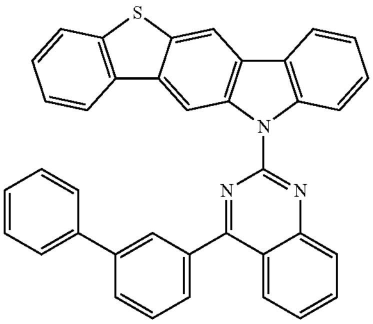
H2-122
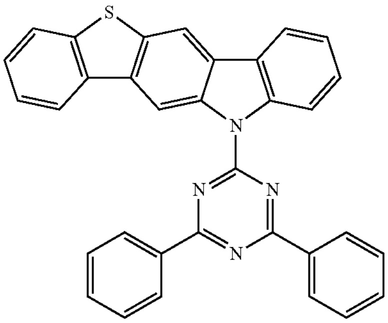
H2-123
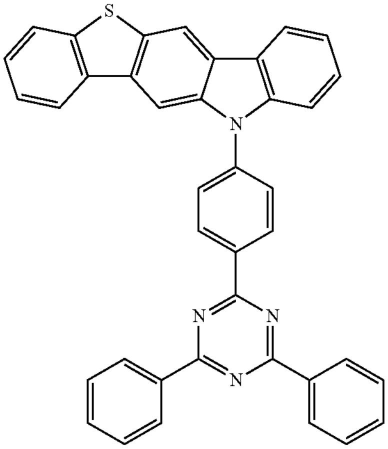
H2-124
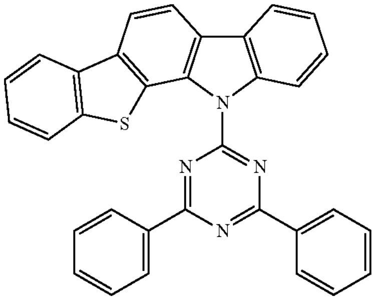
-continued
H2-125
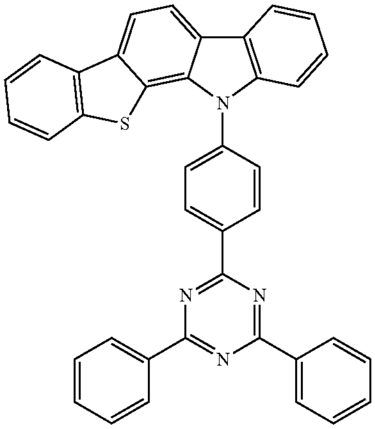
H2-126
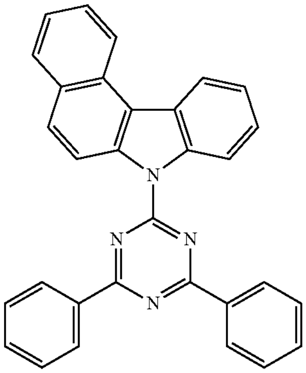
H2-127
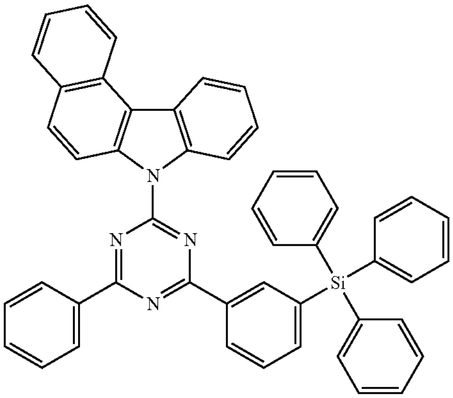
H2-128
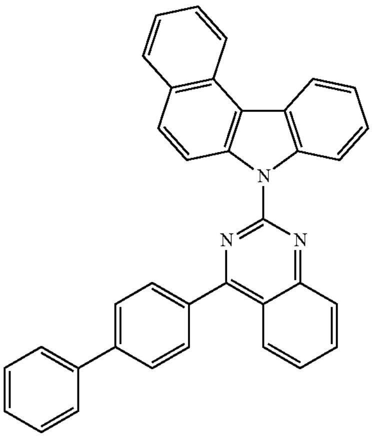

-continued
H2-129
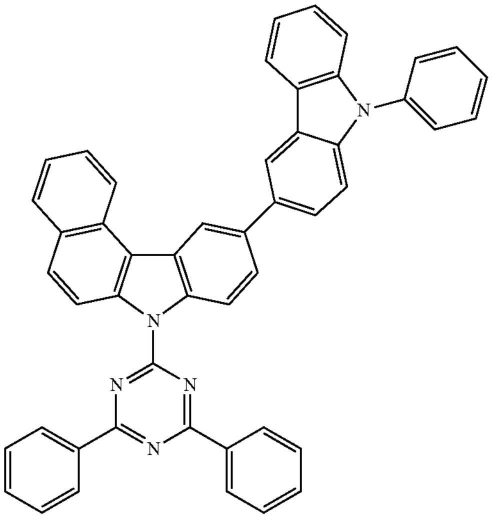
H2-130
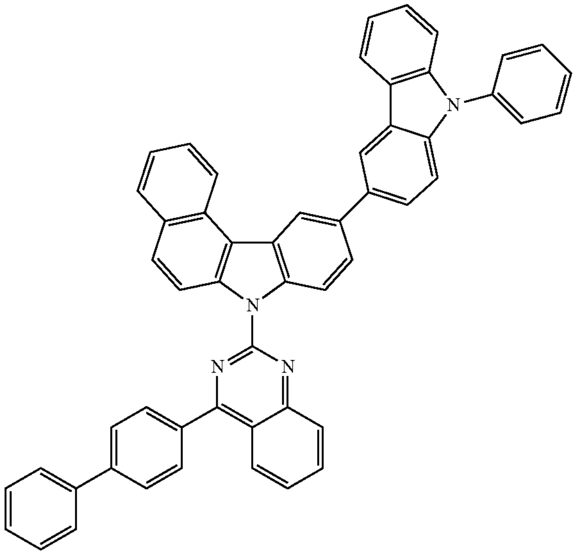
-continued
H2-131
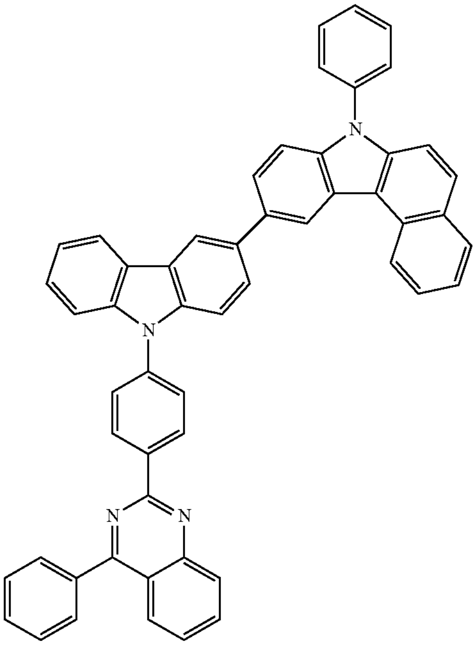
H2-132
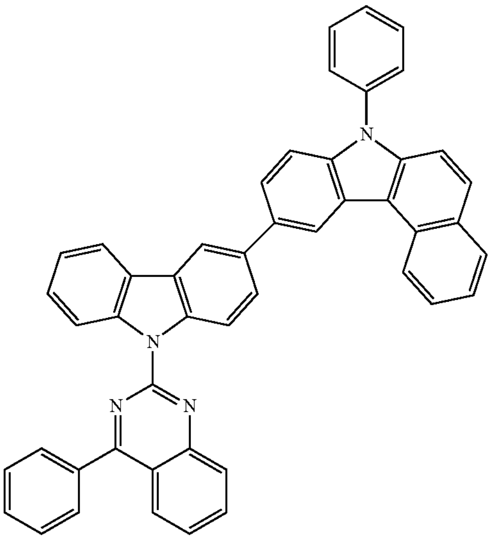

-continued
H2-133
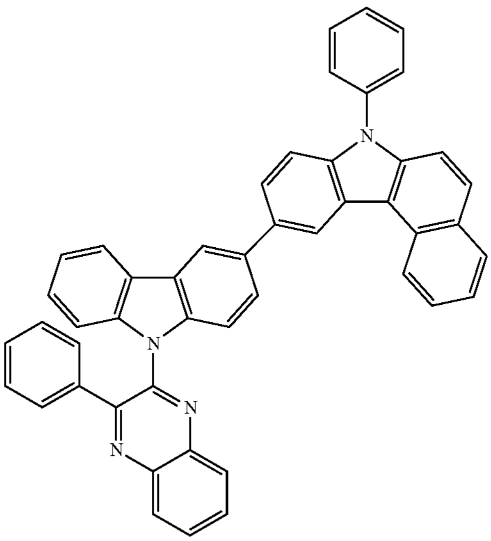
H2-134
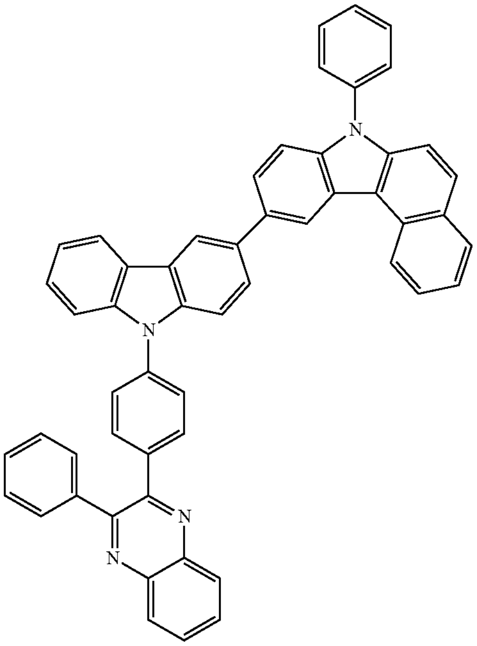
-continued
H2-135
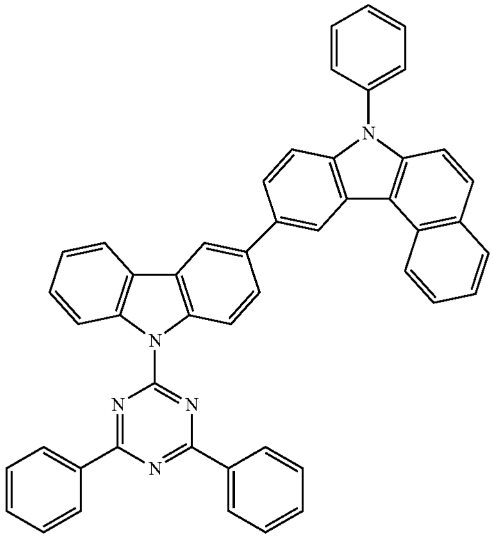
H2-136
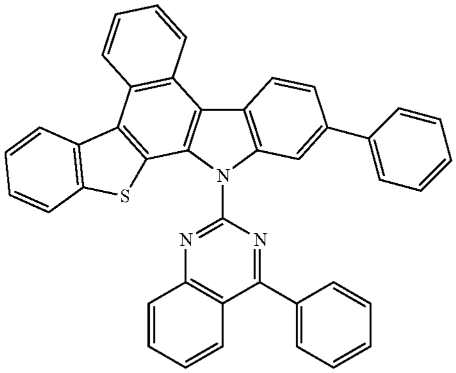
H2-137
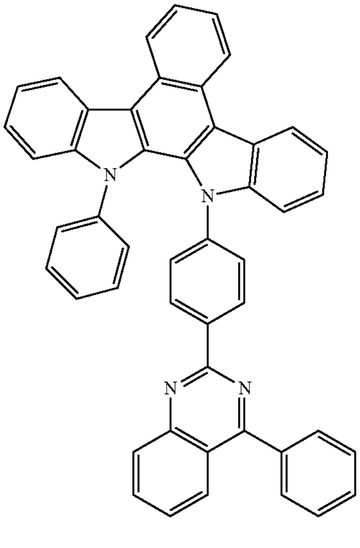

-continued
H2-138
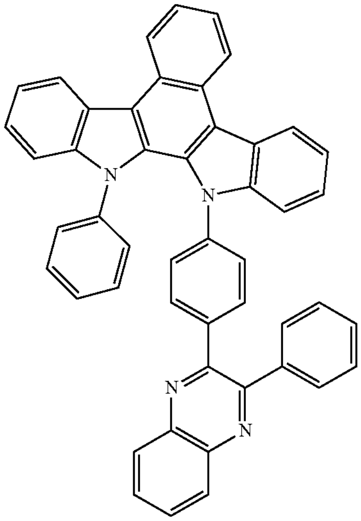
H2-139
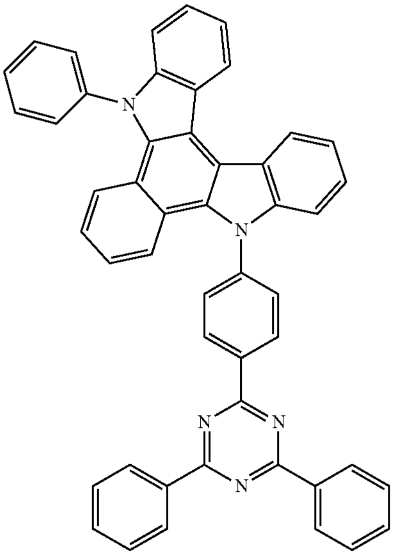
H2-140
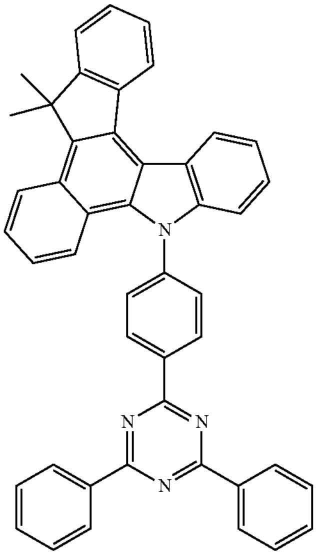
-continued
H2-141
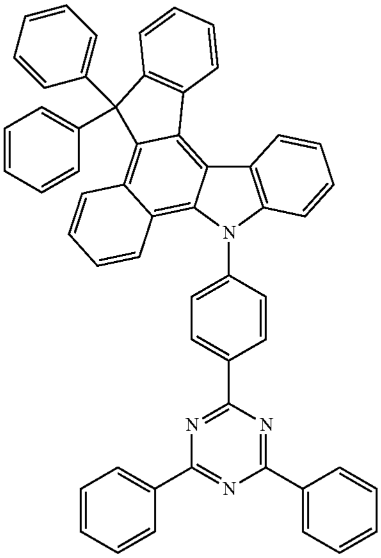
H2-142
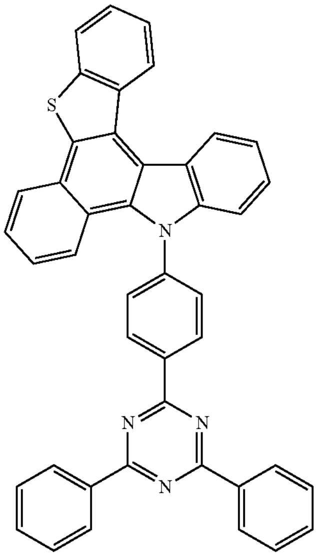
H2-143
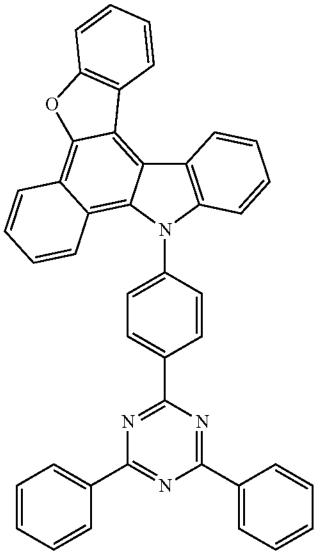

H2-144
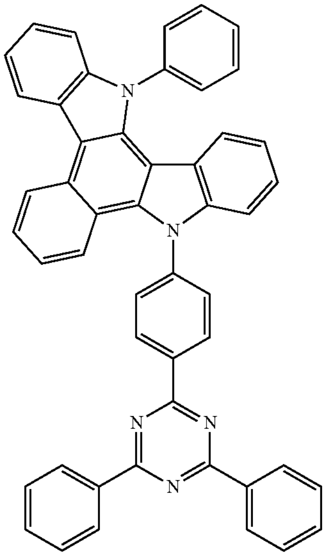
H2-145
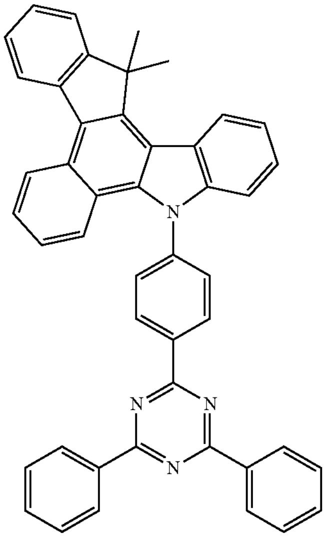
H2-146
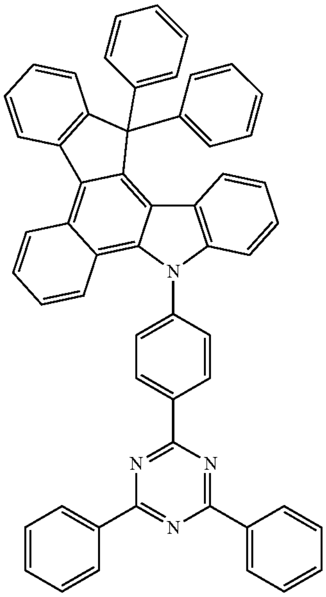
H2-147
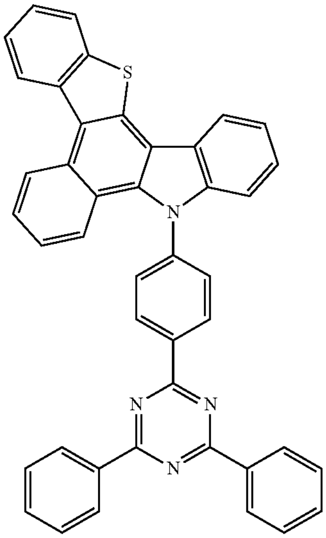

-continued
H2-148
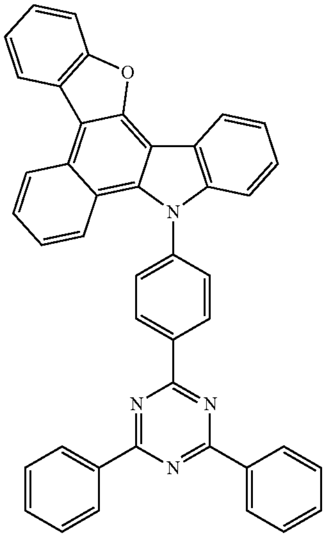
H2-149
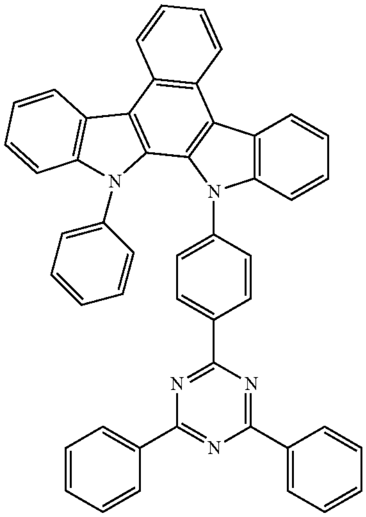
H2-150
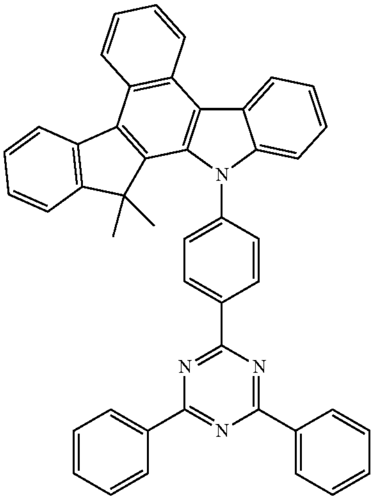
-continued
H2-151
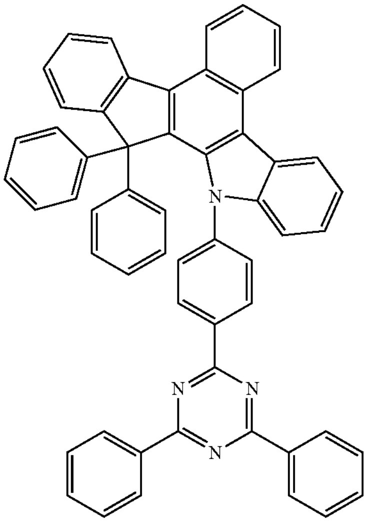
H2-152
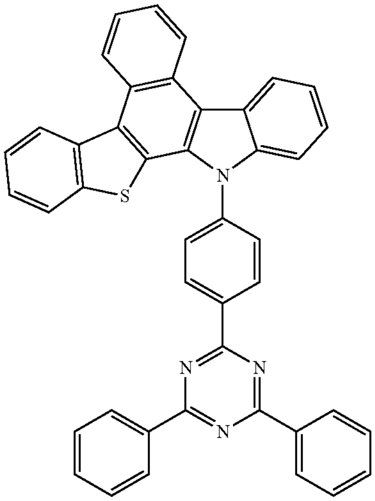
H2-153
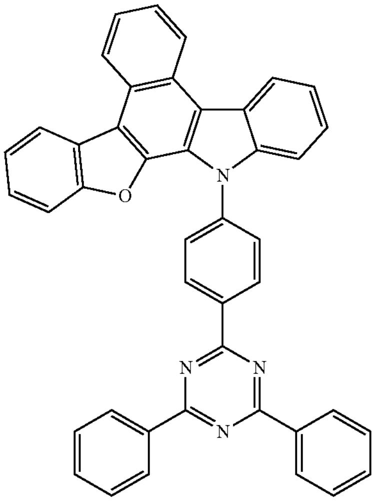

-continued
H2-154
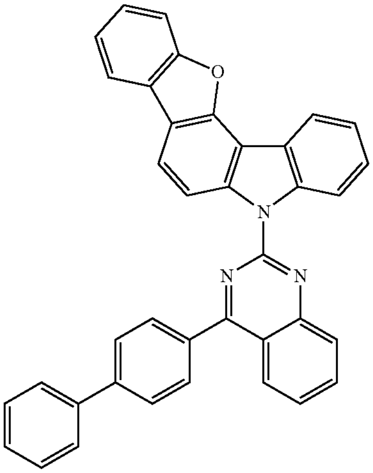
H2-155
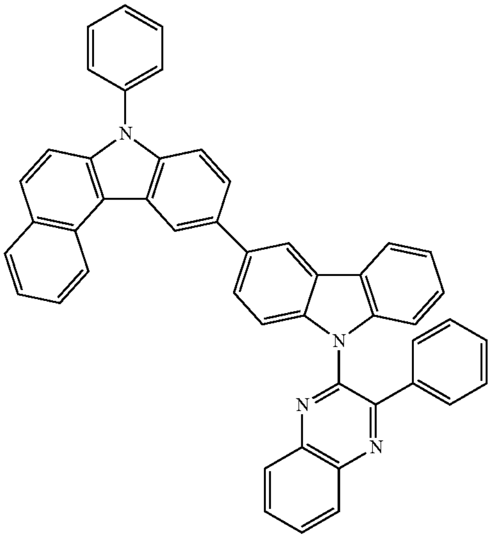
H2-156
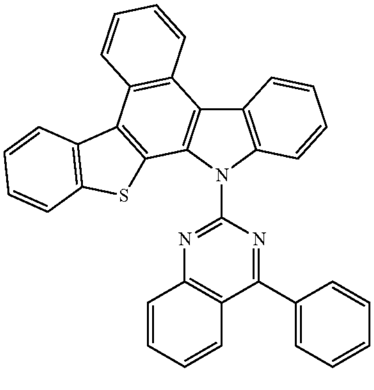
-continued
H2-157
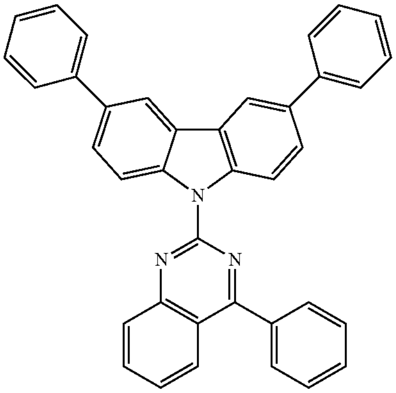
H2-158
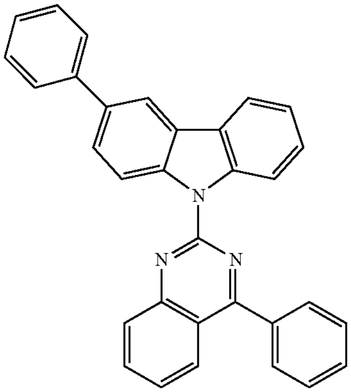
H2-159
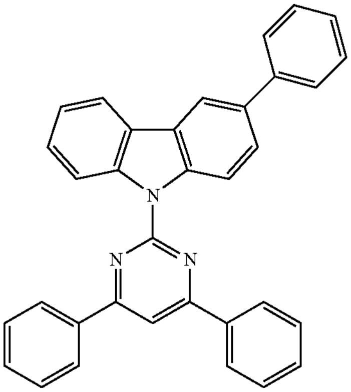
H2-160
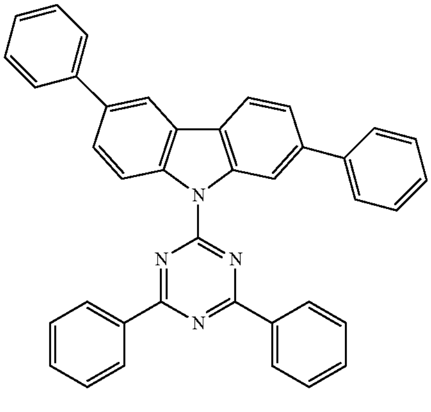

-continued
H2-161
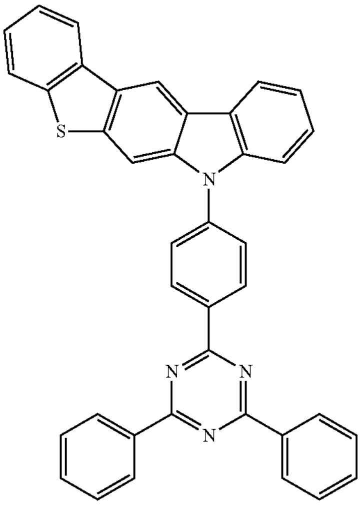
H2-162
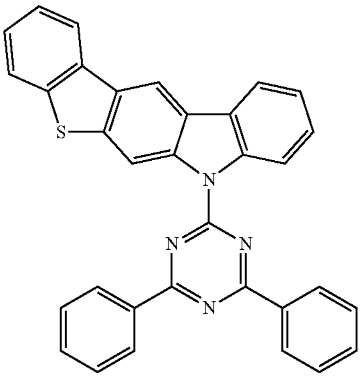
H2-163
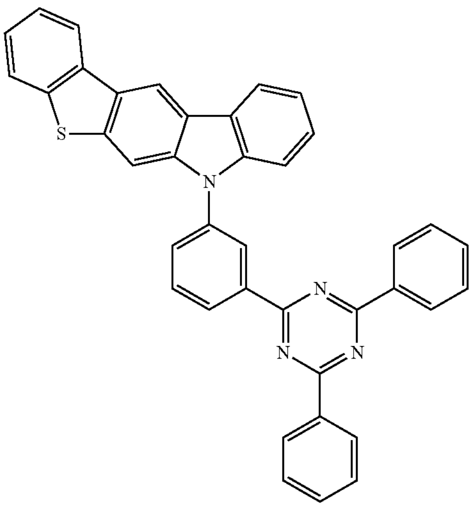
-continued
H2-164
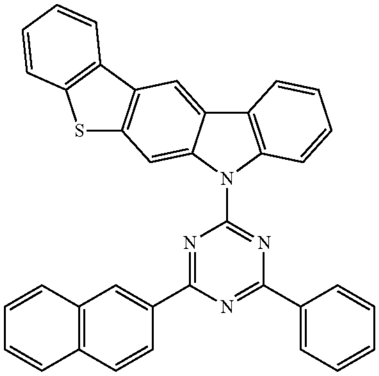
H2-165
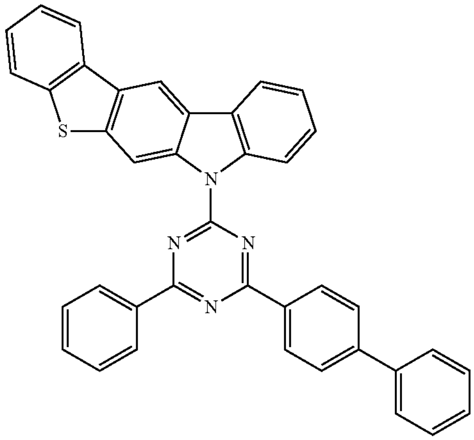
H2-166
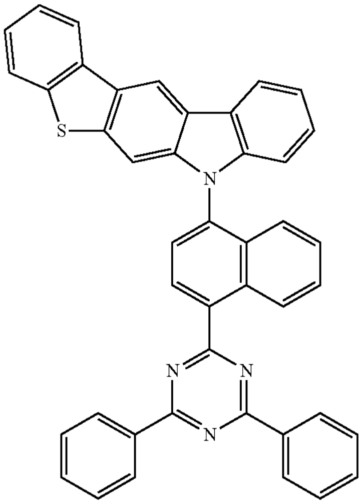

-continued
H2-167
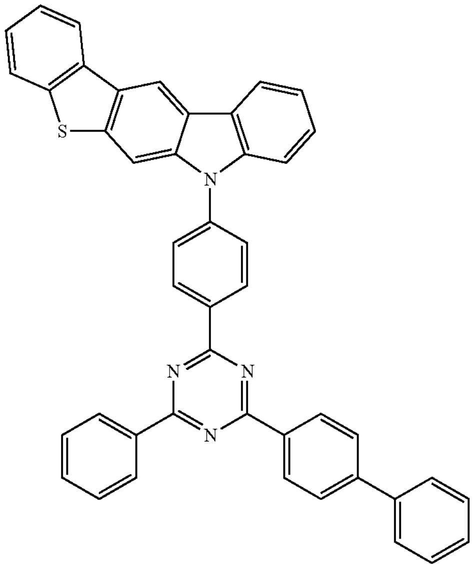
H2-168
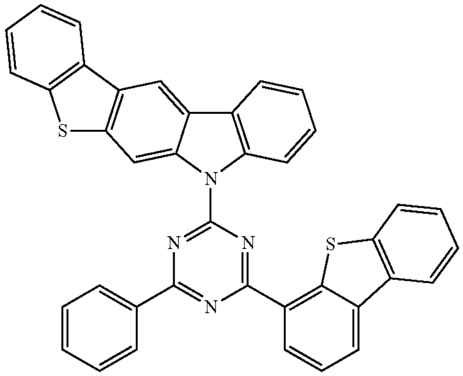
H2-169
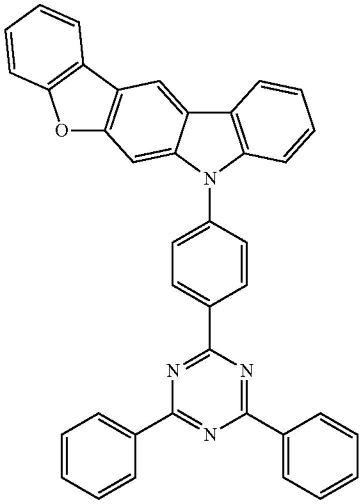
-continued
H2-170
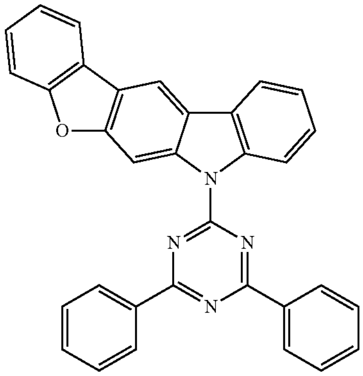
H2-171
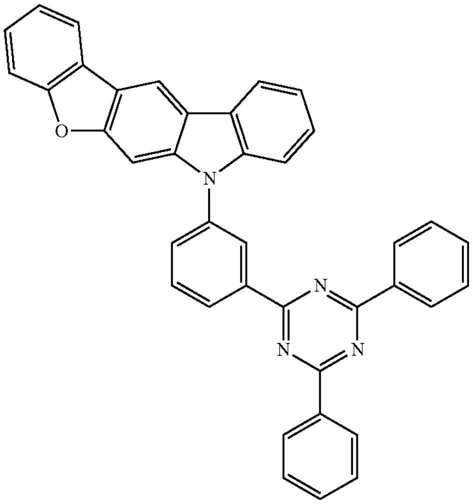
H2-172
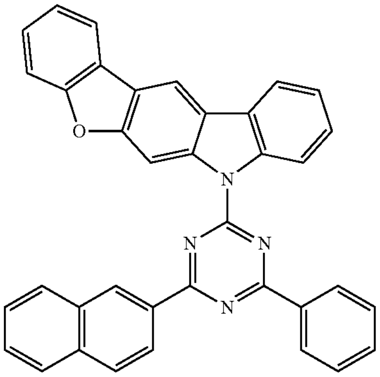

-continued
H2-173
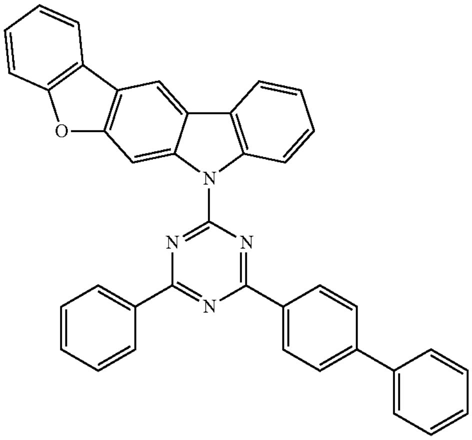
H2-174
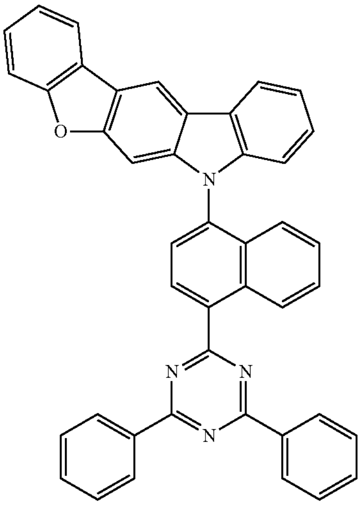
H2-175
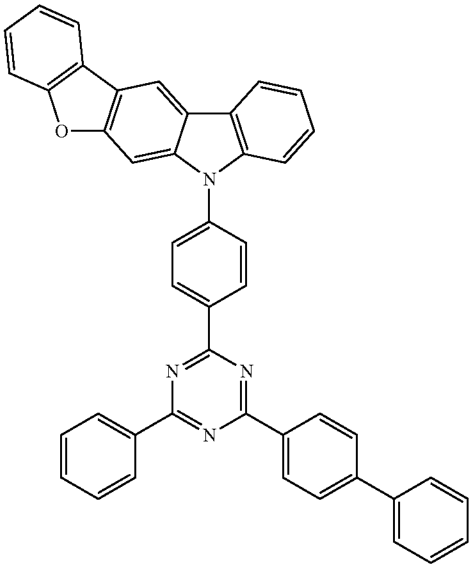
-continued
H2-176
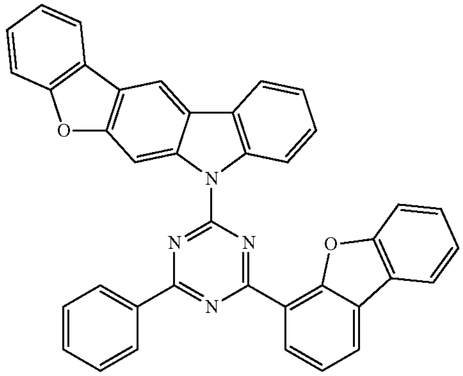
H2-177
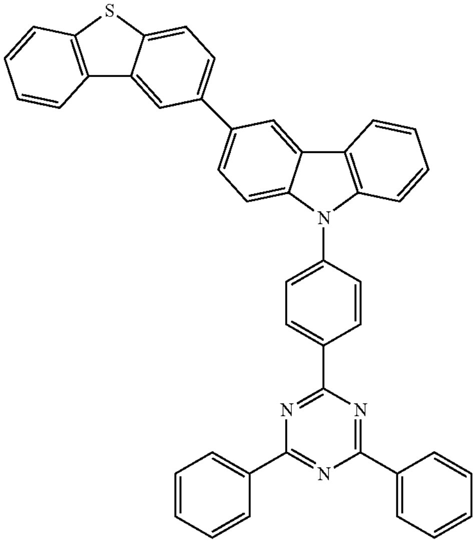
H2-178
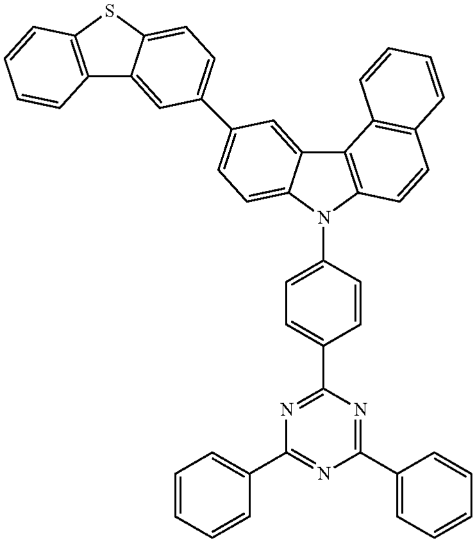

-continued
H2-179
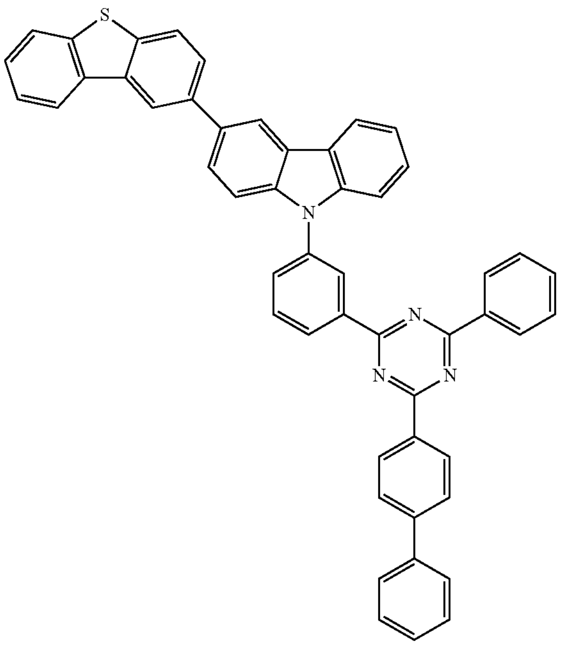
H2-180
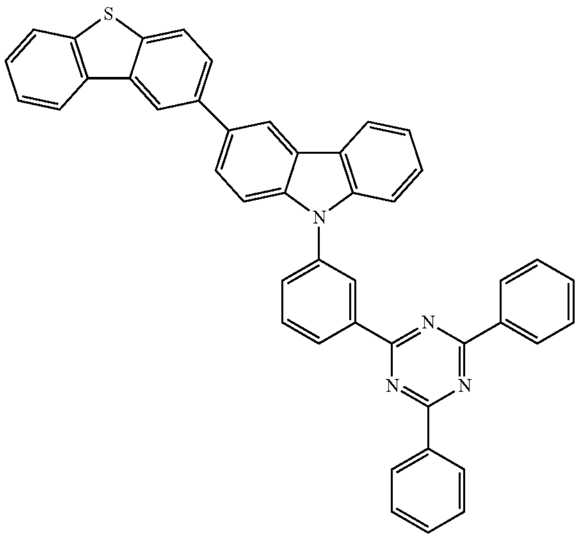
-continued
H2-181
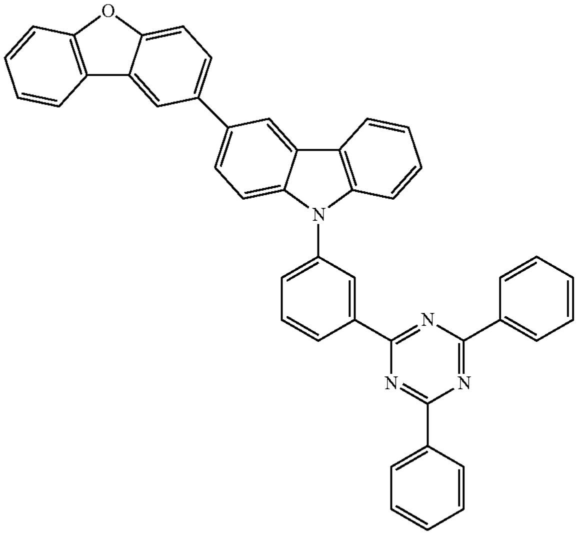
H2-182
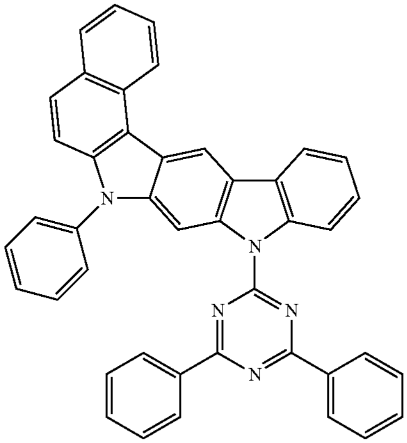
H2-183
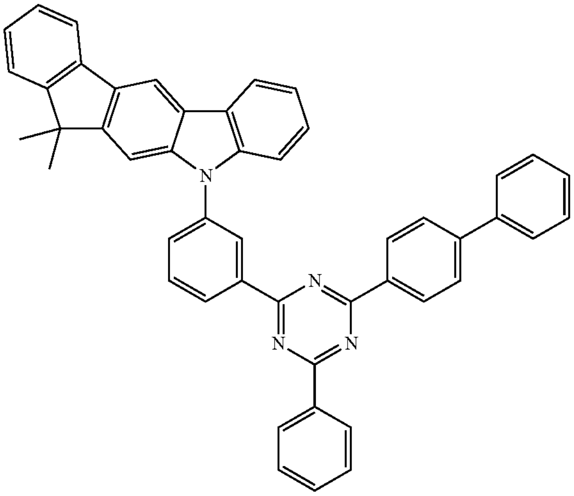

-continued
H2-184
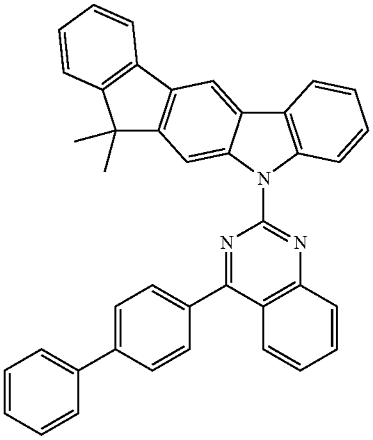
H2-185
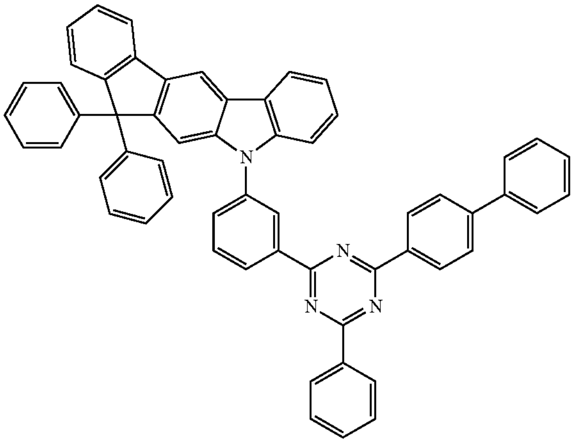
H2-186
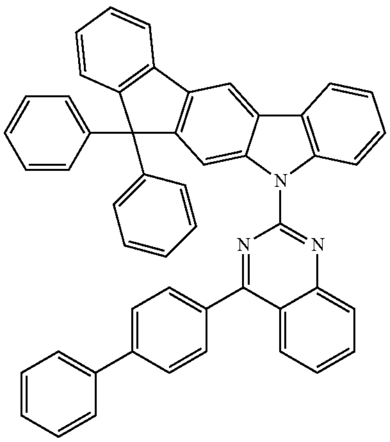
-continued
H2-187
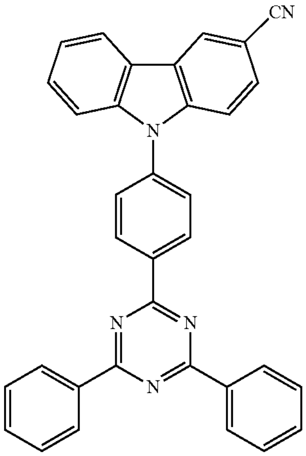
H2-188
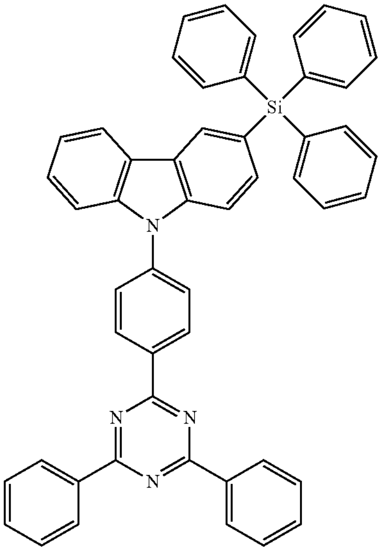
H2-189
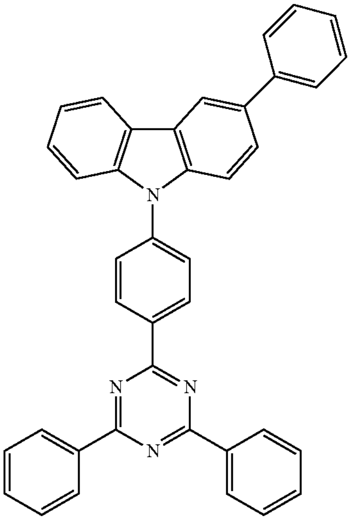

-continued
H2-190
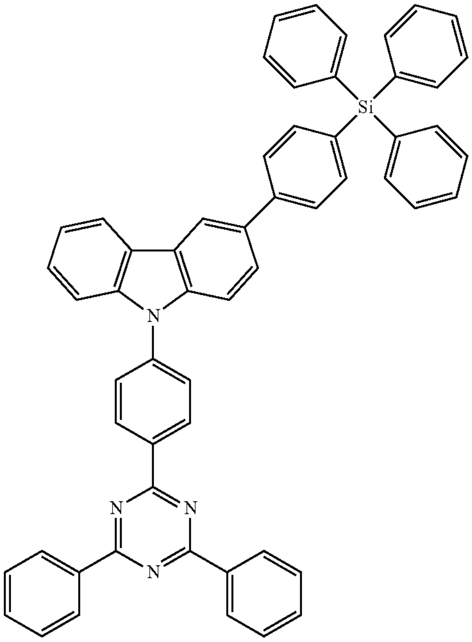
H2-191
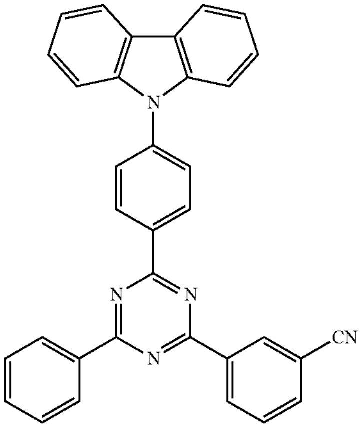
H2-192
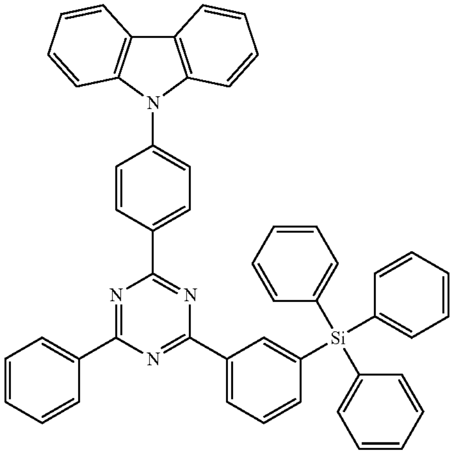
-continued
H2-193
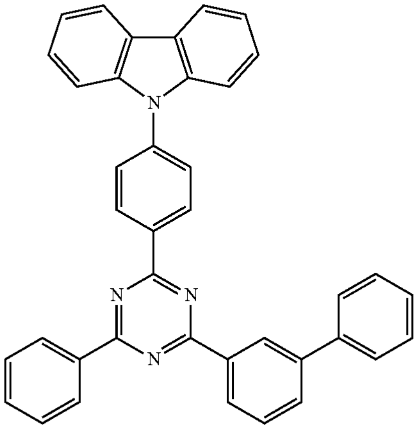
H2-194
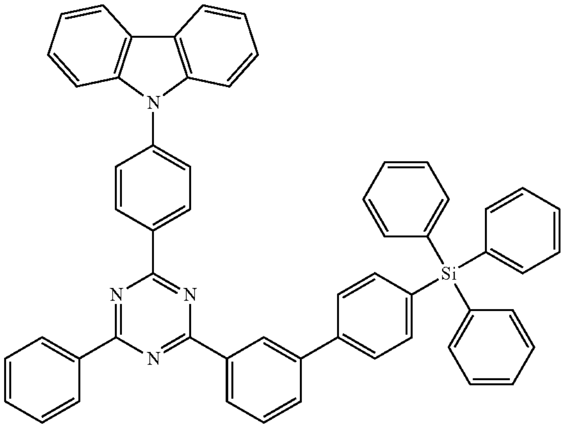
H2-195
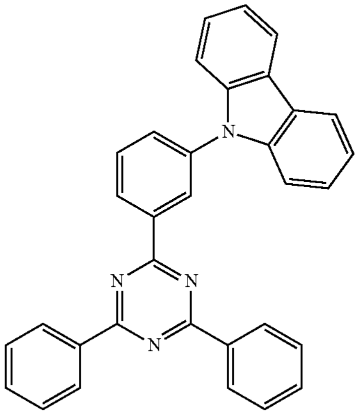

-continued
H2-196
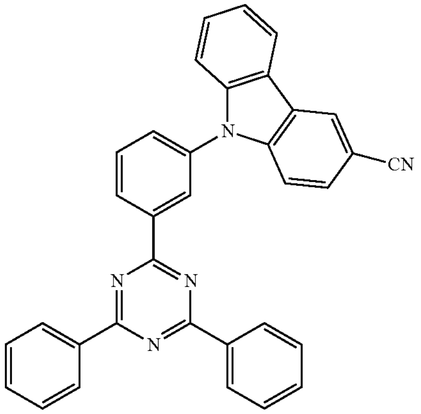
H2-197
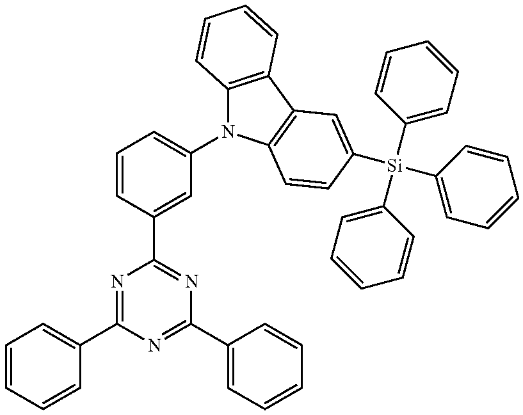
H2-198
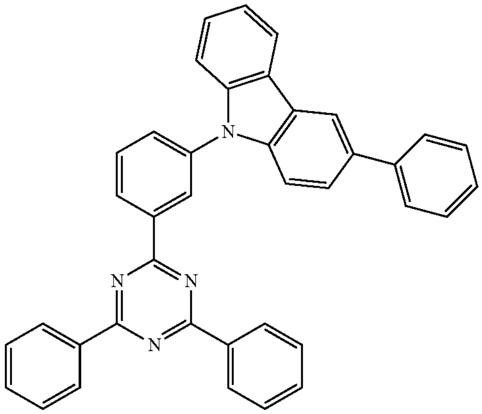
-continued
H2-199
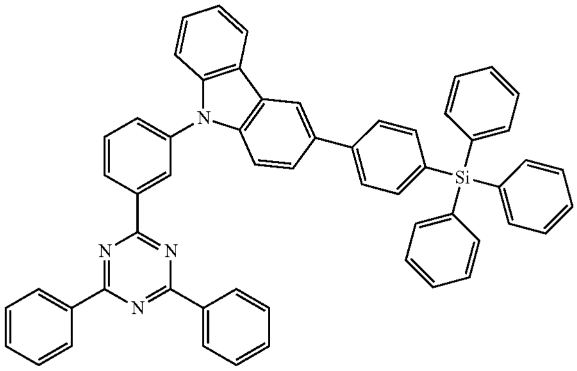
H2-200
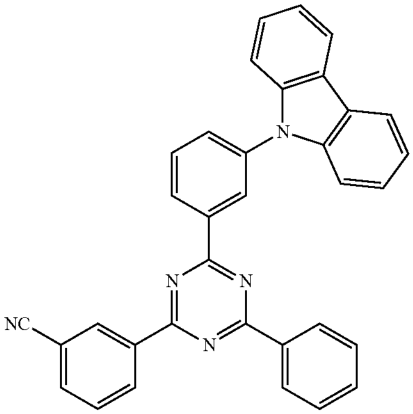
H2-201
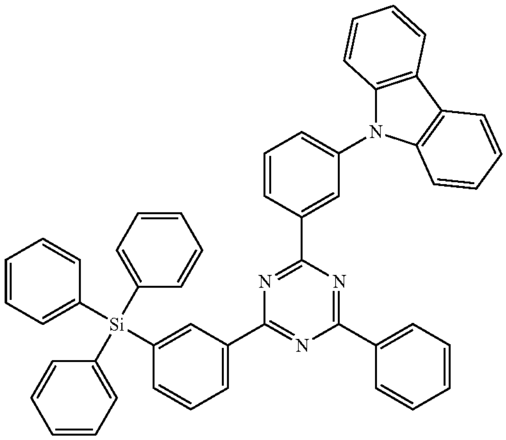

-continued
H2-202
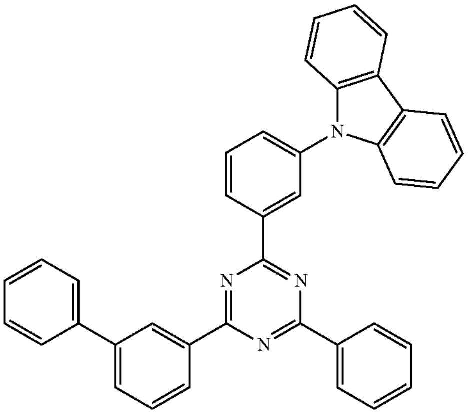
H2-203
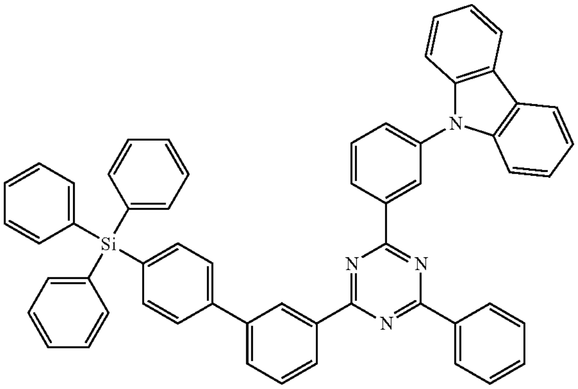
H2-204
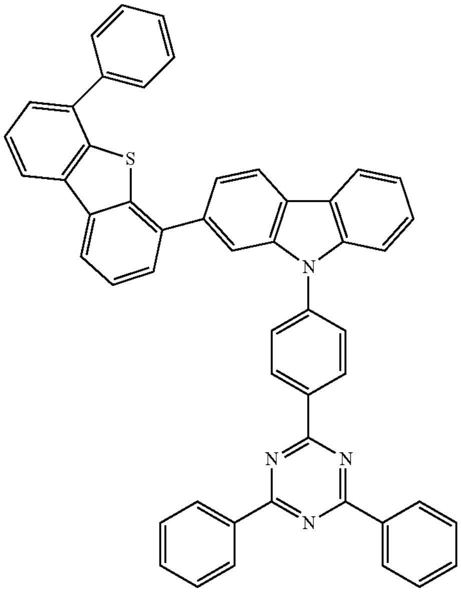
-continued
H2-205
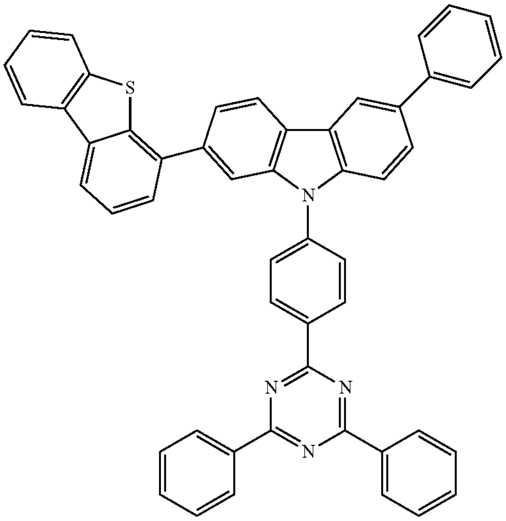
H2-206
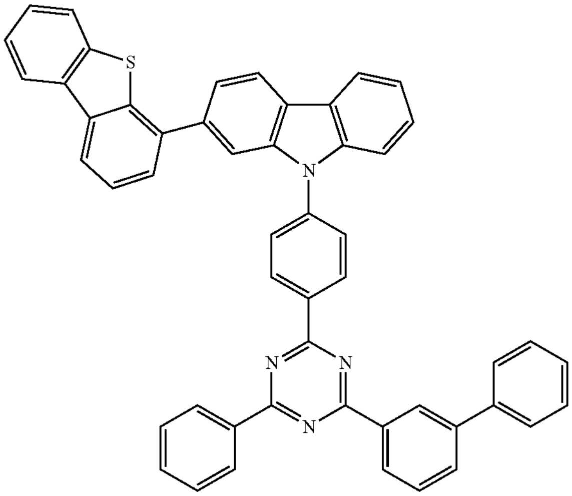
H2-207
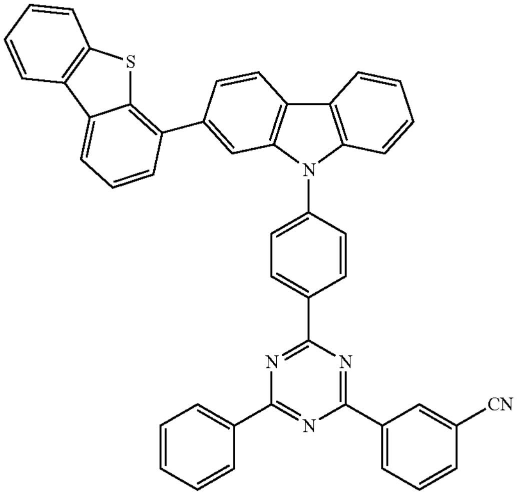

-continued
H2-208
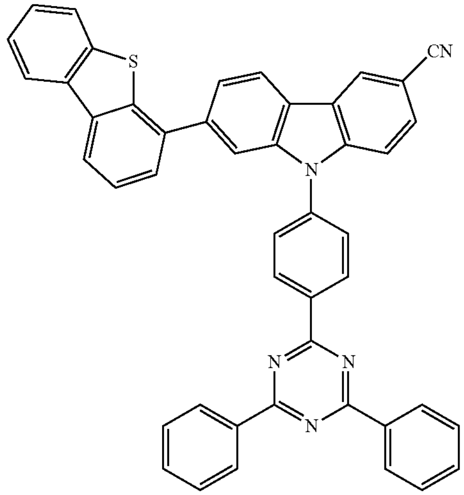
H2-209
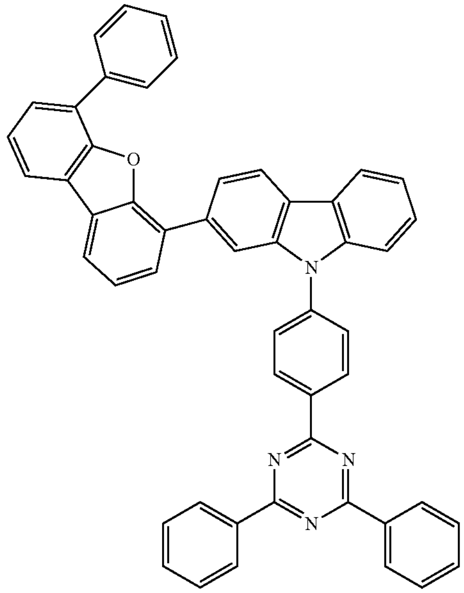
H2-210
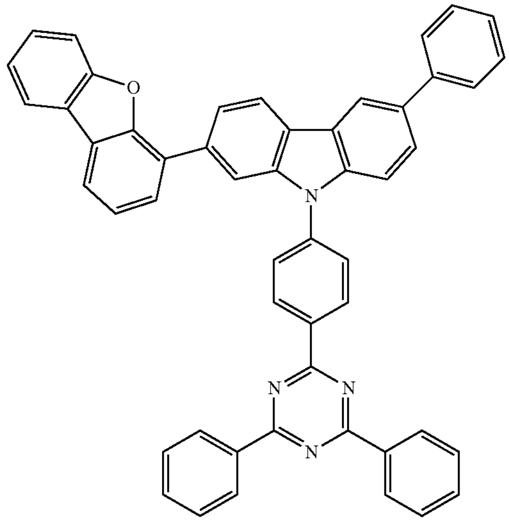
-continued
H2-211
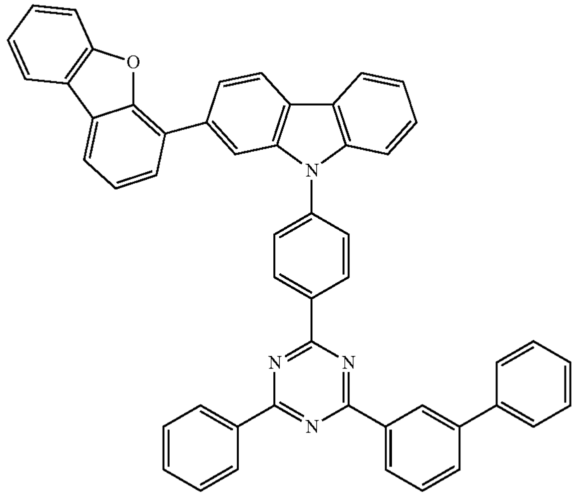
H2-212
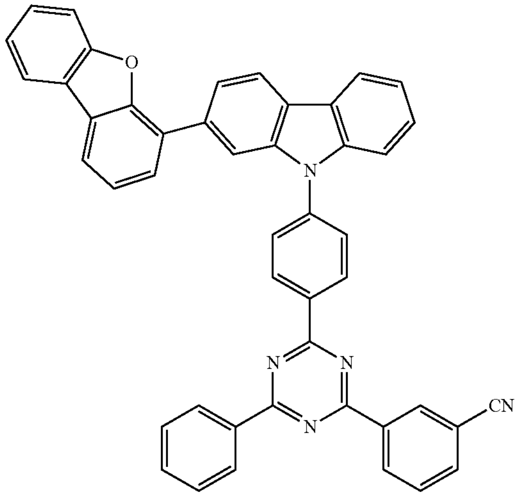
H2-213
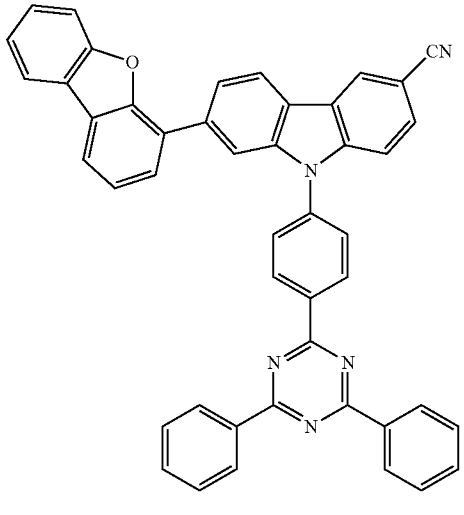

-continued
H2-214
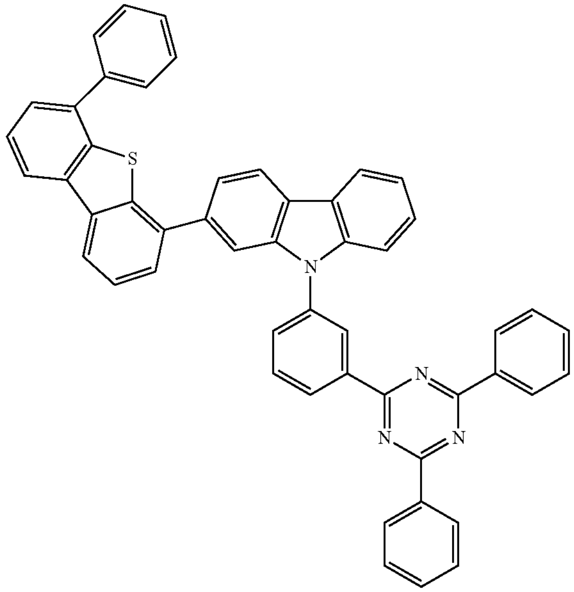
H2-215
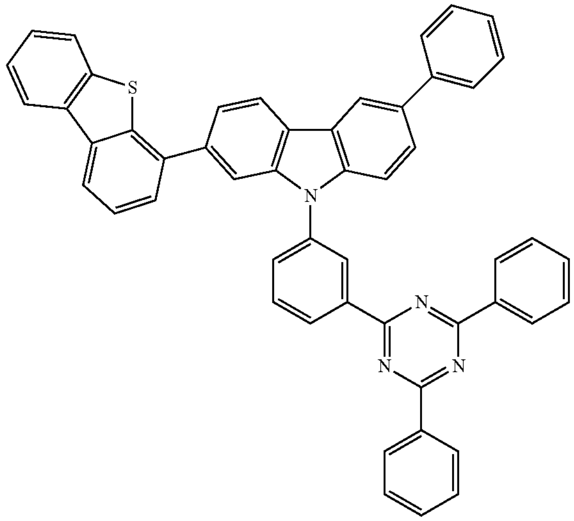
H2-216
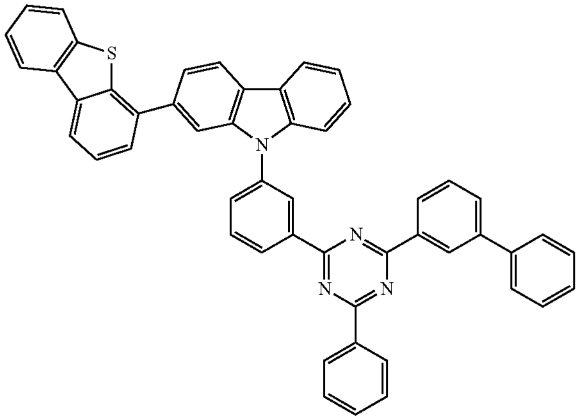
-continued
H2-217
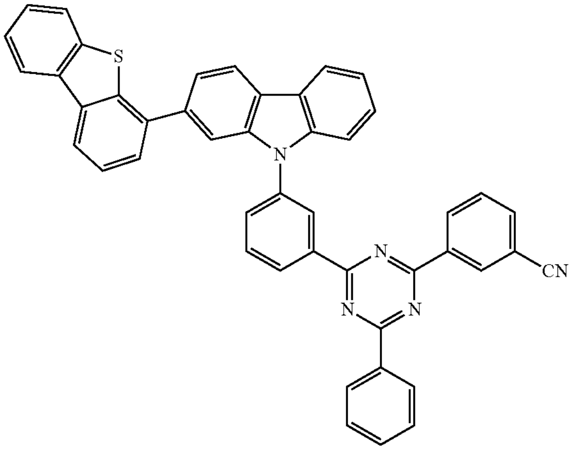
H2-218
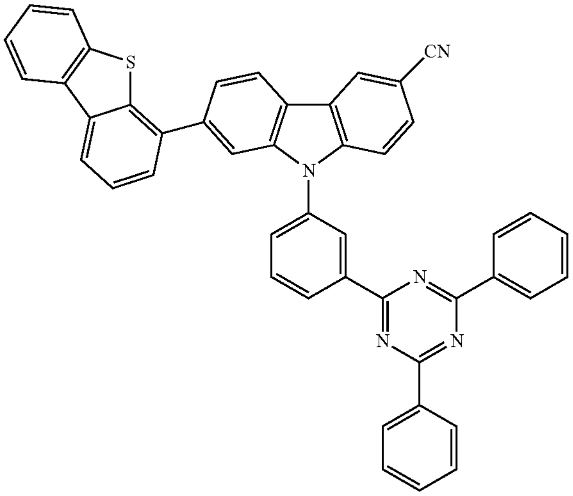
H2-219
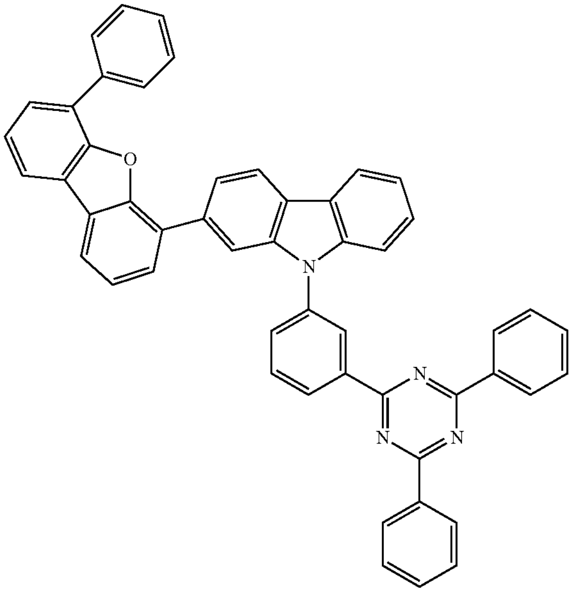

-continued
H2-220
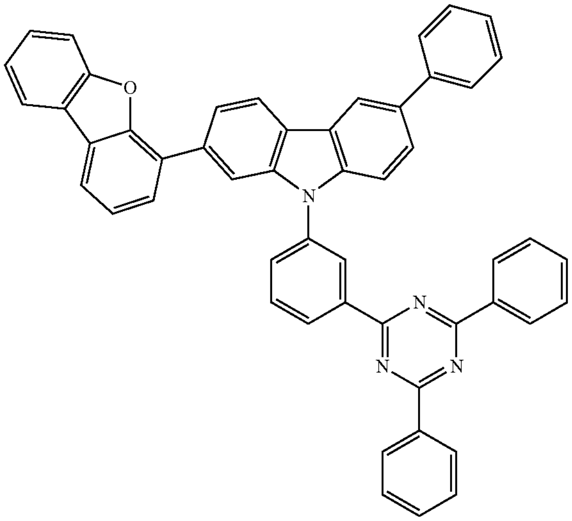
H2-221
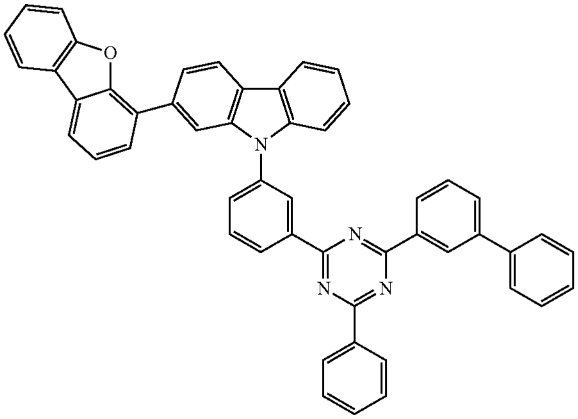
H2-222
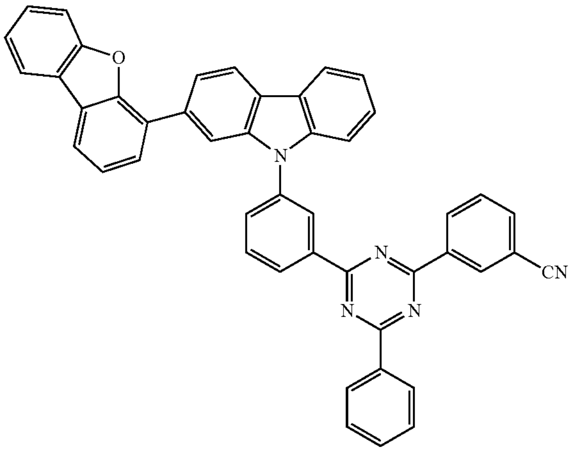
-continued
H2-223
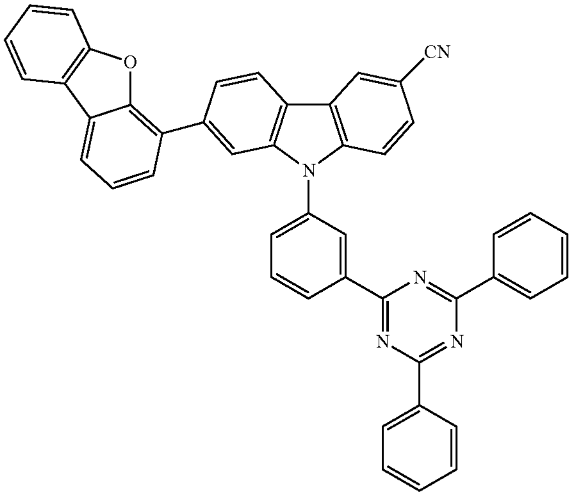
H2-224
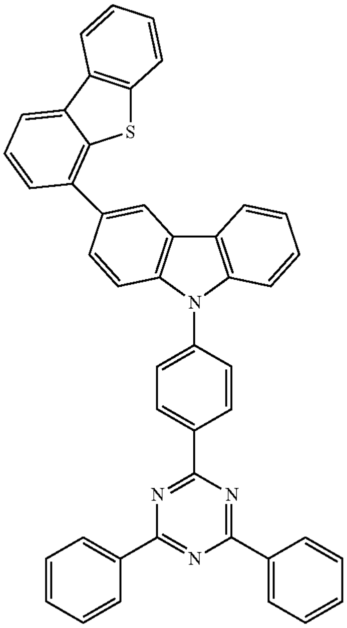

-continued
H2-225
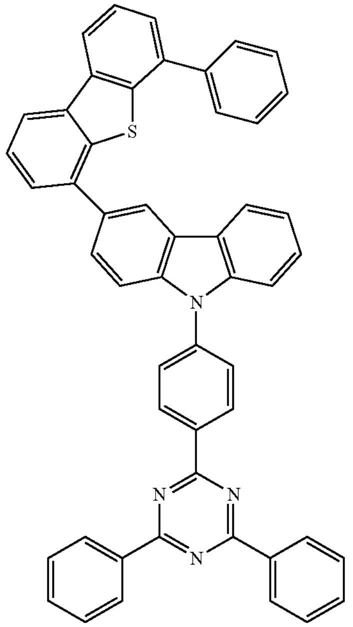
H2-226
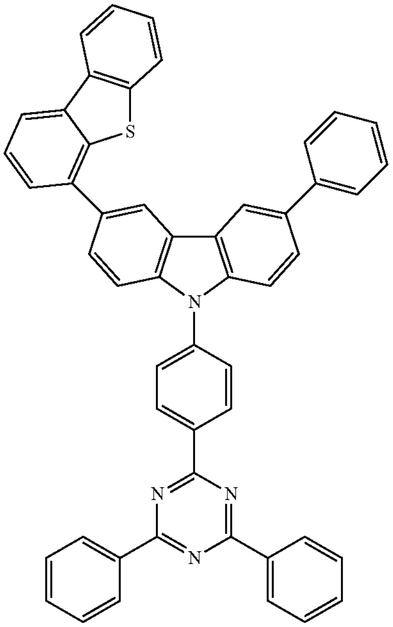
-continued
H2-227
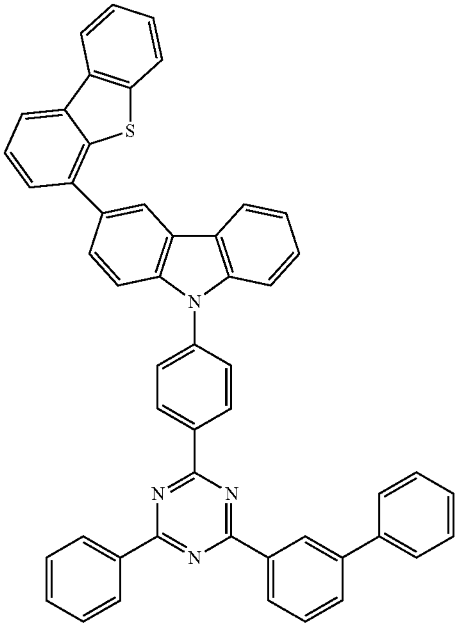
H2-228
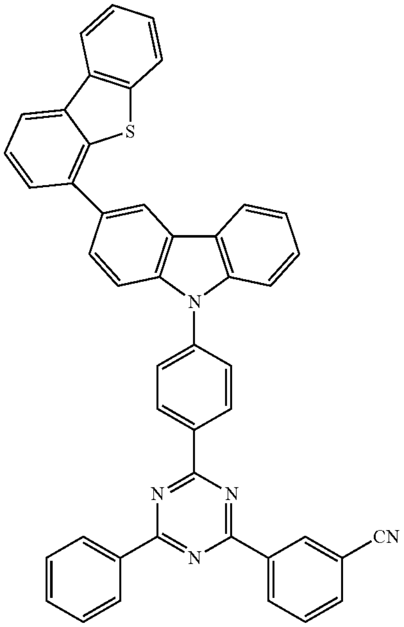

-continued
H2-229
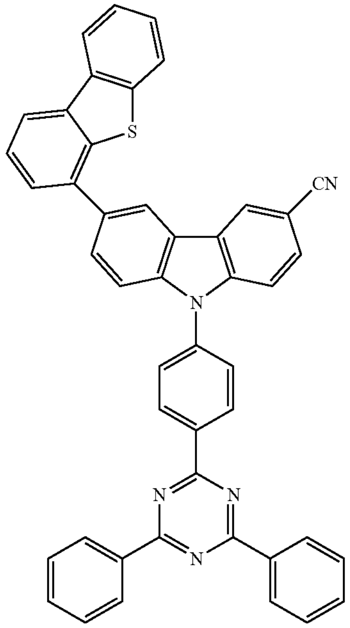
H2-230
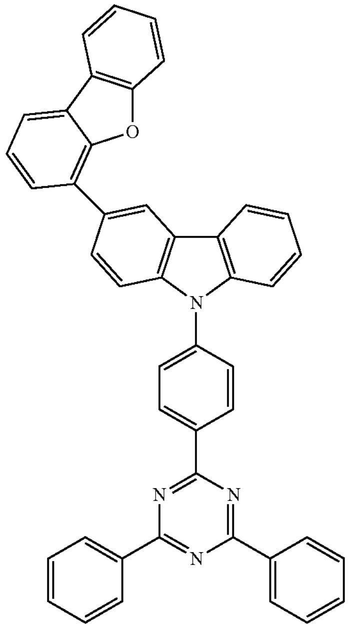
-continued
H2-231
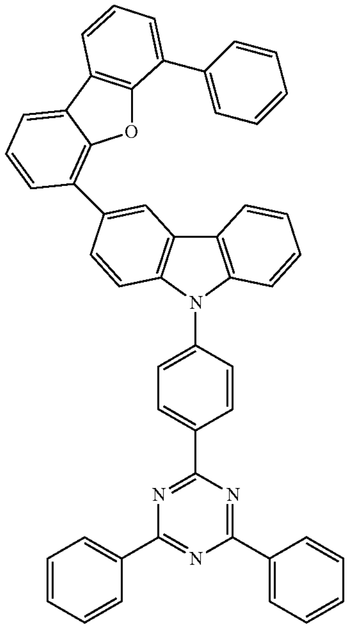
H2-232
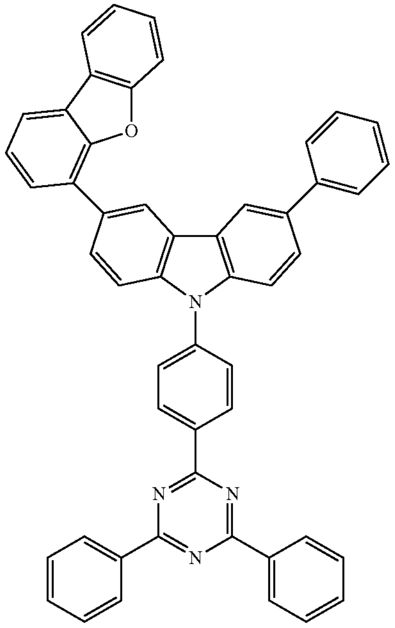

-continued
H2-233
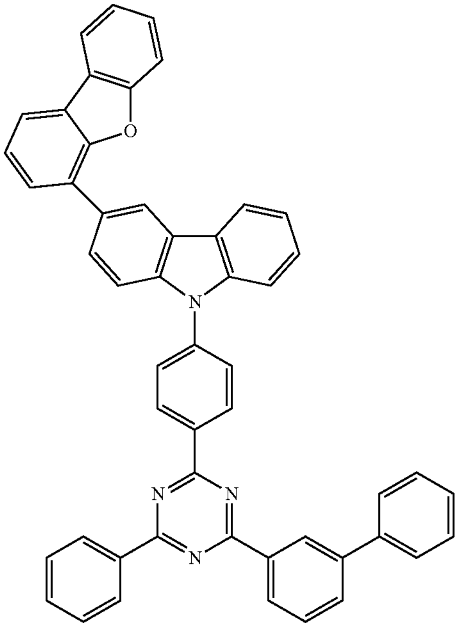
H2-234
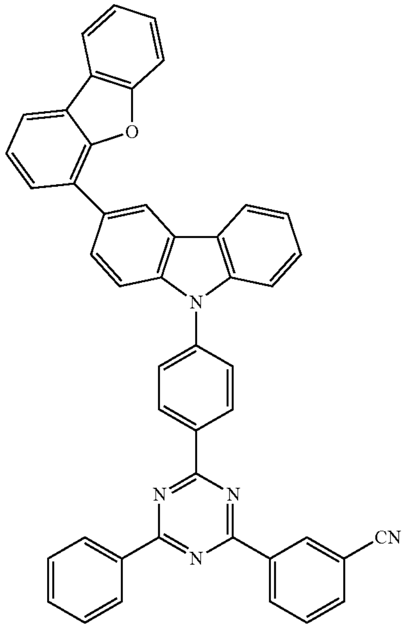
-continued
H2-235
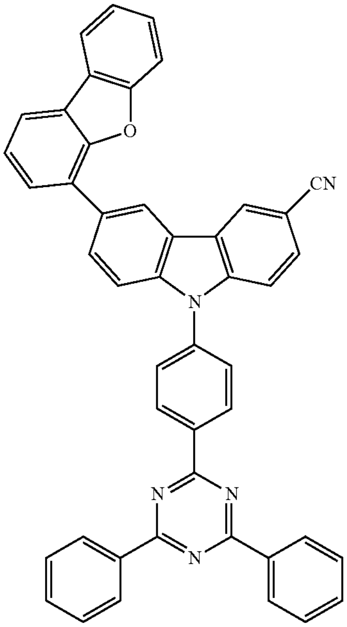
H2-236
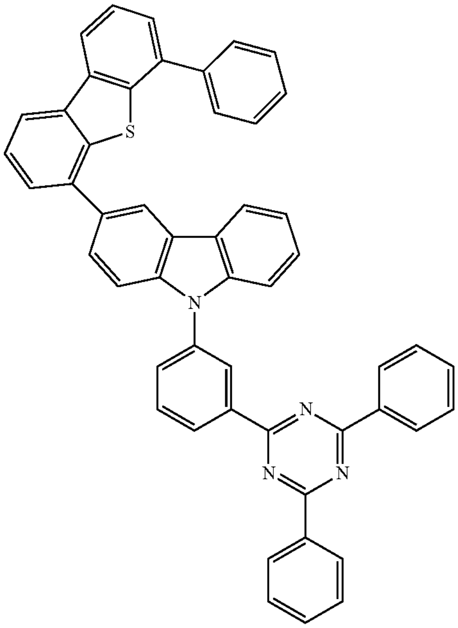

-continued
H2-237
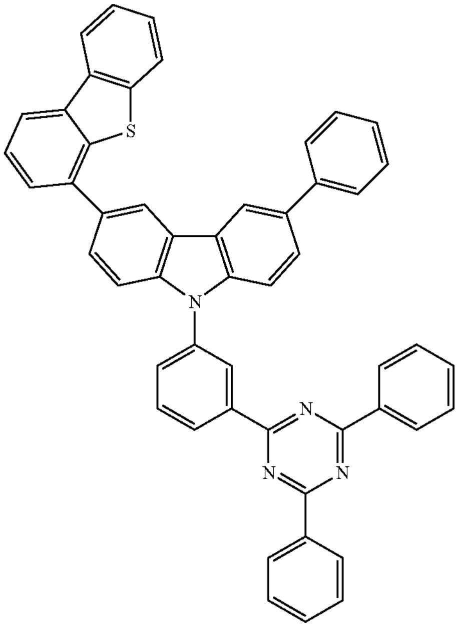
H2-238
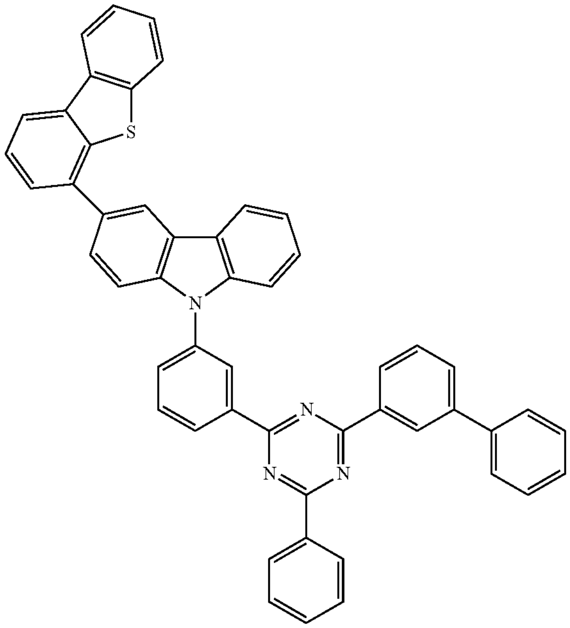
-continued
H2-239
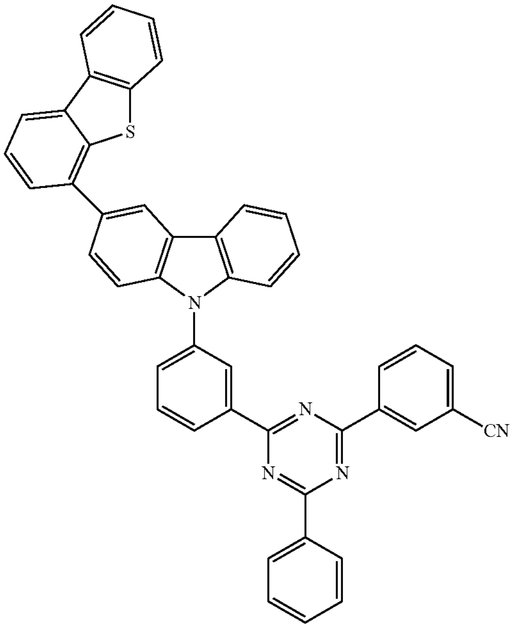
H2-240
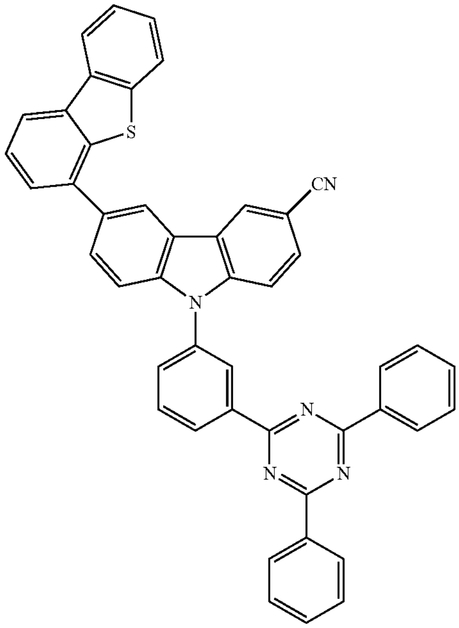

-continued
H2-241
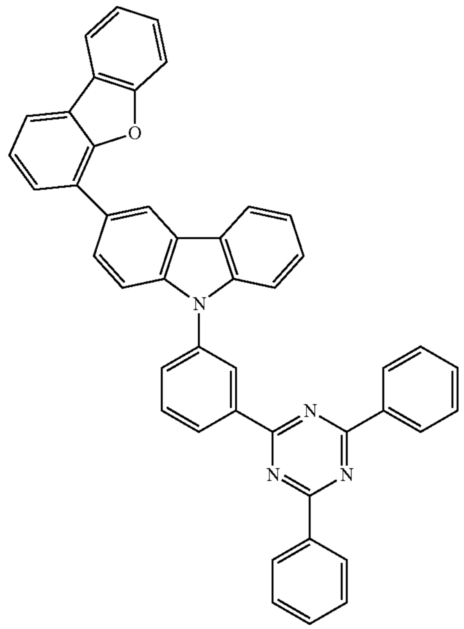
H2-242
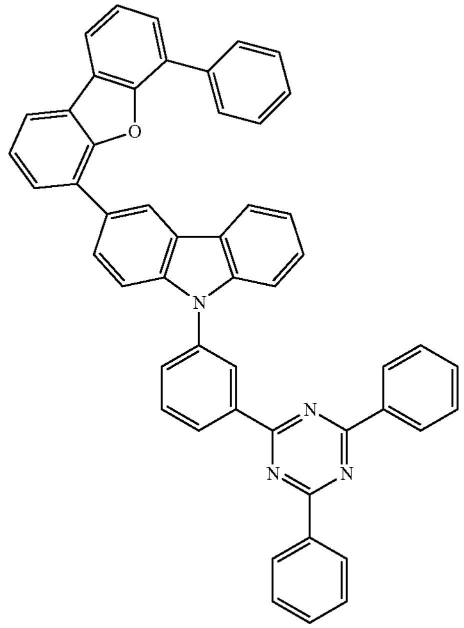
-continued
H2-243
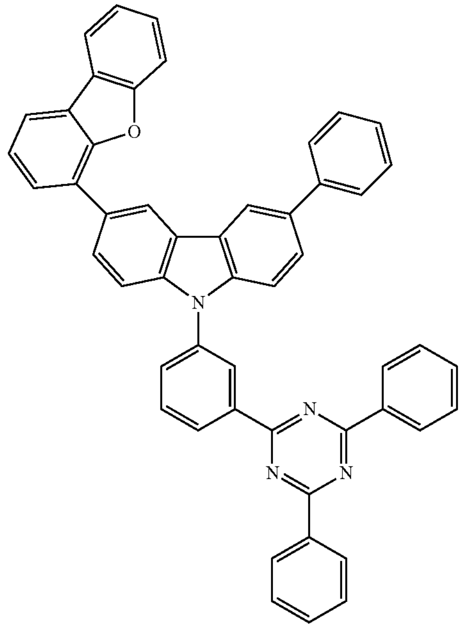
H2-244
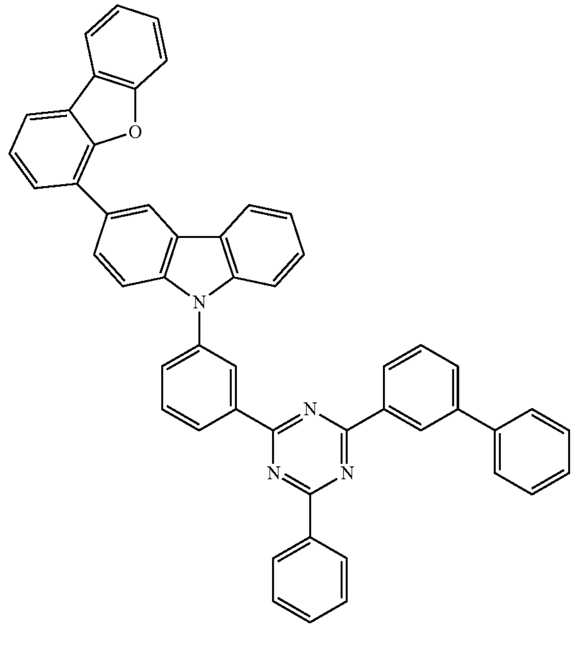

-continued
H2-245
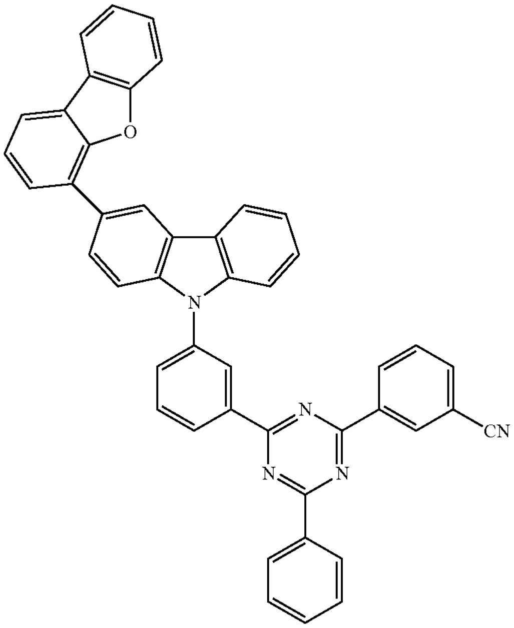
H2-246
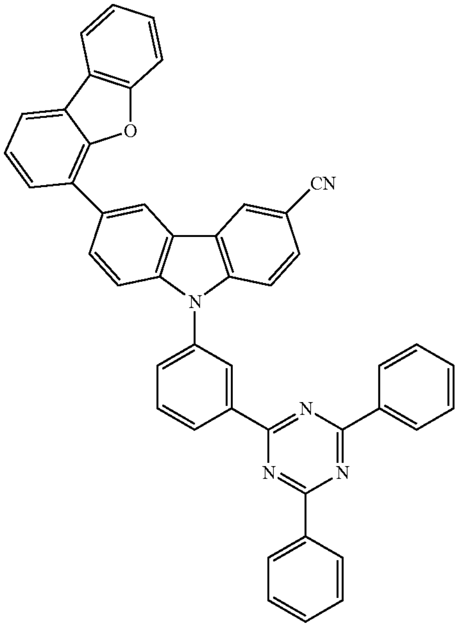
H2-247
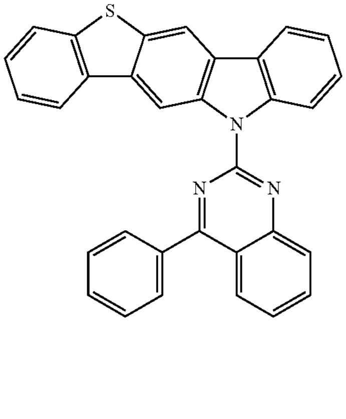
-continued
H2-248
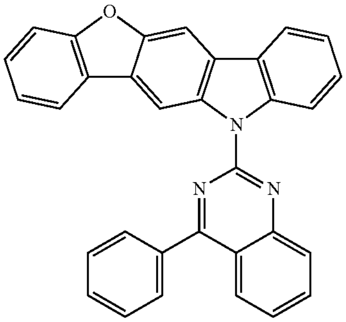
H2-249
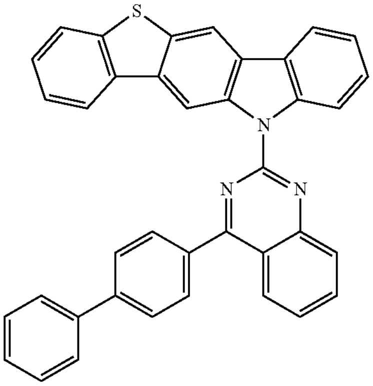
H2-250
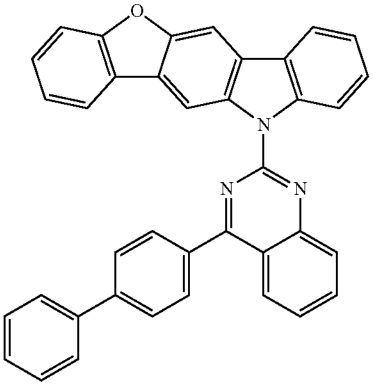
H2-251
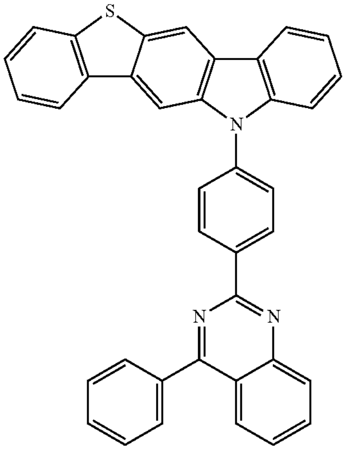

-continued
H2-252
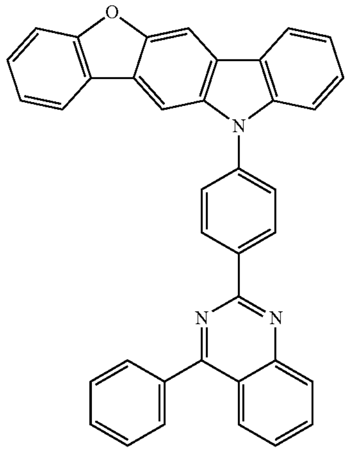
H2-253
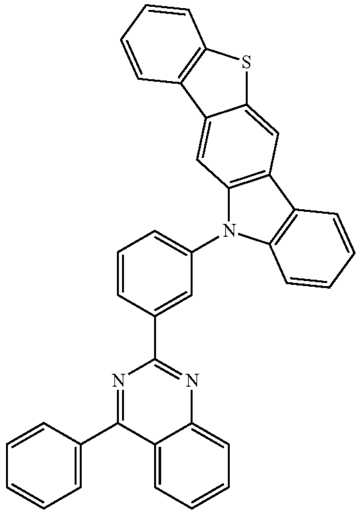
H2-254
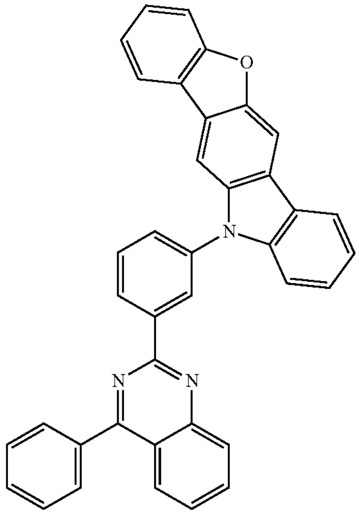
-continued
H2-255
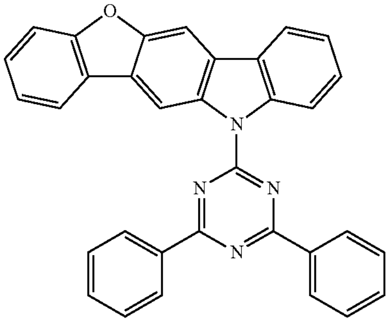
H2-256
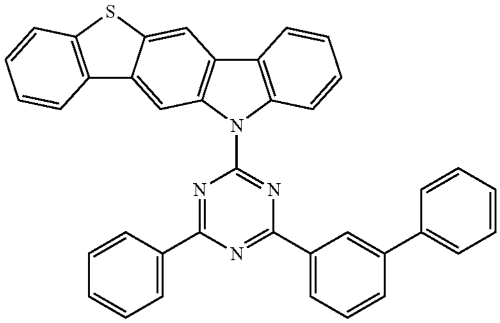
H2-257
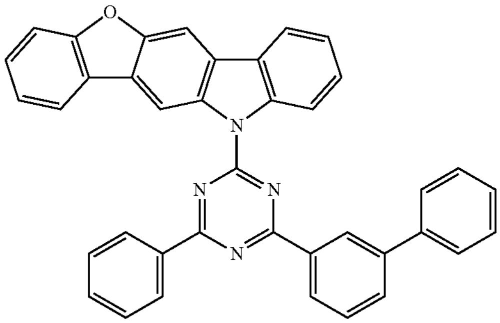
H2-258
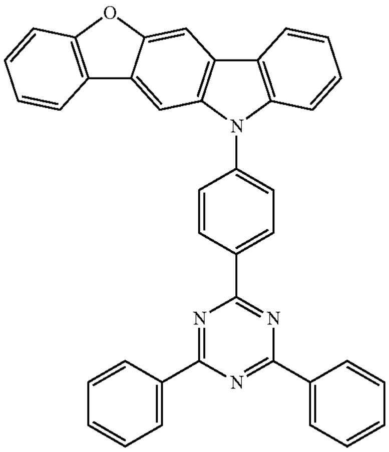

-continued
H2-259
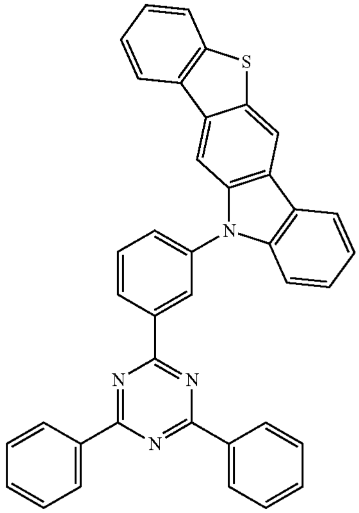
H2-260
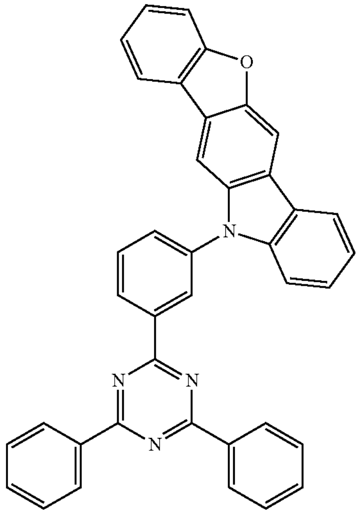
H2-261
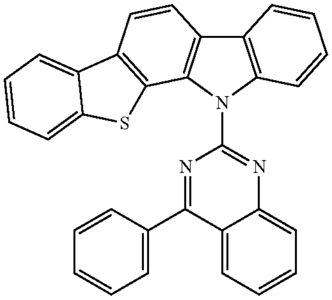
H2-262
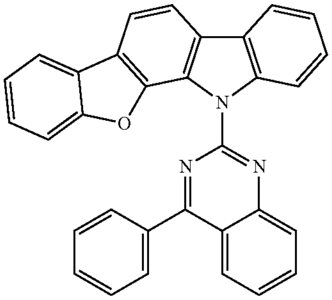
-continued
H2-263
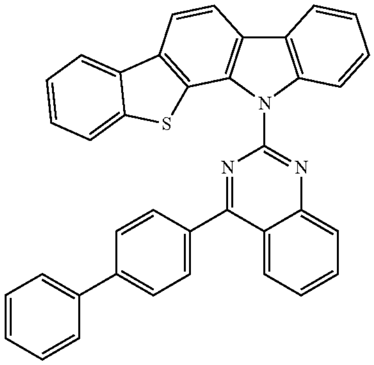
H2-264
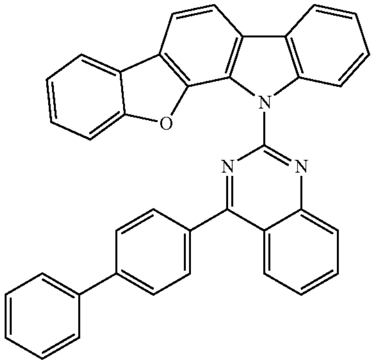
H2-265
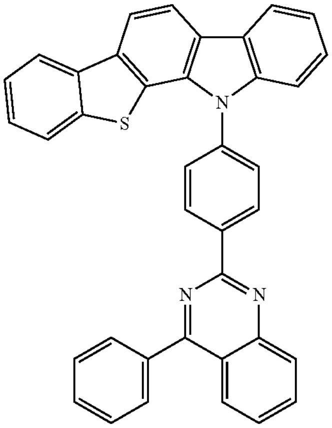
H2-266
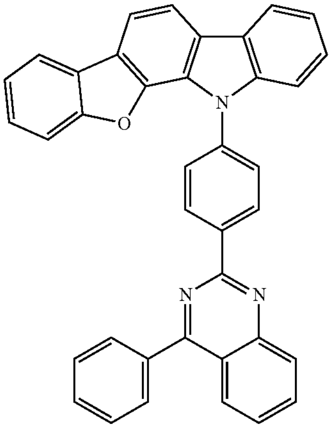

-continued
H2-267
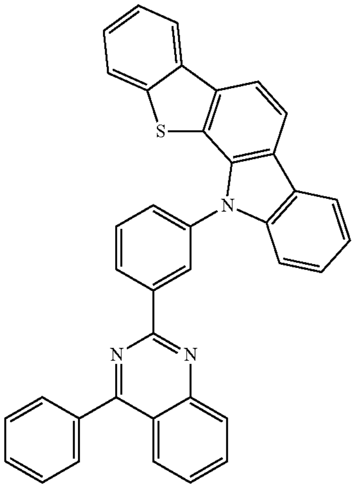
H2-268
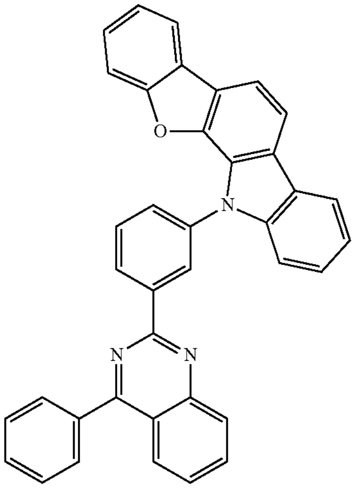
H2-269
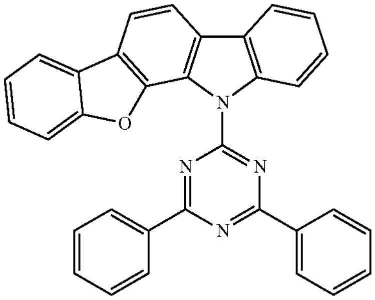
H2-270
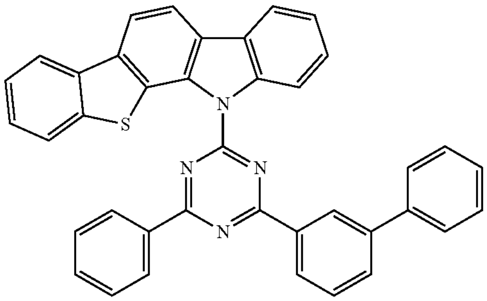
-continued
H2-271
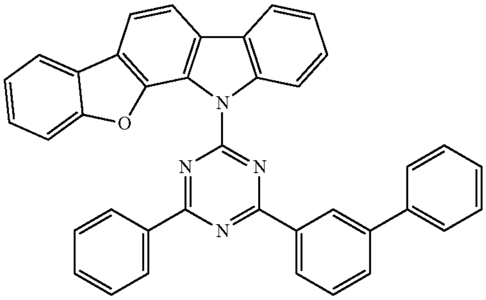
H2-272
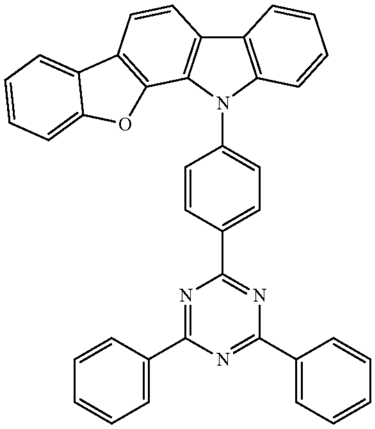
H2-273
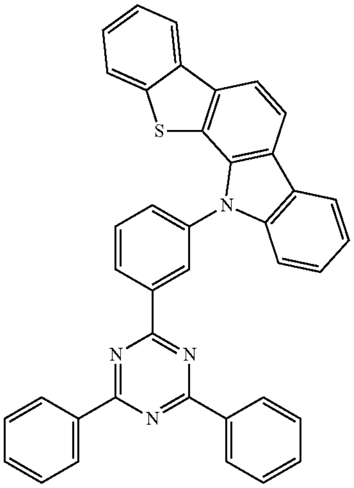

-continued
H2-274
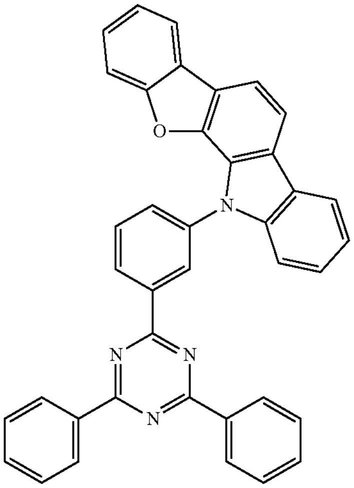
H2-275
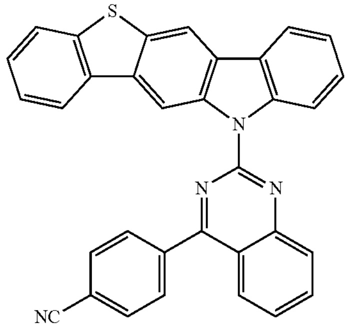
H2-276
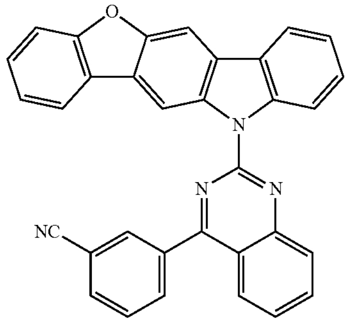
H2-277
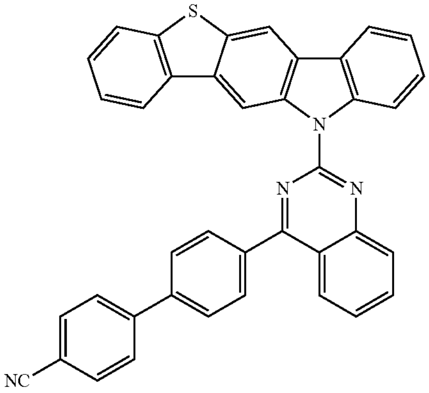
-continued
H2-278
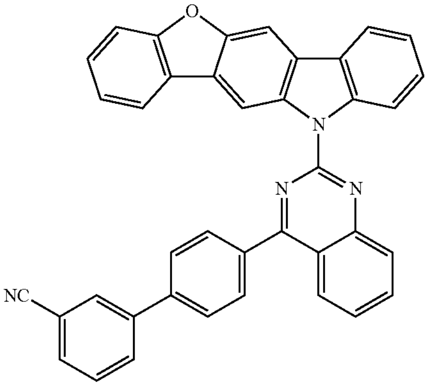
H2-279
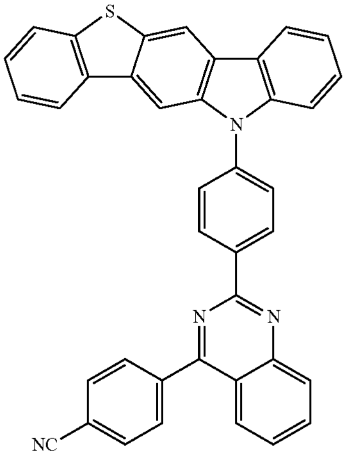
H2-280
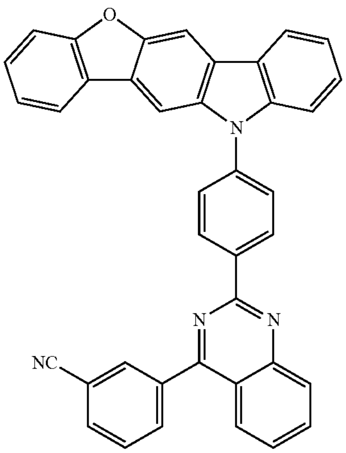

-continued
H2-281
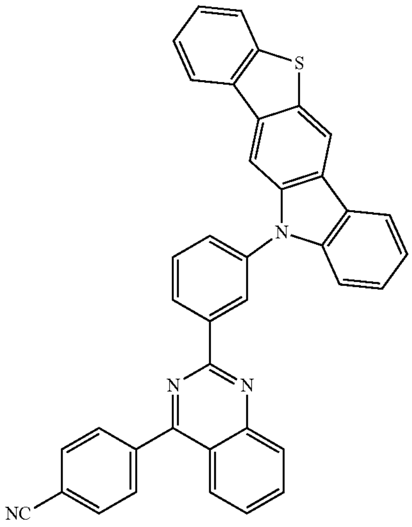
H2-282
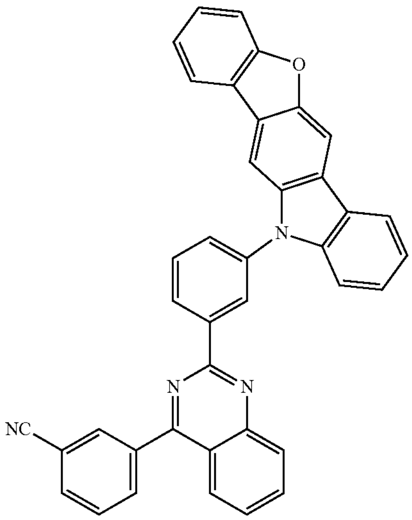
H2-283
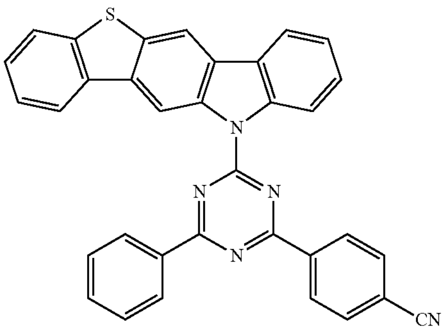
-continued
H2-284
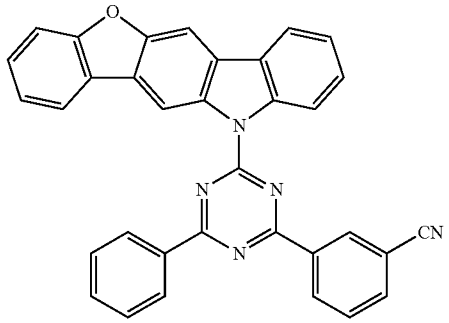
H2-285
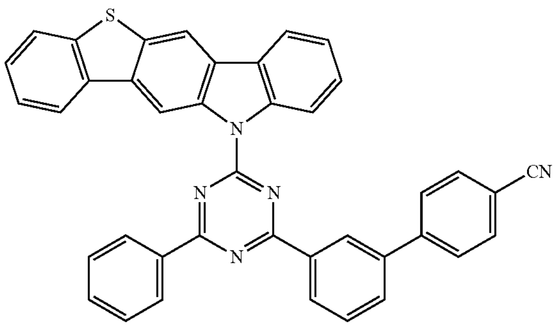
H2-286
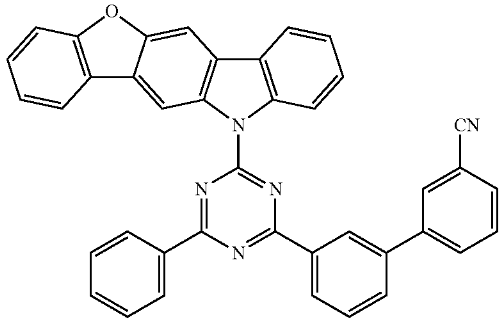
H2-287
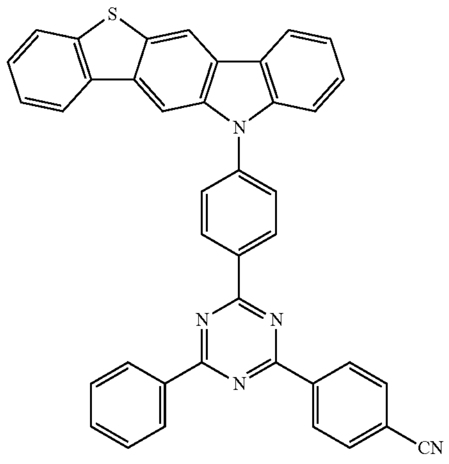

-continued
H2-288
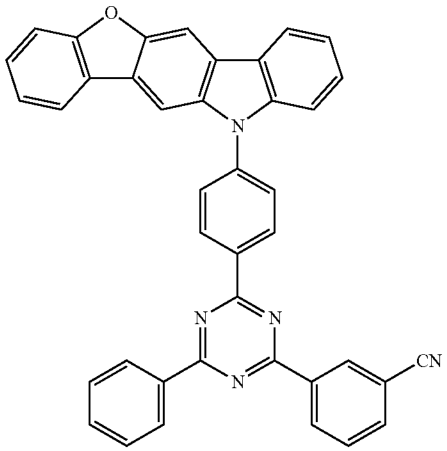
H2-289
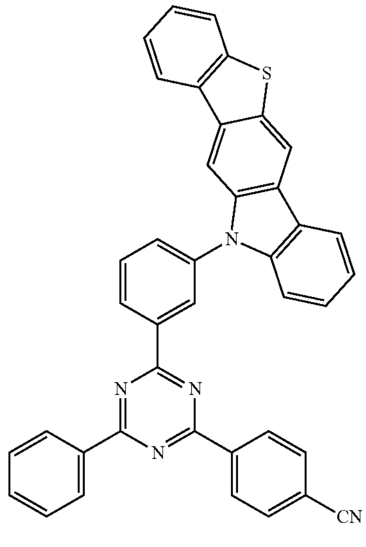
H2-290
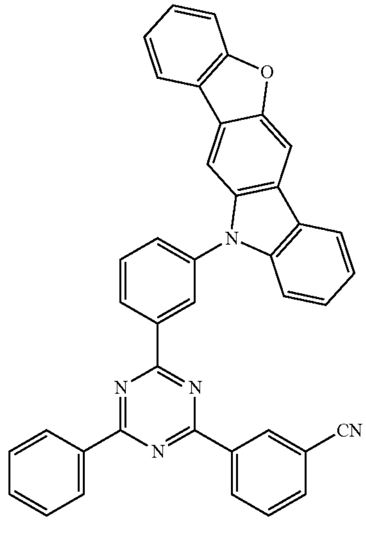
-continued
H2-291
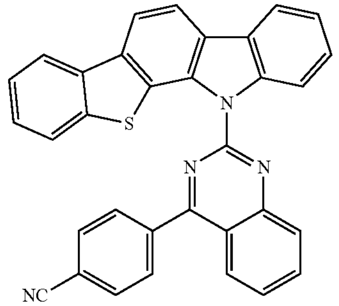
H2-292
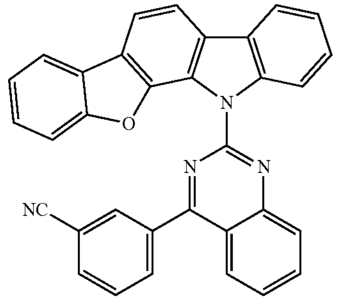
H2-293
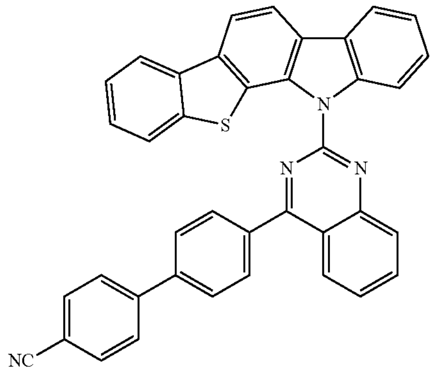
H2-294
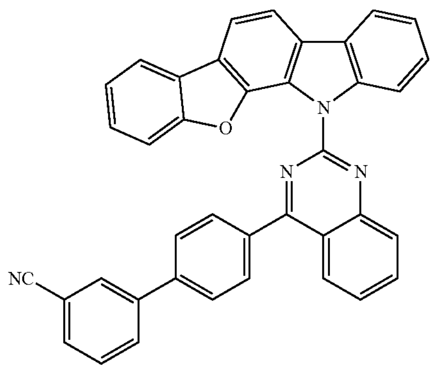

-continued
H2-295
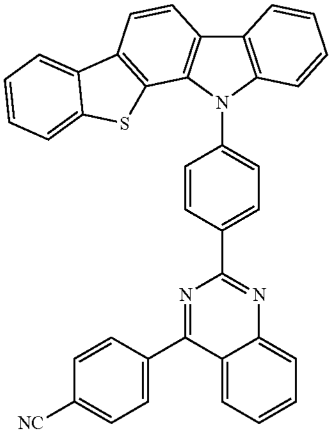
H2-296
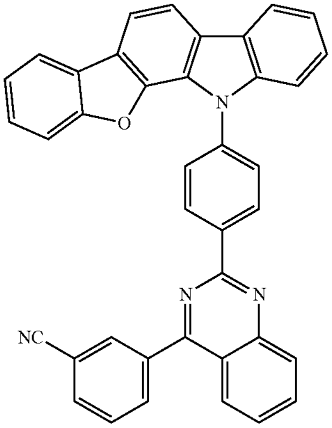
H2-297
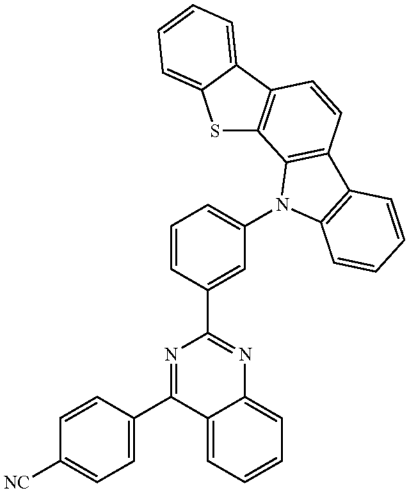
-continued
H2-298
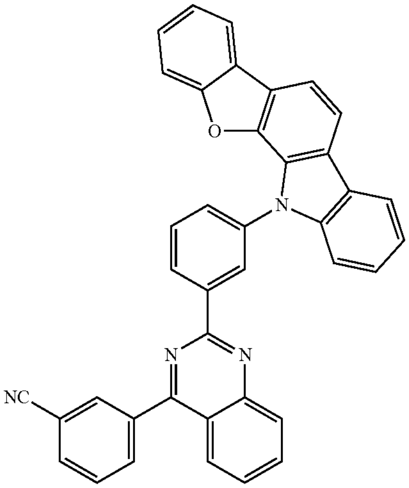
H2-299
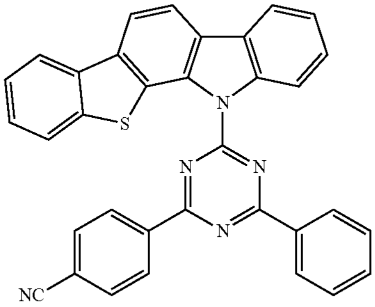
H2-300
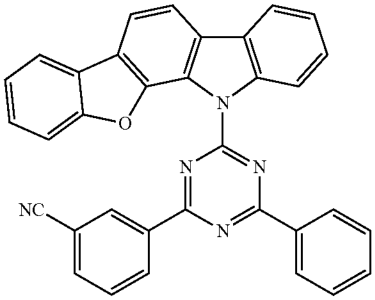
H2-301
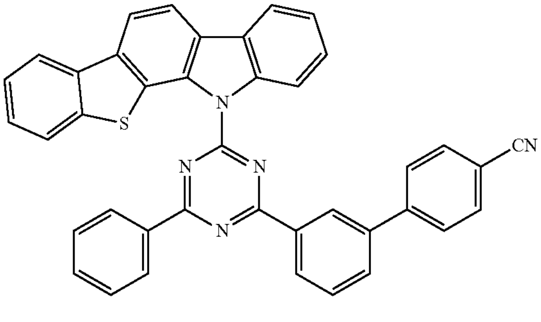

-continued
H2-302
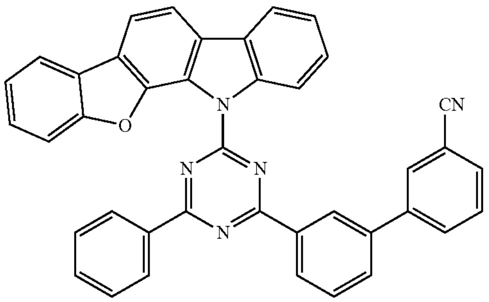
H2-303
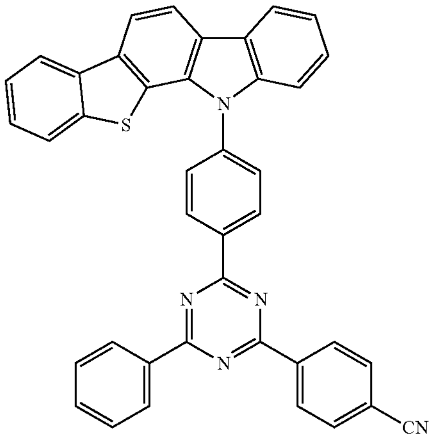
H2-304
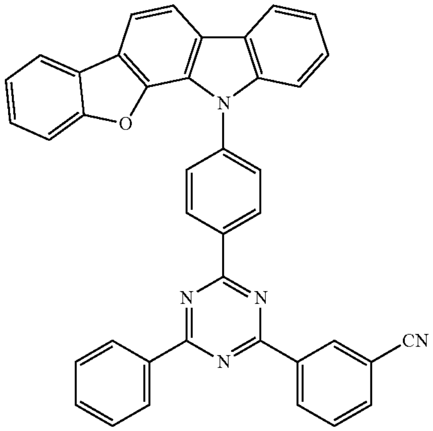
-continued
H2-305
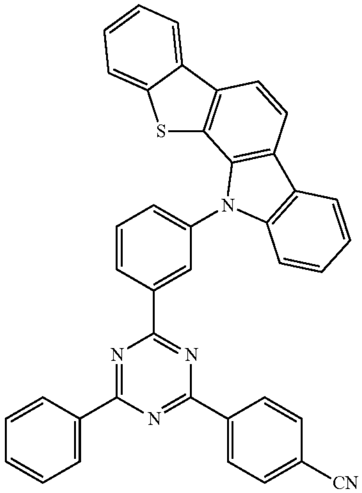
H2-306
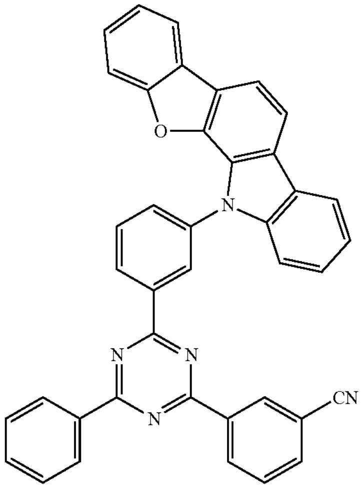
H2-307
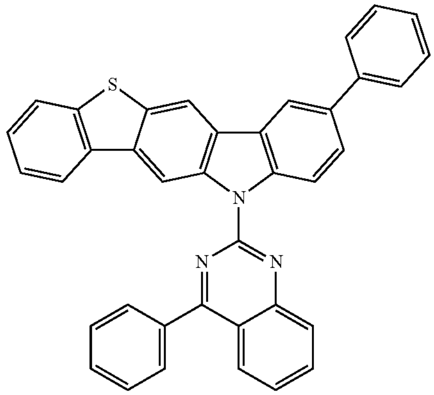

-continued
H2-308
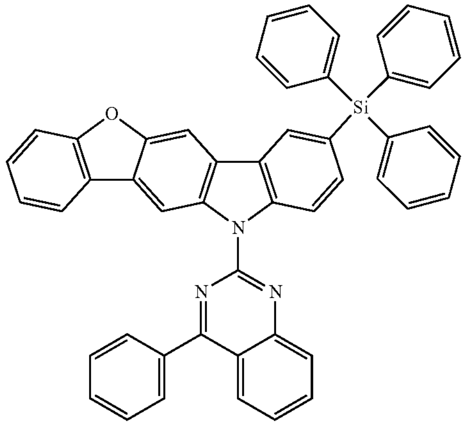
H2-309
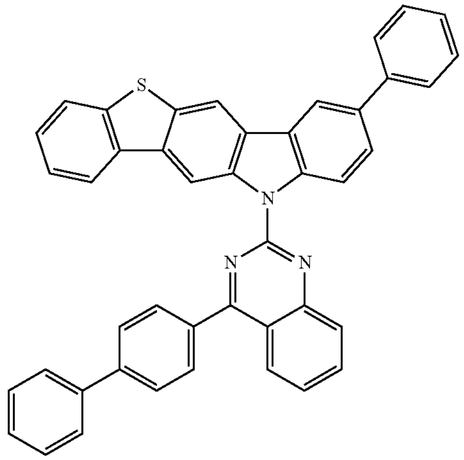
H2-310
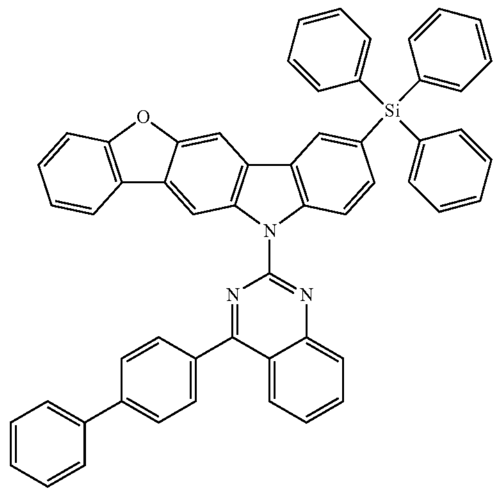
-continued
H2-311
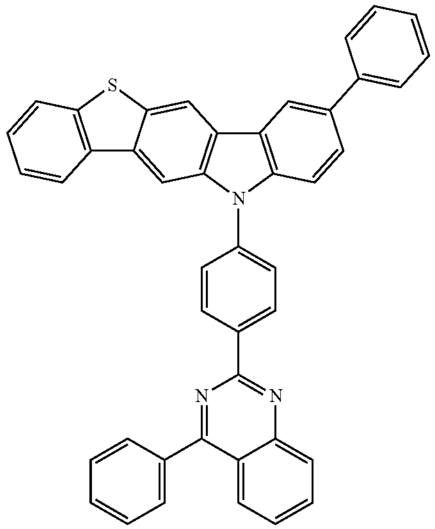
H2-312
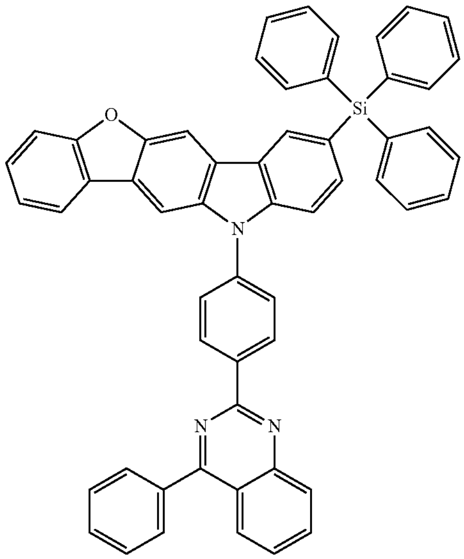
H2-313
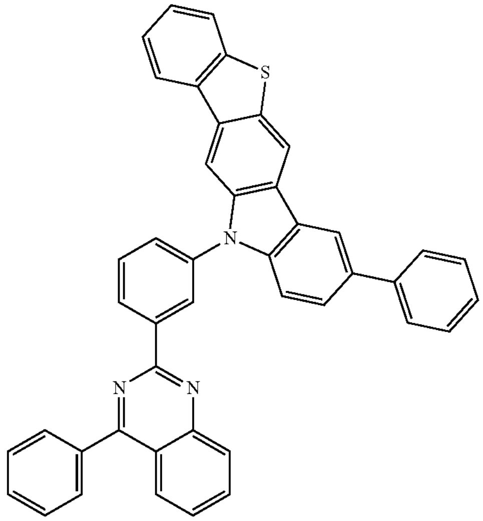

-continued
H2-314
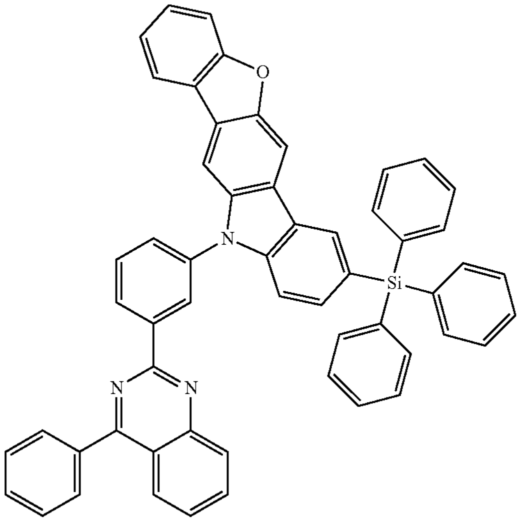
H2-315
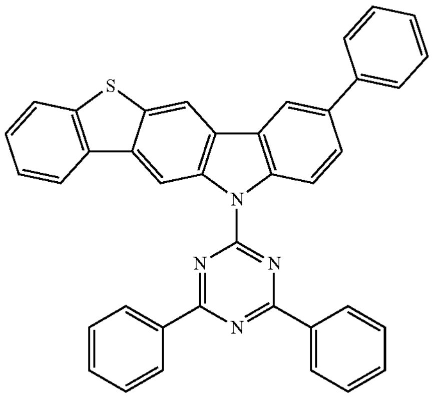
H2-316
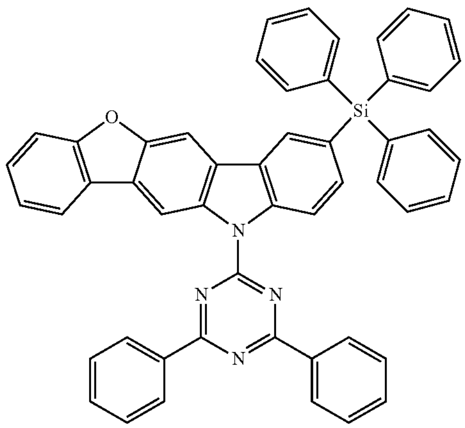
-continued
H2-317
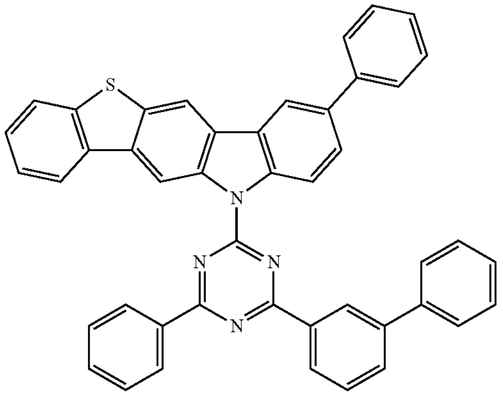
H2-318
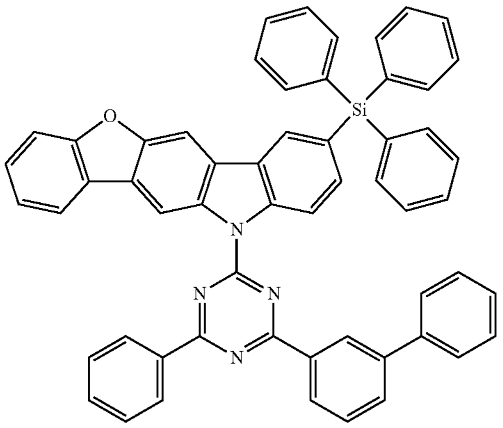
H2-319
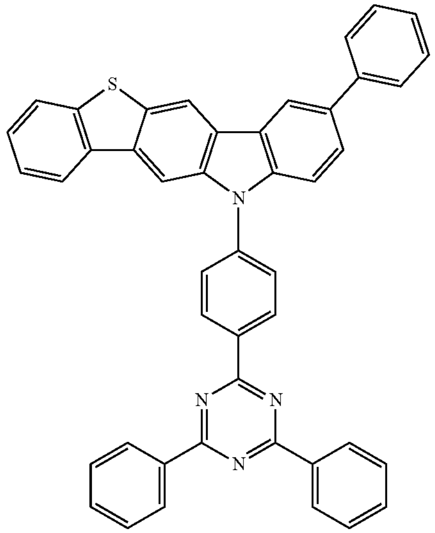

-continued
H2-320
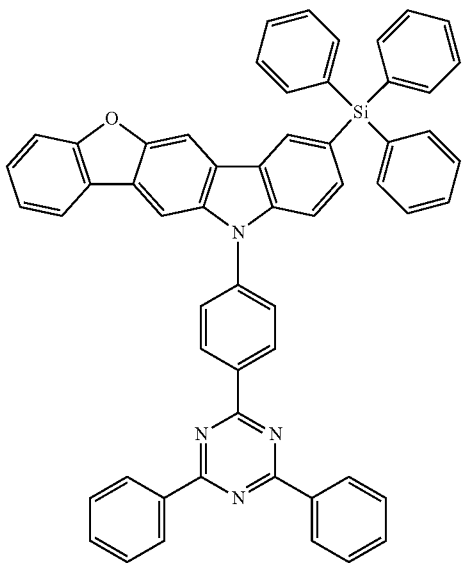
H2-321
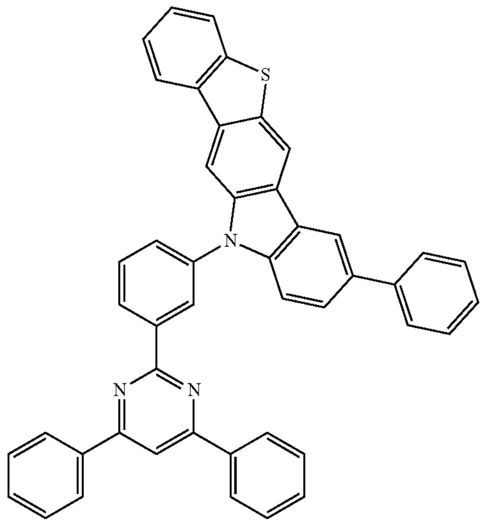
H2-322
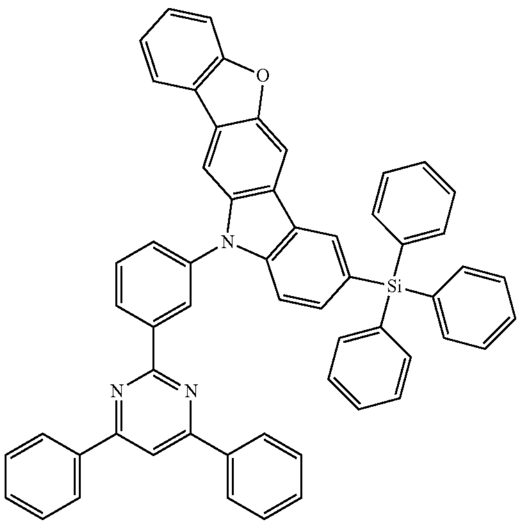
-continued
H2-323
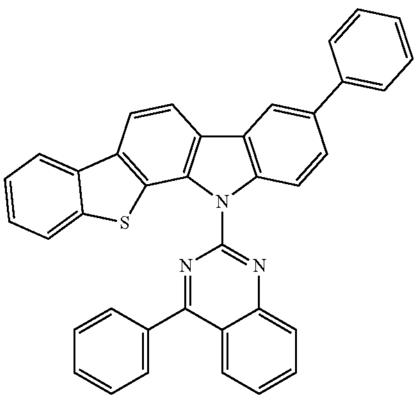
H2-324
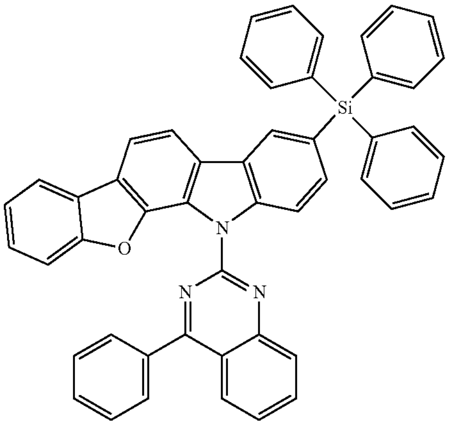
H2-325
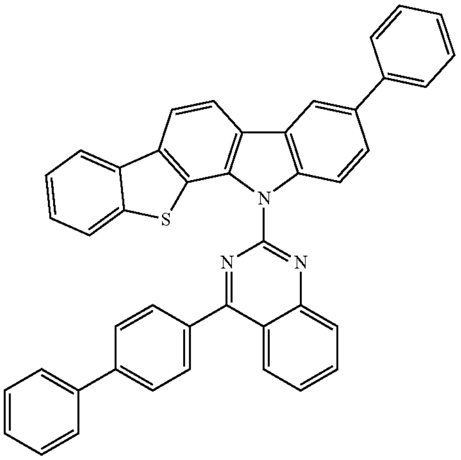

-continued
H2-326
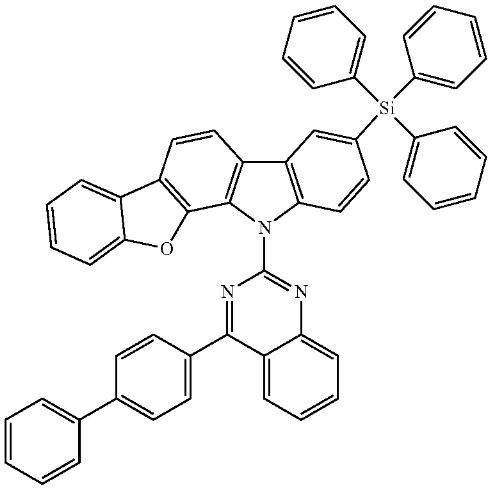
H2-327
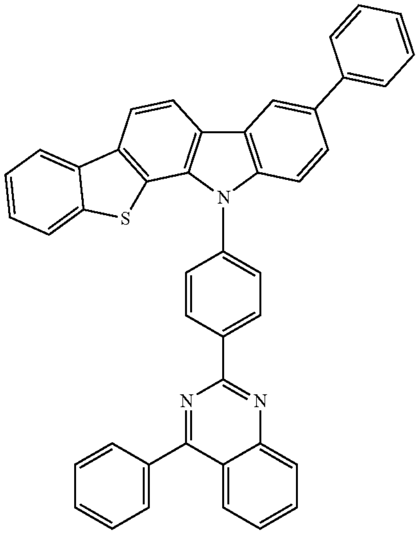
H2-328
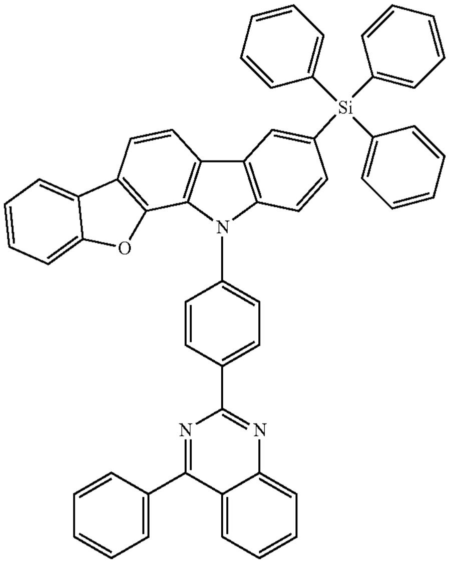
-continued
H2-329
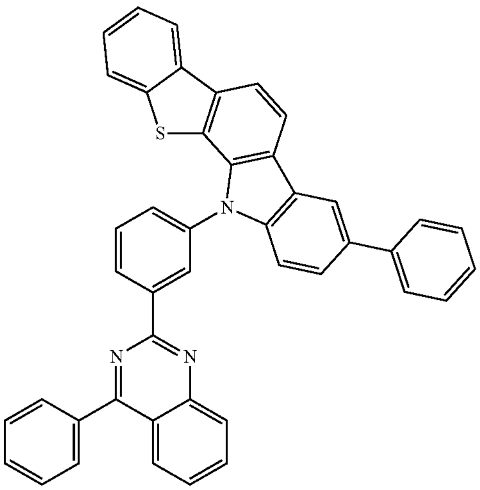
H2-330
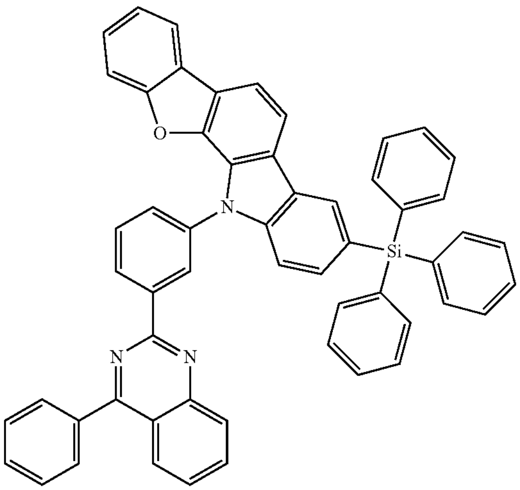
H2-331
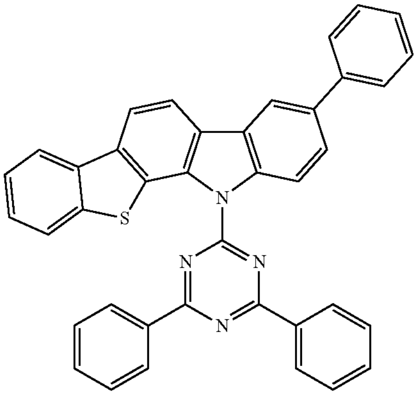

-continued
H2-332
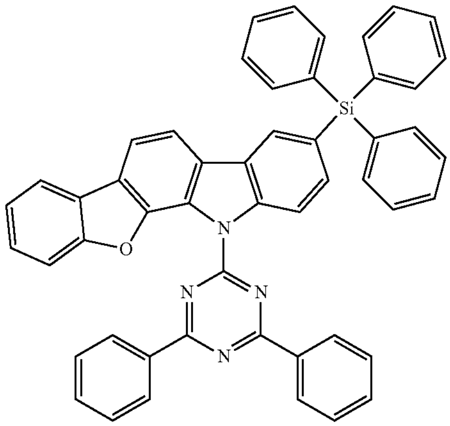
H2-333
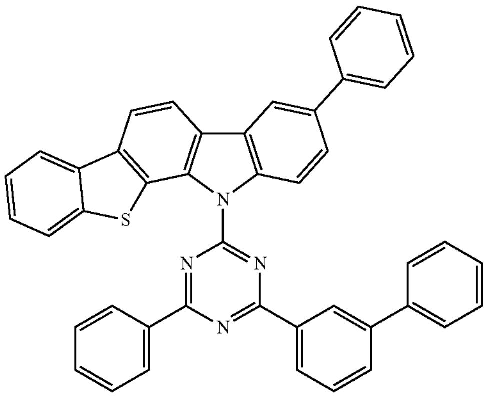
H2-334
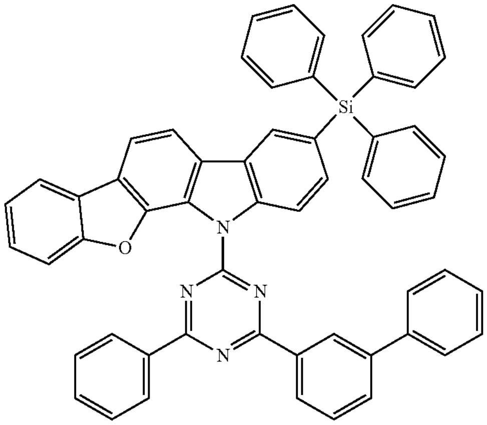
-continued
H2-335
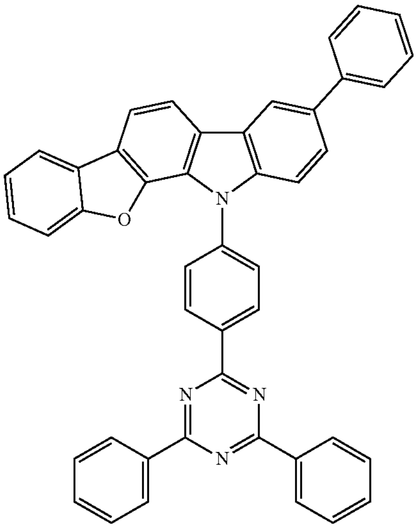
H2-336
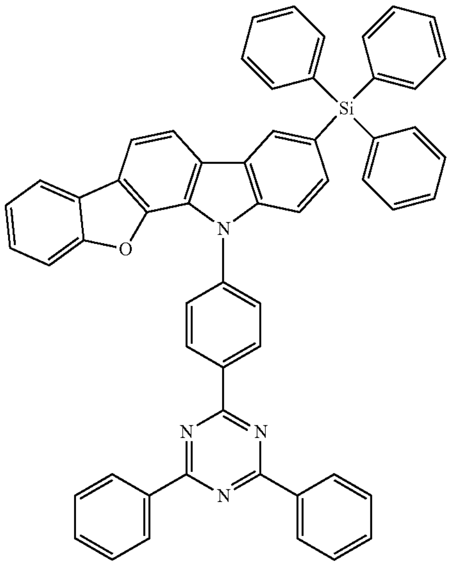
H2-337
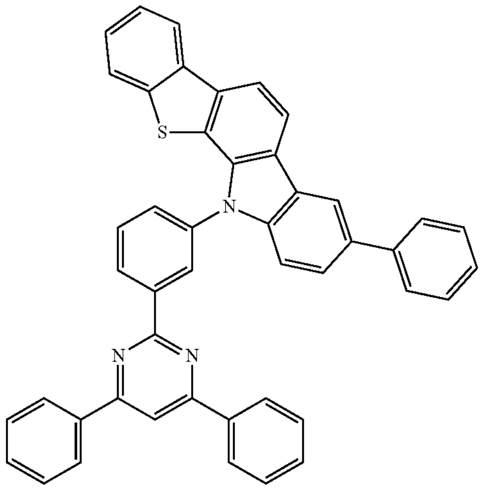

-continued
H2-338
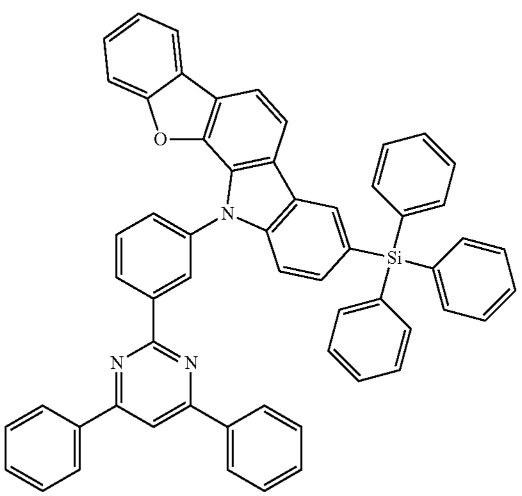
H2-339
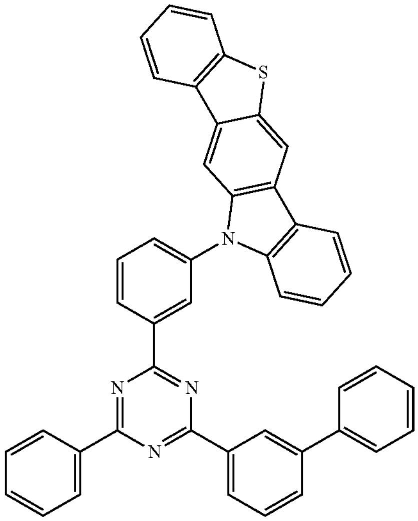
H2-340
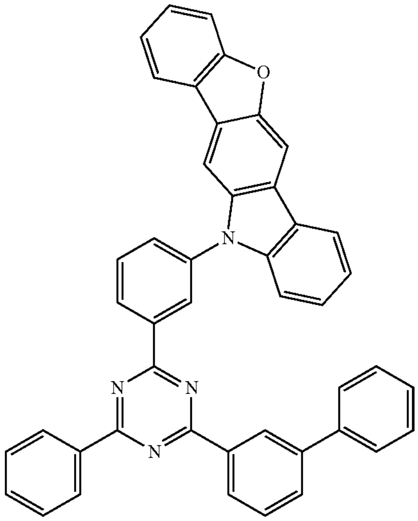
-continued
H2-341
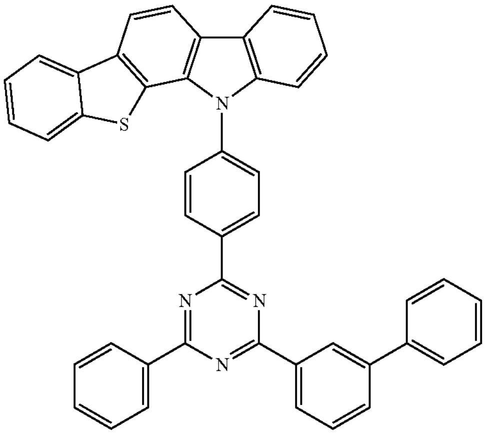
H2-342
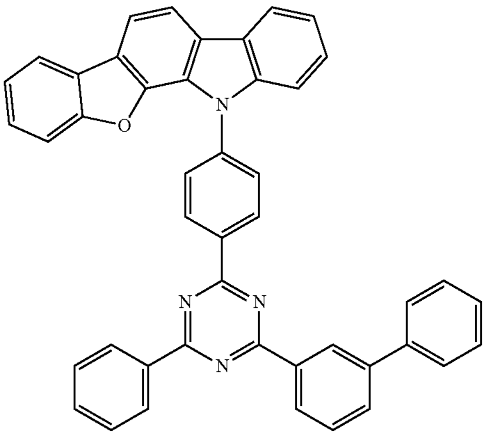
H2-343
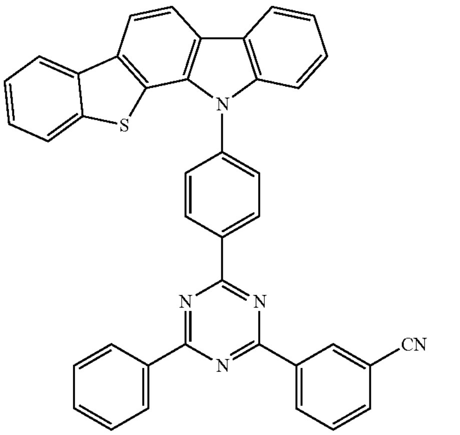

-continued
H2-344
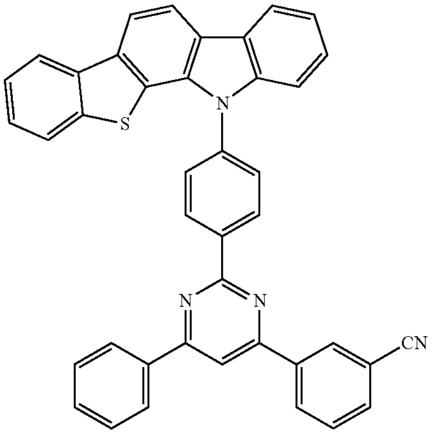
H2-345
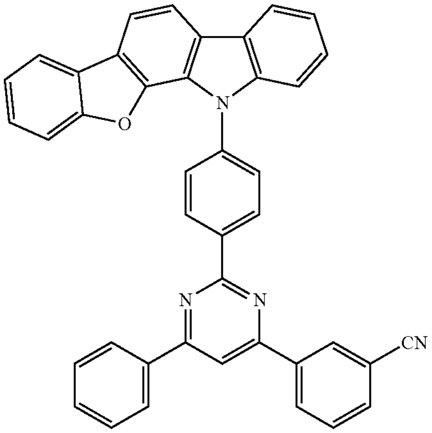
H2-346
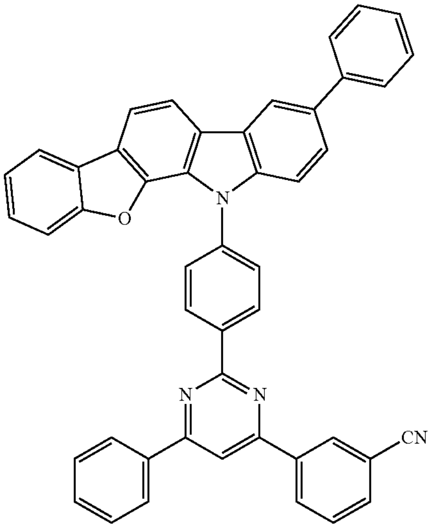
-continued
H2-347
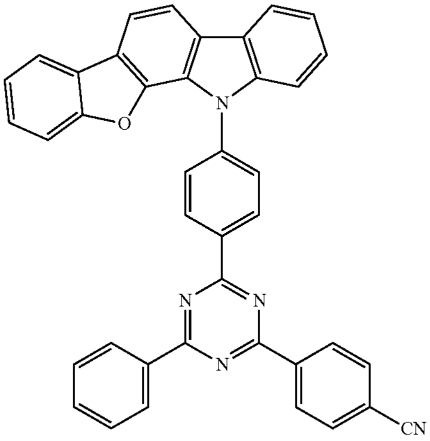
H2-348
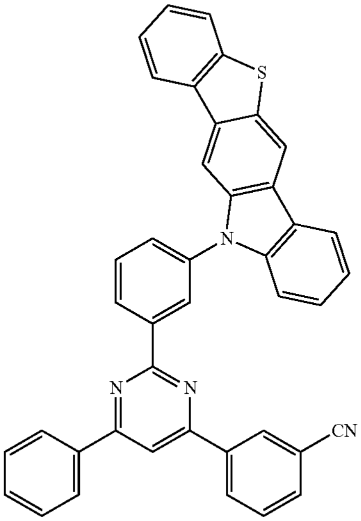
H2-349
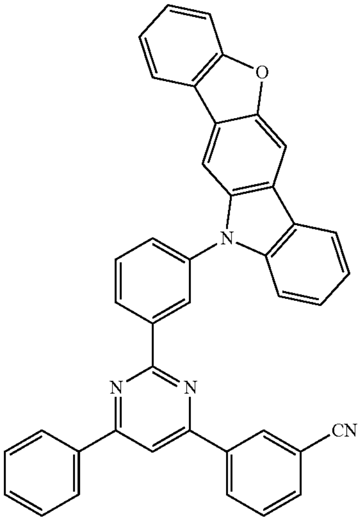

-continued
H2-350
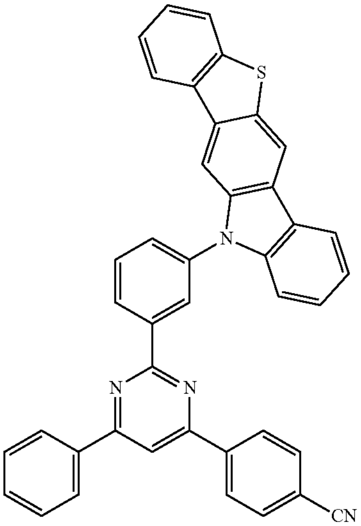
H2-351
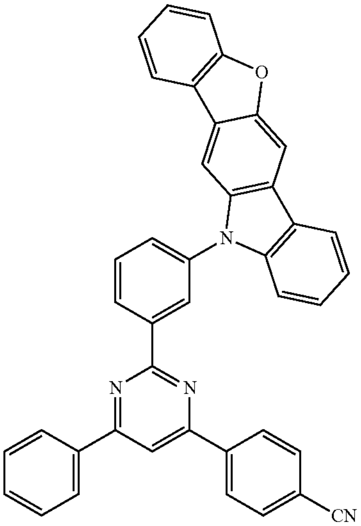
H2-352
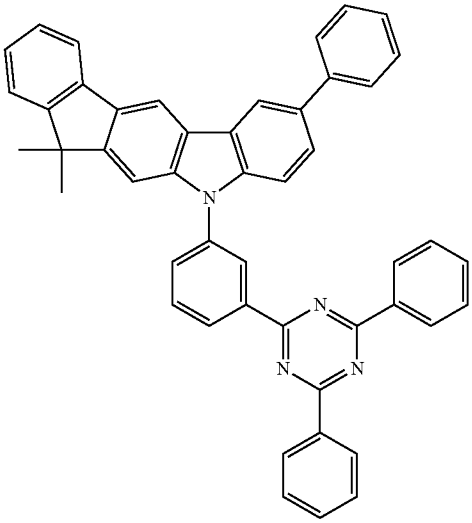
-continued
H2-353
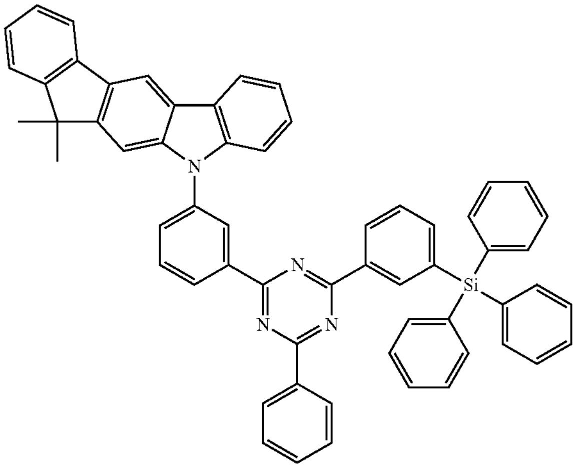
H2-354
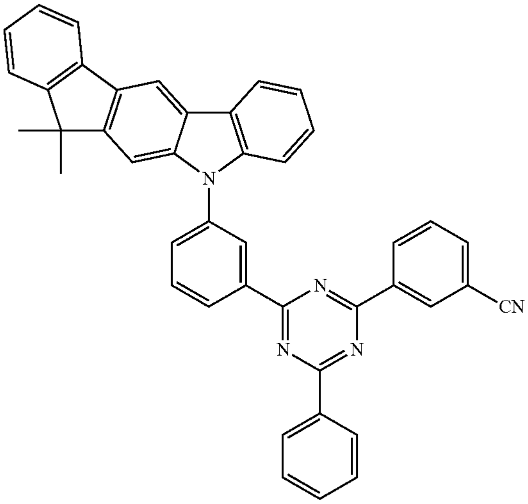
H2-355
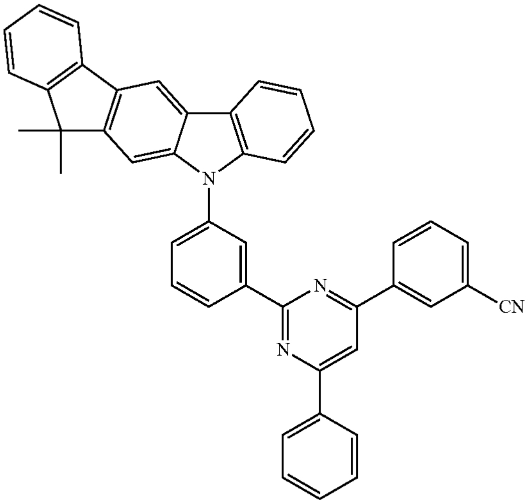

-continued
H2-356
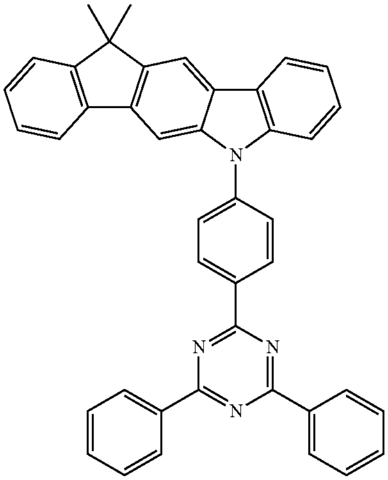
H2-357
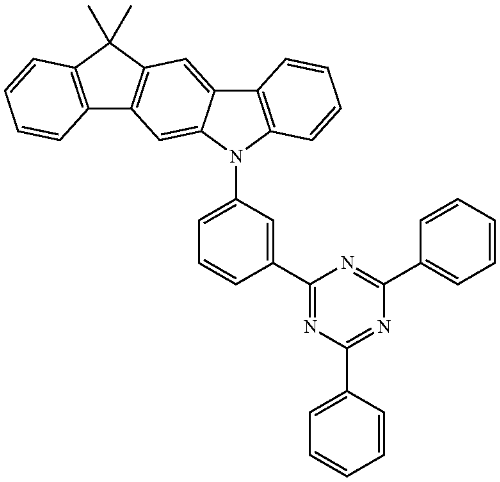
H2-358
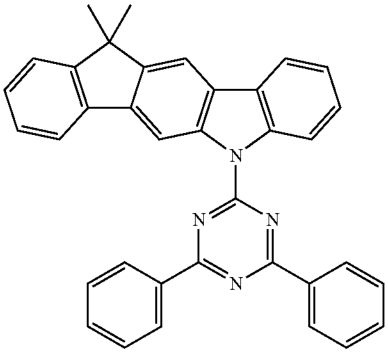
-continued
H2-359
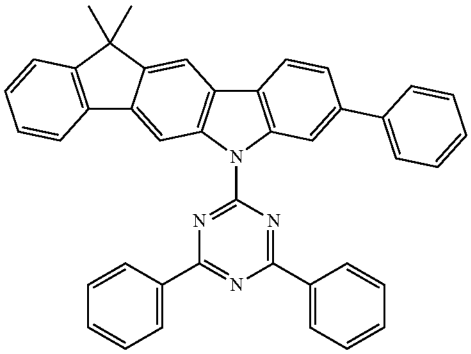
H2-360
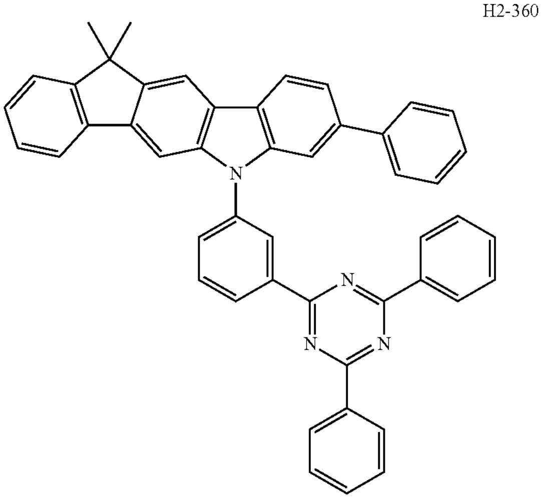
H2-361
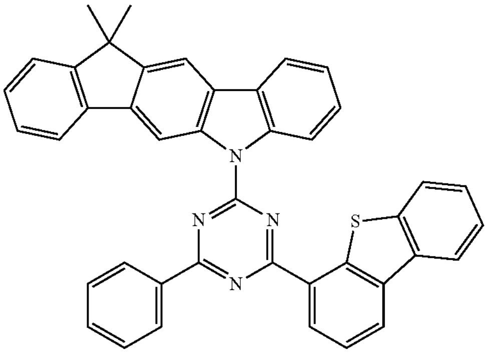
H2-362
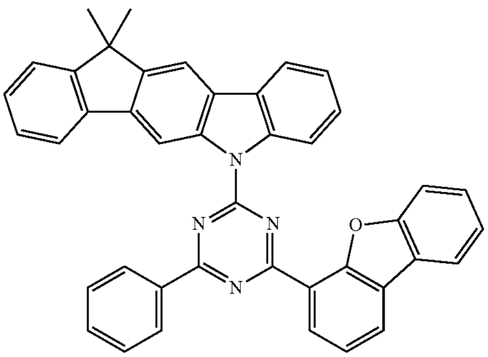

H2-363
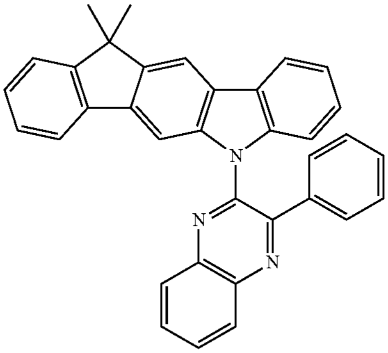
H2-364
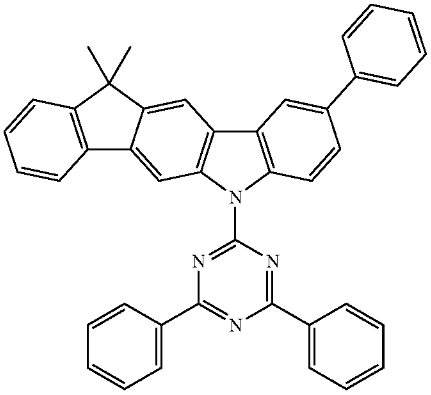
H2-365
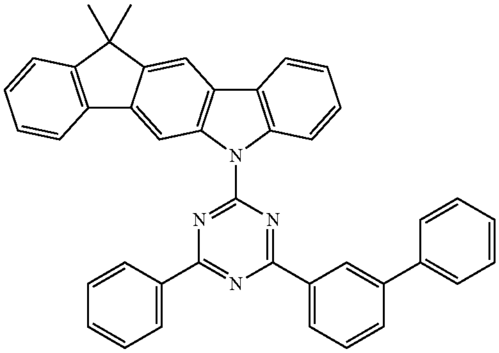
H2-366
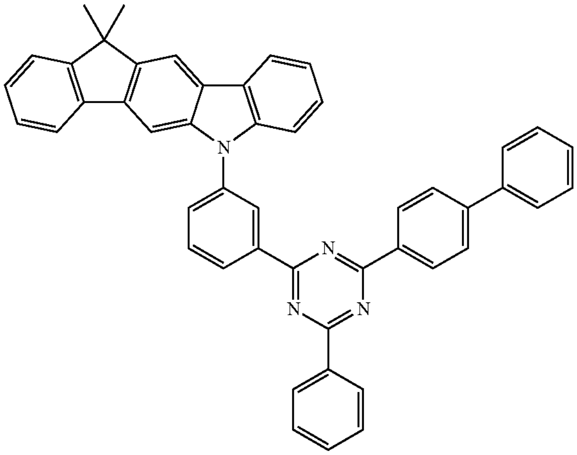
H2-367
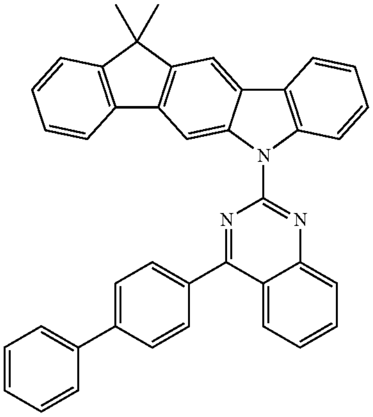
H2-368
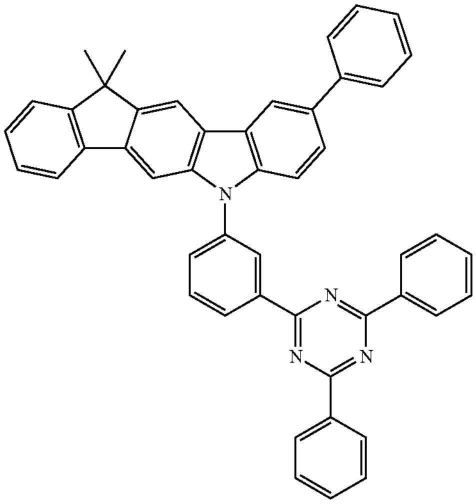
H2-369
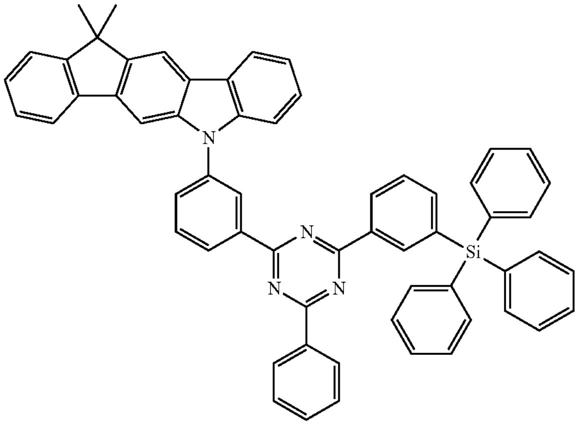

-continued
H2-370
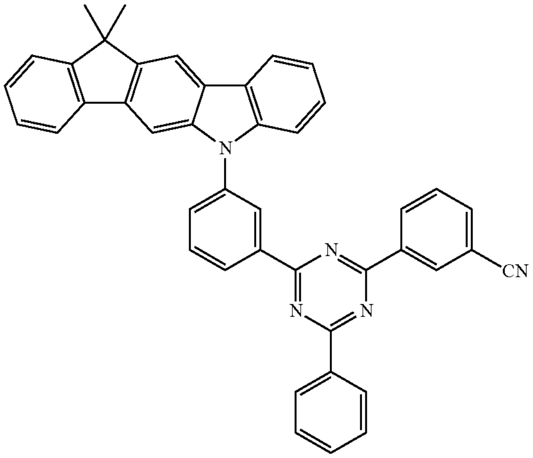
H2-371
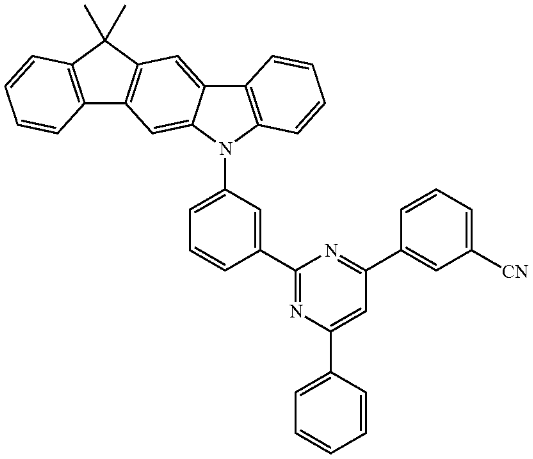
H2-372
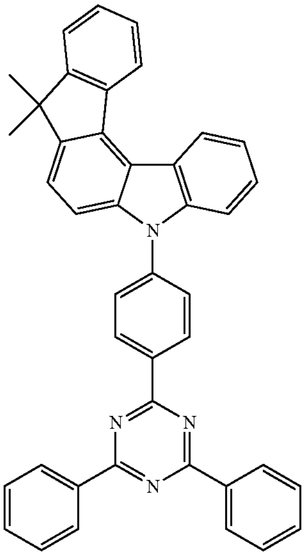
-continued
H2-373
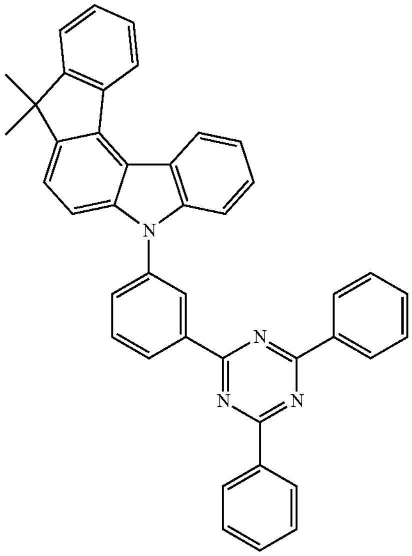
H2-374
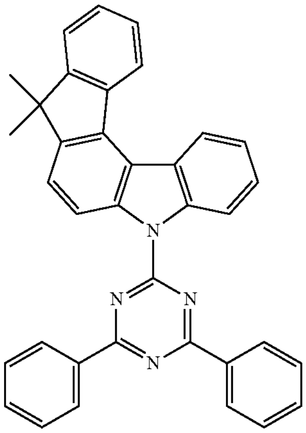
H2-375
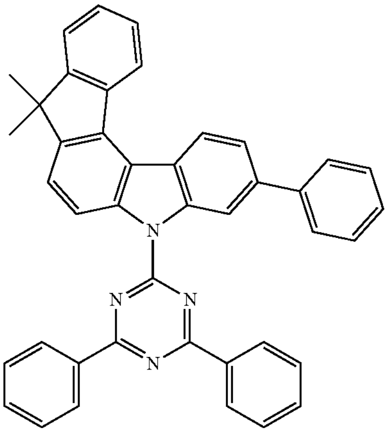

-continued
H2-376
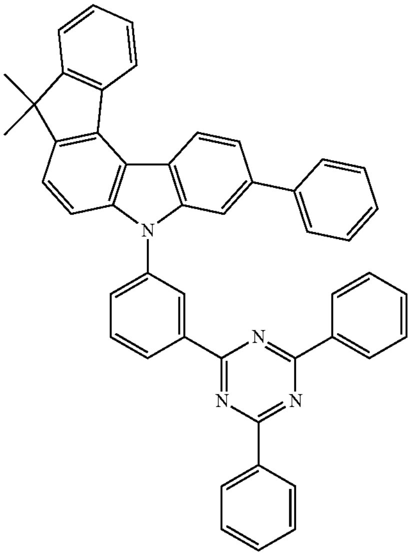
H2-377
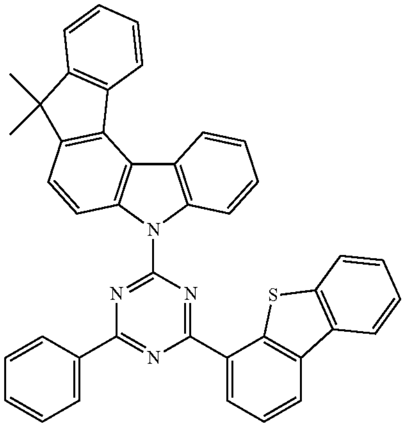
H2-378
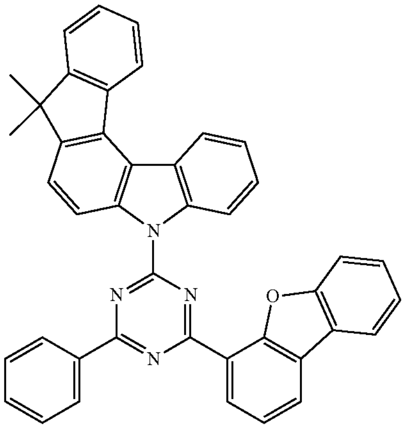
-continued
H2-379
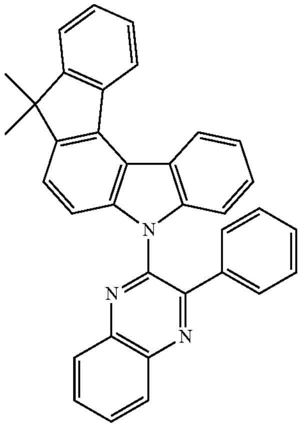
H2-380
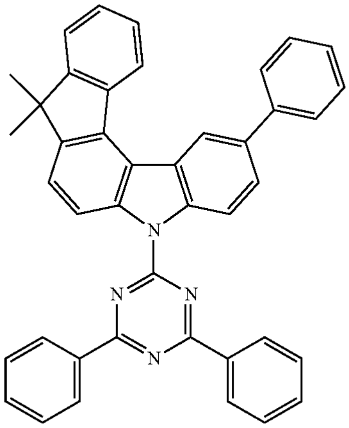
H2-381
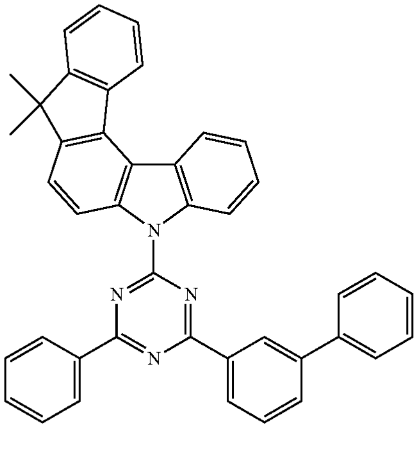

-continued
H2-382
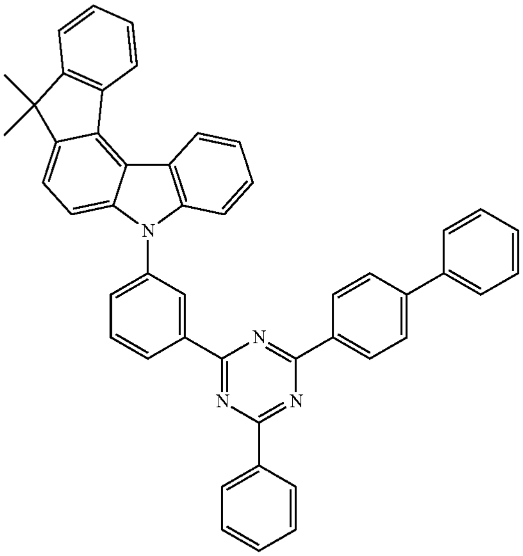
H2-383
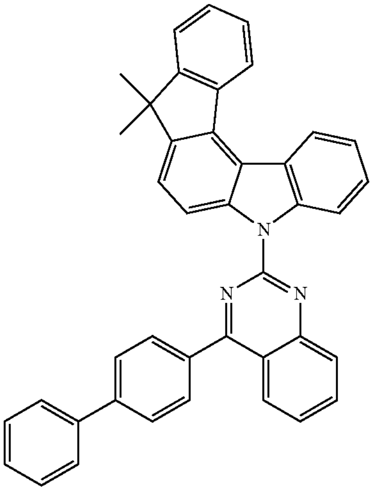
H2-384
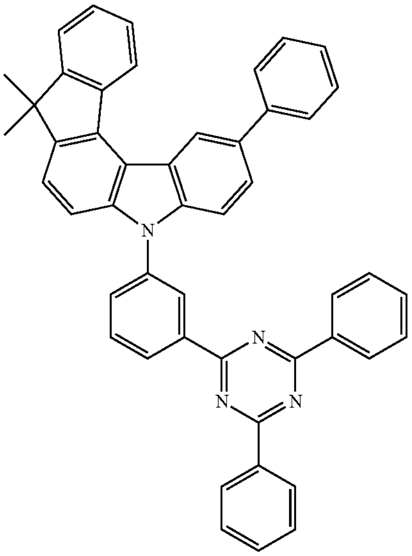
-continued
H2-385
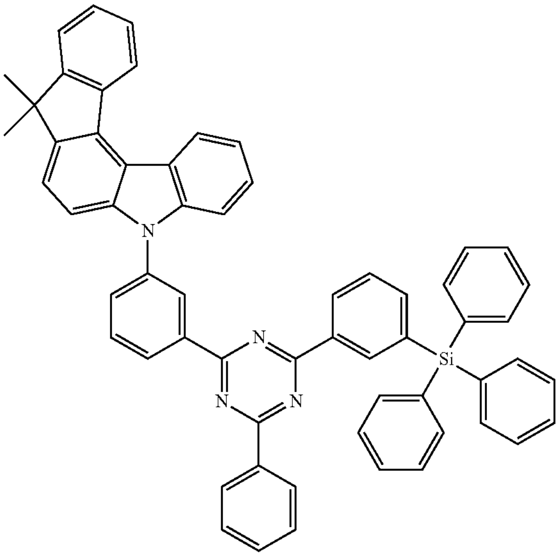
H2-386
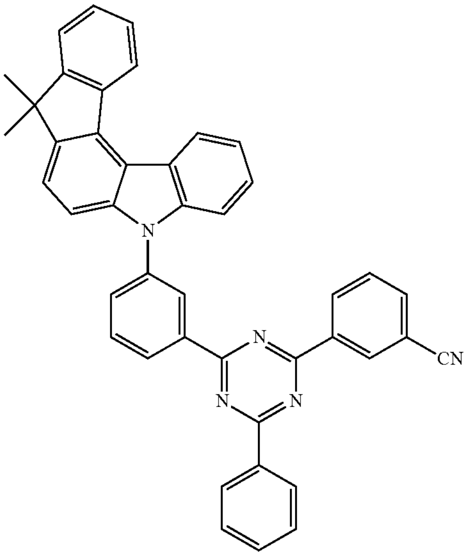

-continued
H2-387
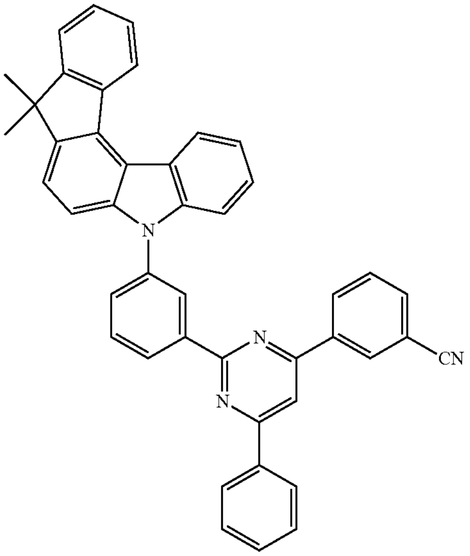
H2-388
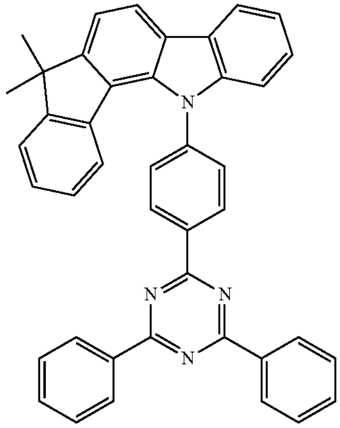
H2-389
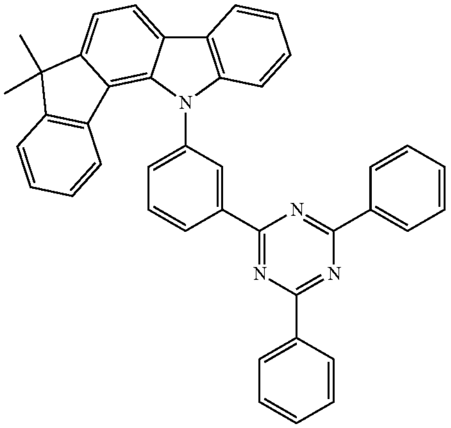
-continued
H2-390
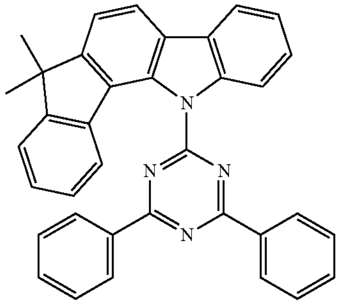
H2-391
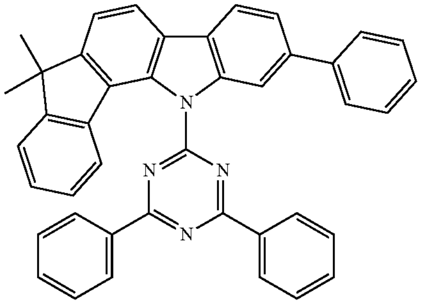
H2-392
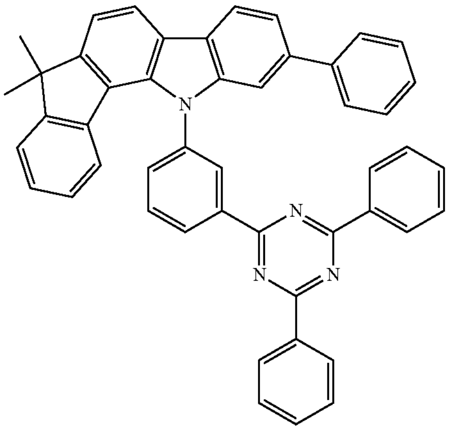
H2-393
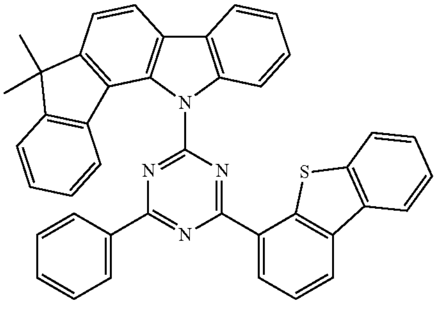

H2-394
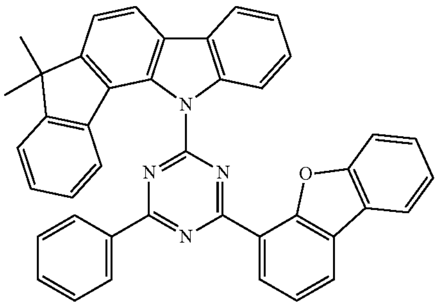
H2-395
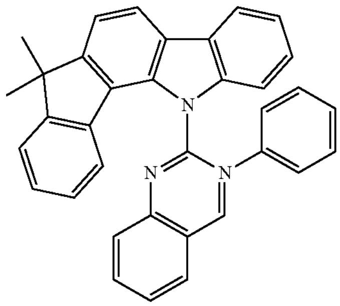
H2-396
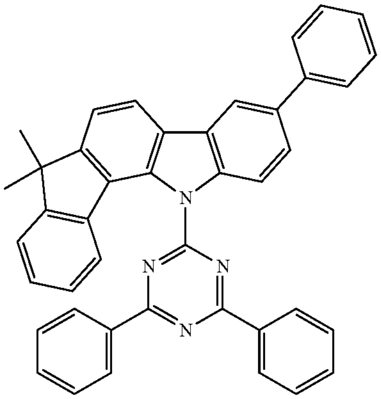
H2-397
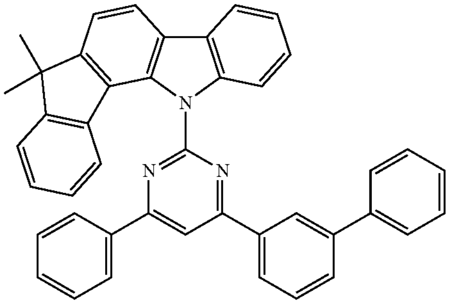
H2-398
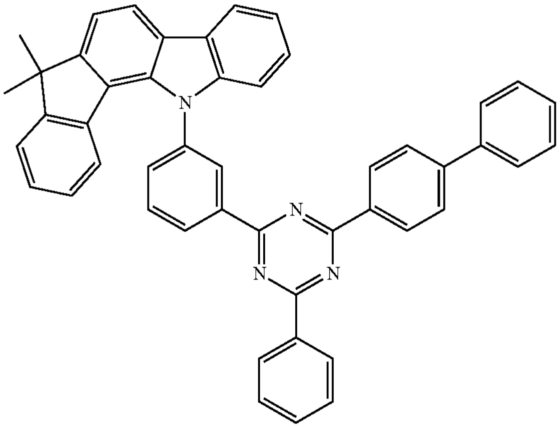
H2-399
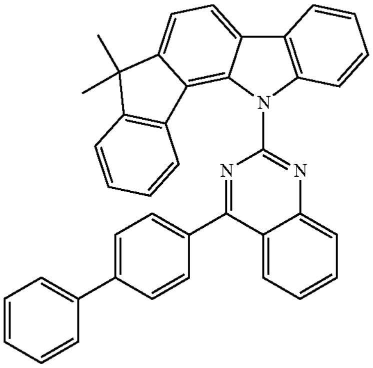
H2-400
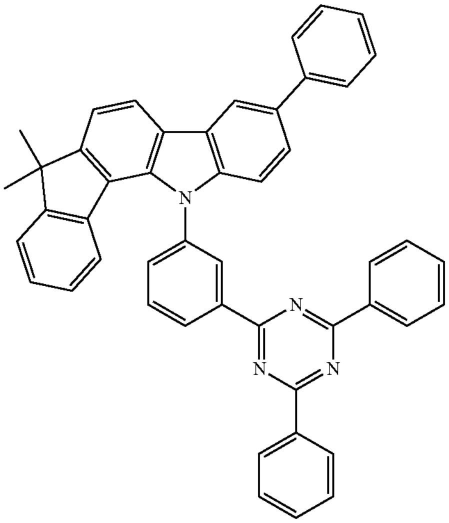

H2-401
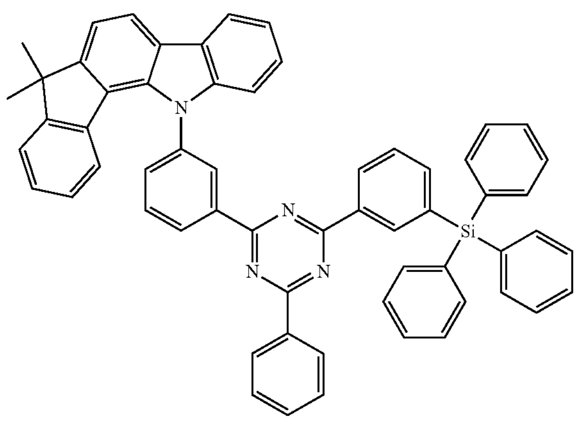
H2-402
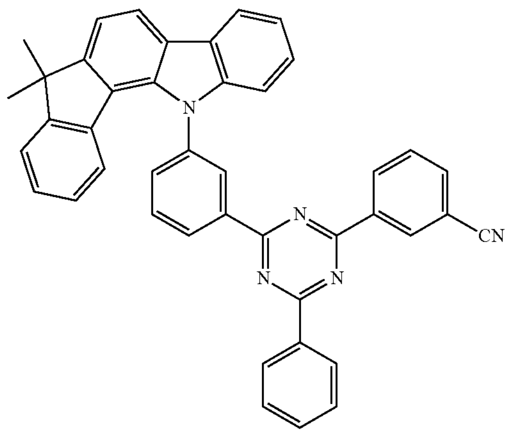
H2-403
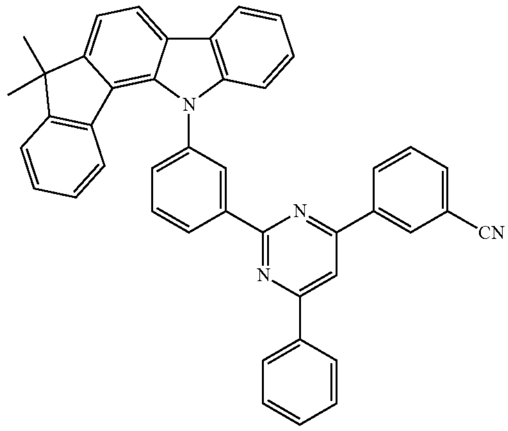
H2-404
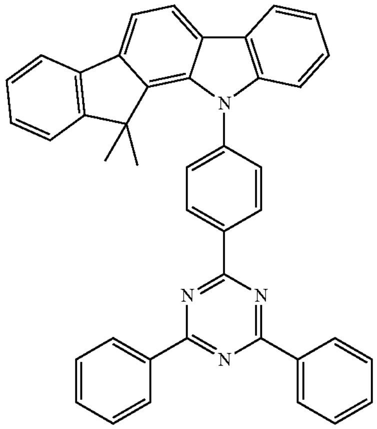
H2-405
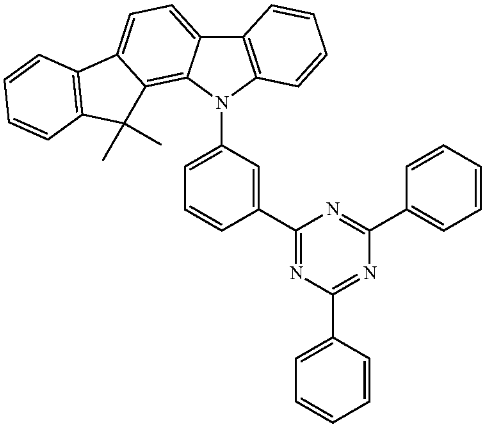
H2-406
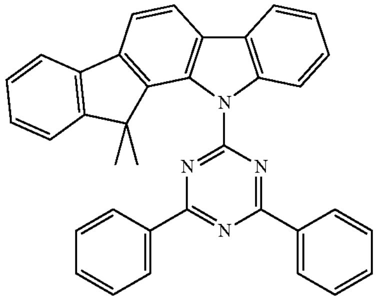
H2-407
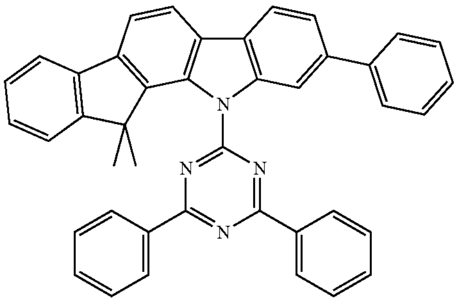

-continued
H2-408
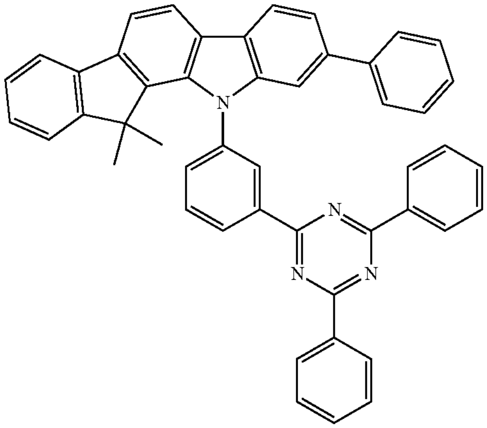
H2-409
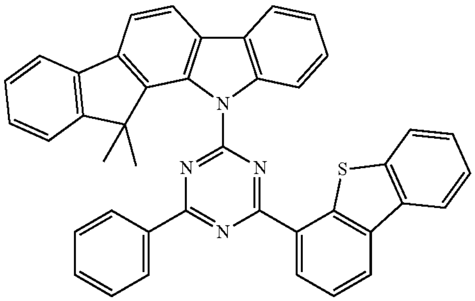
H2-410
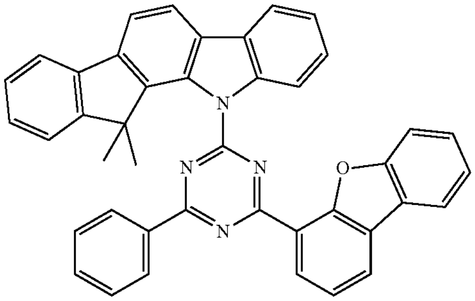
H2-411
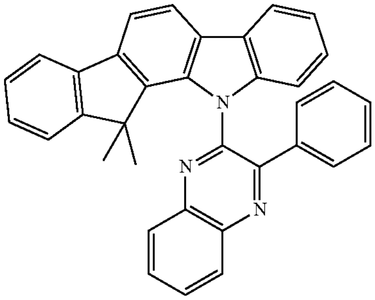
-continued
H2-412
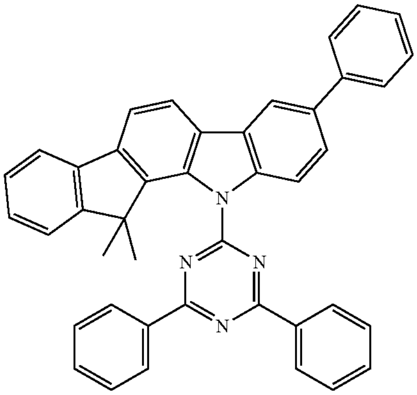
H2-413
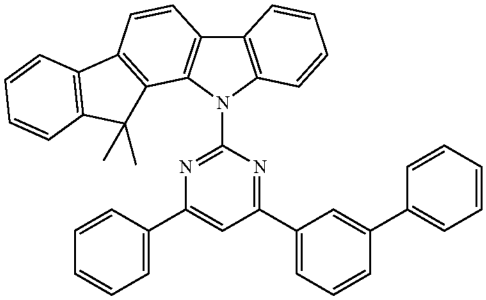
H2-414
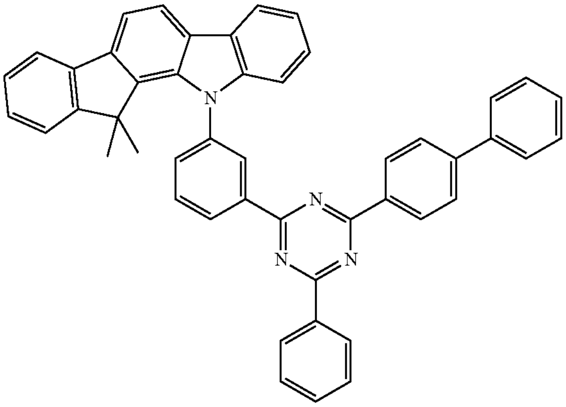
H2-415
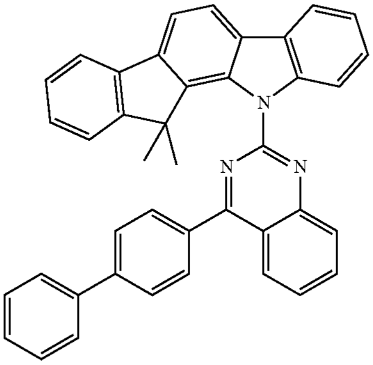

-continued
H2-416
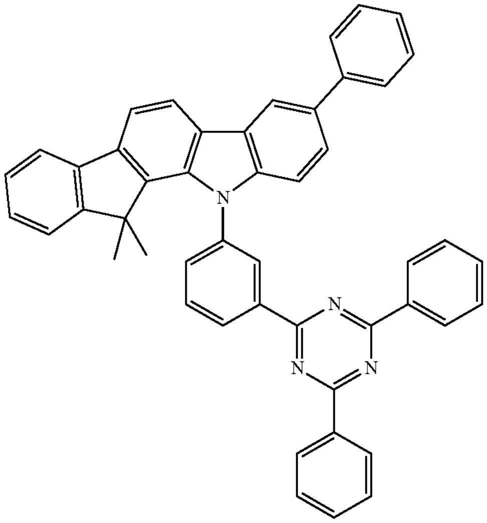
H2-417
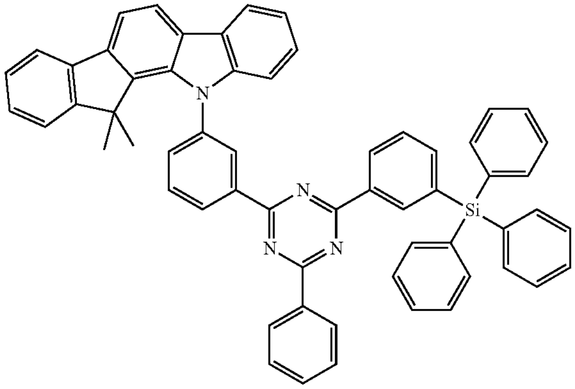
H2-418
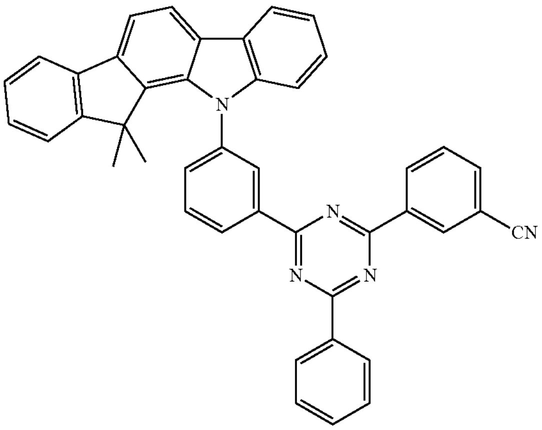
-continued
H2-419
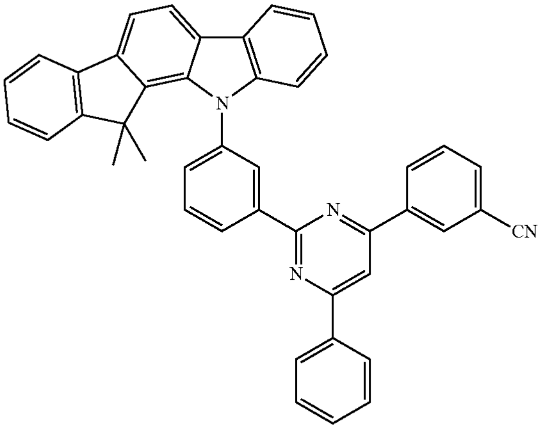
H2-420
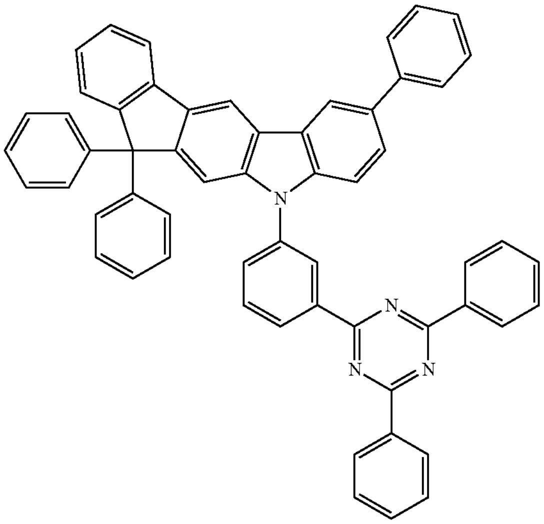
H2-421
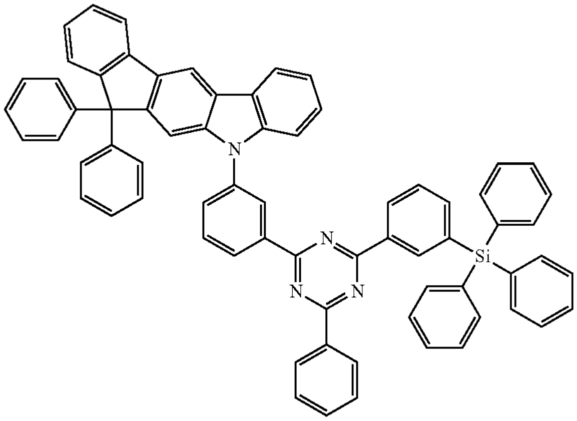

-continued
H2-422
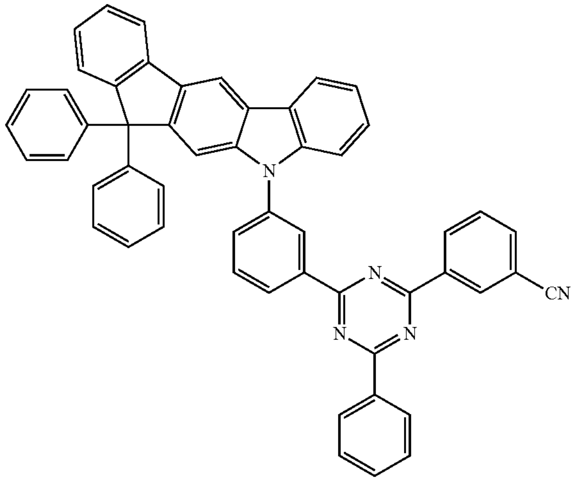
H2-423
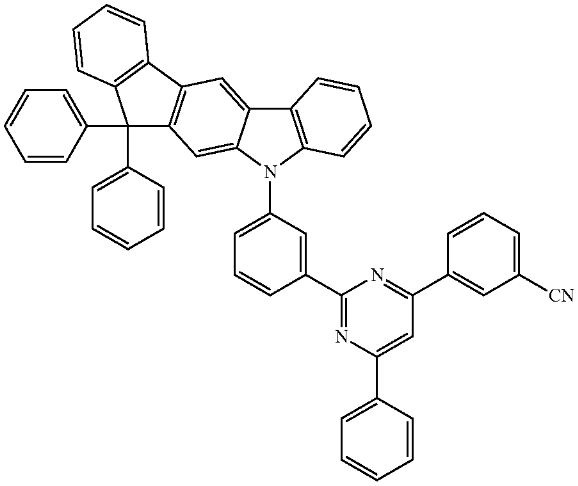
H2-424
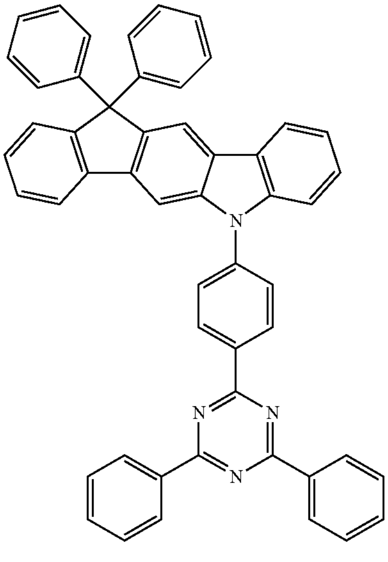
-continued
H2-425
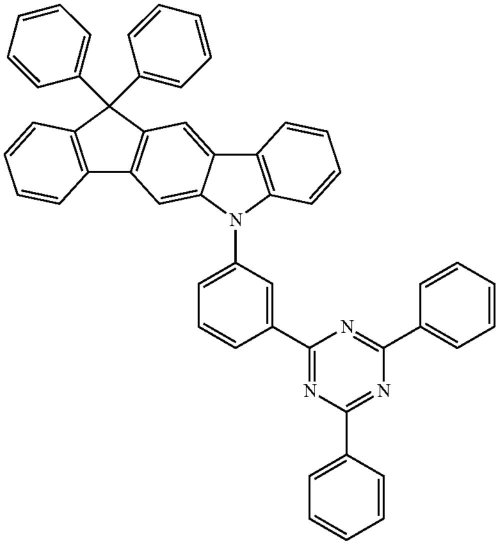
H2-426
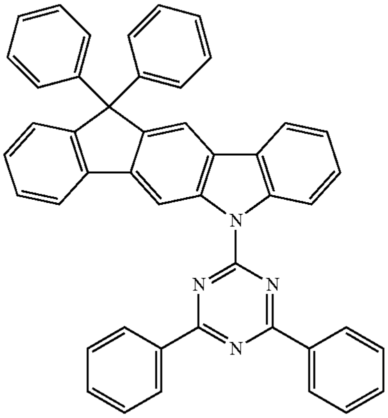
H2-427
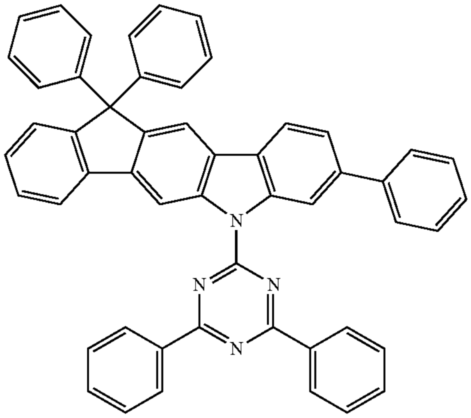

-continued
H2-428
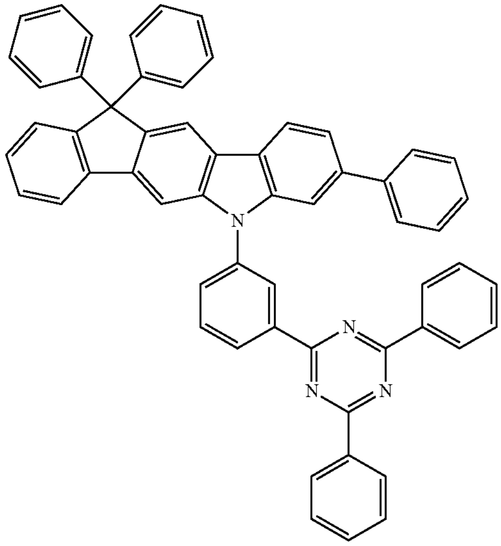
H2-429
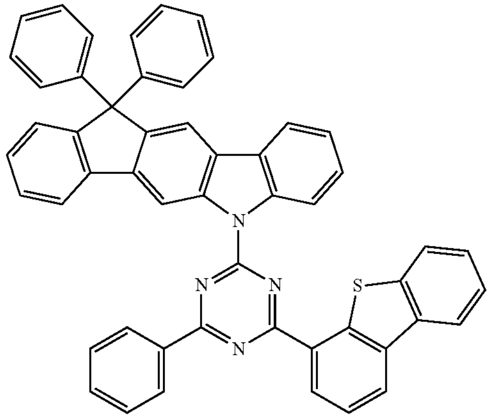
H2-430
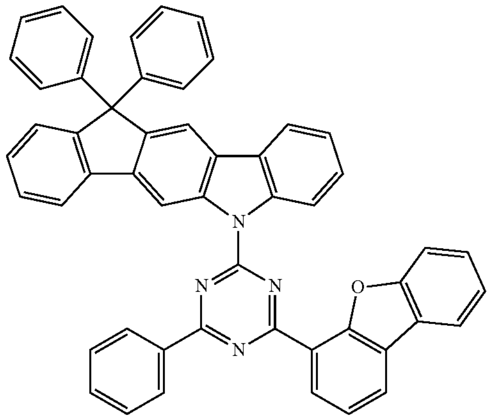
-continued
H2-431
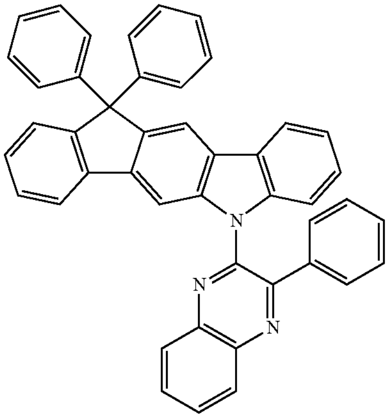
H2-432
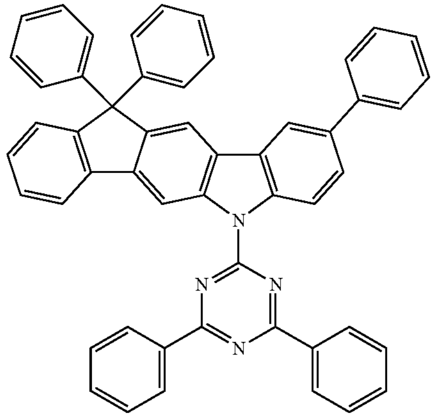
H2-433
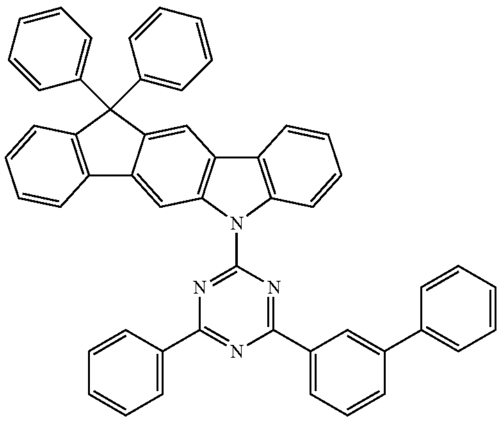

-continued
H2-434
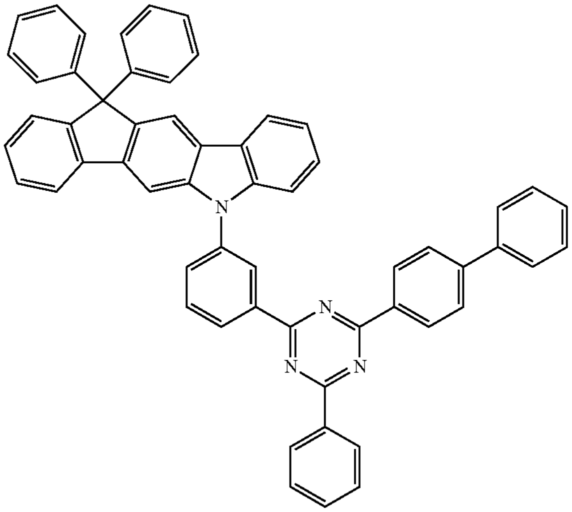
H2-435
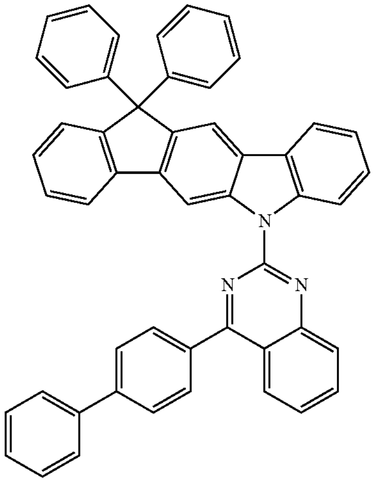
H2-436
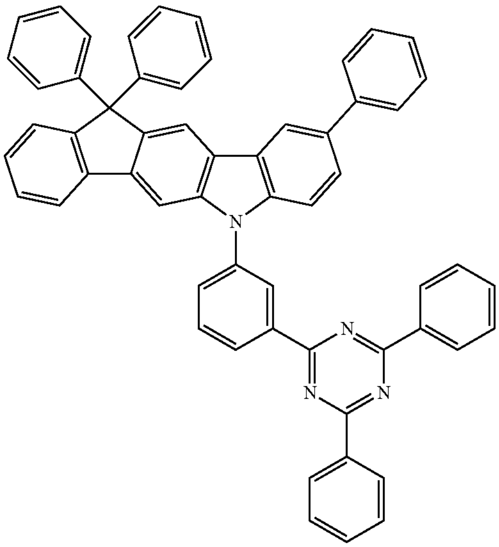
-continued
H2-437
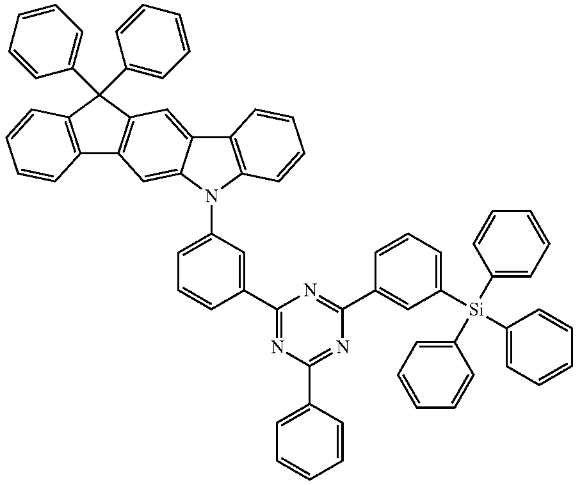
H2-438
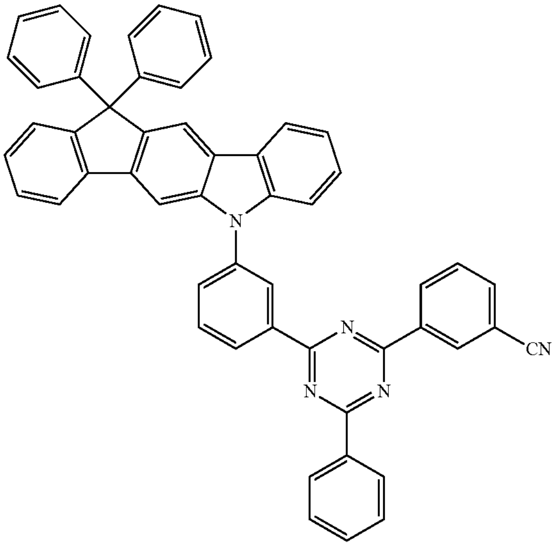
H2-439
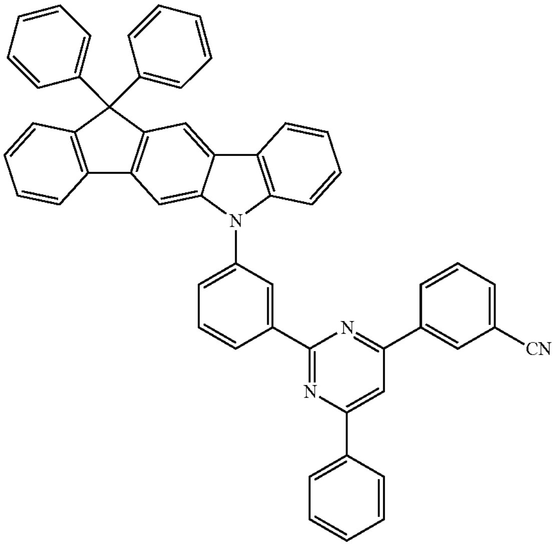

-continued
H2-440
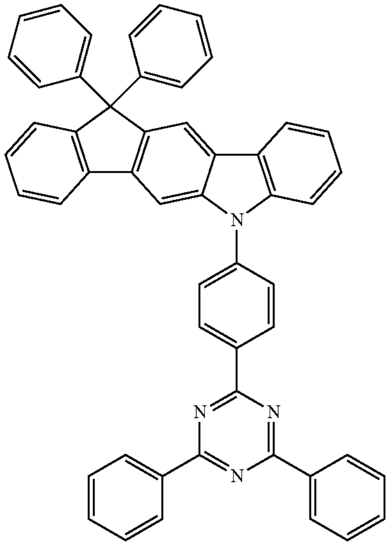
H2-441
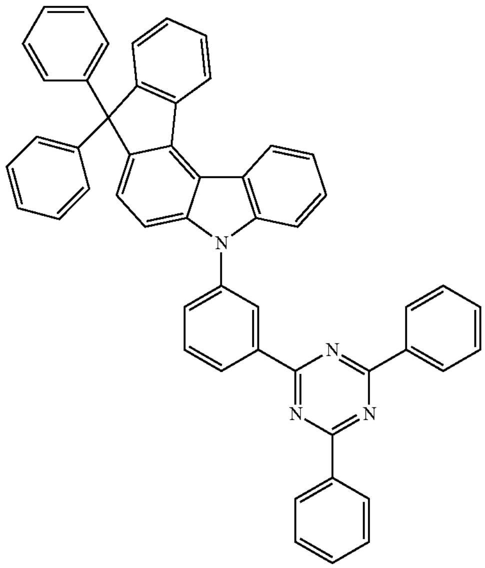
H2-442
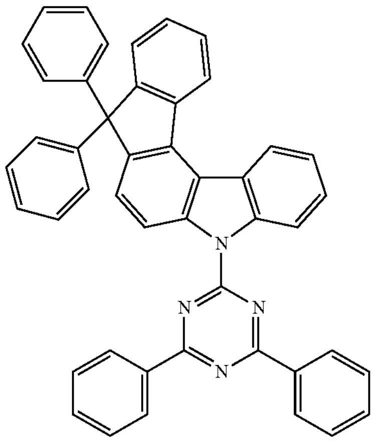
-continued
H2-443
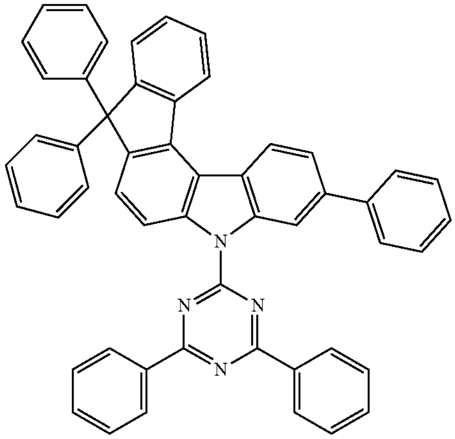
H2-444
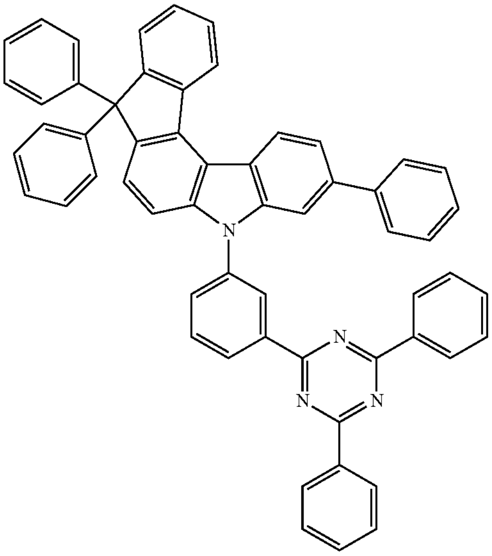
H2-445
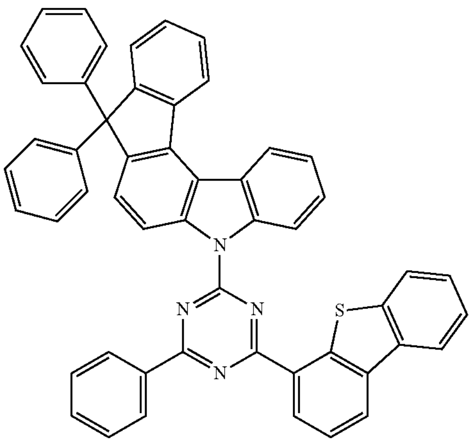

-continued
H2-446
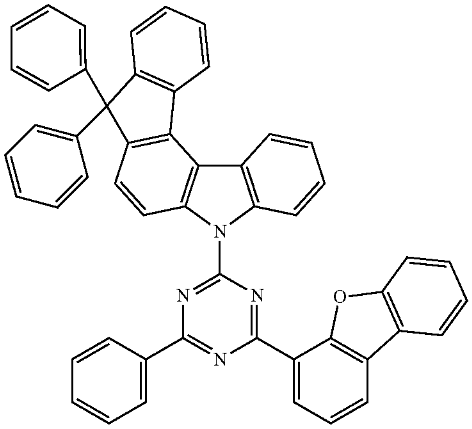
H2-447
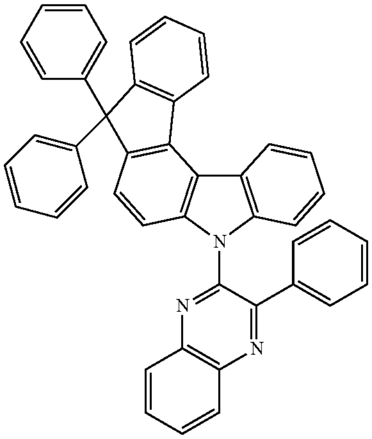
H2-448
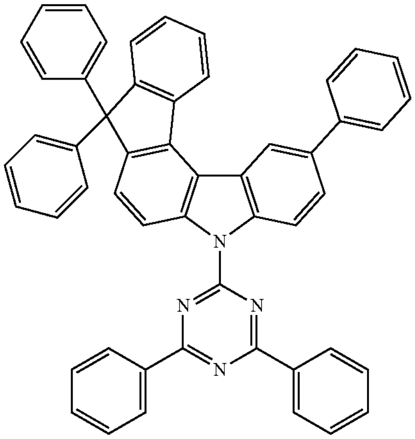
-continued
H2-449
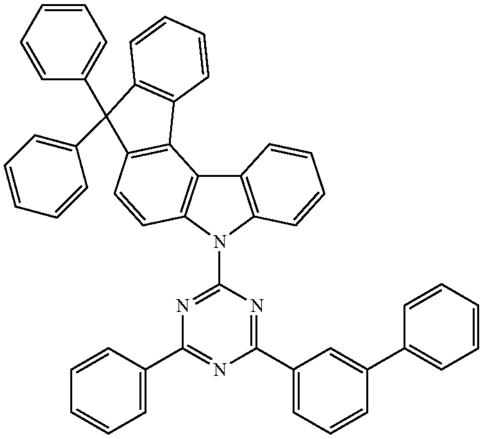
H2-450
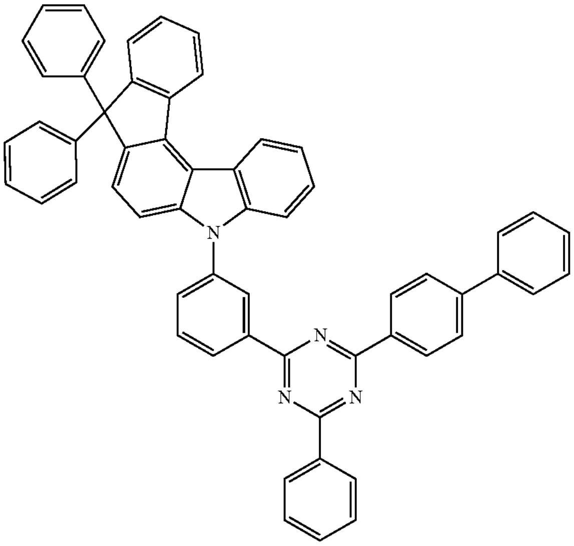
H2-451
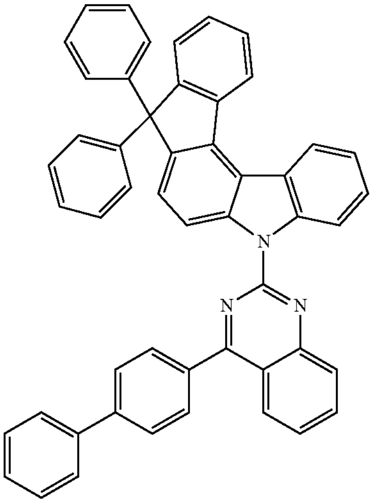

-continued
H2-452
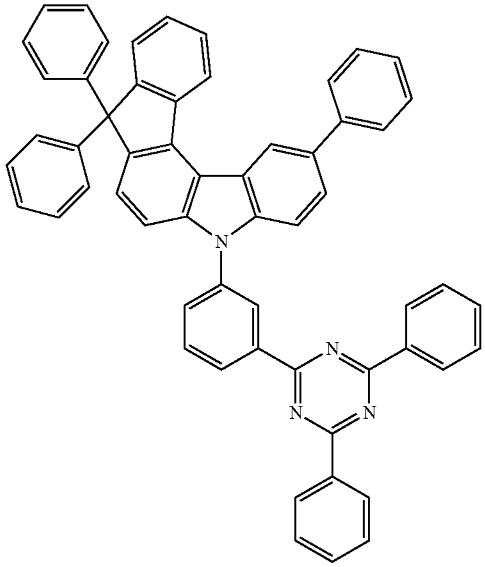
H2-453
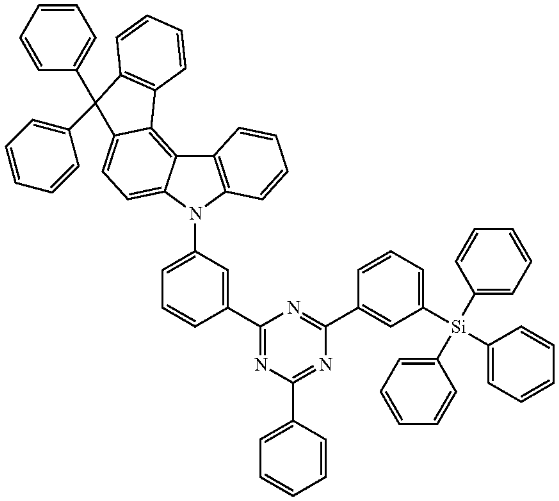
-continued
H2-454
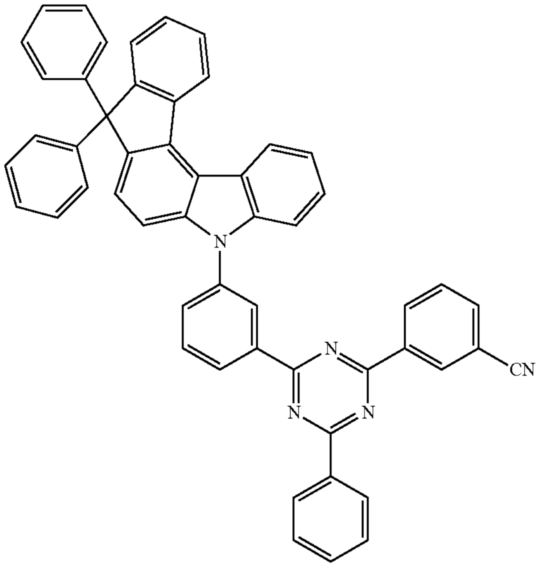
H2-455
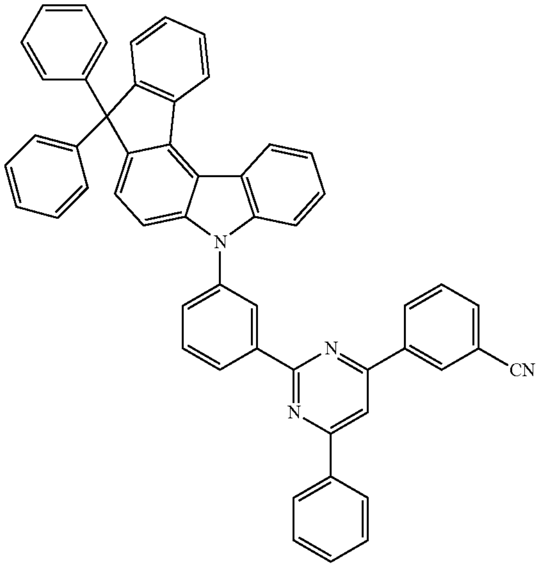
H2-456
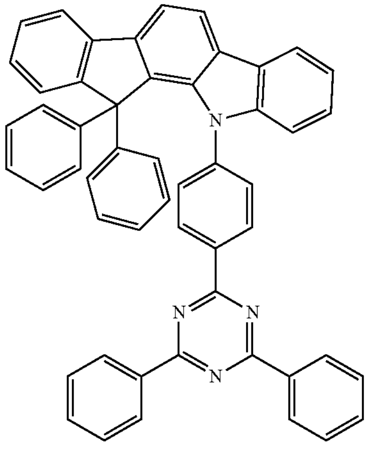

-continued
H2-457
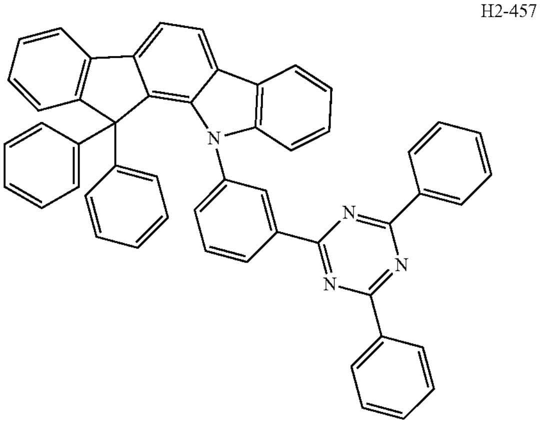
H2-458
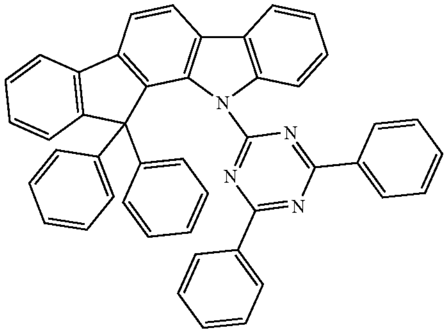
H2-459
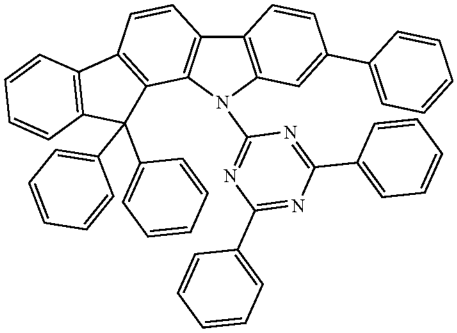
H2-460
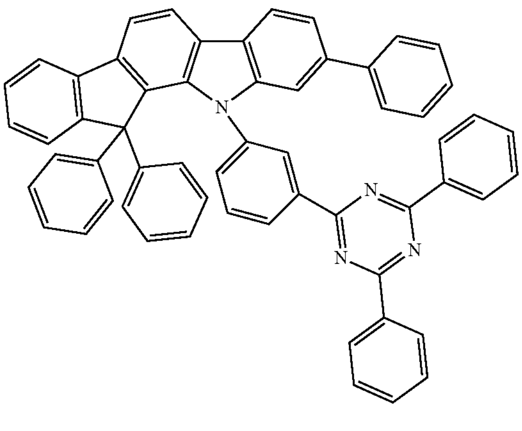
-continued
H2-461
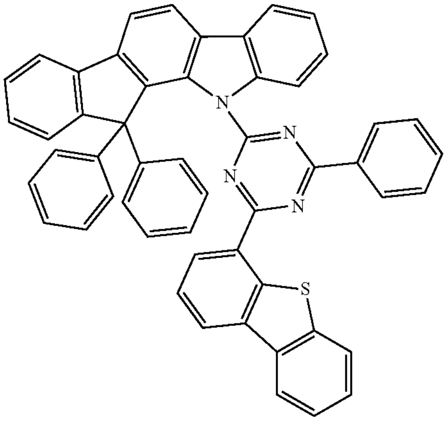
H2-462
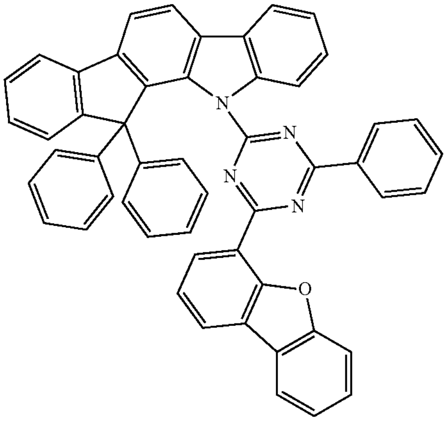
H2-463
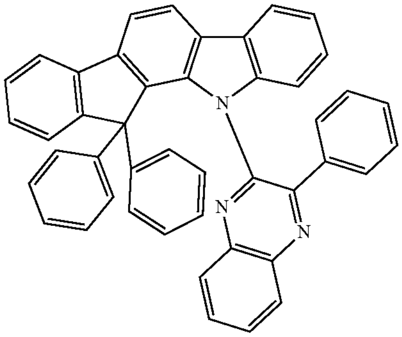
H2-464
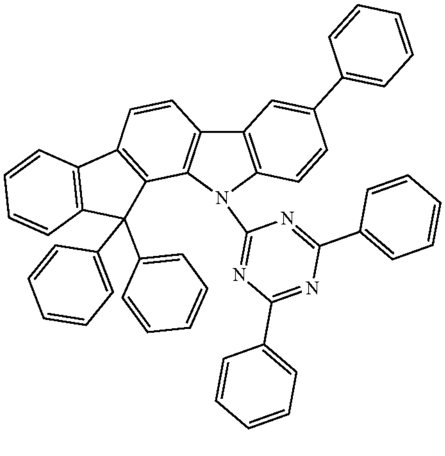

-continued
H2-465
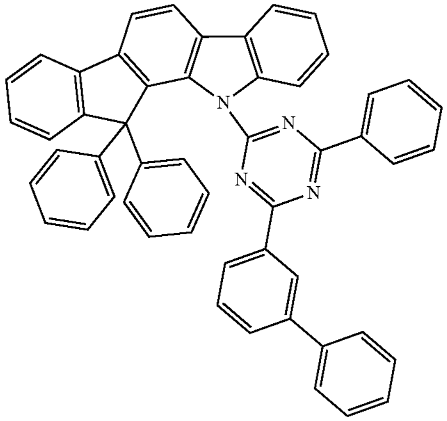
H2-466
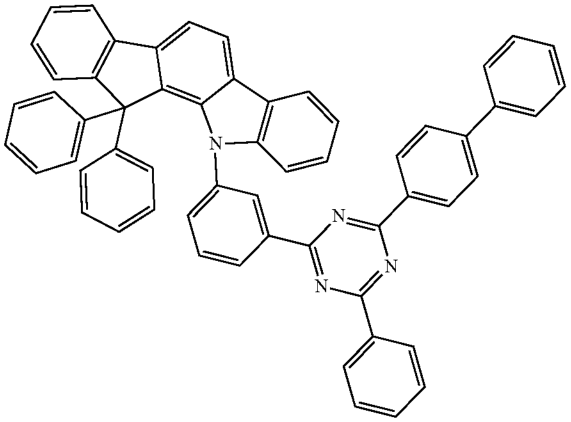
H2-467
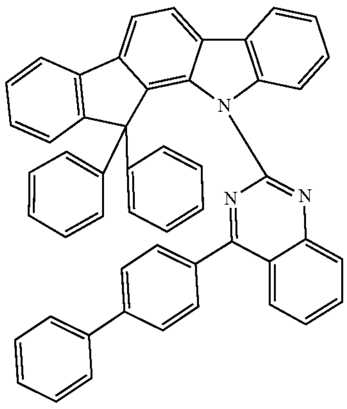
-continued
H2-468
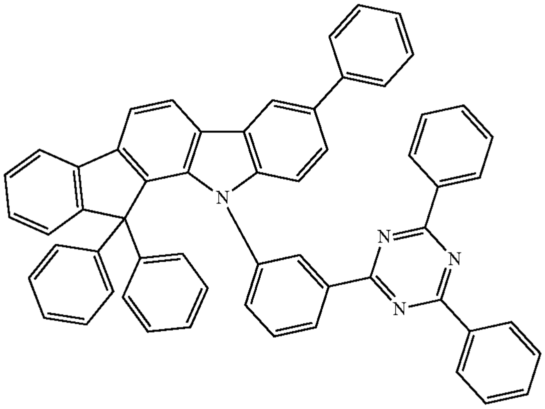
H2-469
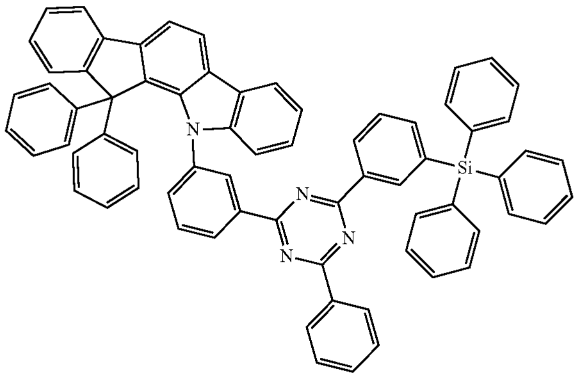
H2-470
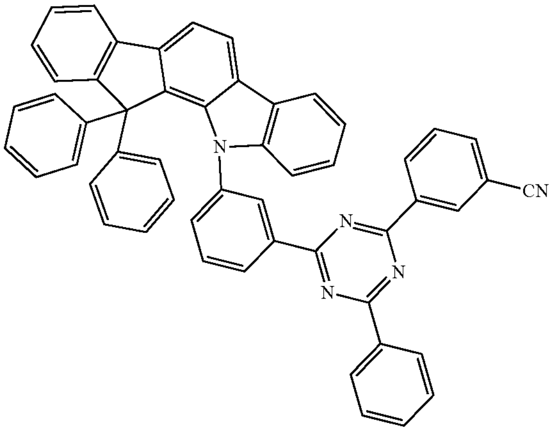

-continued
H2-471
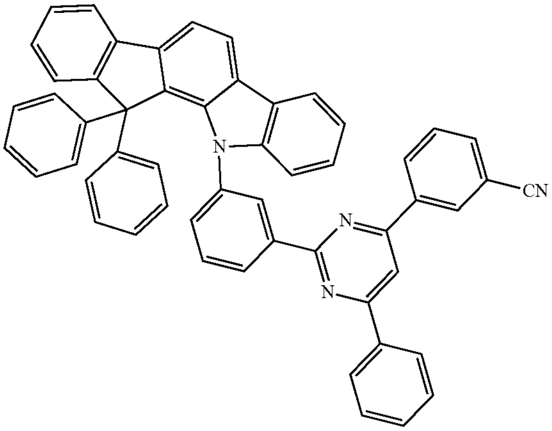
H2-472
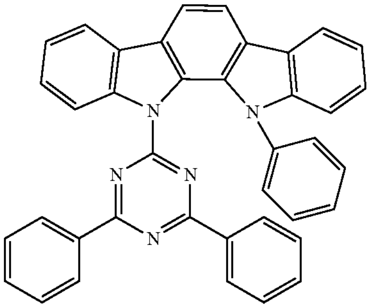
H2-473
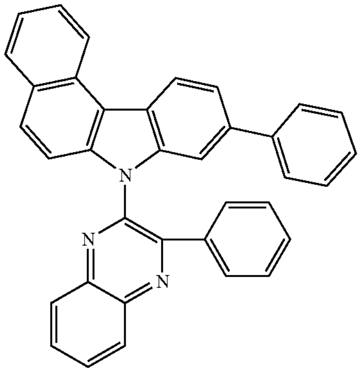
H2-474
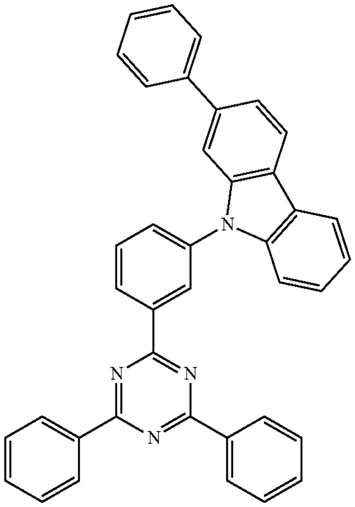
-continued
H2-475
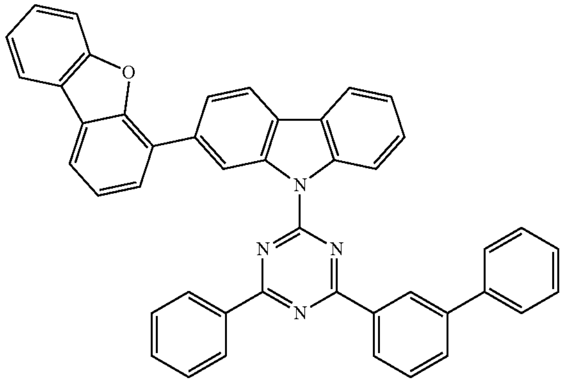
H2-476
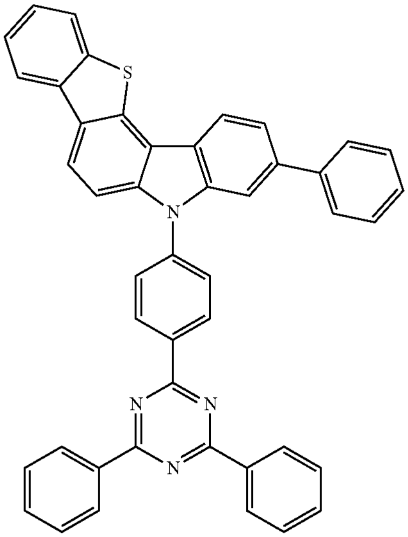
H2-477
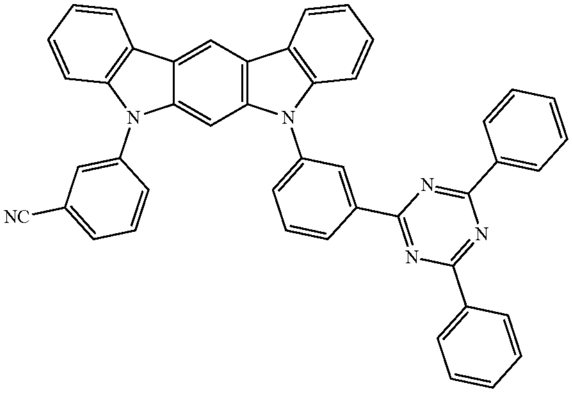

-continued
H2-478
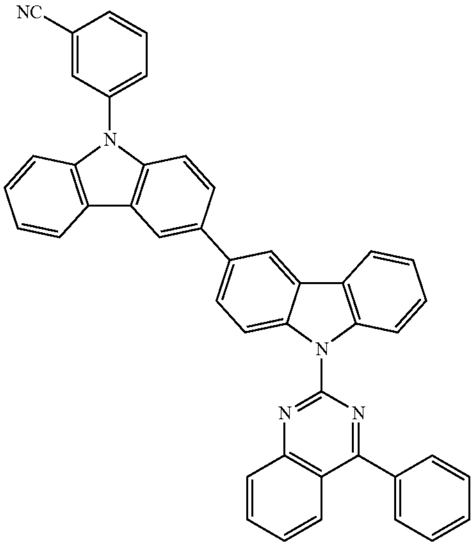
H2-479
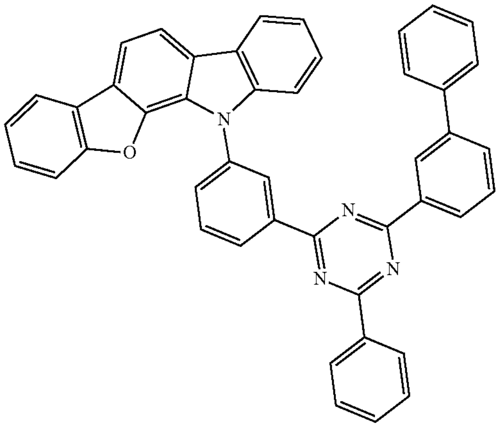
H2-480
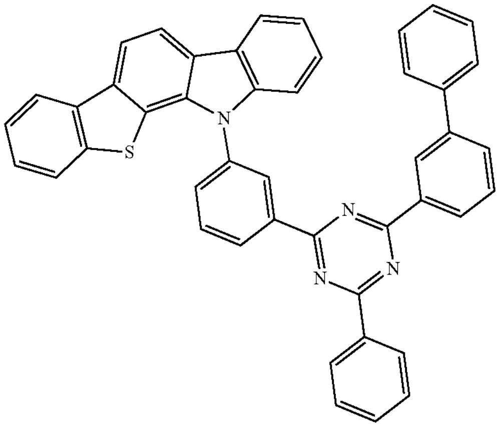
-continued
H2-481
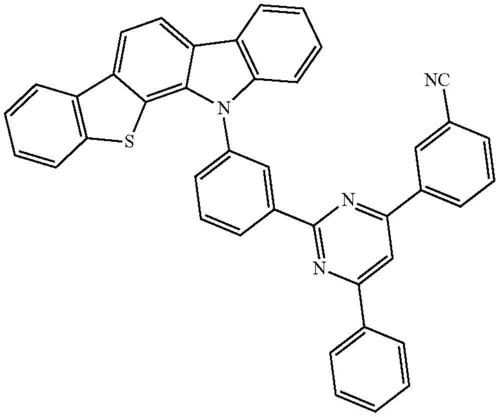
H2-482
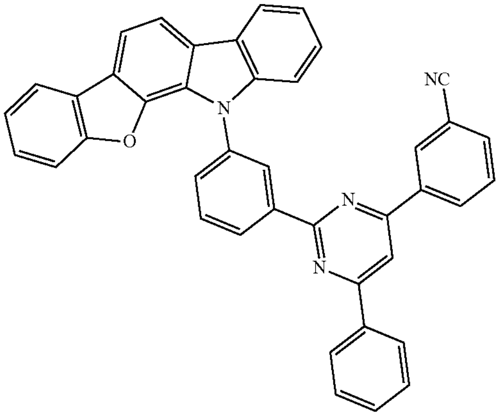
H2-483
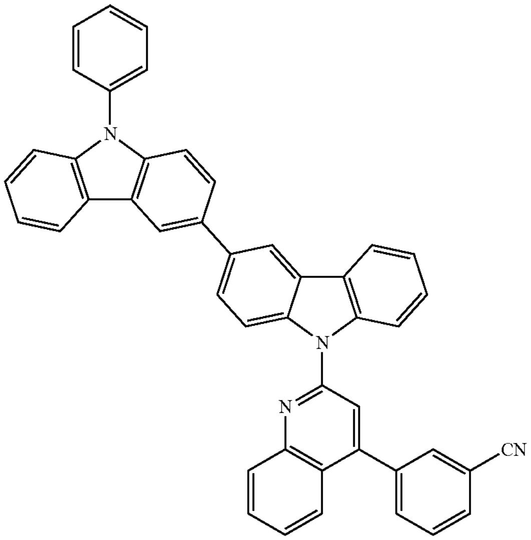

H2-484
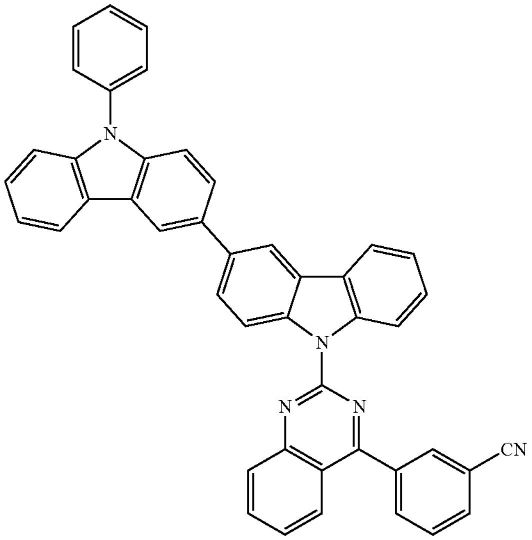
H2-485
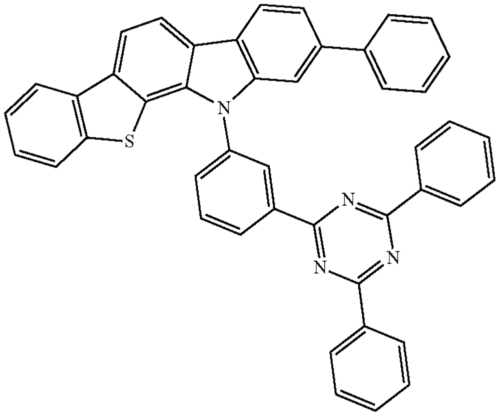
H2-486
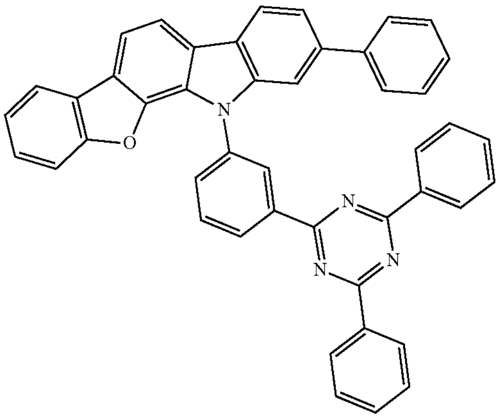
H2-487
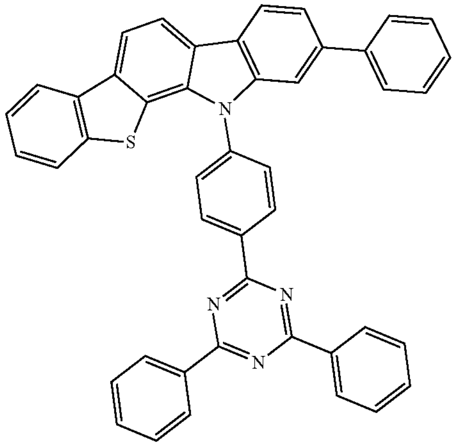
H2-488
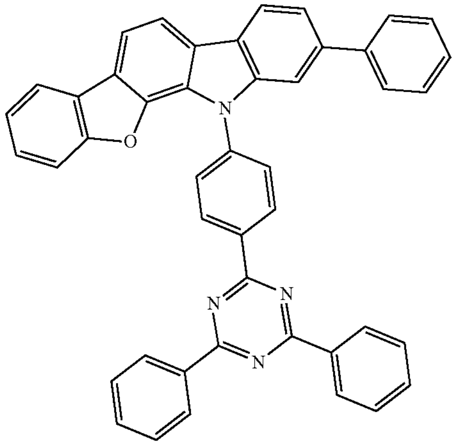
H2-489
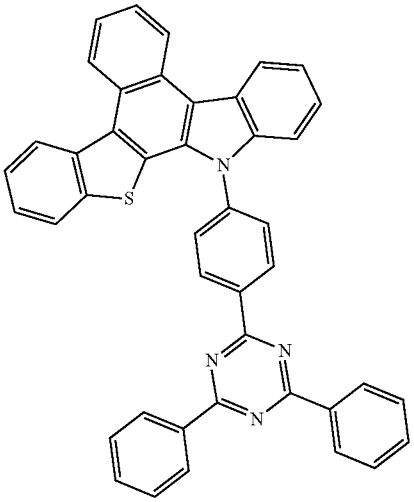

-continued

H2-490

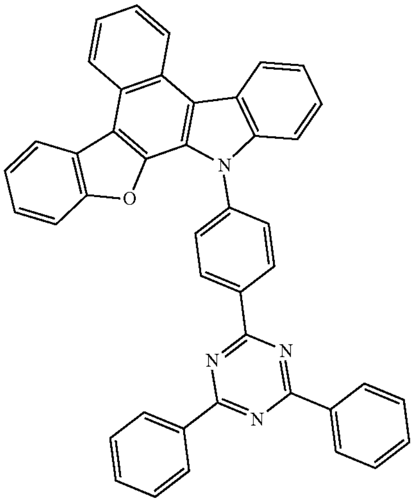

H2-491

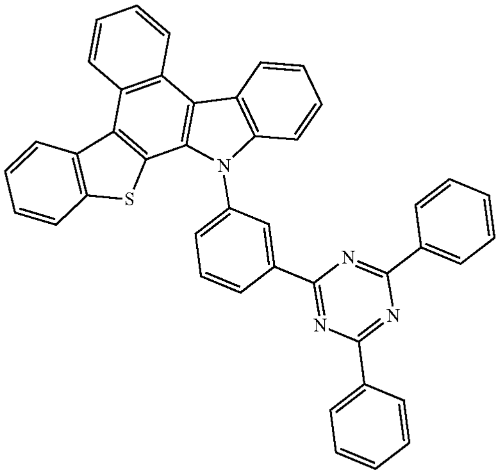

H2-492

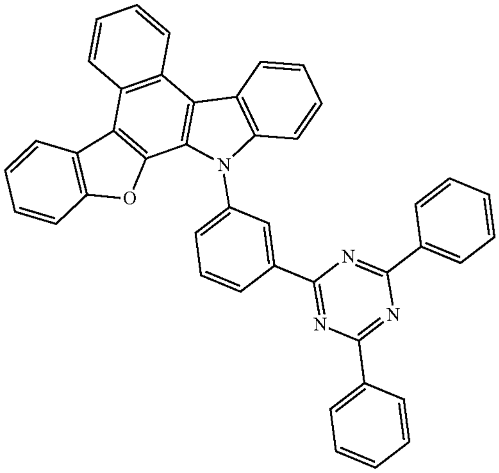

The organic electroluminescent device according to the present invention comprises an anode; a cathode; and at least one organic layer between the anode and the cathode. The organic layer comprises a light-emitting layer, and the light-emitting layer comprises a host and a phosphorescent dopant. The host consists of multi-component host compounds, at least a first host compound of the multi-component host compounds is represented by formula 1, and a second host compound is represented by formula 2.

The light-emitting layer is a layer from which light is emitted, and can be a single layer or a multi layer of which two or more layers are stacked. In the light-emitting layer, it is preferable that the doping concentration of the dopant compound based on the host compound is less than 20 wt %.

The organic layer comprises a light-emitting layer, and may further comprise at least one layer selected from the group consisting of a hole injection layer, a hole transport layer, an electron transport layer, an electron injection layer, an interlayer, a hole blocking layer, and an electron blocking layer.

According to the organic electroluminescent device of the present invention, the weight ratio of the first host material to the second host material is in the range of 1:99 to 99:1.

The dopant is preferably at least one phosphorescent dopant. The dopant materials applied to the organic electroluminescent device according to the present invention are not limited, but may be preferably selected from metallated complex compounds of iridium, osmium, copper and platinum, more preferably selected from ortho-metallated complex compounds of iridium, osmium, copper and platinum, and even more preferably ortho-metallated iridium complex compounds.

The phosphorescent dopant is preferably selected from compounds represented by the following formulae 101 to 103.

(101)

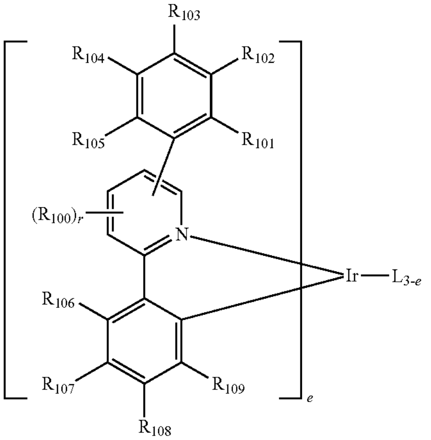

(102)

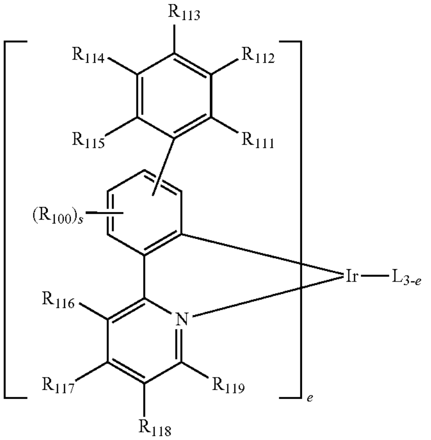

-continued (103)

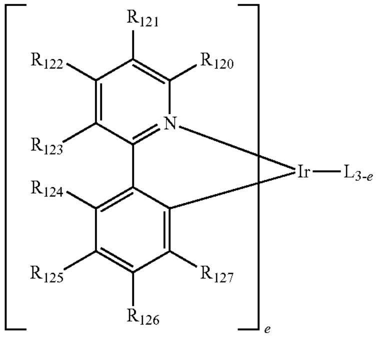

wherein L is selected from the following structures:

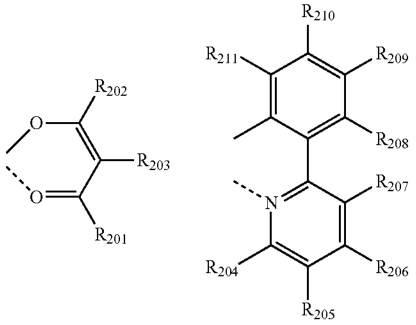

$R_{100}$ represents hydrogen, a substituted or unsubstituted (C1-C30)alkyl, or a substituted or unsubstituted (C3-C30)cycloalkyl;

$R_{101}$ to $R_{109}$, and $R_{111}$ to $R_{123}$ each independently represent hydrogen, deuterium, a halogen, a (C1-C30)alkyl unsubstituted or substituted with deuterium or a halogen(s), a cyano, a substituted or unsubstituted (C1-C30) alkoxy, a substituted or unsubstituted (C6-C30)aryl, or a substituted or unsubstituted (C3-C30)cycloalkyl; adjacent substituents of $R_{106}$ to $R_{109}$ may be linked to each other to form a substituted or unsubstituted fused ring, e.g., fluorene unsubstituted or substituted with alkyl, dibenzothiophene unsubstituted or substituted with alkyl, or dibenzofuran unsubstituted or substituted with alkyl; and adjacent substituents of $R_{120}$ to $R_{123}$ may be linked to each other to form a substituted or unsubstituted fused ring, e.g., quinoline unsubstituted or substituted with halogen, alkyl, or aryl;

$R_{124}$ to $R_{127}$ each independently represent hydrogen, deuterium, a halogen, a substituted or unsubstituted (C1-C30)alkyl, or a substituted or unsubstituted (C6-C30) aryl; and adjacent substituents of $R_{124}$ to $R_{127}$ may be linked to each other to form a substituted or unsubstituted fused ring, e.g., fluorene unsubstituted or substituted with alkyl, dibenzothiophene unsubstituted or substituted with alkyl, or dibenzofuran unsubstituted or substituted with alkyl;

$R_{201}$ to $R_{211}$ each independently represent hydrogen, deuterium, a halogen, a (C1-C30)alkyl unsubstituted or substituted with deuterium or a halogen(s), a substituted or unsubstituted (C3-C30)cycloalkyl, or a substituted or unsubstituted (C6-C30)aryl; and adjacent substituents of $R_{208}$ to $R_{211}$ may be linked to each other to form a substituted or unsubstituted fused ring, e.g., fluorene unsubstituted or substituted with alkyl, dibenzothiophene unsubstituted or substituted with alkyl, or dibenzofuran unsubstituted or substituted with alkyl;

r and s each independently represent an integer of 1 to 3; where r or s is an integer of 2 or more, each of $R_{100}$ may be the same or different; and e represents an integer of 1 to 3.

Specifically, the phosphorescent dopant materials include the following:

D-1

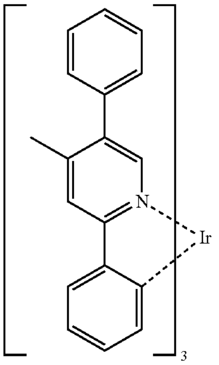

D-2

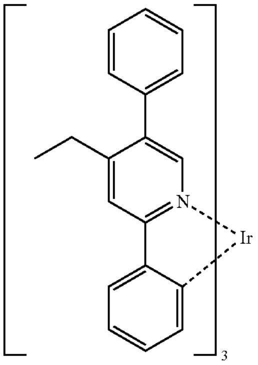

D-3

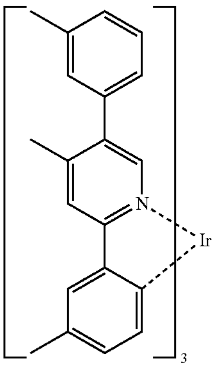

-continued
D-4
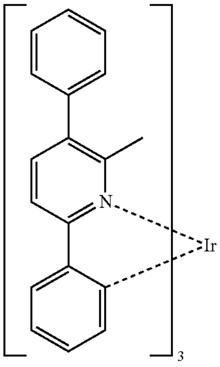
D-5
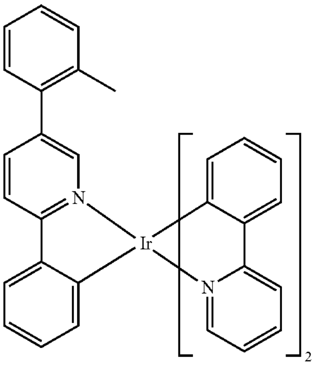
D-6
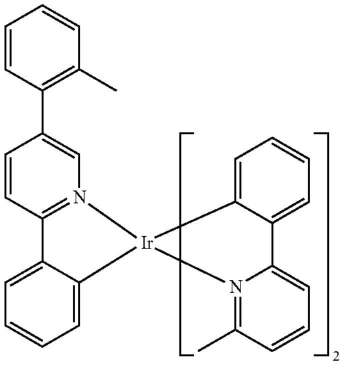
D-7
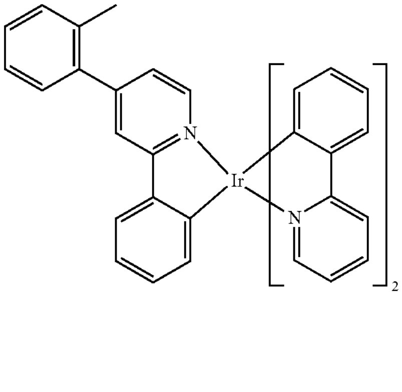
-continued
D-8
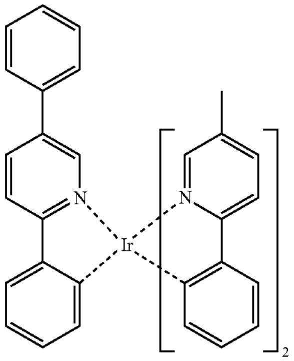
D-9
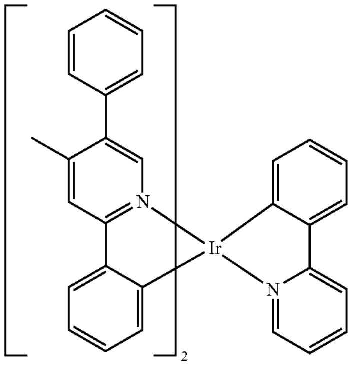
D-10
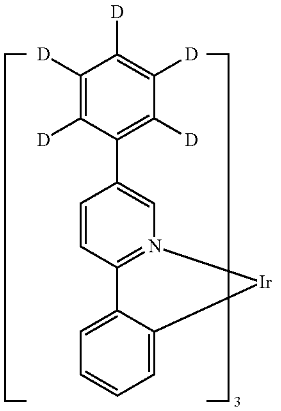
D-11
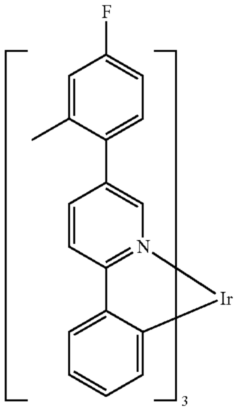

-continued
D-12
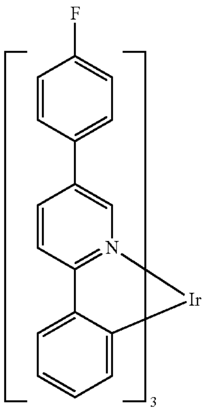
D-13
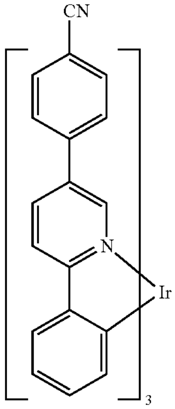
D-14
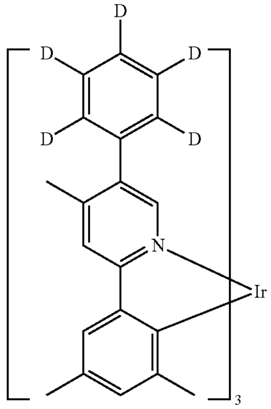
D-15
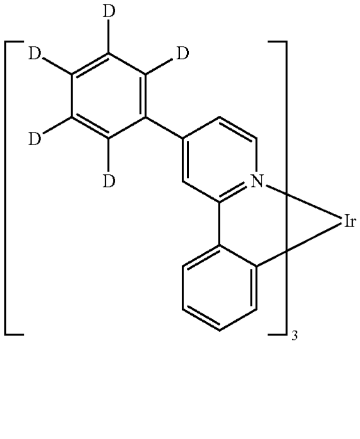
-continued
D-16
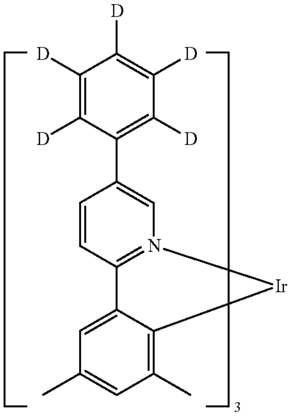
D-17
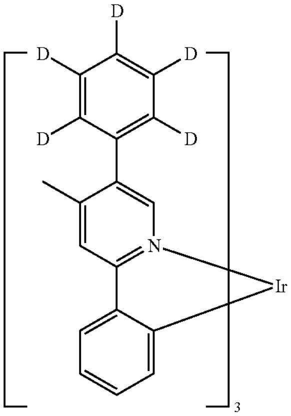
D-18
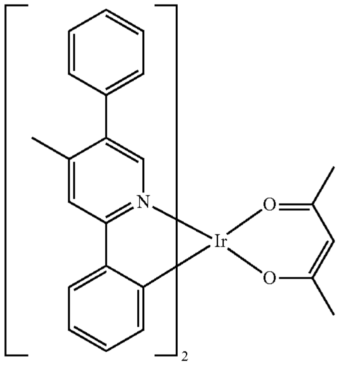
D-19
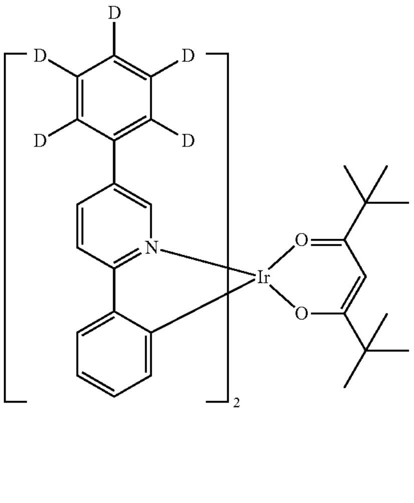

-continued
D-20
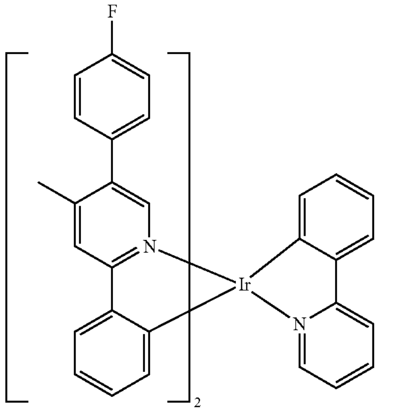
D-21
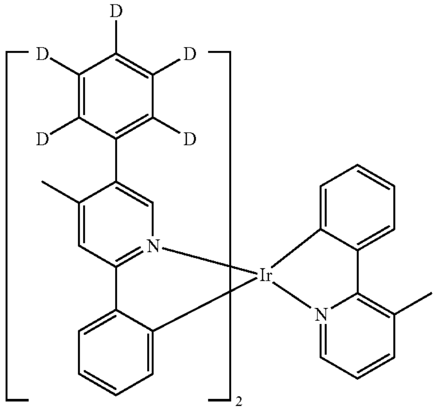
D-22
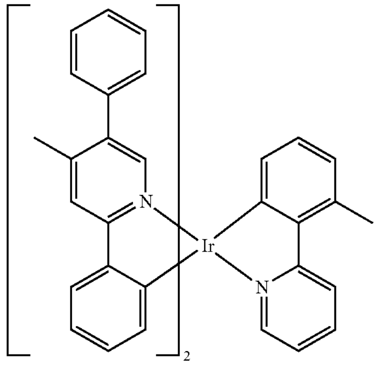
D-23
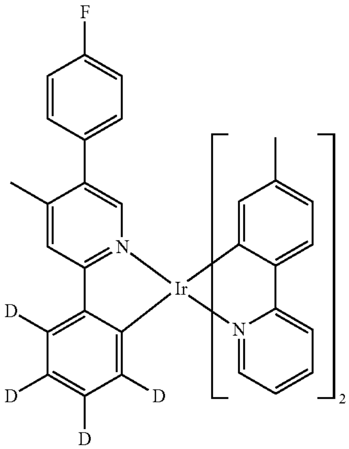
-continued
D-24
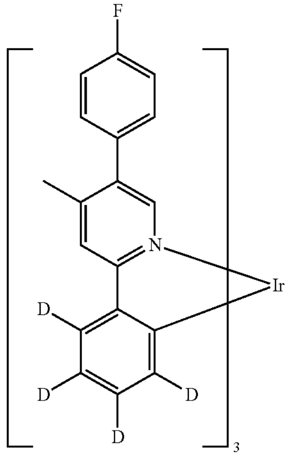
D-25
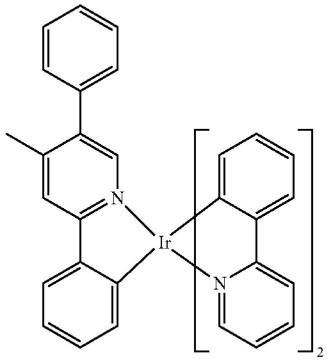
D-26
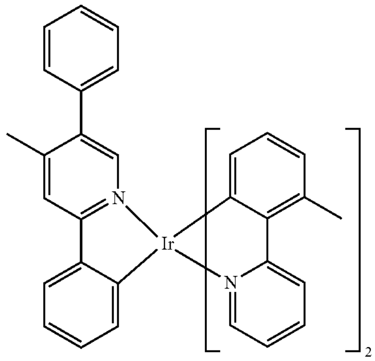
D-27
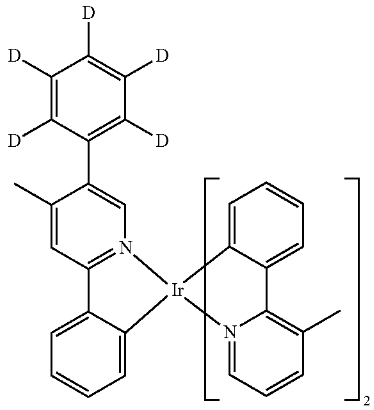

-continued
D-28
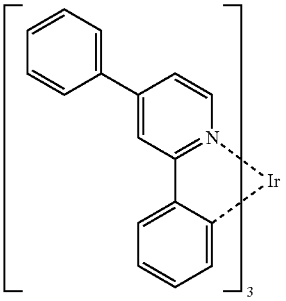
D-29
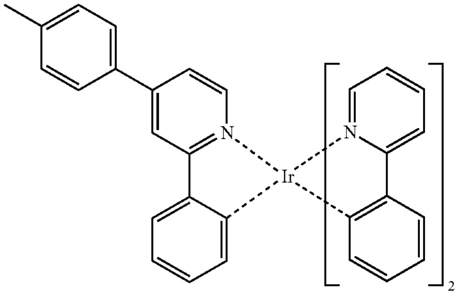
D-30
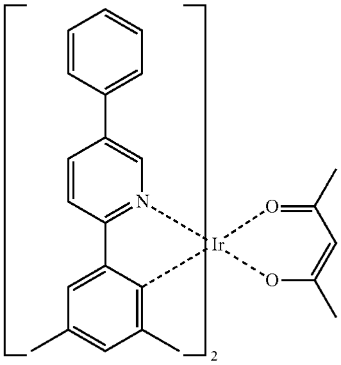
D-31
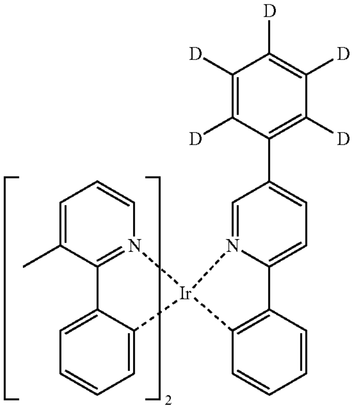
-continued
D-32
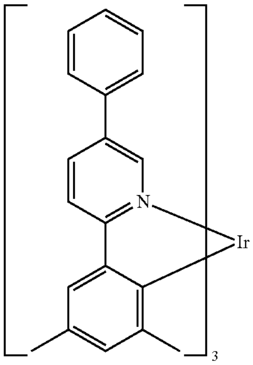
D-33
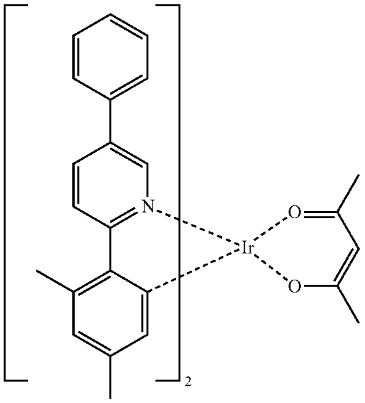
D-34
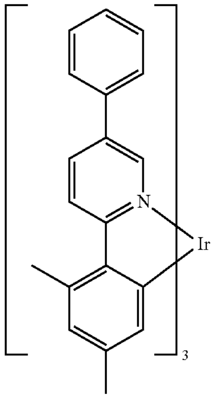
D-35
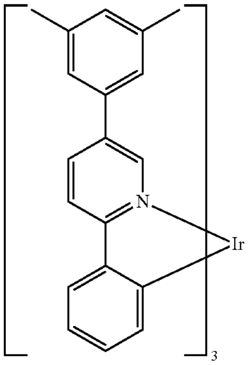

-continued
D-36
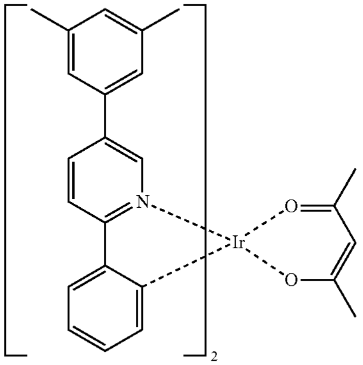
D-37
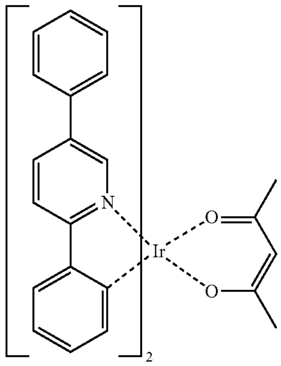
D-38
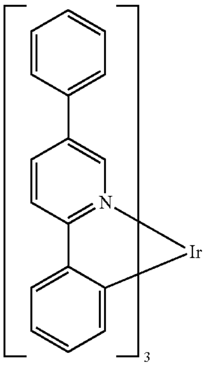
D-39
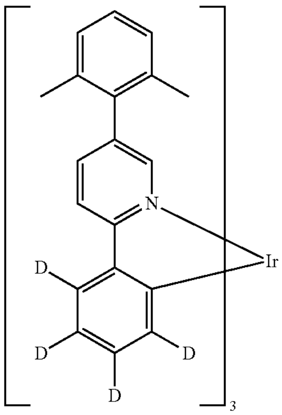
-continued
D-40
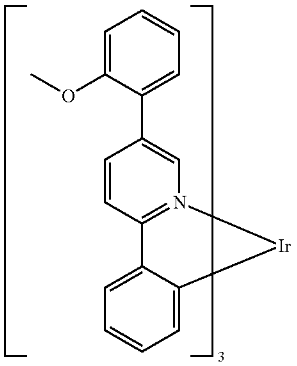
D-41
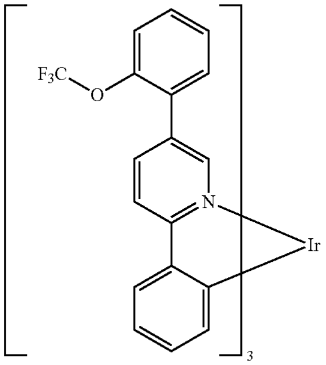
D-42
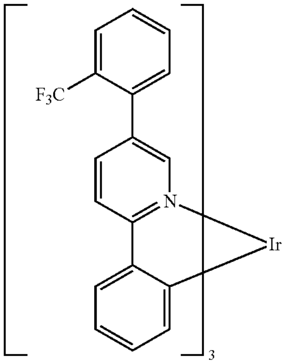
D-43
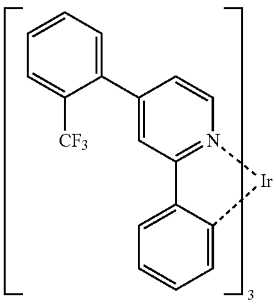

-continued
D-44
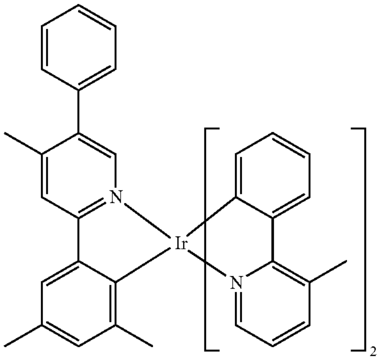
D-45
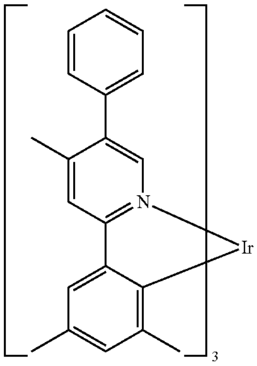
D-46
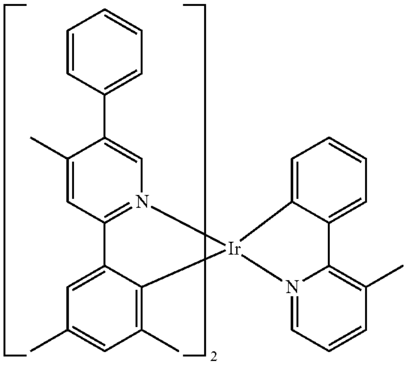
D-47
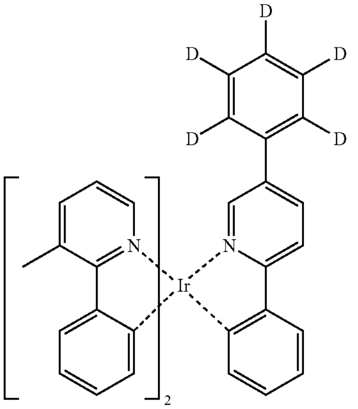
-continued
D-48
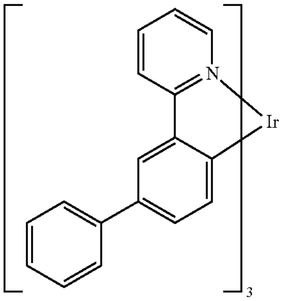
D-49
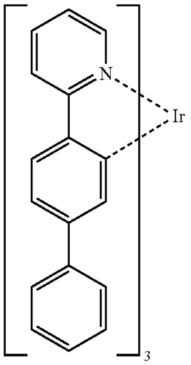
D-50
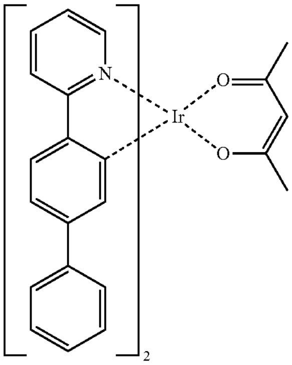
D-51
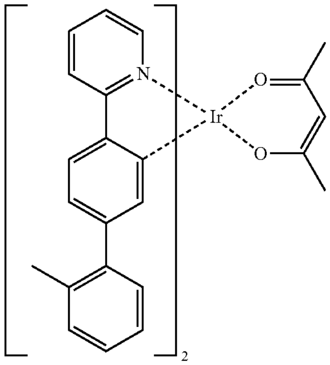

-continued
D-52
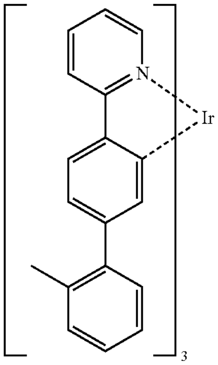
D-53
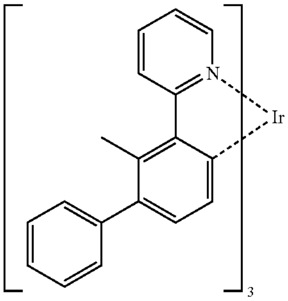
D-54
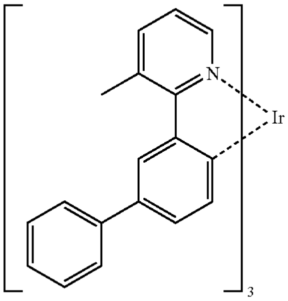
D-55
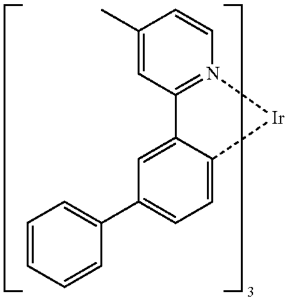
D-56
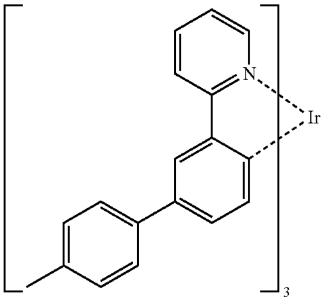
-continued
D-57
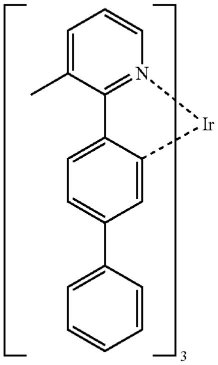
D-58
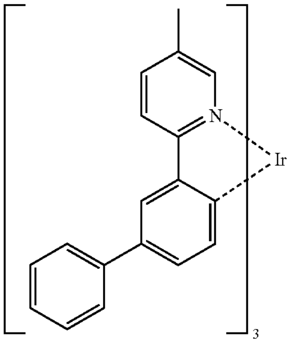
D-59
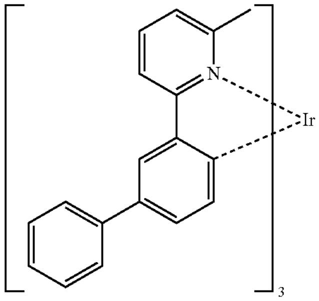
D-60
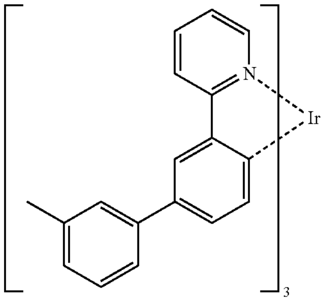

-continued
D-61
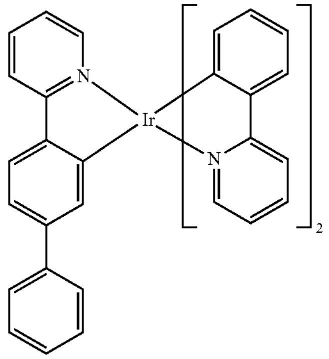
D-62
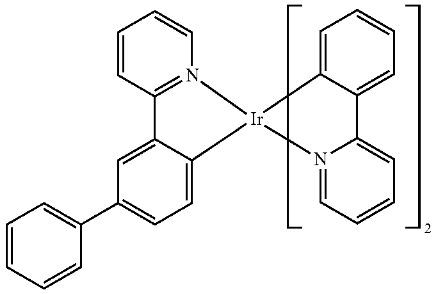
D-63
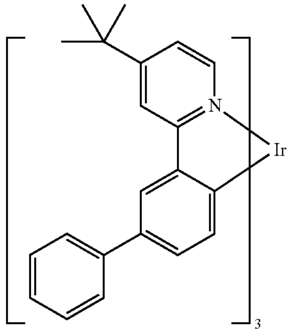
D-64
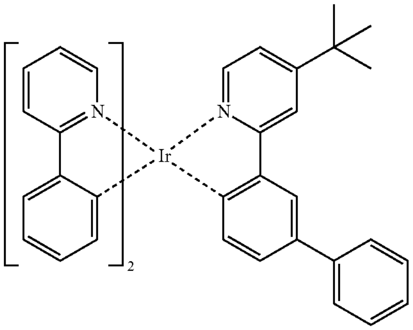
-continued
D-65
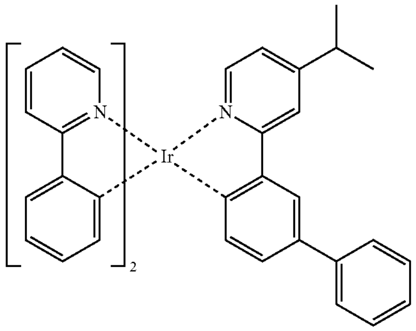
D-66
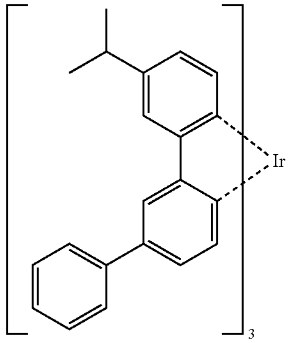
D-67
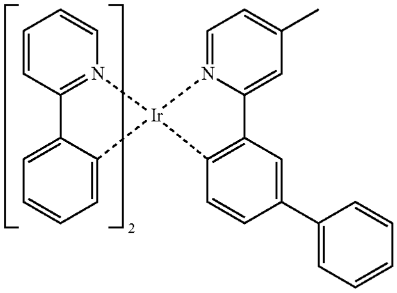
D-68
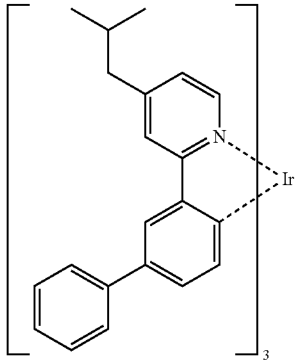

D-69
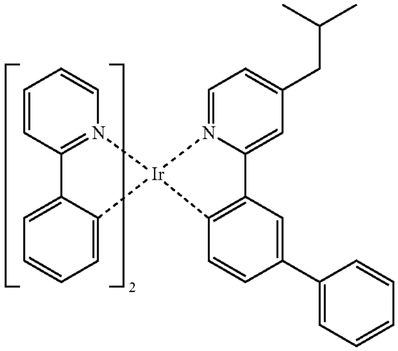
D-70
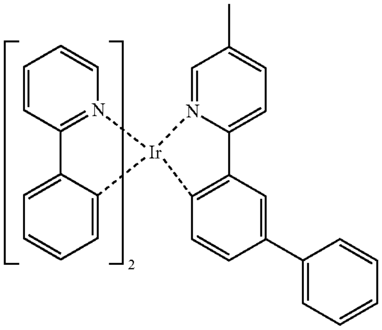
D-71
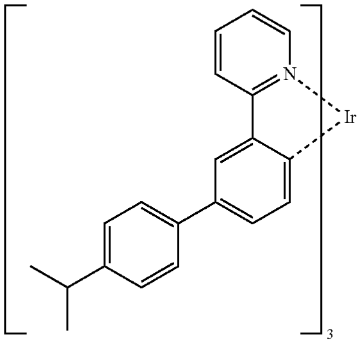
D-72
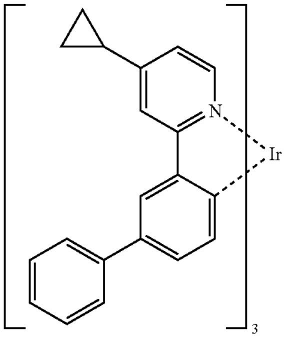
D-73
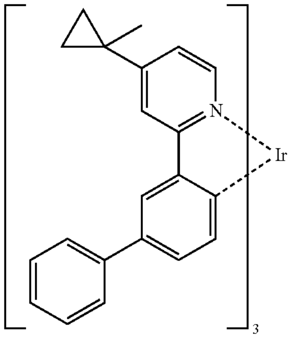
D-74
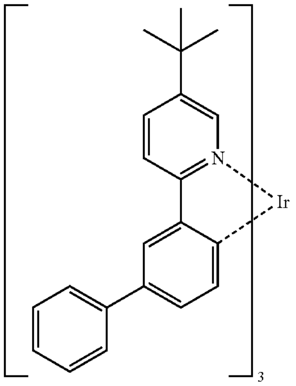
D-75
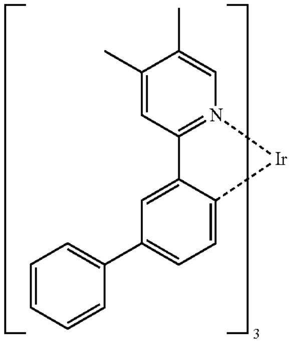
D-76
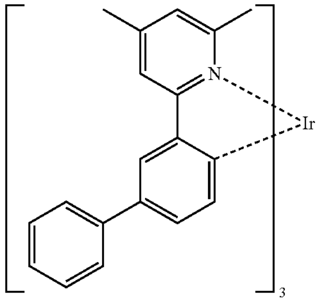

-continued
D-77
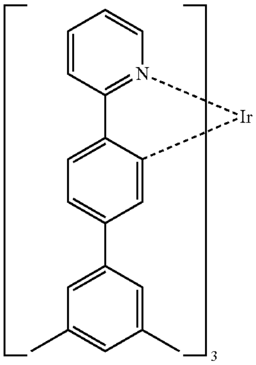
D-78
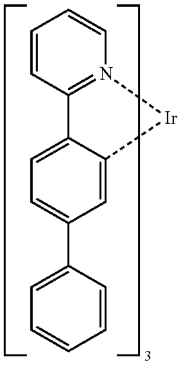
D-79
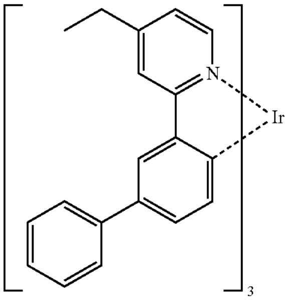
D-80
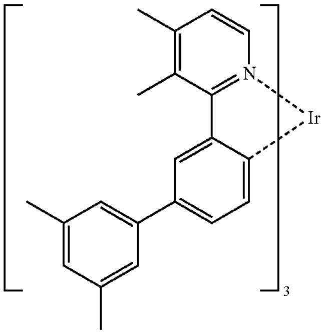
-continued
D-81
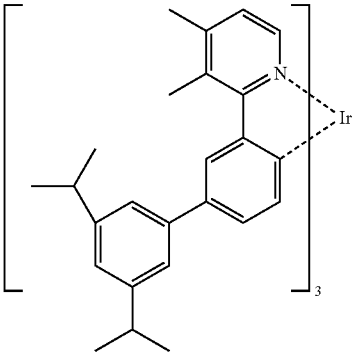
D-82
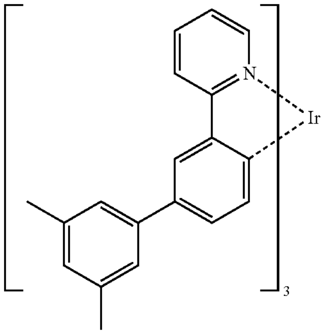
D-83
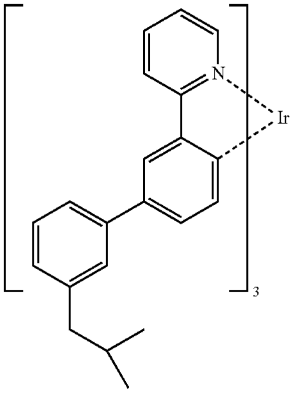
D-84
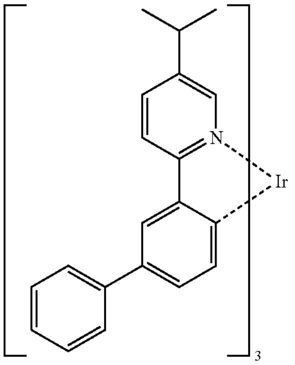

-continued
D-85
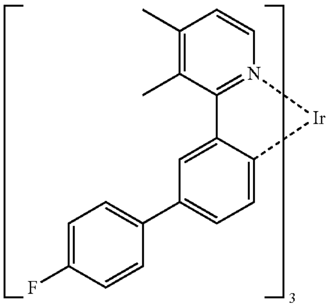
D-86
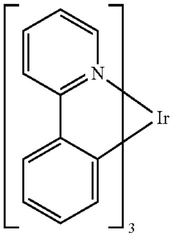
D-87
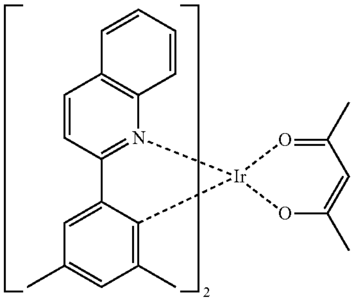
D-88
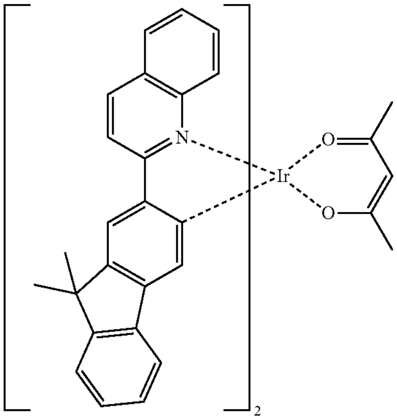
D-89
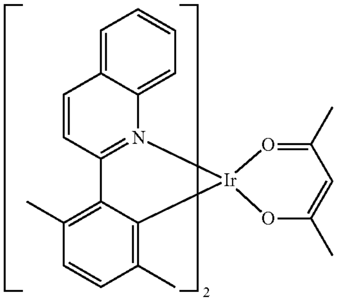
-continued
D-90
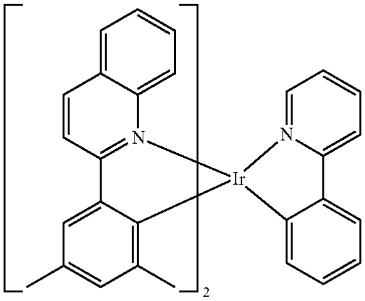
D-91
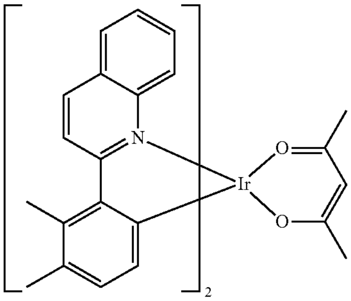
D-92
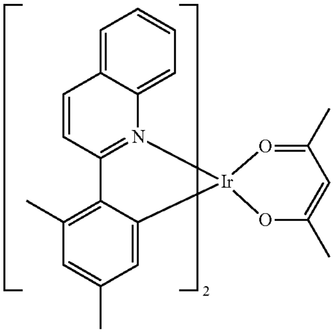
D-93
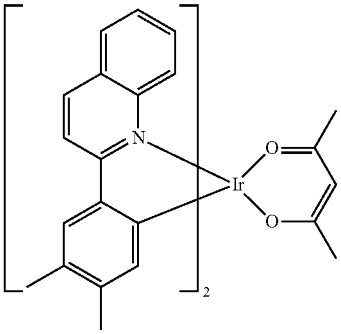

-continued
D-94
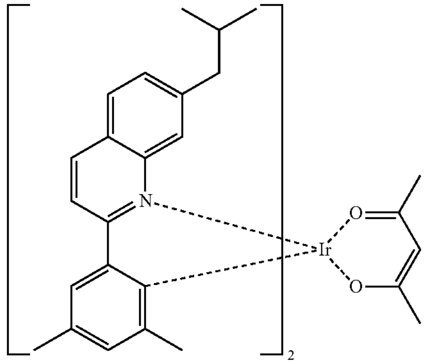
D-95
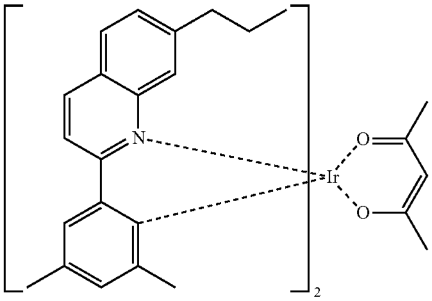
D-96
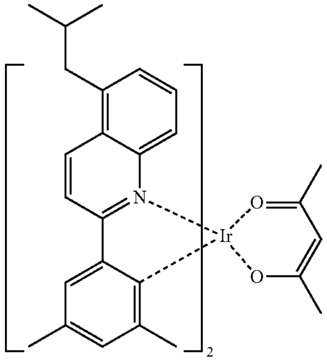
D-97
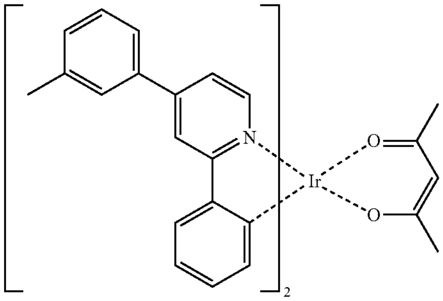
-continued
D-98
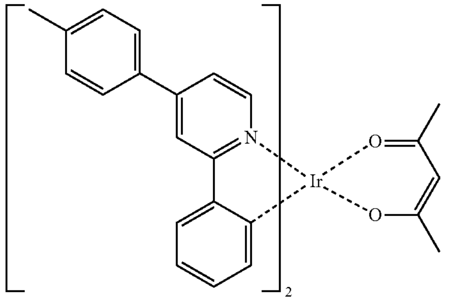
D-99
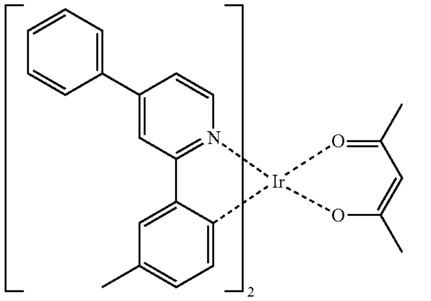
D-100
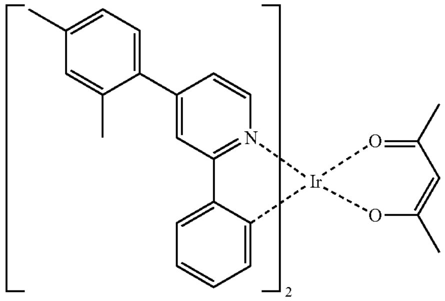
D-101
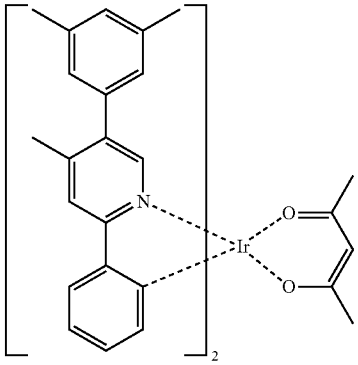
D-102
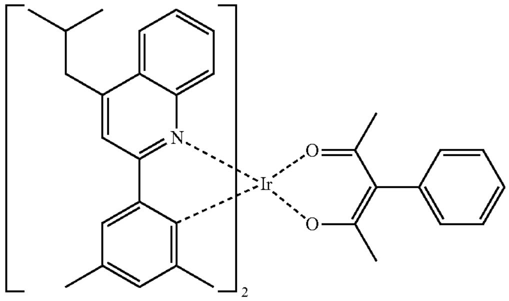

-continued
D-103
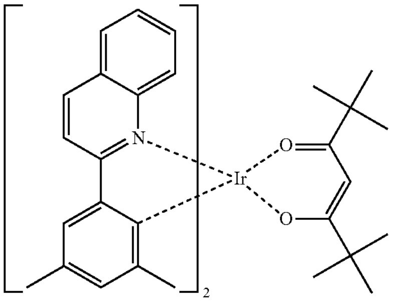
D-104
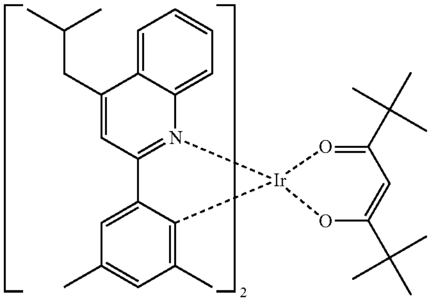
D-105
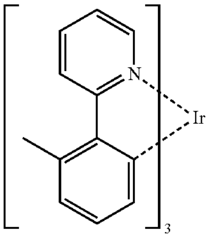
D-106
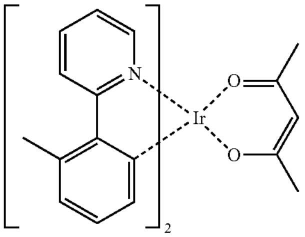
D-107
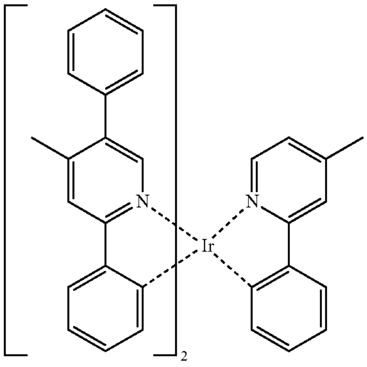
-continued
D-108
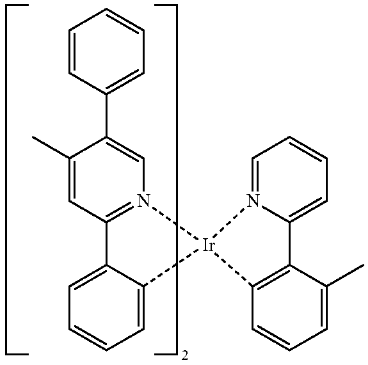
D-109
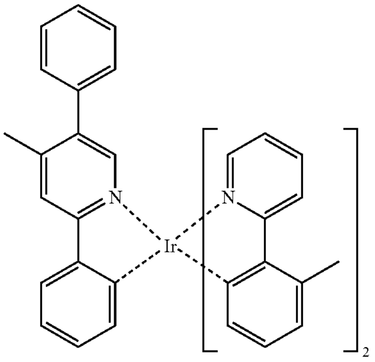
D-110
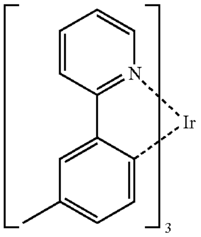
D-111
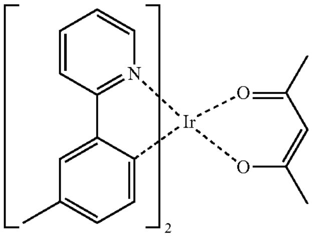
D-112
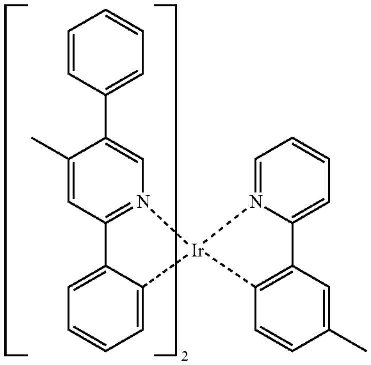

-continued
D-113
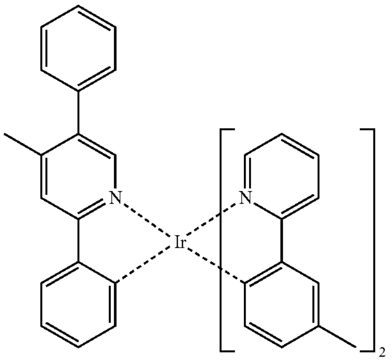
D-114
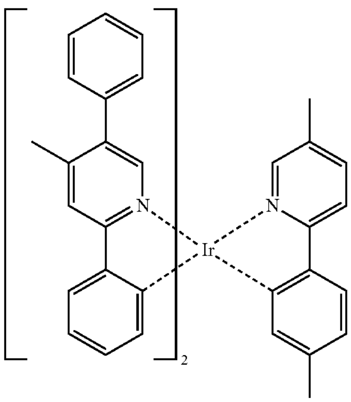
D-115
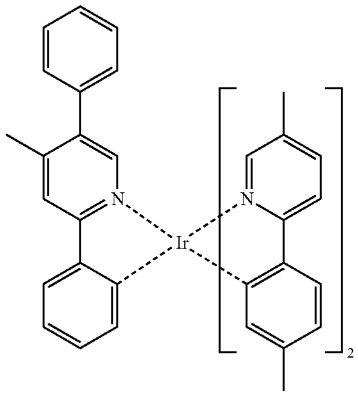
D-116
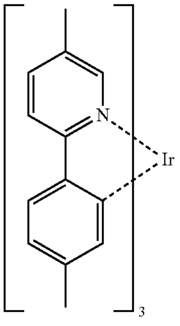
-continued
D-117
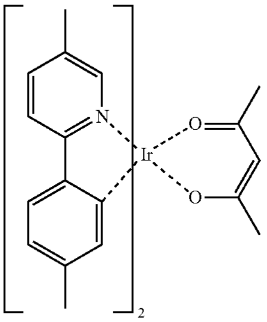
D-118
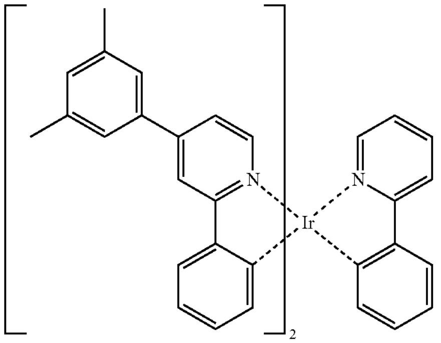
D-119
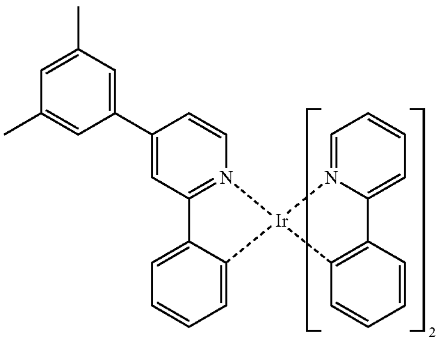
D-120
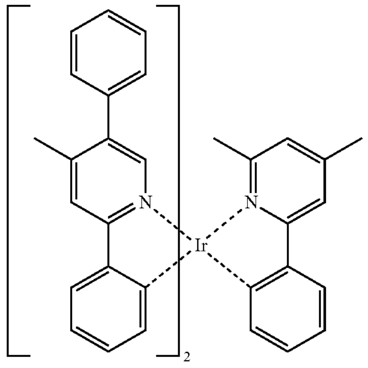

-continued
D-121
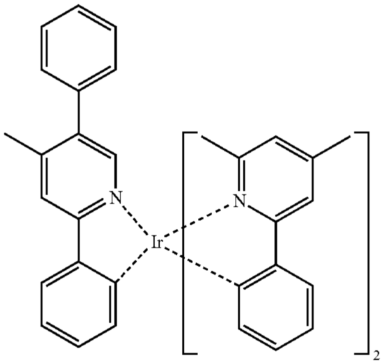
D-122
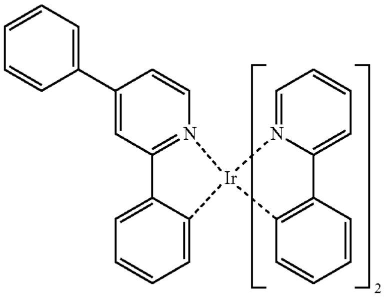
D-123
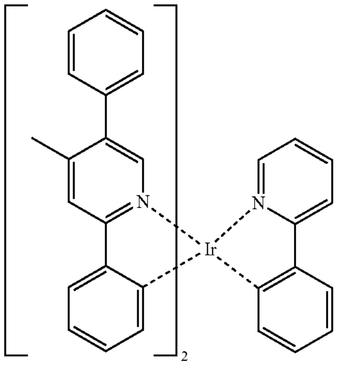
D-124
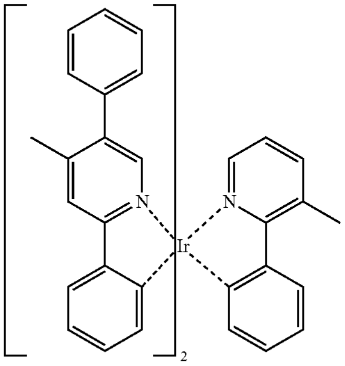
-continued
D-125
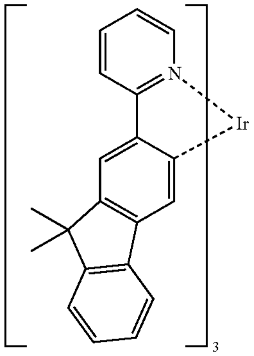
D-126
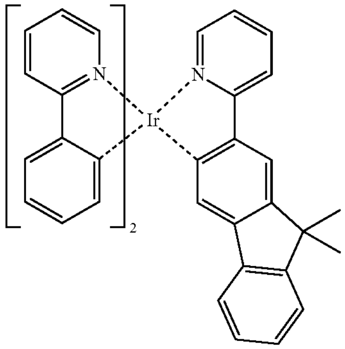
D-127
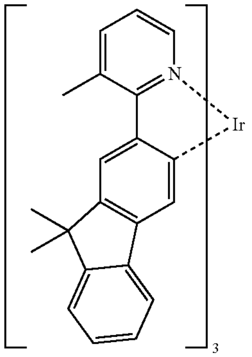
D-128
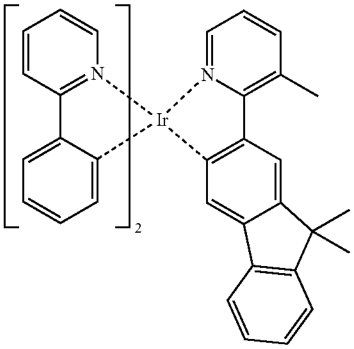

-continued
D-129
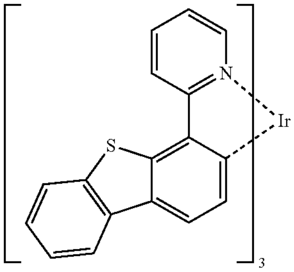
D-130
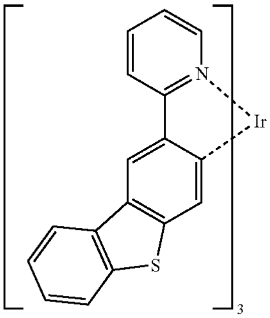
D-131
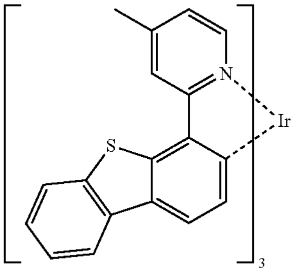
D-132
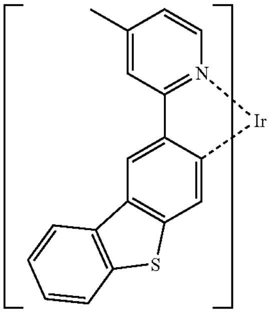
D-133
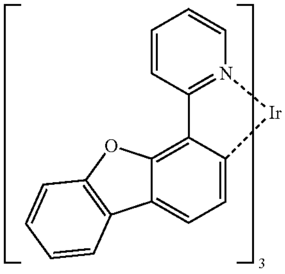
-continued
D-134
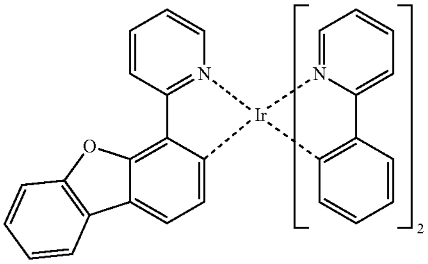
D-135
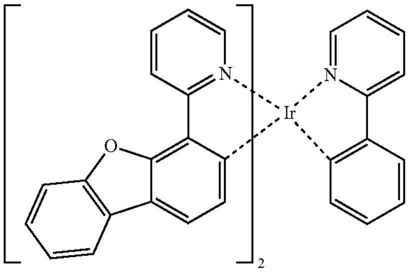
D-136
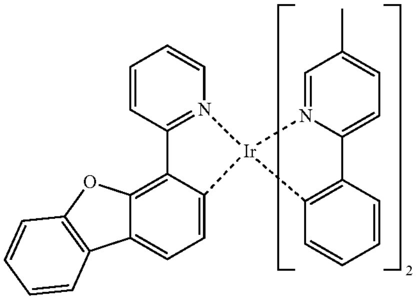
D-137
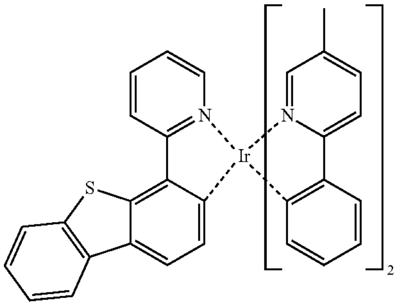
D-138
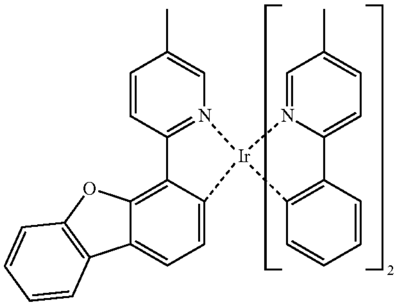

-continued
D-139
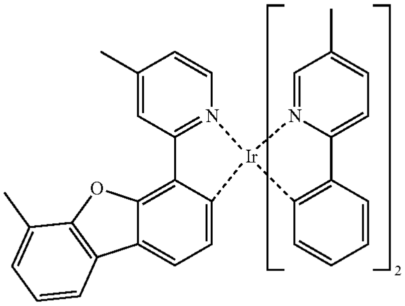
D-140
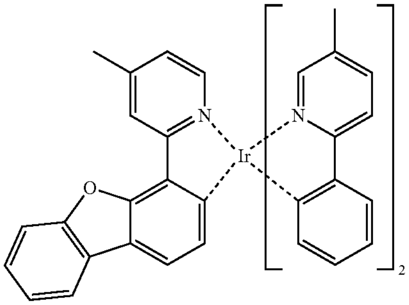
D-141
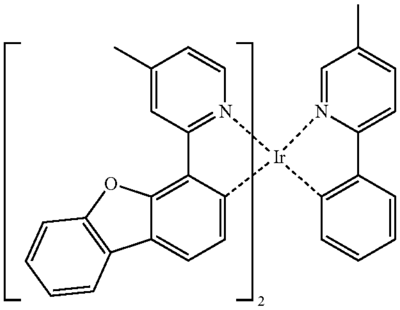
D-142
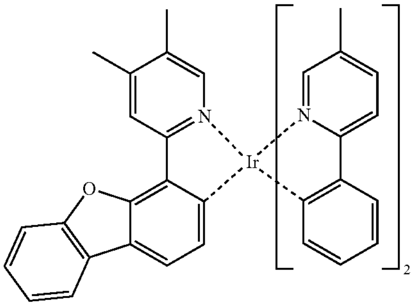
D-143
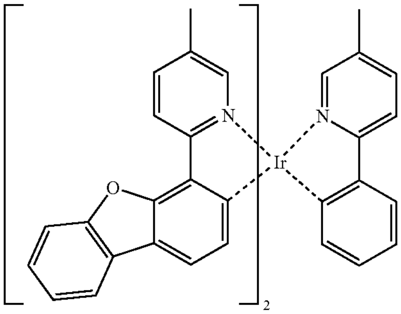
-continued
D-144
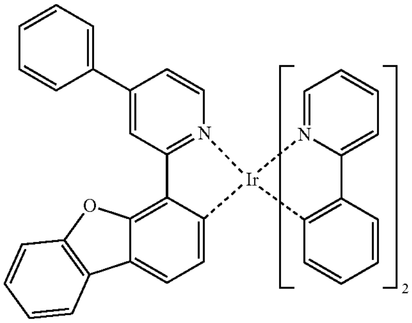
D-145
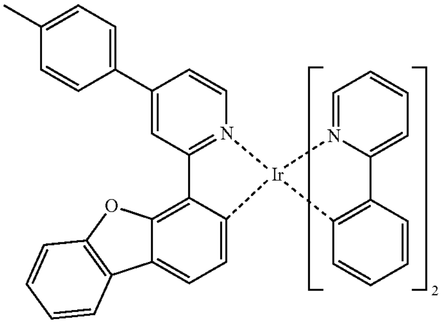
D-146
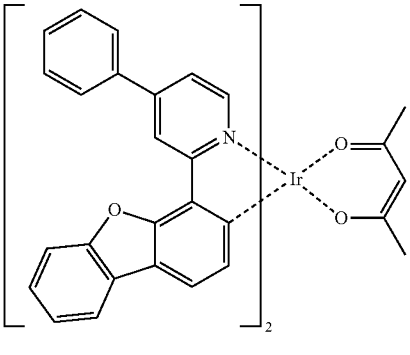
D-147
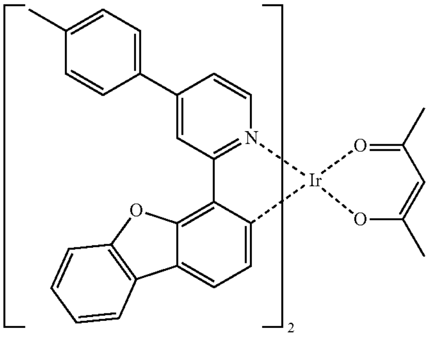

-continued
D-148
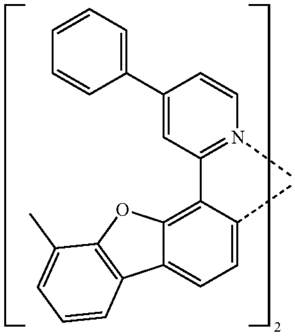
D-149
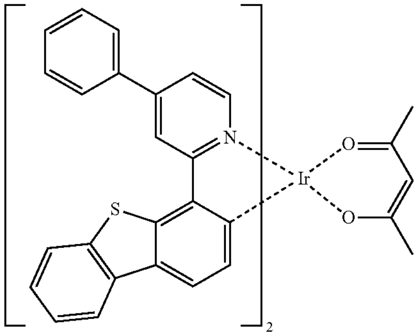
D-150
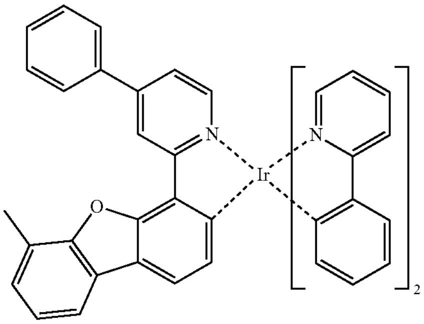
D-151
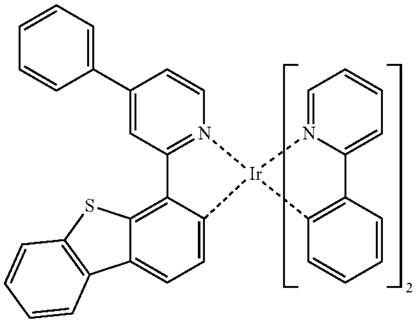
D-152
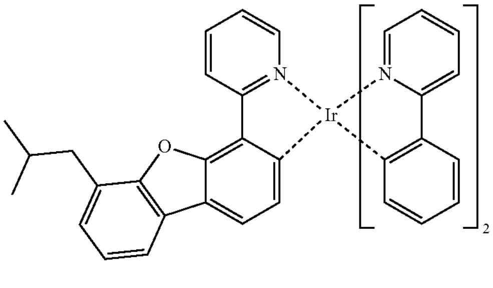
-continued
D-153
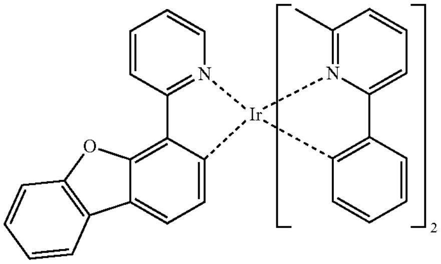
D-154
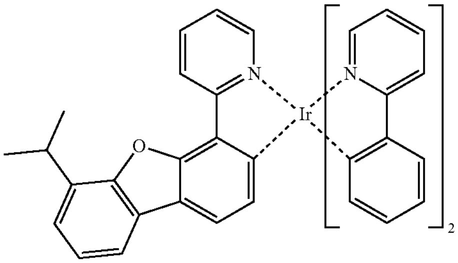
D-155
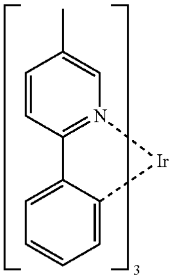
D-156
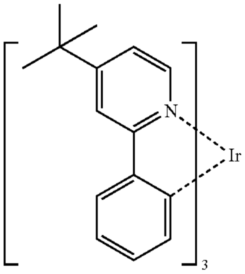
D-157
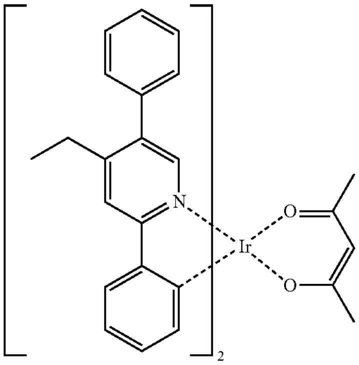

-continued
D-158
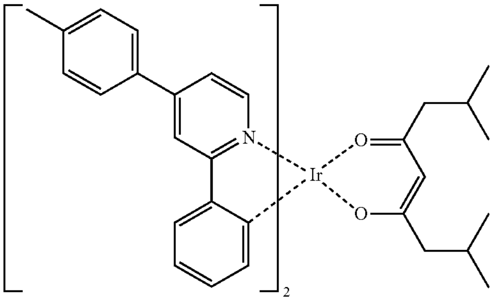
D-159
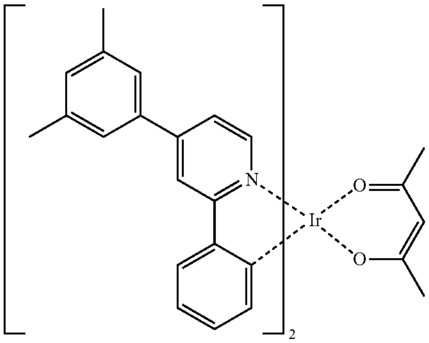
D-160
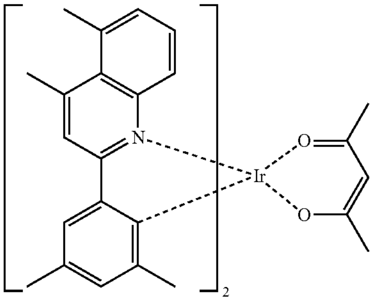
D-161
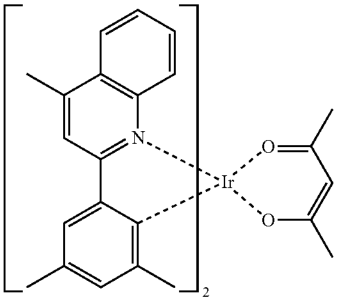
D-162
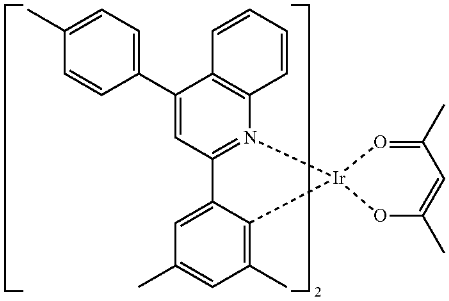
-continued
D-163
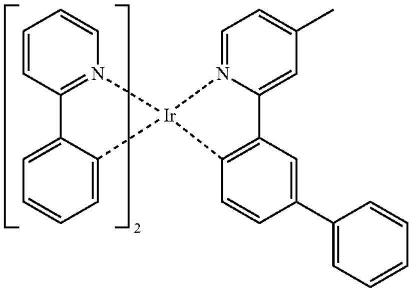
D-164
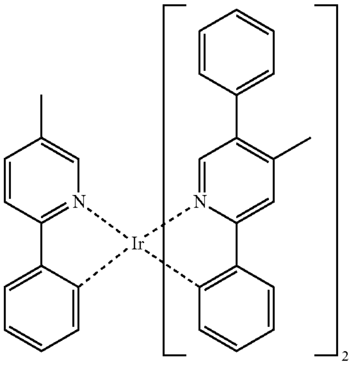
D-165
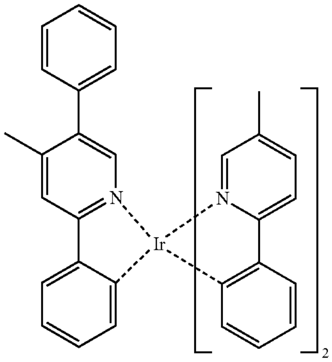
D-166
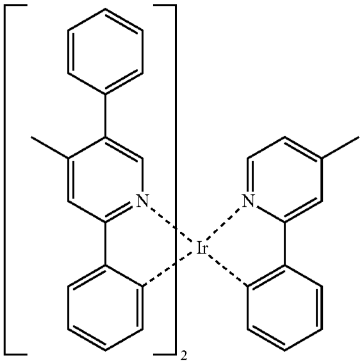

-continued
D-167
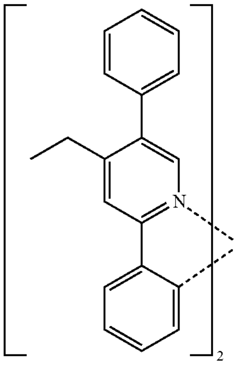
D-168
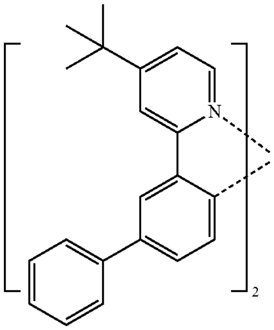
D-169
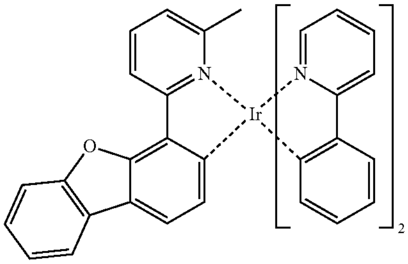
D-170
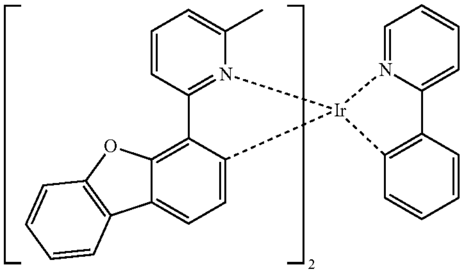
D-171
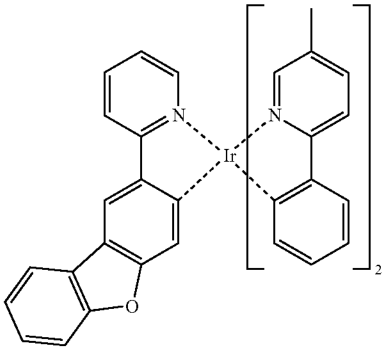
-continued
D-172
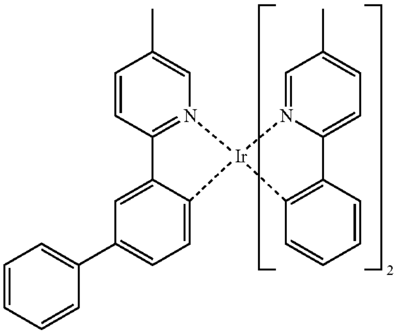
D-173
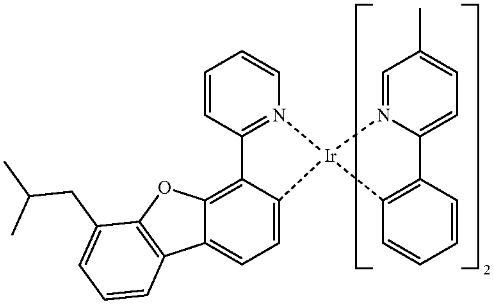
D-174
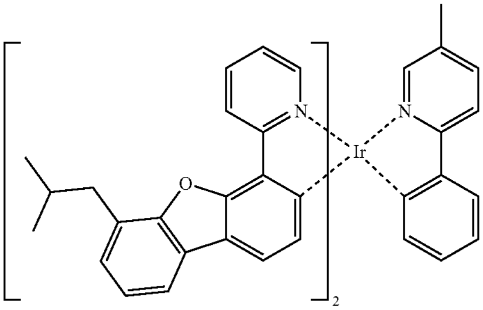
D-175
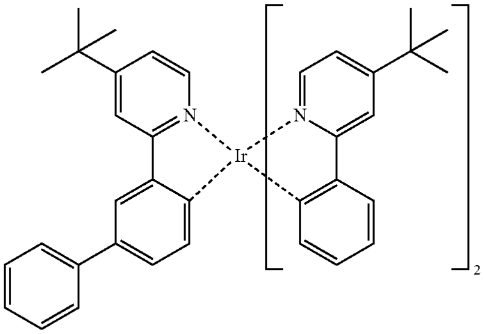

-continued
D-176
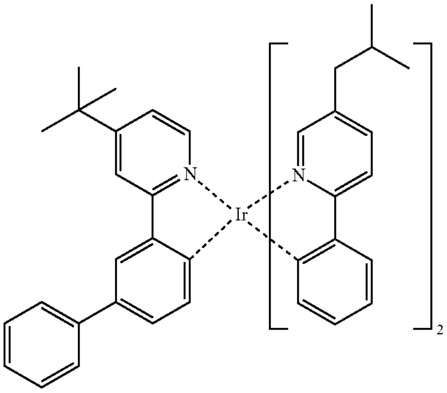
D-177
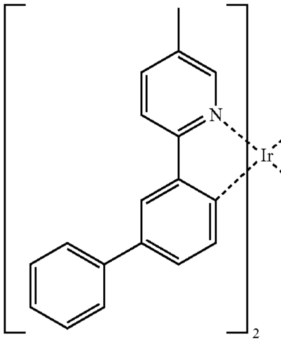
D-178
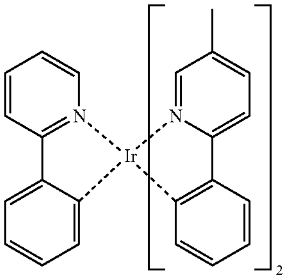
D-179
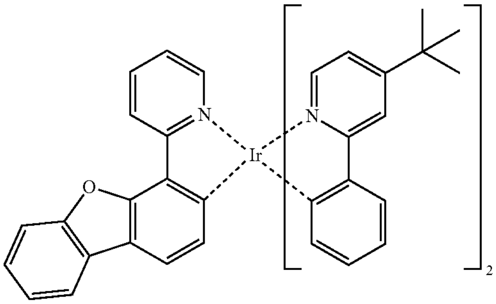
-continued
D-180
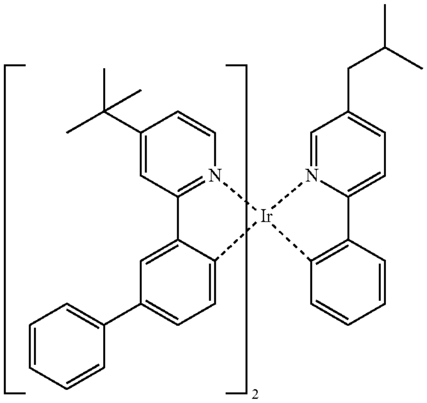
D-181
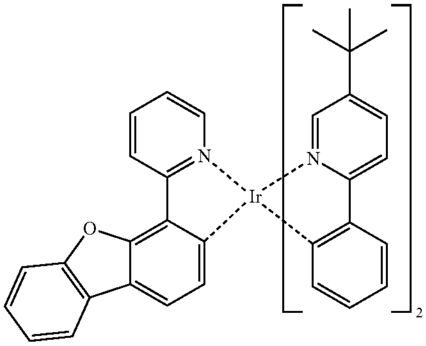
D-182
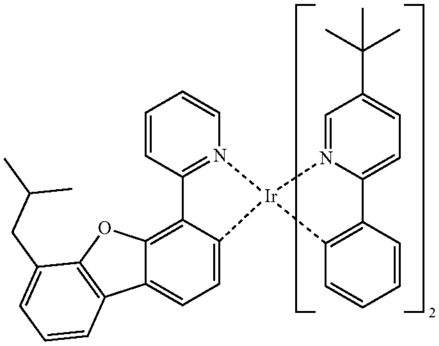
D-183
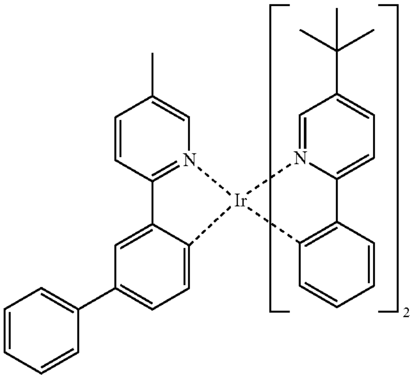

-continued
D-184
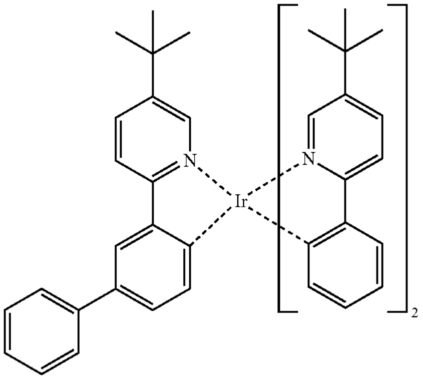
D-185
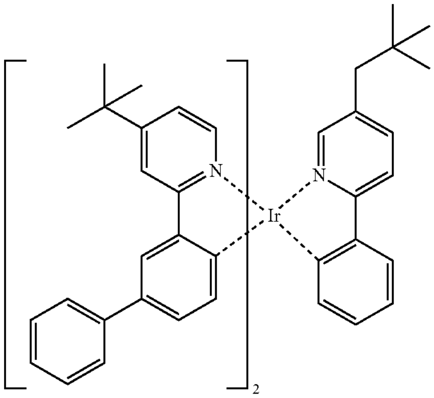
D-186
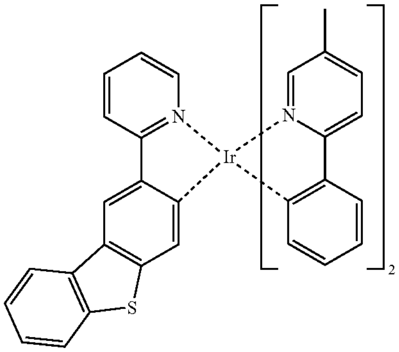
D-187
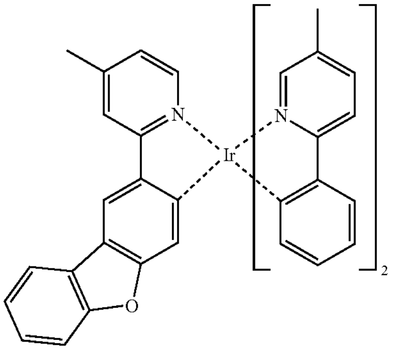
-continued
D-188
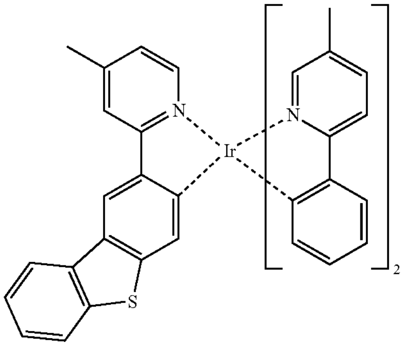
D-189
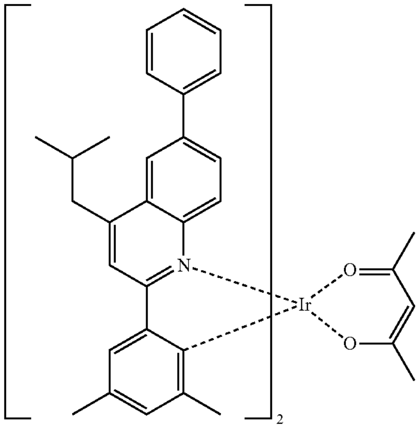
D-190
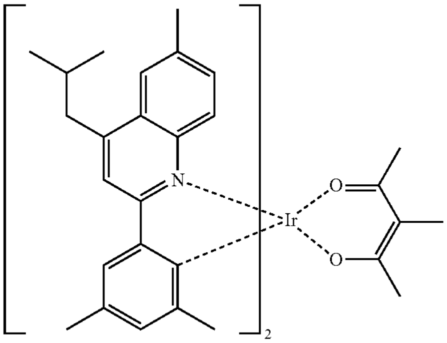
D-191
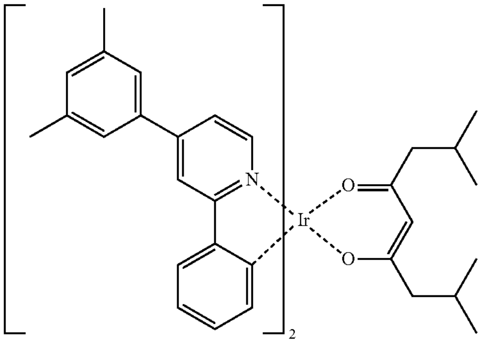

D-192
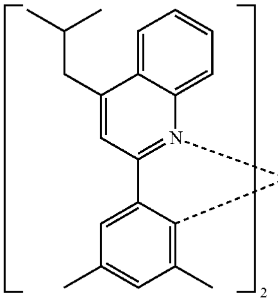
D-193
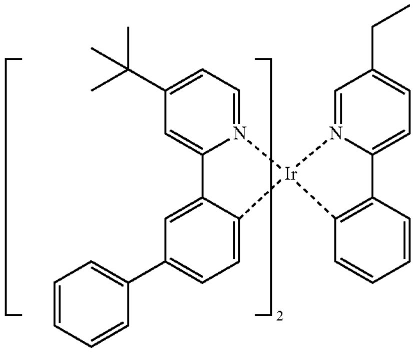
D-194
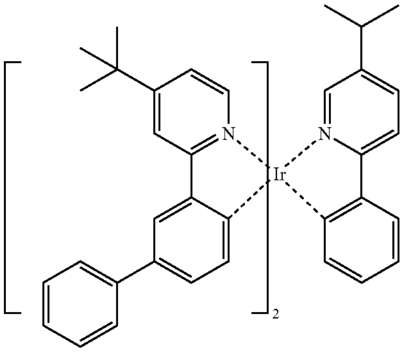
D-195
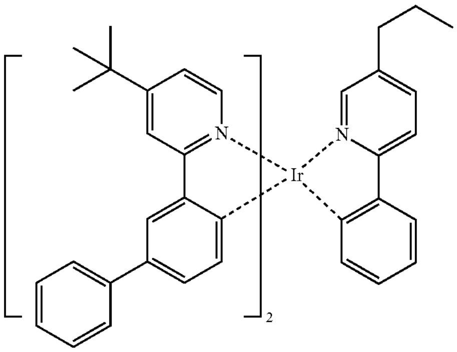
D-196
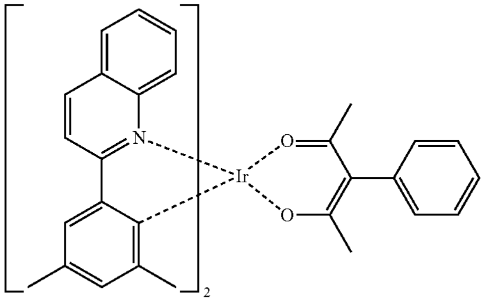
D-197
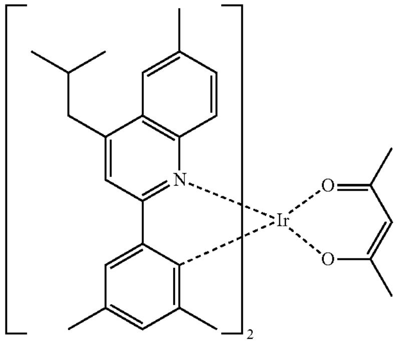
D-198
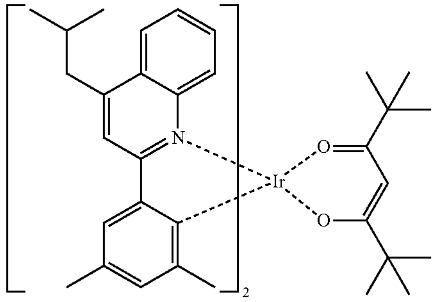
D-199
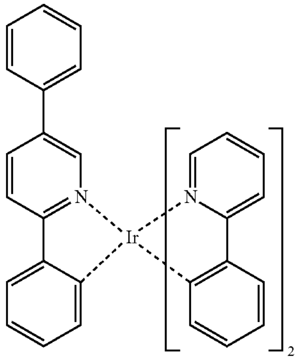
D-200
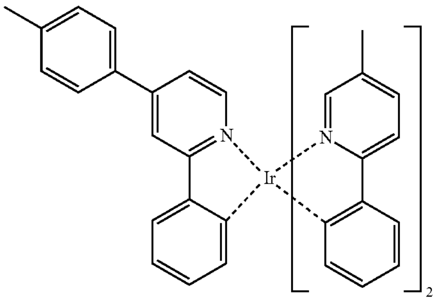

-continued
D-201
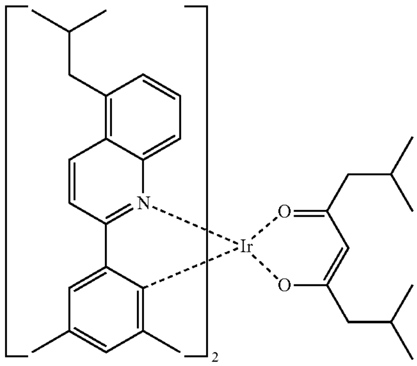
D-202
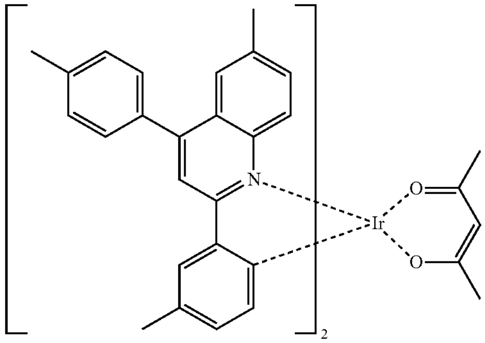
D-203
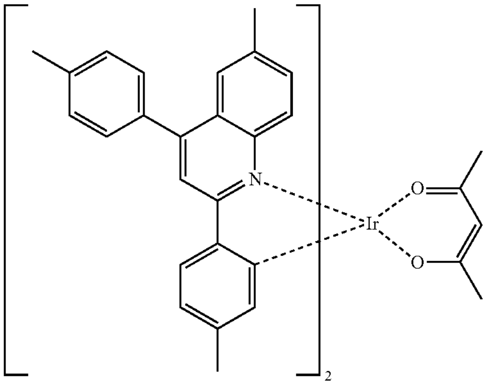
D-204
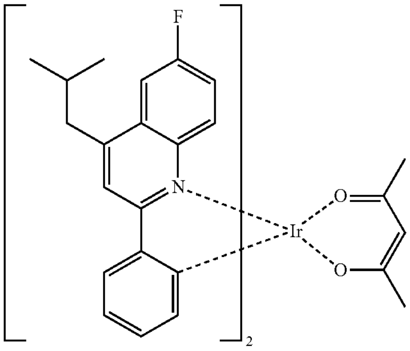
-continued
D-205
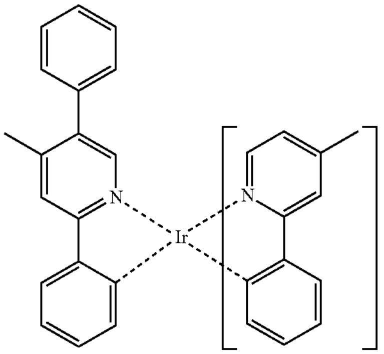
D-206
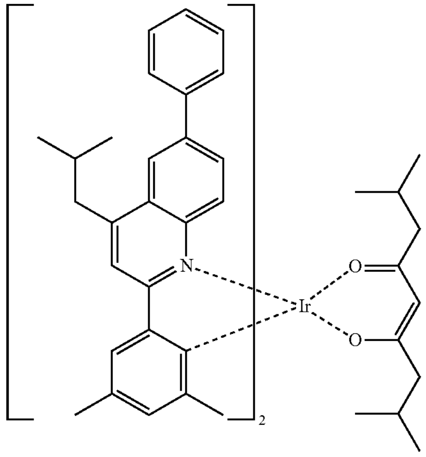
D-207
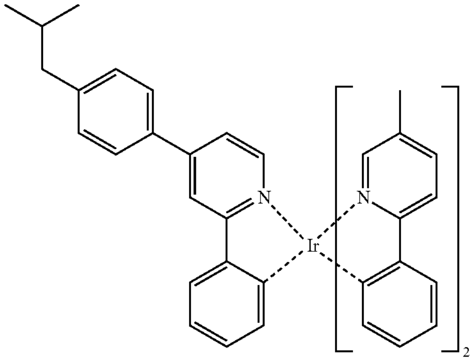
D-208
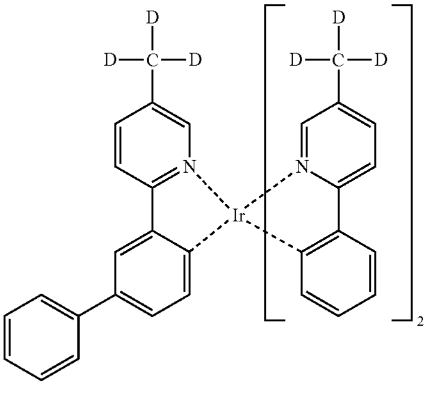

-continued

D-209

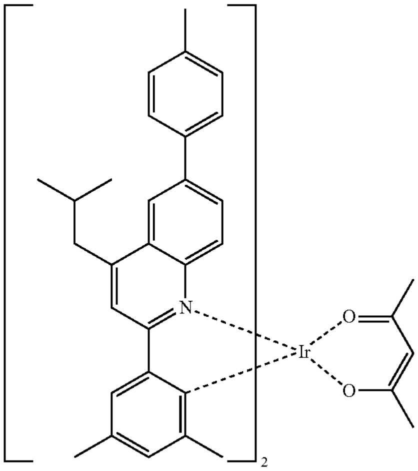

D-210

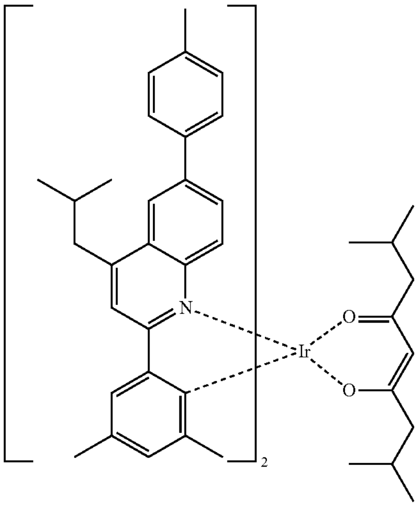

D-211

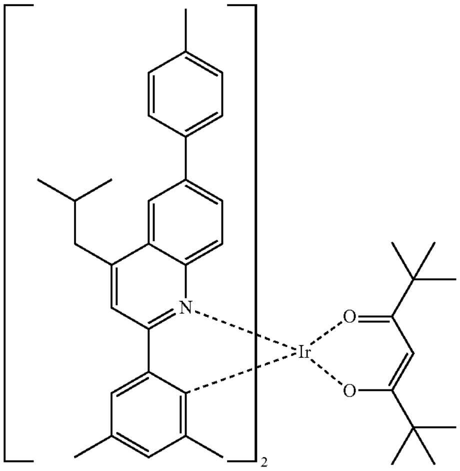

-continued

D-212

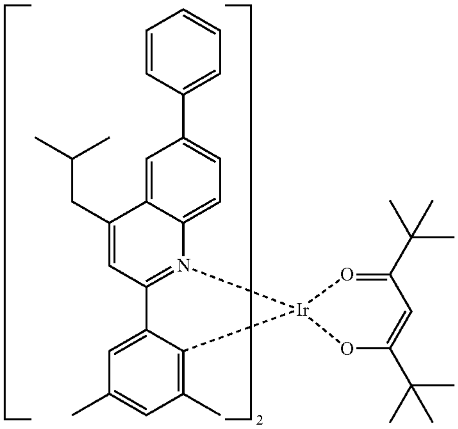

The organic electroluminescent device according to the present invention may further comprise at least one compound selected from the group consisting of arylamine-based compounds and styrylarylamine-based compounds in the organic layer.

In addition, in the organic electroluminescent device according to the present invention, the organic layer may further comprise at least one metal selected from the group consisting of metals of Group 1, metals of Group 2, transition metals of the $4^{th}$ period, transition metals of the $5^{th}$ period, lanthanides and organic metals of d-transition elements of the Periodic Table, or at least one complex compound comprising said metal.

According to the present invention, at least one layer (hereinafter, "a surface layer") is preferably placed on an inner surface(s) of one or both electrode(s); selected from a chalcogenide layer, a metal halide layer and a metal oxide layer. Specifically, a chalcogenide (including oxides) layer of silicon or aluminum is preferably placed on an anode surface of an electroluminescent medium layer, and a metal halide layer or a metal oxide layer is preferably placed on a cathode surface of an electroluminescent medium layer. Such a surface layer provides operation stability for the organic electroluminescent device. Preferably, said chalcogenide includes $SiO_x(1 \le X \le 2)$, $AlO_x(1 \le X \le 1.5)$, SiON, SiAlON, etc.; said metal halide includes LiF, $MgF_2$, $CaF_2$, a rare earth metal fluoride, etc.; and said metal oxide includes $Cs_2O$, $Li_2O$, MgO, SrO, BaO, CaO, etc.

Between the anode and the light-emitting layer, a layer selected from a hole injection layer, a hole transport layer, or an electron blocking layer, or formed by a combination thereof can be used. Multi layers can be used for the hole injection layer in order to lower the hole injection barrier (or hole injection voltage) from the anode to the hole transport layer or the electron blocking layer. Two compounds can be simultaneously used in each layer. The hole transport layer and the electron blocking layer can also be formed of multi layers.

Between the light-emitting layer and the cathode, a layer selected from an electron buffer layer, a hole blocking layer, an electron transport layer, or an electron injection layer, or formed by a combination thereof can be used. Multi layers can be used for the electron buffer layer in order to control the injection of the electrons and enhance the interfacial characteristics between the light-emitting layer and the electron injection layer. Two compounds can be simultaneously used in each layer. The hole blocking layer and the electron transport layer can also be formed of multi layers, and each layer can comprise two or more compounds.

In the organic electroluminescent device according to the present invention, a mixed region of an electron transport compound and a reductive dopant, or a mixed region of a hole transport compound and an oxidative dopant is preferably placed on at least one surface of a pair of electrodes. In this case, the electron transport compound is reduced to an anion, and thus it becomes easier to inject and transport electrons from the mixed region to an electroluminescent medium. Further, the hole transport compound is oxidized to a cation, and thus it becomes easier to inject and transport holes from the mixed region to the electroluminescent medium. Preferably, the oxidative dopant includes various Lewis acids and acceptor compounds; and the reductive dopant includes alkali metals, alkali metal compounds, alkaline earth metals, rare-earth metals, and mixtures thereof. A reductive dopant layer may be employed as a charge generating layer to prepare an electroluminescent device having two or more electroluminescent layers and emitting white light.

In order to form each layer of the organic electroluminescent device of the present invention, dry film-forming methods such as vacuum evaporation, sputtering, plasma and ion plating methods, or wet film-forming methods such as ink jet printing, nozzle printing, slot coating, spin coating, dip coating, and flow coating methods can be used. The first and second host compounds of the present invention may be co-evaporated or mixture-evaporated.

When using a wet film-forming method, a thin film can be formed by dissolving or diffusing materials forming each layer into any suitable solvent such as ethanol, chloroform, tetrahydrofuran, dioxane, etc. The solvent can be any solvent where the materials forming each layer can be dissolved or diffused, and where there are no problems in film-formation capability.

Herein, a co-evaporation indicates a process for two or more materials to be deposited as a mixture, by introducing each of the two or more materials into respective crucible cells, and applying an electric current to the cells for each of the materials to be evaporated. Herein, a mixture-evaporation indicates a process for two or more materials to be deposited as a mixture, by mixing the two or more materials in one crucible cell before the deposition, and applying an electric current to the cell for the mixture to be evaporated.

By using the organic electroluminescent device of the present invention, a display system or a lighting system can be produced.

Hereinafter, the luminescent properties of the device comprising the host compound of the present invention will be explained in detail with reference to the following examples.

Device Examples 1-1 to 1-6: Preparation of an OLED Device by Co-Evaporating the First Host Compound and the Second Host Compound of the Present Invention An OLED device was produced using the organic electroluminescent compound according to the present invention. A transparent electrode indium tin oxide (ITO) thin film (10 Ω/sq) on a glass substrate for an organic light-emitting diode (OLED) device (Geomatec) was subjected to an ultrasonic washing with trichloroethylene, acetone, ethanol, and distilled water, sequentially, and then was stored in isopropanol. The ITO substrate was then mounted on a substrate holder of a vacuum vapor depositing apparatus. $N^4$,$N^{4'}$-diphenyl-$N^4$,$N^{4'}$-bis(9-phenyl-9H-carbazol-3-yl)-[1,1'-biphenyl]-4,4'-diamine (compound HI-1) was introduced into a cell of said vacuum vapor depositing apparatus, and then the pressure in the chamber of said apparatus was controlled to $10^{-6}$ torr. Thereafter, an electric current was applied to the cell to evaporate the above introduced material, thereby forming a first hole injection layer having a thickness of 80 nm on the ITO substrate. Next, 1,4,5,8,9,12-hexaazatriphenylene-hexacarbonitrile (compound HI-2) was introduced into another cell of said vacuum vapor depositing apparatus, and was evaporated by applying an electric current to the cell, thereby forming a second hole injection layer having a thickness of 5 nm on the first hole injection layer. N-([1,1'-biphenyl]-4-yl)-9,9-dimethyl-N-(4-(9-phenyl-9H-carbazol-3-yl)phenyl)-9H-fluorene-2-amine (compound HT-1) was then introduced into another cell of said vacuum vapor depositing apparatus, and was evaporated by applying an electric current to the cell, thereby forming a first hole transport layer having a thickness of 10 nm on the second hole injection layer. Afterwards, N,N-di([1,1'-biphenyl]-4-yl)-4'-(9H-carbazol-9-yl)-[1,1'-biphenyl]-4-amine (compound HT-2) was introduced into another cell of said vacuum vapor depositing apparatus, and was evaporated by applying an electric current to the cell, thereby forming a second hole transport layer having a thickness of 60 nm on the first hole transport layer. As a host material, a first host compound and a second host compound were introduced into two cells of the vacuum vapor depositing apparatus, respectively. A dopant compound D-96 was introduced into another cell. The two host materials were evaporated at 1:1 rate, while the dopant was evaporated at a different rate from the host materials, so that the dopant was deposited in a doping amount of 3 wt % based on the total amount of the host and dopant to form a light-emitting layer having a thickness of 40 nm on the hole transport layer. 2,4-bis(9,9-dimethyl-9H-fluoren-2-yl)-6-(naphthalen-2-yl)-1,3,5-triazine (compound ET-1) and lithium quinolate (compound EI-1) were then introduced into two cells of the vacuum vapor depositing apparatus, respectively, and evaporated at 1:1 rate to form an electron transport layer having a thickness of 30 nm on the light-emitting layer. After depositing lithium quinolate (compound EI-1) as an electron injection layer having a thickness of 2 nm on the electron transport layer, an Al cathode having a thickness of 80 nm was deposited by another vacuum vapor deposition apparatus. Thus, an OLED device was produced.

HI-1

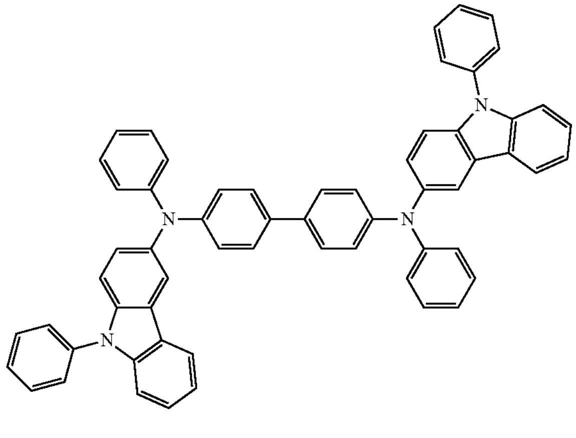

-continued
HI-2
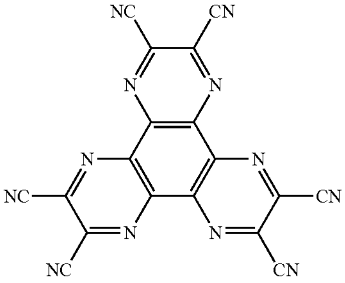
HT-1
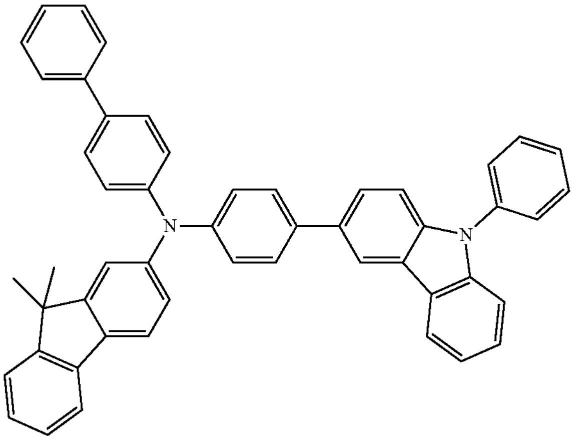
HT-2
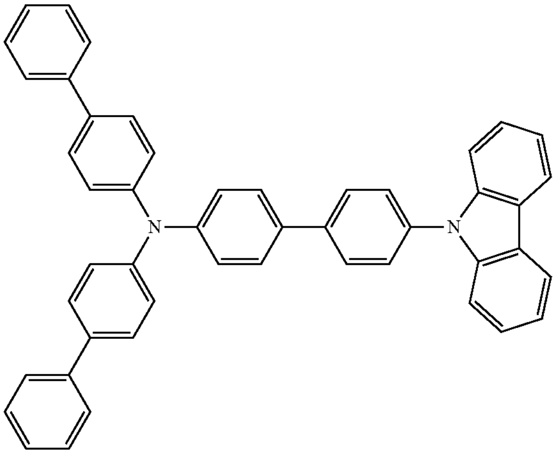
-continued
HT-3
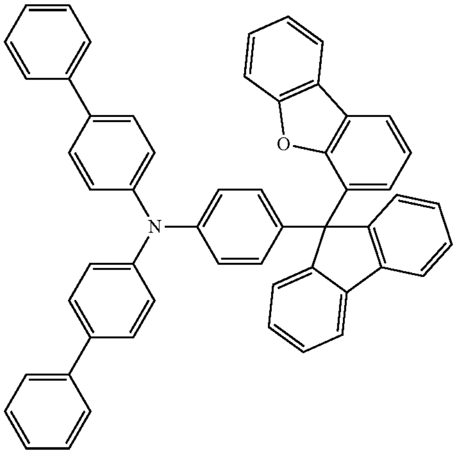
HT-4
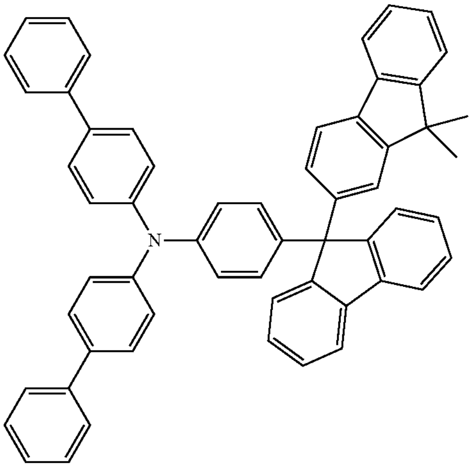
ET-1
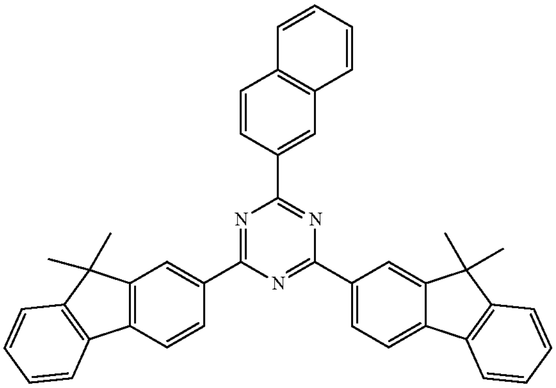
EI-1
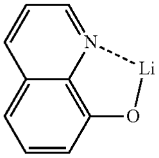

Comparative Examples 1-1 to 1-3: Preparation of an OLED Device Using Only the Second Host Compound as a Host An OLED device was produced in the same manner as in Device Examples 1-1 to 1-6, except for using only the second host compound as a host of the light-emitting layer.

The driving voltage at 1,000 nit, luminous efficiency, CIE color coordinate, and the time taken for the luminance at 5,000 nit to be reduced from 100% to 80% at a constant current of the OLEDs produced as above were measured.

Table 1 below shows the luminous characteristics of the organic electroluminescent devices produced as in the examples above.

TABLE 1

| Device No. | HTL | Host | Dopant | Voltage [V] | Efficiency [cd/A] | Color Coordinate (x, y) | Lifespan [hr] |
|---|---|---|---|---|---|---|---|
| Example 1-1 | HT-1/HT-2 | H1-1: H2-2 | D-96 | 4.4 | 27.5 | 0.664, 0.335 | 1,280 |
| Example 1-2 | HT-1/HT-2 | H1-7: H2-29 | D-96 | 3.9 | 27.7 | 0.665, 0.332 | 550 |
| Example 1-3 | HT-1/HT-2 | H1-19: H2-29 | D-96 | 4.1 | 24.6 | 0.664, 0.332 | 470 |
| Example 1-4 | HT-1/HT-2 | H1-36: H2-154 | D-96 | 4.6 | 27.8 | 0.663, 0.335 | 1,530 |
| Example 1-5 | HT-1/HT-2 | H1-36: H2-29 | D-96 | 3.7 | 28.2 | 0.666, 0.331 | 780 |
| Example 1-6 | HT-1/HT-2 | H1-36: H2-155 | D-96 | 4.6 | 26.9 | 0.664, 0.335 | 970 |
| Comp. Ex. 1-1 | HT-1/HT-2 | H2-2 | D-96 | 4.1 | 28.2 | 0.662, 0.337 | 300 |
| Comp. Ex. 1-2 | HT-1/HT-2 | H2-154 | D-96 | 4.5 | 27.1 | 0.662, 0.337 | 420 |
| Comp. Ex. 1-3 | HT-1/HT-2 | H2-29 | D-96 | 3.6 | 27.5 | 0.668, 0.331 | 310 |

Device Examples 2-1 to 2-7: Preparation of an OLED Device by Co-Evaporating the First Host Compound and the Second Host Compound of the Present Invention An OLED device was produced in the same manner as in Device Examples 1-1 to 1-6, except for forming the second hole injection layer of 3 nm; forming the first hole transport layer of 40 nm; not forming the second hole transport layer; doping compound D-25 as the dopant of the light-emitting layer in a doping amount of 15 wt % based on the total amount of the host and dopant; forming the electron transport layer of 35 nm by evaporating 2,4-bis(9,9-dimethyl-9H-fluoren-2-yl)-6-(naphthalen-2-yl)-1,3,5-triazine and lithium quinolate at a rate of 4:6; and using other combinations for the first host compound and the second host compound used in the host of the light-emitting layer.

Device Examples 2-8 to 2-9: Preparation of an OLED Device by Co-Evaporating the First Host Compound and the Second Host Compound of the Present Invention An OLED device was produced in the same manner as in Device Examples 1-1 to 1-6, except for forming the second hole injection layer of 3 nm; forming the first hole transport layer of 40 nm; not forming the second hole transport layer; doping compound D-1 as the dopant of the light-emitting layer in a doping amount of 15 wt % based on the total amount of the host and dopant; forming the electron transport layer of 35 nm by evaporating 2,4-bis(9,9-dimethyl-9H-fluoren-2-yl)-6-(naphthalen-2-yl)-1,3,5-triazine and lithium quinolate at a rate of 4:6; and using other combinations for the first host compound and the second host compound used in the host of the light-emitting layer.

Device Example 2-10: Preparation of an OLED Device by Co-Evaporating the First Host Compound and the Second Host Compound of the Present Invention An OLED device was produced in the same manner as in Device Examples 1-1 to 1-6, except for forming the second hole injection layer of 3 nm; forming the first hole transport layer of 40 nm; not forming the second hole transport layer; doping compound D-136 as the dopant of the light-emitting layer in a doping amount of 15 wt % based on the total amount of the host and dopant; forming the electron transport layer of 35 nm by evaporating 2,4-bis(9,9-dimethyl-9H-fluoren-2-yl)-6-(naphthalen-2-yl)-1,3,5-triazine and lithium quinolate at a rate of 4:6; and using other combinations for the first host compound and the second host compound used in the host of the light-emitting layer.

Device Examples 3-1 to 3-3: Preparation of an OLED Device by Co-Evaporating the First Host Compound and the Second Host Compound of the Present Invention An OLED device was produced in the same manner as in Device Examples 2-1 to 2-7, except for forming the first hole injection layer of 10 nm; forming the second hole transport layer of 30 nm using compound HT-3; using compound D-136 as the dopant of the light-emitting layer; and using other combinations for the first host compound and the second host compound used in the host of the light-emitting layer.

Device Example 3-4: Preparation of an OLED Device by Co-Evaporating the First Host Compound and the Second Host Compound of the Present Invention An OLED device was produced in the same manner as in Device Examples 2-1 to 2-7, except for forming the first hole injection layer of 10 nm; forming the second hole transport layer of 30 nm using compound HT-3; using compound D-168 as the dopant of the light-emitting layer; and using other combinations for the first host compound and the second host compound used in the host of the light-emitting layer.

Comparative Examples 2-1 to 2-3: Preparation of an OLED Device Using Only the First Host Compound as a Host An OLED device was produced in the same manner as in Device Examples 2-1 to 2-7, except for using only the first host compound as a host of the light-emitting layer.

Comparative Examples 3-1 to 3-3: Preparation of an OLED Device Using Only the Second Host Compound as a Host An OLED device was produced in the same manner as in Device Examples 2-1 to 2-7, except for using only the second host compound as a host of the light-emitting layer.

Comparative Examples 3-4 to 3-6: Preparation of an OLED Device Using Only the Second Host Compound as a Host An OLED device was produced in the same manner as in Device Examples 2-8 to 2-9, except for using only the second host compound as a host of the light-emitting layer.

Comparative Examples 4-1 to 4-3: Preparation of an OLED Device Using Only the Second Host Compound as a Host An OLED device was produced in the same manner as in Device Examples 3-1 to 3-3, except for using only the second host compound as a host of the light-emitting layer.

The driving voltage at 1,000 nit, luminous efficiency, CIE color coordinate, and the time taken for the luminance at 15,000 nit to be reduced from 100% to 80% at a constant current of the OLEDs produced as above were measured.

Table 2 below shows the luminous characteristics of the organic electroluminescent devices produced as in the examples above.

TABLE 2

| Device No. | HTL | Host | Dopant | Voltage [V] | Efficiency [cd/A] | Color Coordinate (x, y) | Lifespan [hr] |
|---|---|---|---|---|---|---|---|
| Example 2-1 | HT-1 | H1-1: H2-25 | D-25 | 3.2 | 49.8 | 0.301, 0.658 | 350 |
| Example 2-2 | HT-1 | H1-1: H2-31 | D-25 | 3 | 57.1 | 0.308, 0.655 | 380 |
| Example 2-3 | HT-1 | H1-1: H2-48 | D-25 | 2.9 | 56.8 | 0.305, 0.656 | 400 |
| Example 2-4 | HT-1 | H1-1: H2-101 | D-25 | 3 | 55.5 | 0.303, 0.657 | 230 |
| Example 2-5 | HT-1 | H1-1: H2-34 | D-25 | 3.1 | 58.1 | 0.306, 0.655 | 440 |
| Example 2-6 | HT-1 | H1-4: H2-31 | D-25 | 3 | 53.3 | 0.304, 0.656 | 120 |
| Example 2-7 | HT-1 | H1-37: H2-31 | D-25 | 3 | 53.7 | 0.306, 0.655 | 300 |
| Example 2-8 | HT-1 | H1-1: H2-31 | D-1 | 2.9 | 53 | 0.321, 0.656 | 560 |
| Example 2-9 | HT-1 | H1-1: H2-48 | D-1 | 2.8 | 55.3 | 0.319, 0.657 | 550 |
| Example 2-10 | HT-1 | H1-113: H2-31 | D-136 | 2.8 | 59.4 | 0.331, 0.655 | 600 |
| Example 3-1 | HT-1/HT-3 | H1-1: H2-48 | D-136 | 3.1 | 67.5 | 0.326, 0.658 | 590 |
| Example 3-2 | HT-1/HT-3 | H1-1: H2-273 | D-136 | 3.1 | 66.2 | 0.328, 0.657 | 700 |
| Example 3-3 | HT-1/HT-3 | H1-113: H2-125 | D-136 | 3.1 | 65.8 | 0.329, 0.657 | 700 |
| Example 3-4 | HT-1/HT-3 | H1-1: H2-273 | D-168 | 3.0 | 57.2 | 0.288, 0.665 | 450 |
| Comp. Ex. 2-1 | HT-1 | H1-1 | D-25 | 6.8 | 3.1 | 0.301, 0.653 | × |
| Comp. Ex. 2-2 | HT-1 | H1-4 | D-25 | 7.2 | 3.6 | 0.295, 0.658 | × |
| Comp. Ex. 2-3 | HT-1 | H1-37 | D-25 | 7.0 | 3.0 | 0.302, 0.653 | × |
| Comp. Ex. 3-1 | HT-1 | H2-31 | D-25 | 2.9 | 42.8 | 0.314, 0.652 | 100 |
| Comp. Ex. 3-2 | HT-1 | H2-101 | D-25 | 2.8 | 50.3 | 0.315, 0.651 | 60 |
| Comp. Ex. 3-3 | HT-1 | H2-34 | D-25 | 2.7 | 49.2 | 0.312, 0.652 | 100 |
| Comp. Ex. 3-4 | HT-1 | H2-31 | D-1 | 2.9 | 33.5 | 0.323, 0.653 | 390 |
| Comp. Ex. 3-5 | HT-1 | H2-48 | D-1 | 2.6 | 41.2 | 0.325, 0.653 | 380 |
| Comp. Ex. 3-6 | HT-1 | H2-87 | D-1 | 2.8 | 37.9 | 0.323, 0.653 | 420 |

TABLE 2-continued

| Device No. | HTL | Host | Dopant | Voltage [V] | Efficiency [cd/A] | Color Coordinate (x, y) | Lifespan [hr] |
|---|---|---|---|---|---|---|---|
| Comp. Ex. 4-1 | HT-1/HT-3 | H2-48 | D-136 | 2.6 | 51.9 | 0.334, 0.652 | 490 |
| Comp. Ex. 4-2 | HT-1/HT-3 | H2-125 | D-136 | 3.0 | 64.9 | 0.337, 0.649 | 360 |
| Comp. Ex. 4-3 | HT-1/HT-3 | H2-273 | D-136 | 3.3 | 68.2 | 0.332, 0.654 | 440 |

Device Example 4-1: Preparation of an OLED Device by Co-Evaporating the First Host Compound and the Second Host Compound of the Present Invention An OLED device was produced in the same manner as in Device Examples 1-1 to 1-6, except for using compound HT-4 for the second hole transport layer, and using the compounds as listed in Table 3 below for the first host compound and the second host compound used in the host of the light-emitting layer.

Comparative Example 5-1: Preparation of an OLED Device Using Only the Second Host Compound as a Host An OLED device was produced in the same manner as in Device Example 4-1, except for using only the second host compound of Table 3 as a host of the light-emitting layer.

The driving voltage at 1,000 nit, luminous efficiency, CIE color coordinate, and the time taken for the luminance at 5,000 nit to be reduced from 100% to 90% at a constant current of the OLEDs produced as above were measured.

Table 3 below shows the luminous characteristics of the organic electroluminescent devices produced as in the examples above.

TABLE 3

| Device No. | HTL | Host | Dopant | Voltage [V] | Efficiency [cd/A] | Color Coordinate (x, y) | Lifespan [hr] |
|---|---|---|---|---|---|---|---|
| Example 4-1 | HT-1/HT-4 | H1-7: H2-41 | D-96 | 3.4 | 30.7 | 0.665, 0.333 | 400 |
| Comp. Ex. 5-1 | HT-1/HT-4 | H2-41 | D-96 | 3.1 | 28.3 | 0.668, 0.331 | 300 |

The organic electroluminescent device of the present invention comprises a light-emitting layer comprising a host and a phosphorus dopant, and the host consists of a specific combination of multi-component host compounds. The device of the present invention provides superior lifespan characteristics to conventional devices.

The invention claimed is:

1. An organic electroluminescent device comprising a hole injection layer, a first hole transport layer, a second hole transport layer and at least one light-emitting layer between an anode and a cathode, wherein the first hole transport layer comprises compounds of a fluorene derivative structure and a mono-amine derivative structure, wherein the light-emitting layer comprises a host and a phosphorescent dopant, the host consists of multi-component host compounds, at least a first host compound of the multi-component host compounds is represented by the following formula 4, 5, or 6, and a second host compound is represented by the following formula 2:

(4)

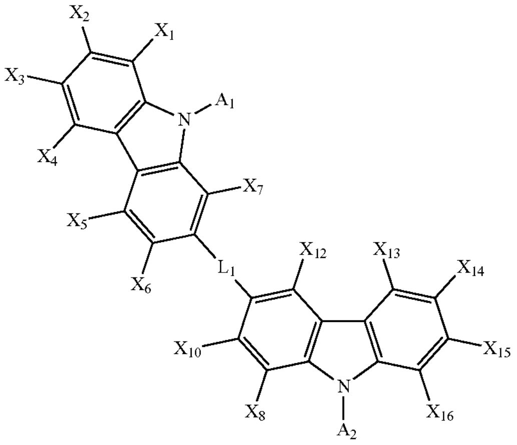

-continued (5)

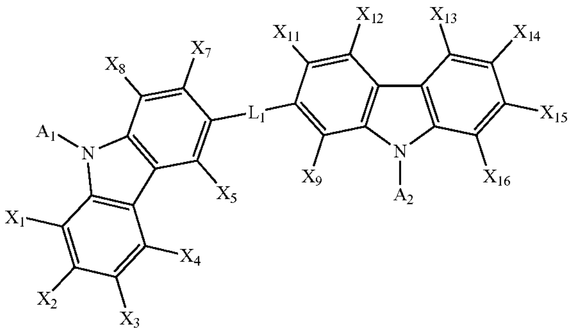

-continued (6)

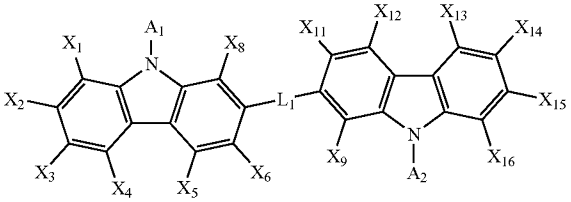

wherein $A_1$ and $A_2$ each independently represent a substituted or unsubstituted (C6-C30) aryl;

$L_1$ is represented by formula 7:

(7)

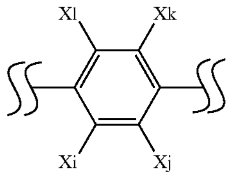

Xi to XI each independently represent hydrogen or deuterium;

$X_1$ to $X_{16}$ each independently represent hydrogen, or deuterium;

(2)

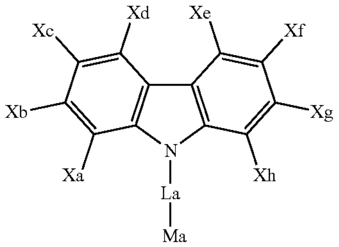

wherein

Ma represents a substituted triazinyl;

La represents a single bond, or one of the following formulae 7 and 8:

(7)

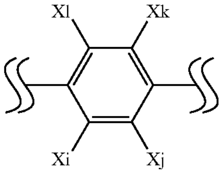

(8)

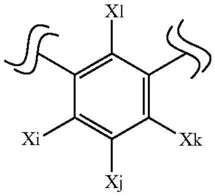

Xi to XI each independently represent hydrogen or deuterium;

Xa to Xh each independently represent hydrogen, deuterium, a halogen, a cyano, a substituted or unsubstituted (C1-C30)alkyl, a substituted or unsubstituted (C2-C30) alkenyl, a substituted or unsubstituted (C2-C30)alkynyl, a substituted or unsubstituted (C3-C30) cycloalkyl, a substituted or unsubstituted (C6-C60) aryl, a substituted or unsubstituted (3- to 30-membered) heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, or a substituted or unsubstituted mono- or di-(C6-C30) arylamino; or are linked to an adjacent substituent(s) to form substituted or unsubstituted benzene, a substituted or unsubstituted indole, or a substituted or unsubstituted benzoindole; and the heteroaryl contains at least one hetero atom selected from B, N, O, S, P(═O), Si, and P.

2. The organic electroluminescent device according to claim 1, wherein in formula 4, 5, or 6, $A_1$ and $A_2$ each independently are selected from the group consisting of phenyl, biphenyl, terphenyl, naphthyl, fluorenyl, phenanthrenyl, anthracenyl, indenyl, triphenylenyl, pyrenyl, tetracenyl, perylenyl, chrysenyl, and fluoranthenyl.

3. The organic electroluminescent device according to claim 1, wherein in formula 2, Xa to Xh each independently represent hydrogen; a cyano; a (C6-C15) aryl unsubstituted or substituted with a tri(C6-C10)arylsilyl; a (10- to 20-membered) heteroaryl unsubstituted or substituted with a (C6-C12) aryl or a cyano (C6-C12) aryl; or an unsubstituted tri(C6-C10)arylsilyl; or are linked to an adjacent substituent(s) to form a substituted or unsubstituted benzene, a substituted or unsubstituted indole, or a substituted or unsubstituted benzoindole.

4. The organic electroluminescent device according to claim 1, wherein the compound represented by formula 2 is selected from the group consisting of:

H2-9

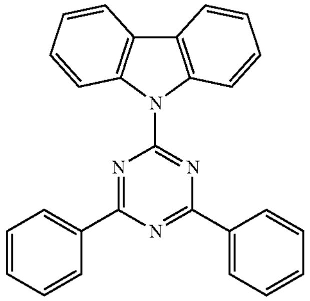

H2-10

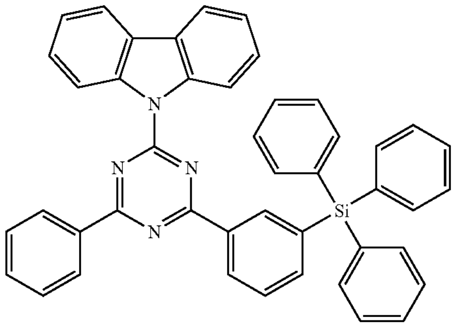

-continued
H2-11
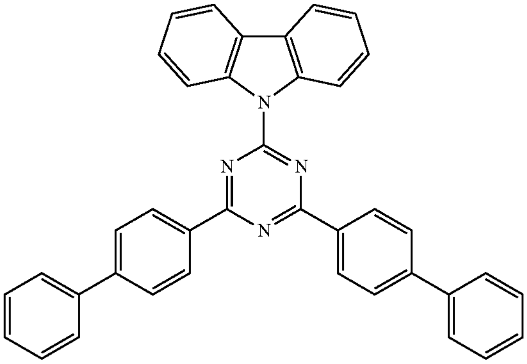
H2-12
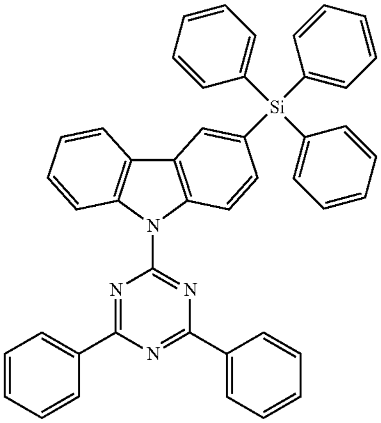
H2-13
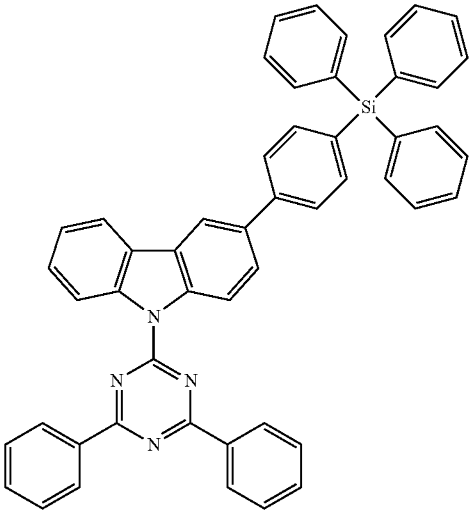
-continued
H2-14
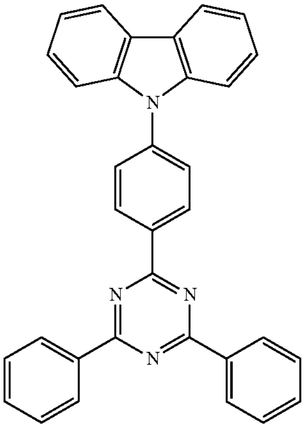
H2-15
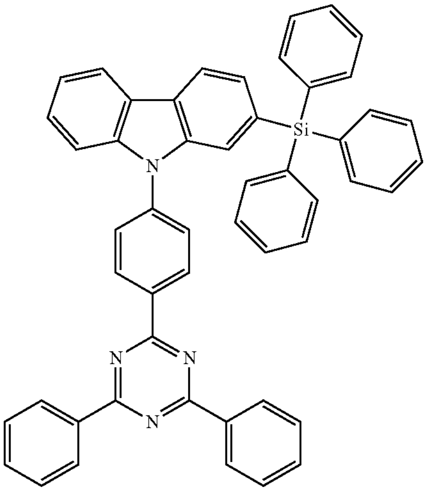
H2-25
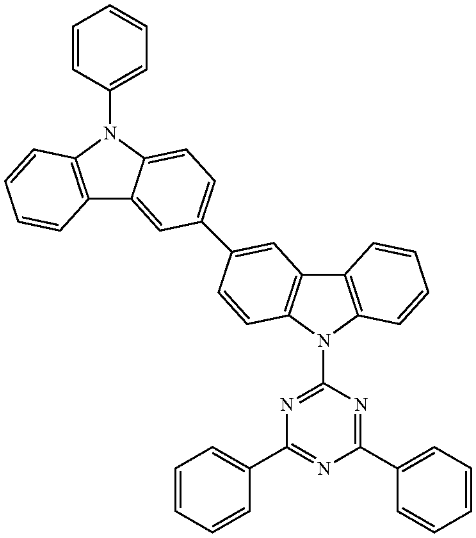

-continued
H2-26
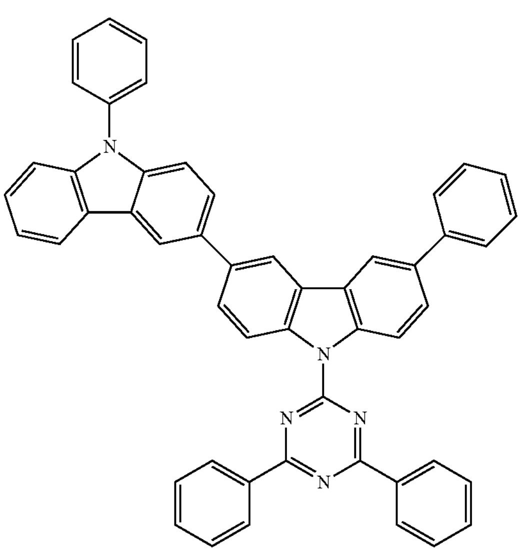
H2-27
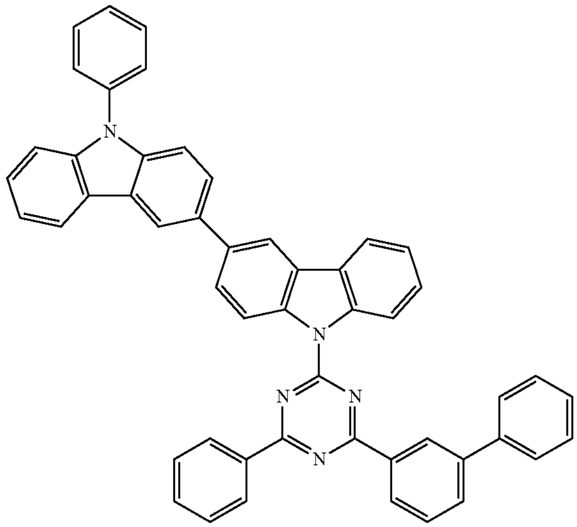
H2-28
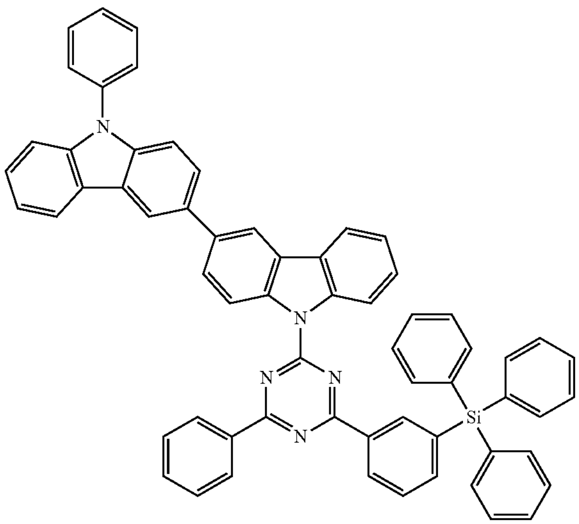
-continued
H2-29
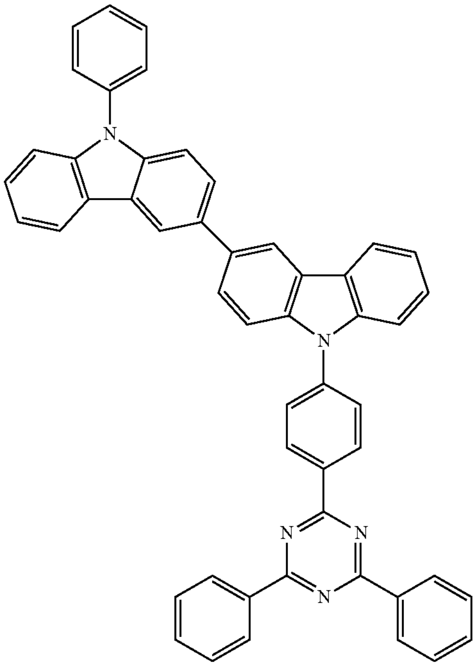
H2-30
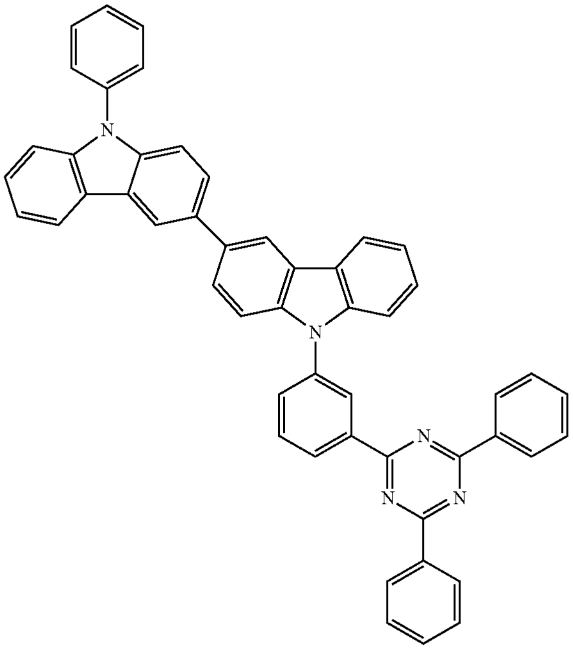

-continued
H2-31
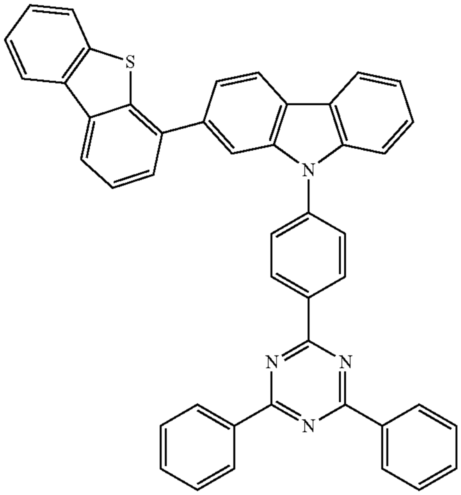
H2-32
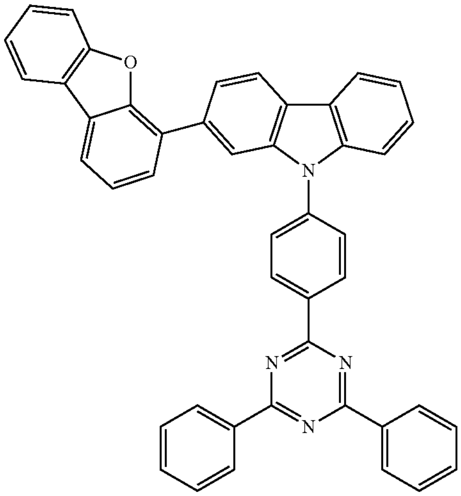
H2-33
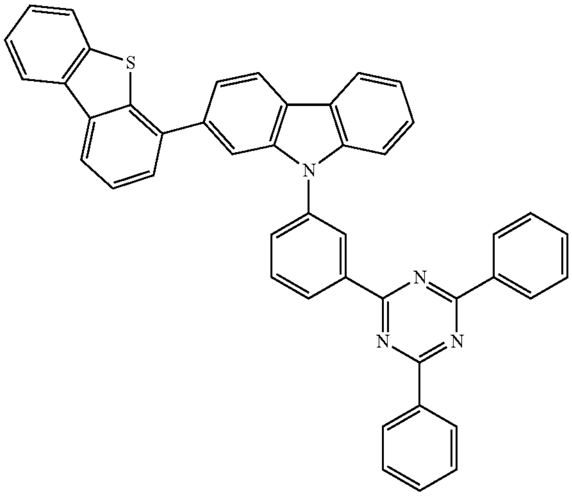
-continued
H2-34
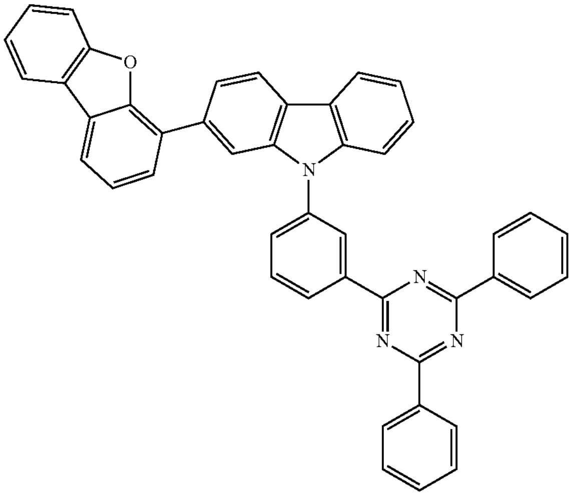
H2-35
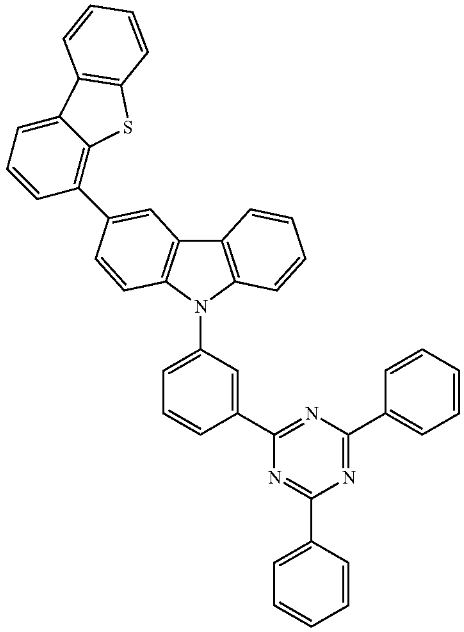
H2-38
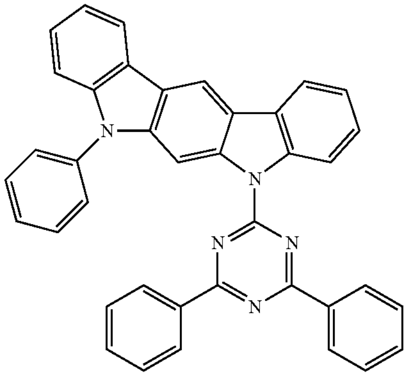

-continued
H2-40
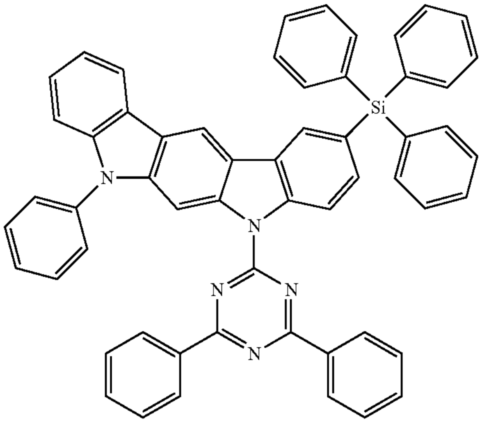
H2-41
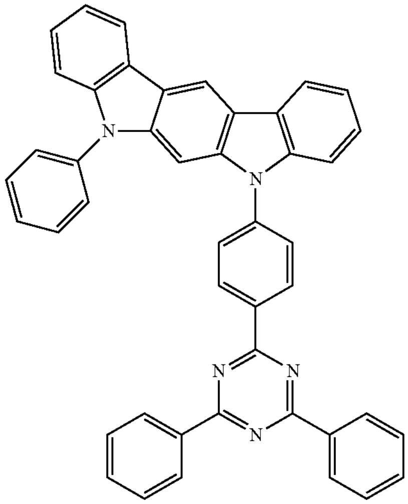
H2--42
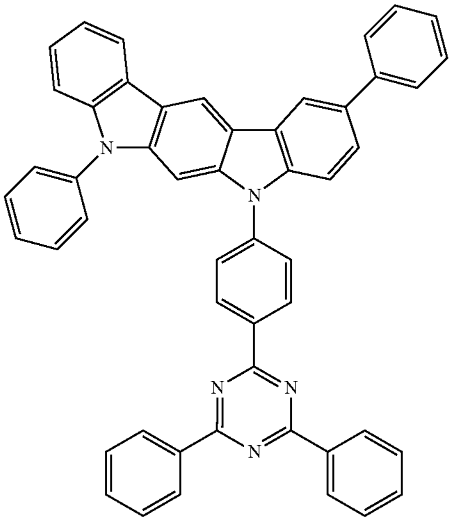
-continued
H2-43
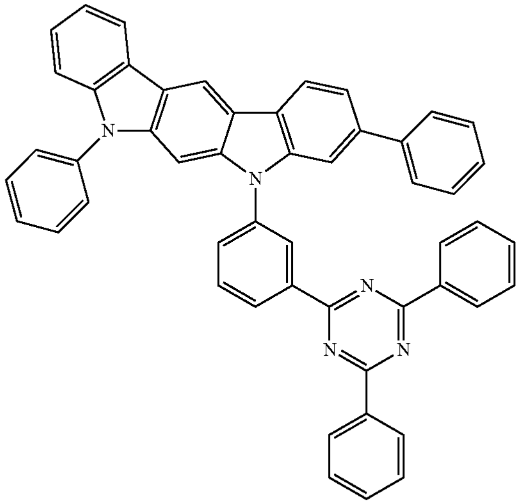
H2-44
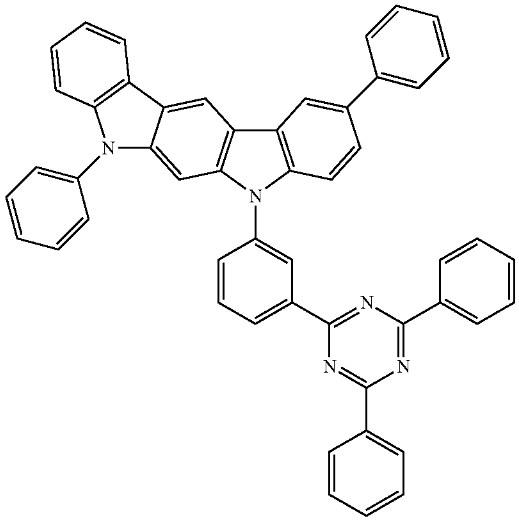
H2-45
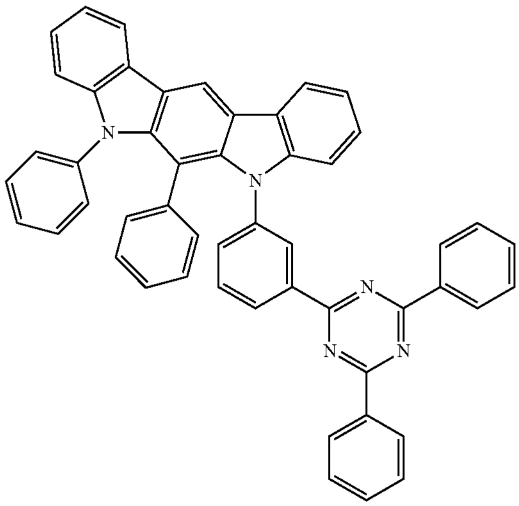

H2-46
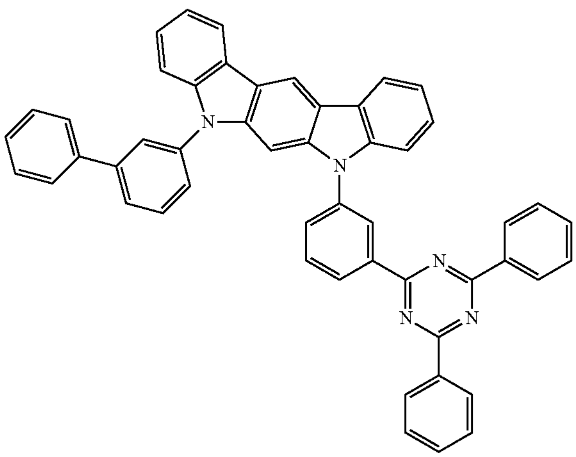
H2-48
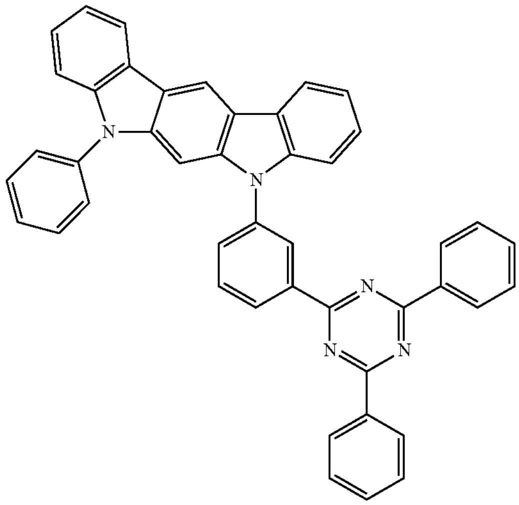
H2-49
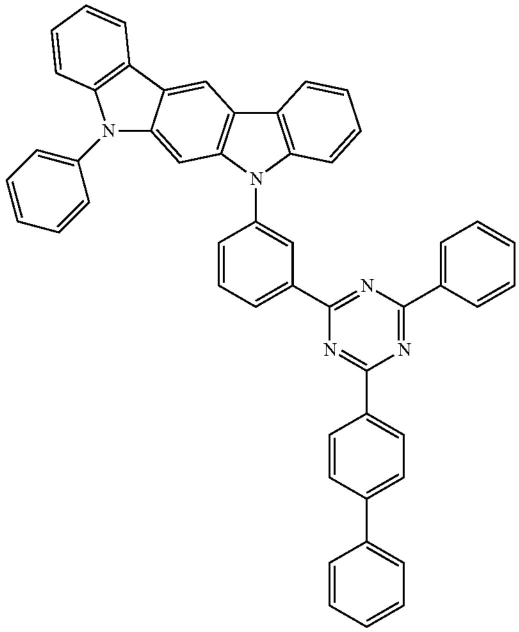
H2-50
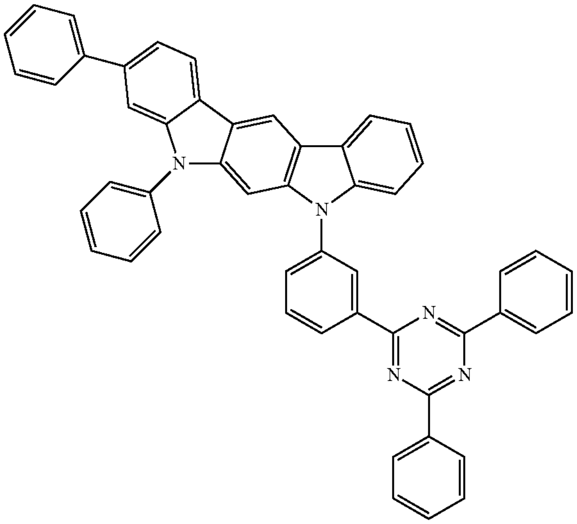
H2-51
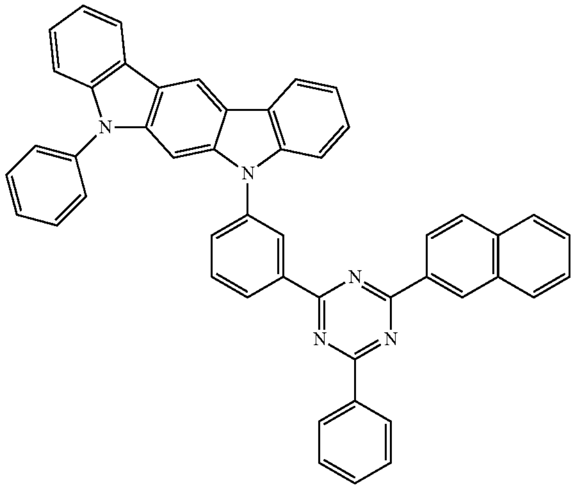
H2-52
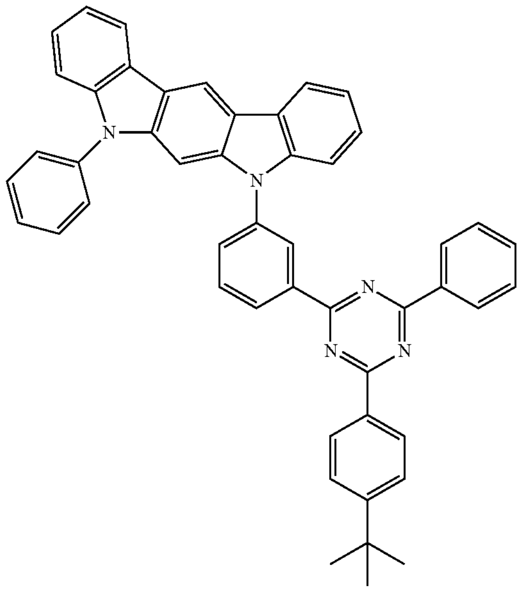

-continued
H2-56
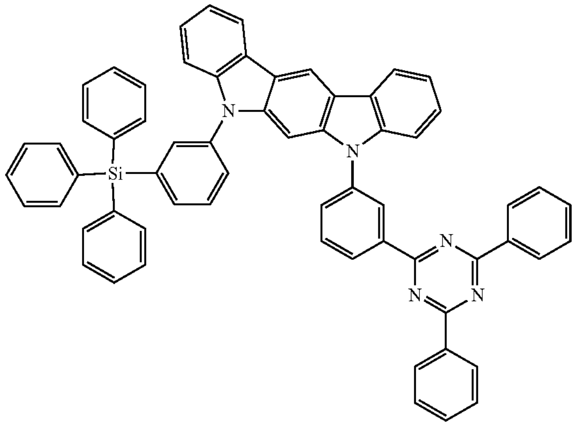
H2-57
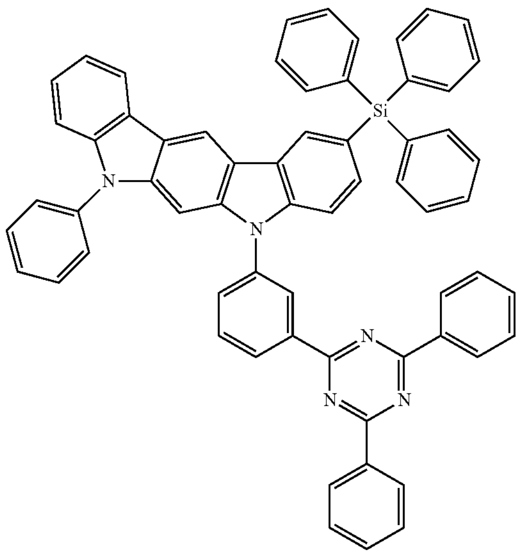
H2-58
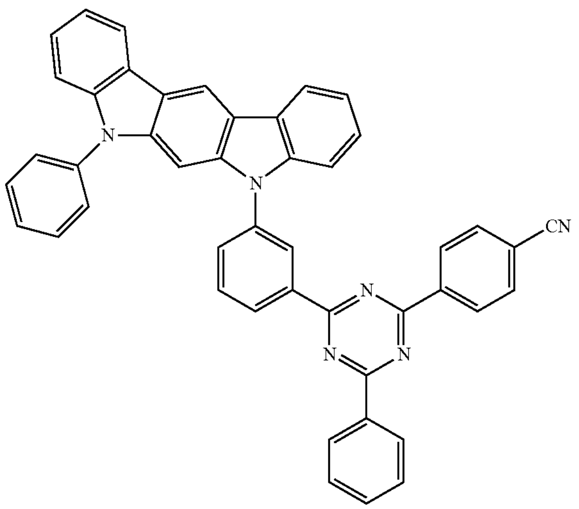
-continued
H2-59
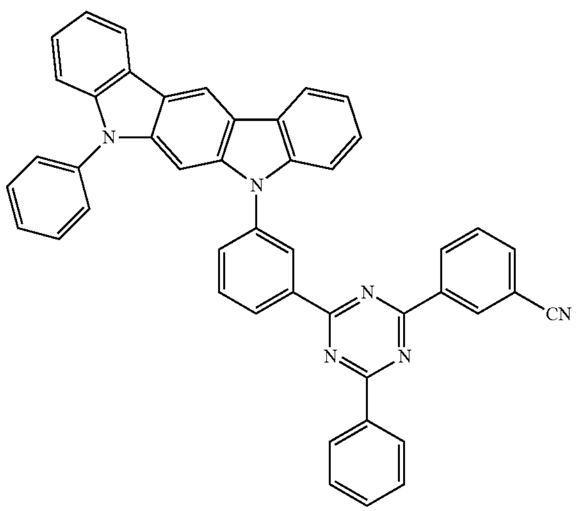
H2-60
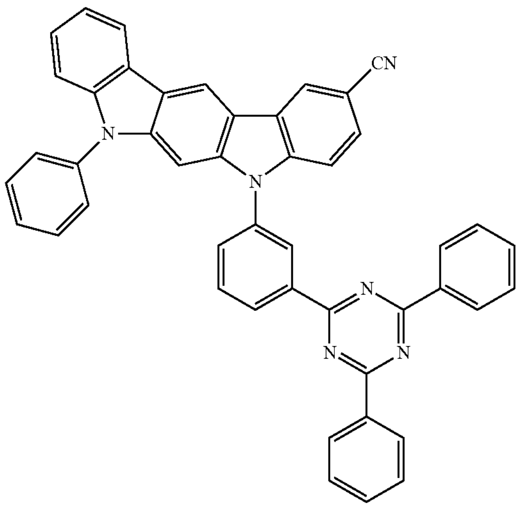
H2-71
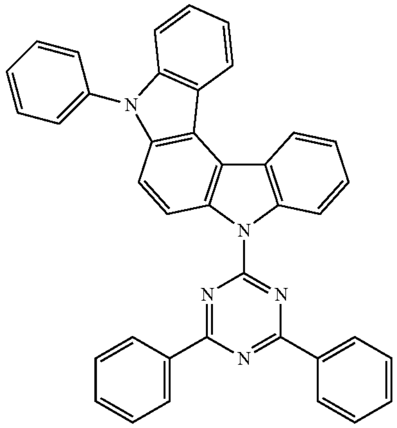

-continued
H2-72
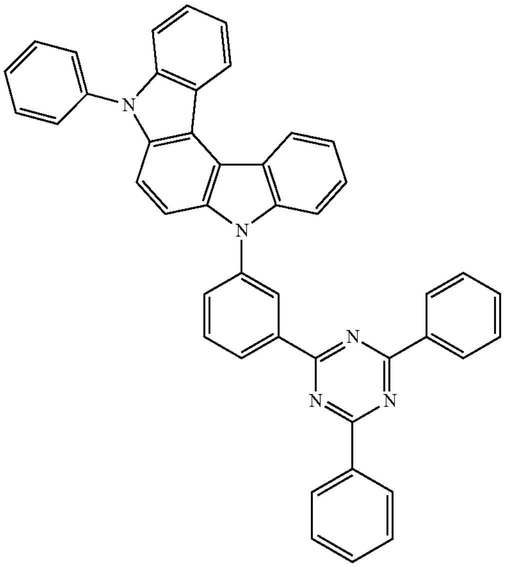
H2-73
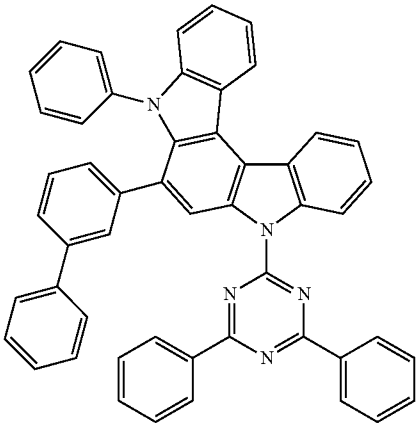
H2-76
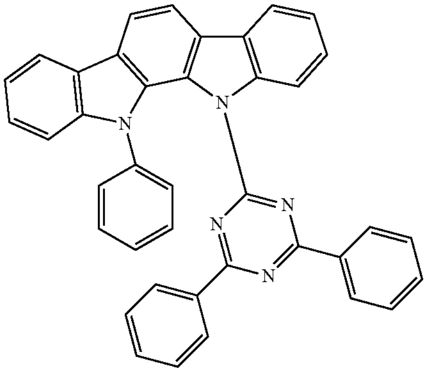
-continued
H2-77
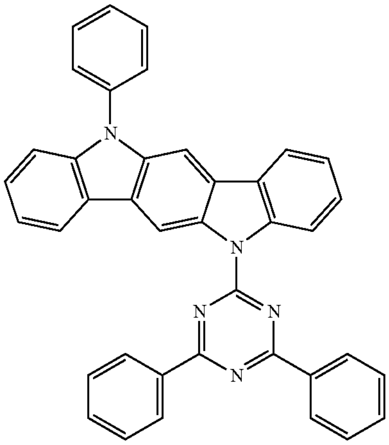
H2-78
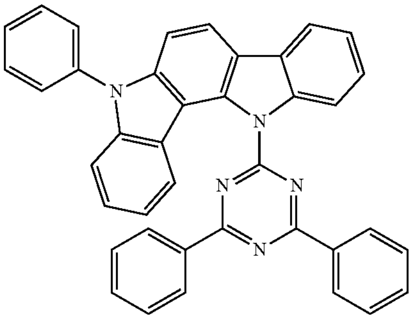
H2-86
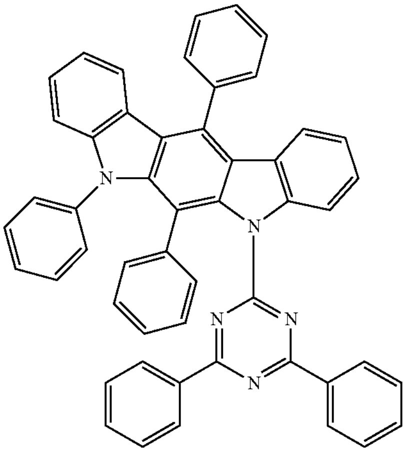

-continued
H2-87
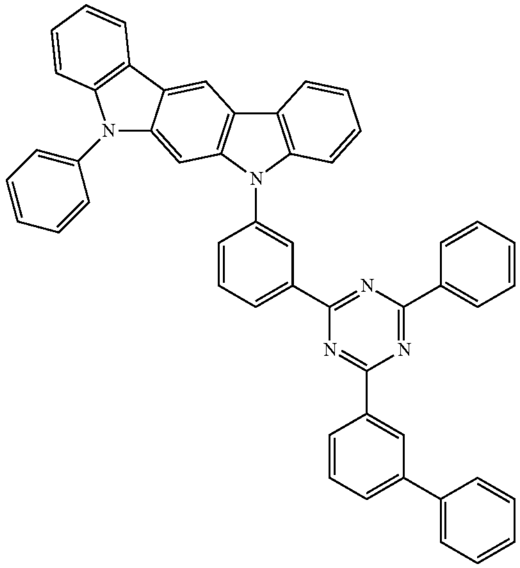
H2-88
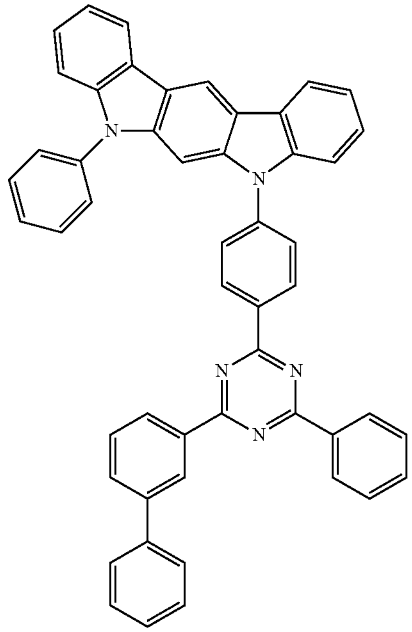
-continued
H2-89
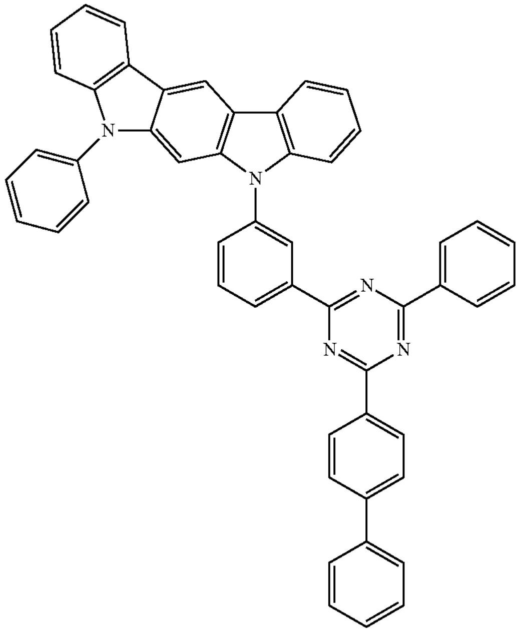
H2-90
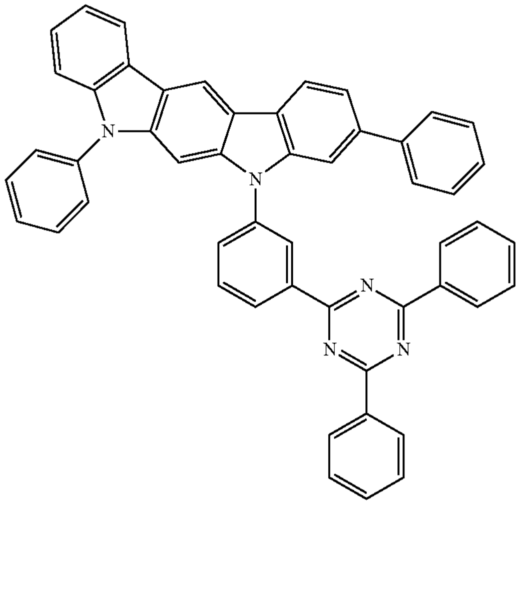

-continued
H2-100
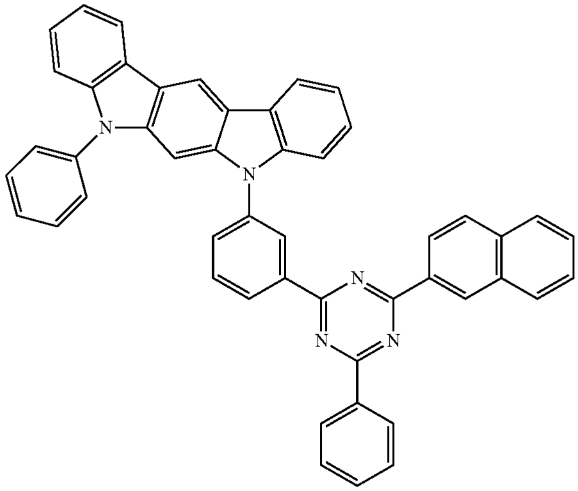
H2-126
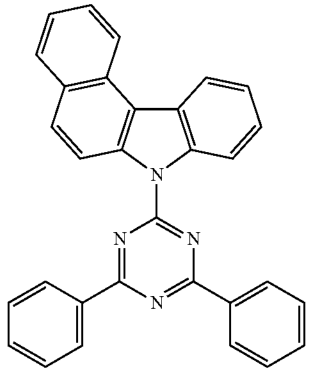
H2-127
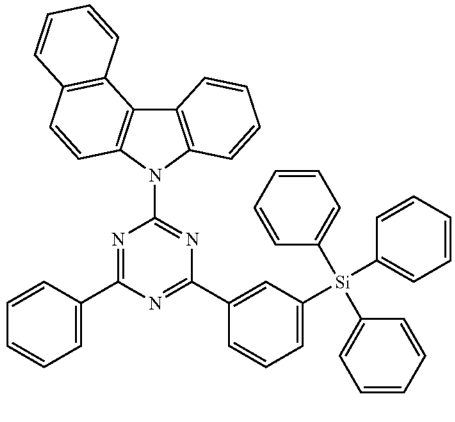
-continued
H2-129
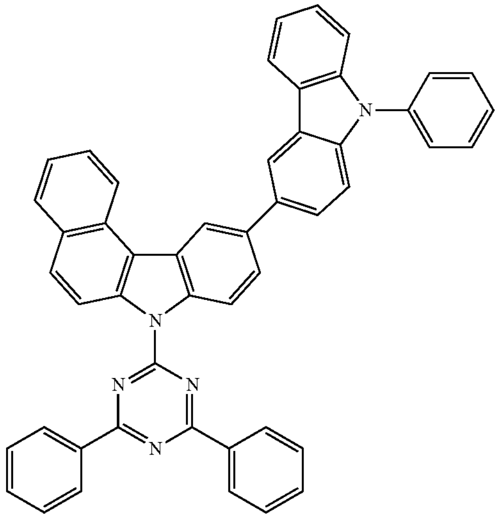
H2-135
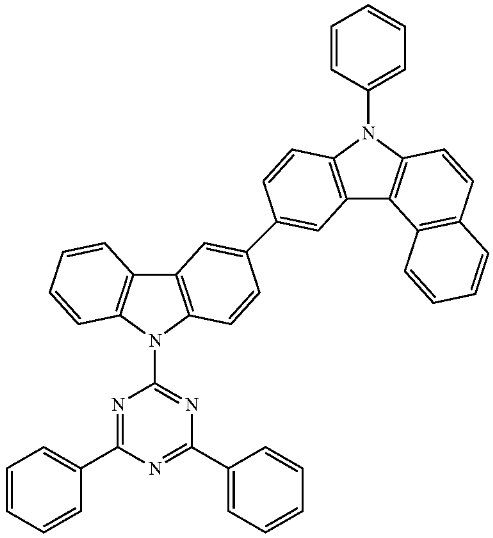
H2-139
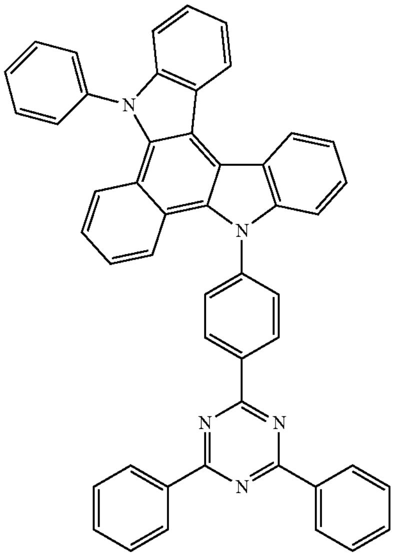

-continued
H2-149
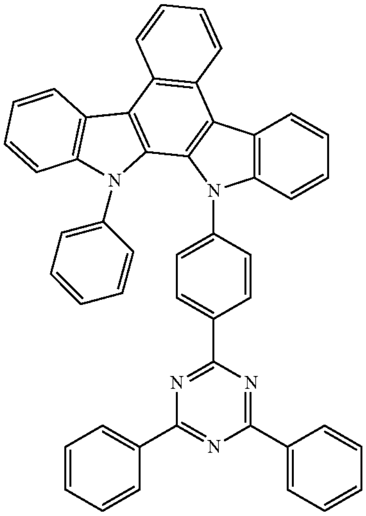
H2-160
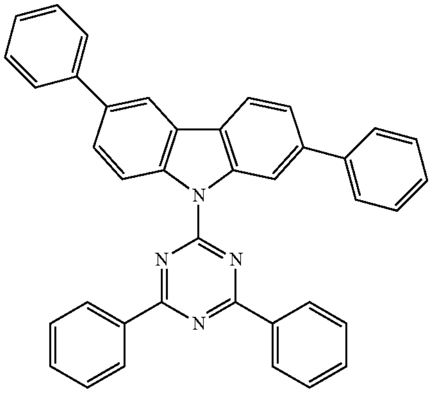
H2-177
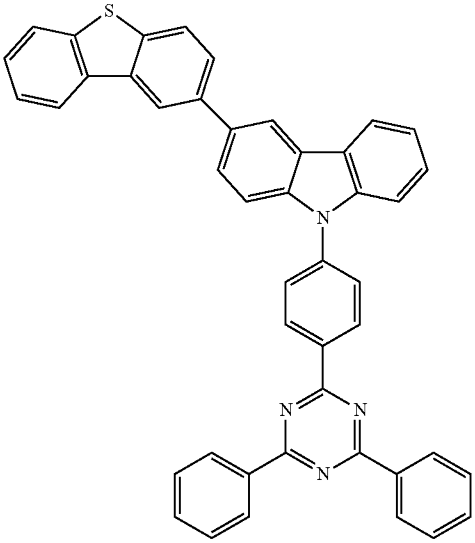
-continued
H2-178
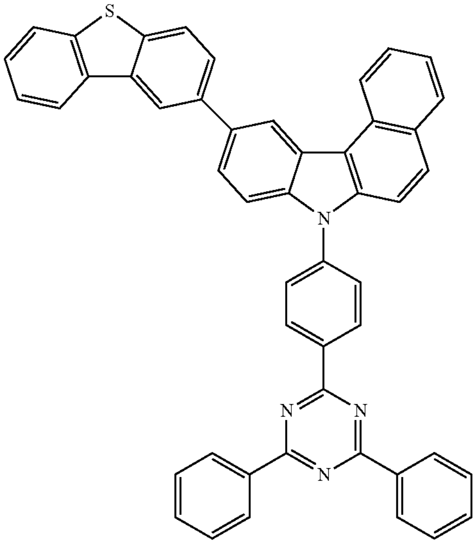
H2-179
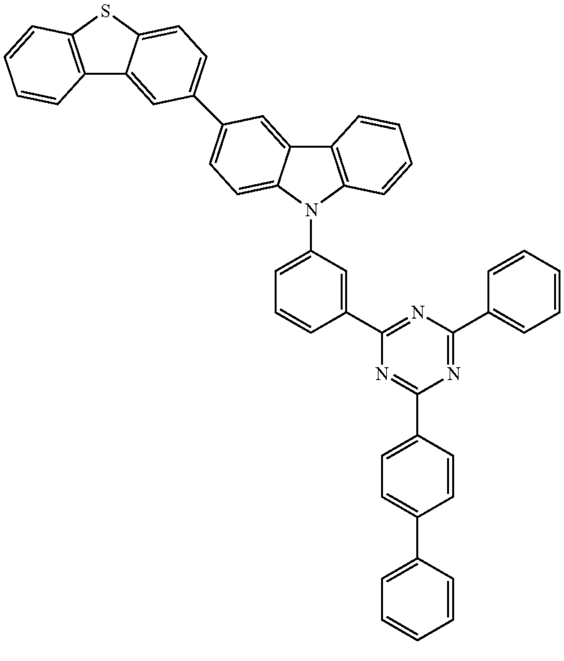

-continued
H2-180
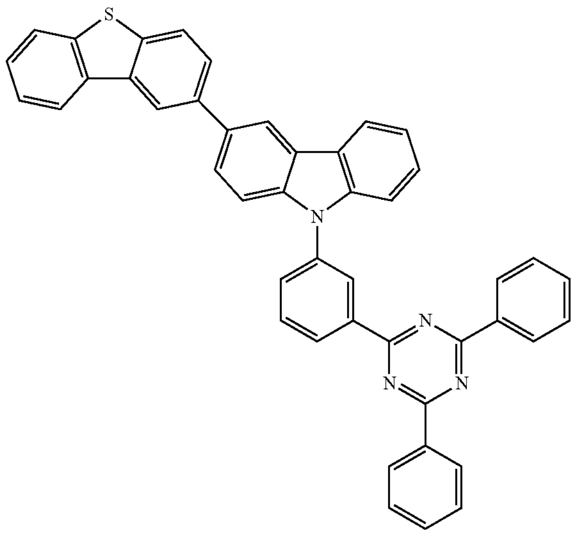
H2-181
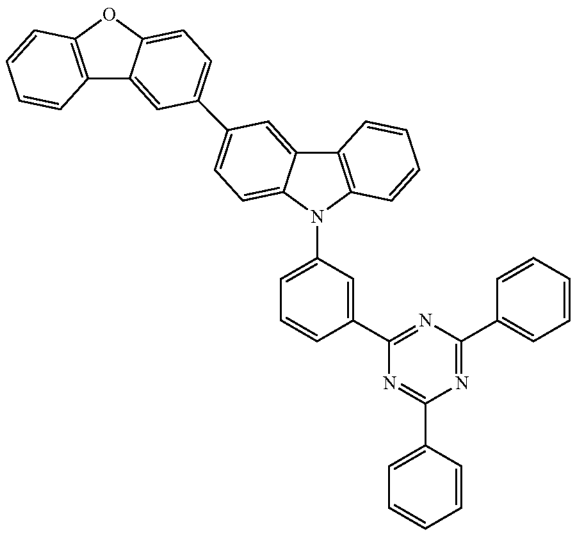
H2-182
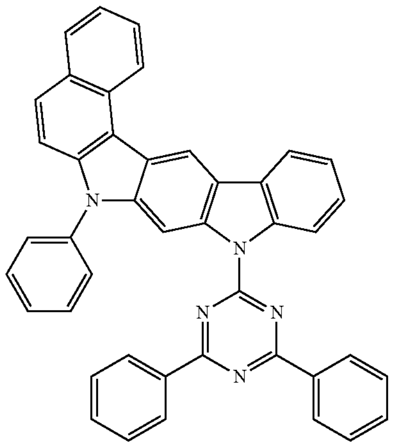
-continued
H2-187
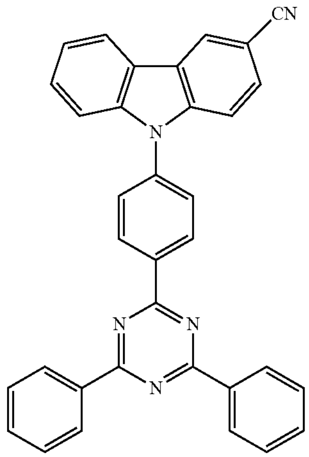
H2-188
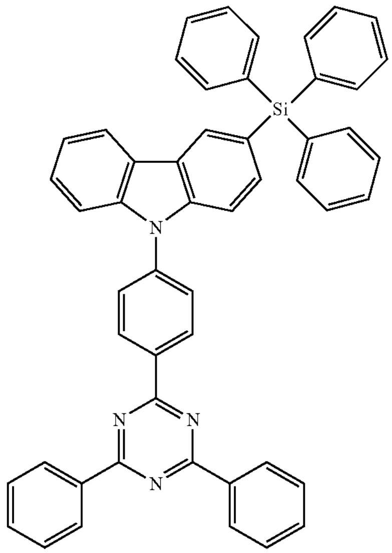
H2-189
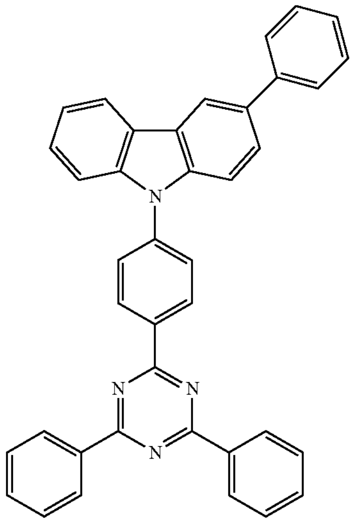

-continued
H2-190
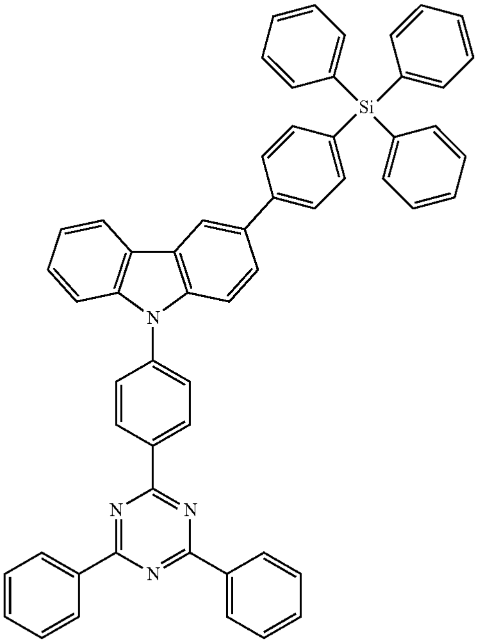
H2-191
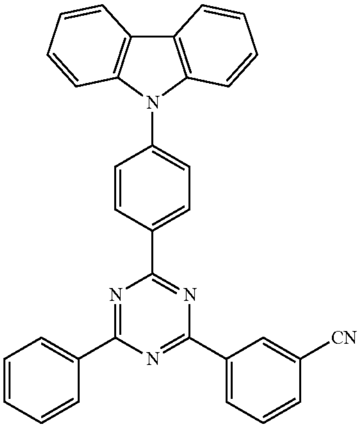
H2-192
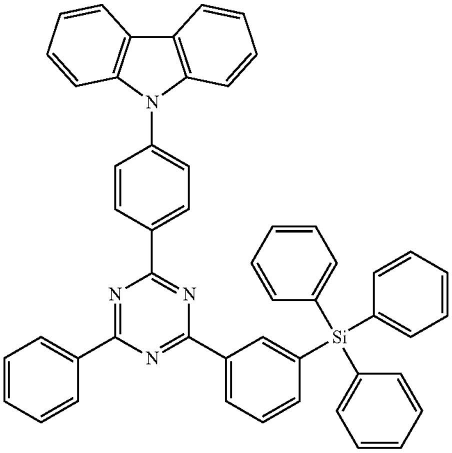
-continued
H2-193
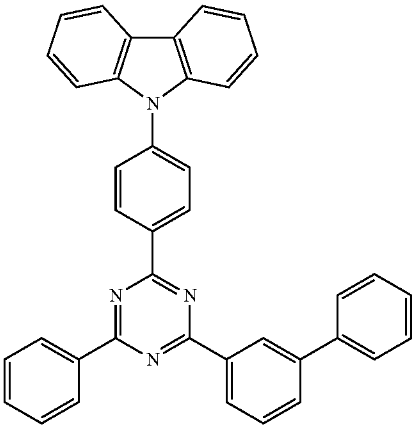
H2-194
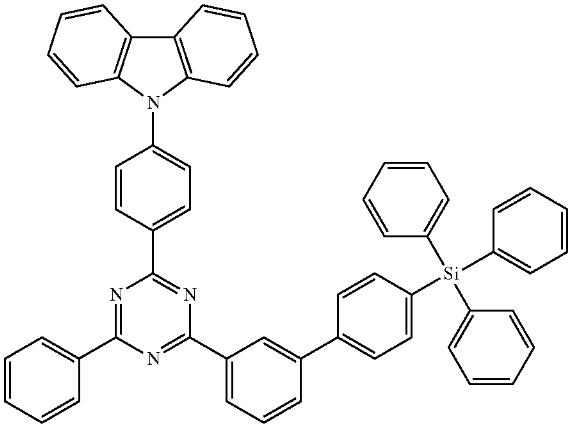
H2-195
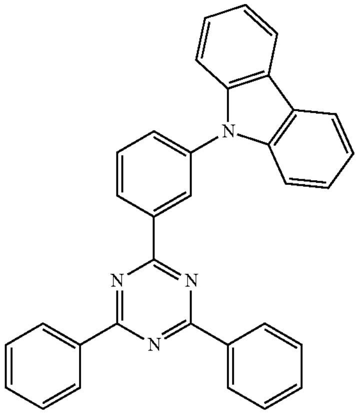

-continued
H2-196
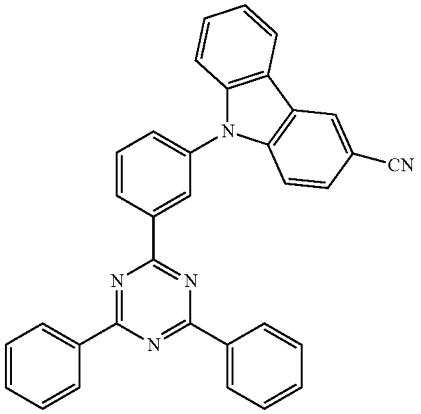
H2-197
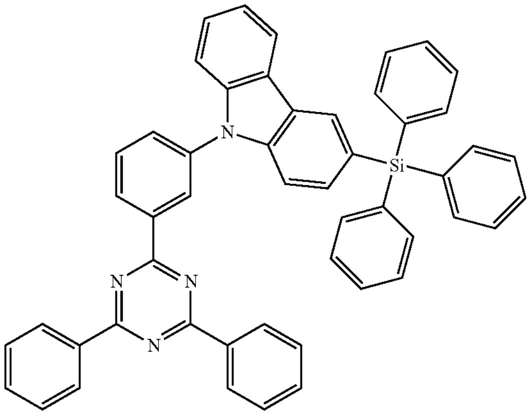
H2-198
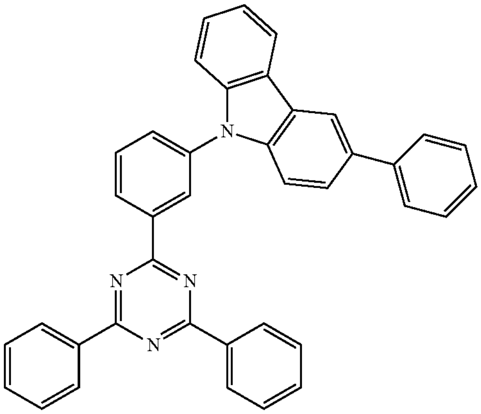
H2-199
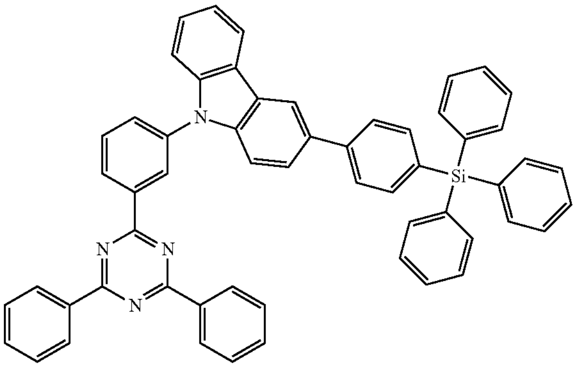
-continued
H2-200
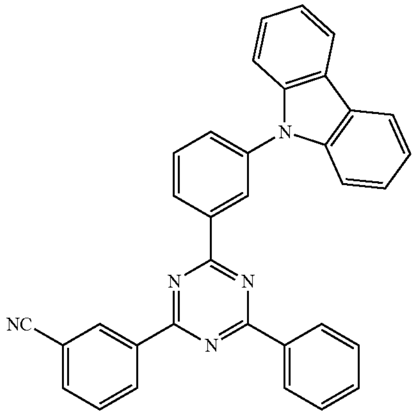
H2-201
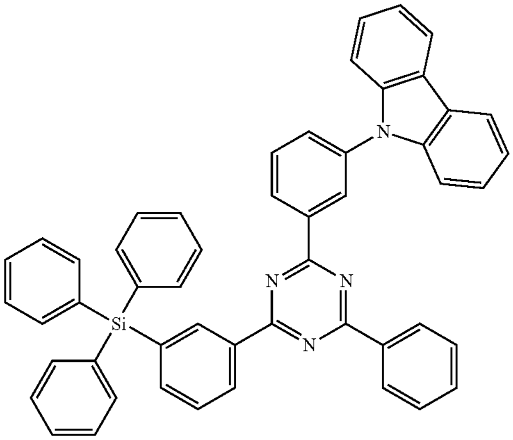
H2-202
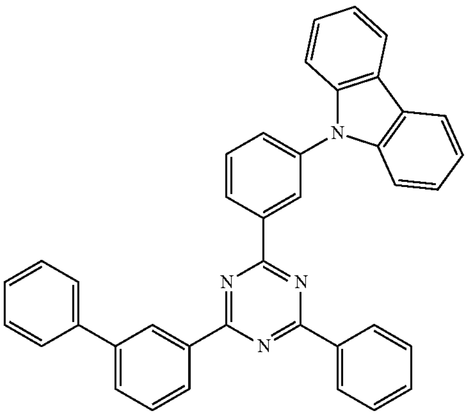

-continued
H2-203
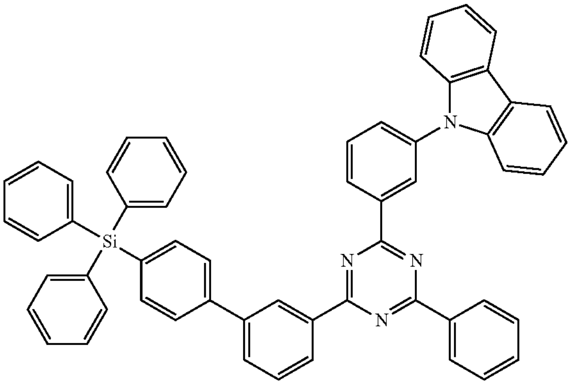
H2-204
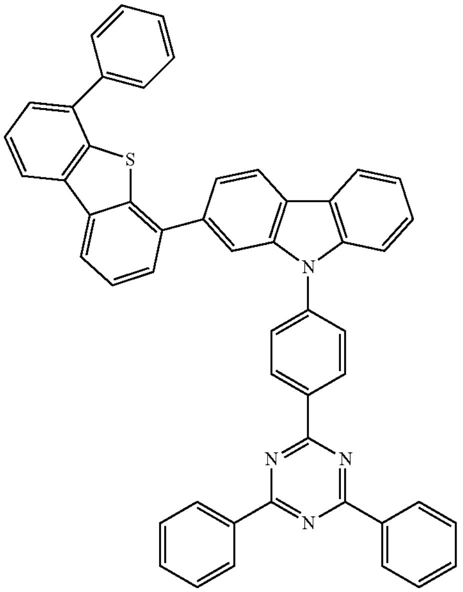
H2-205
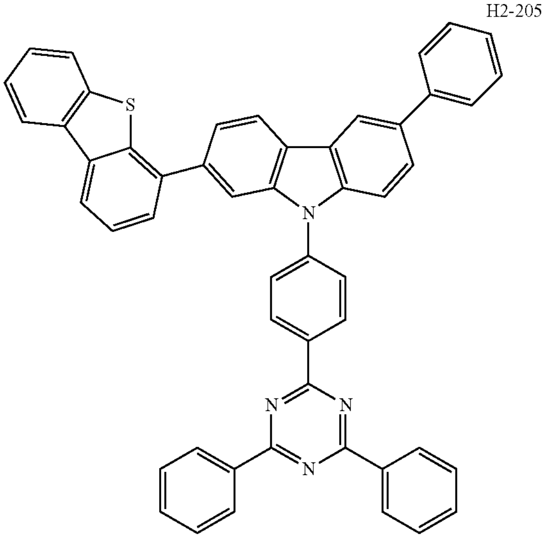
-continued
H2-206
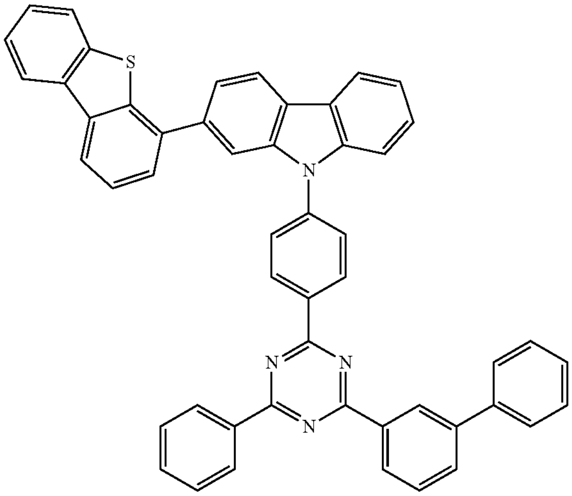
H2-207
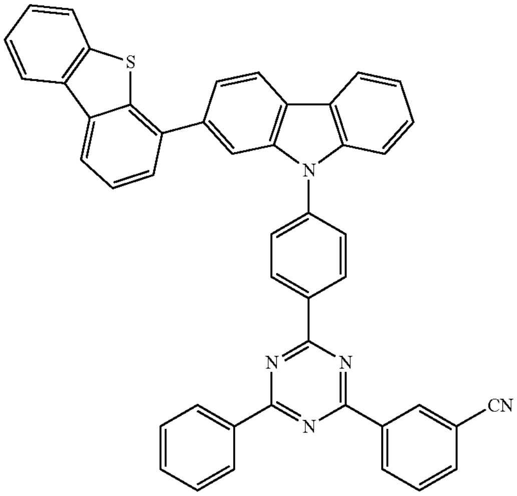
H2-208
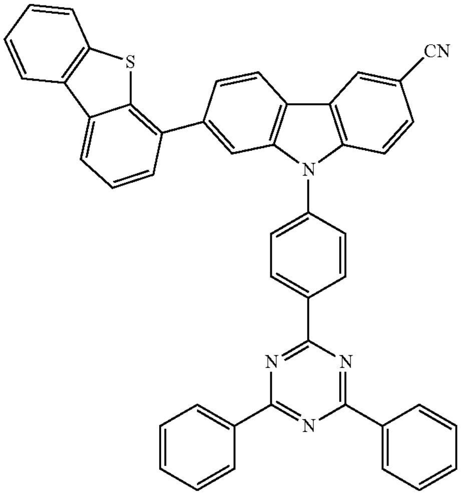

-continued
H2-209
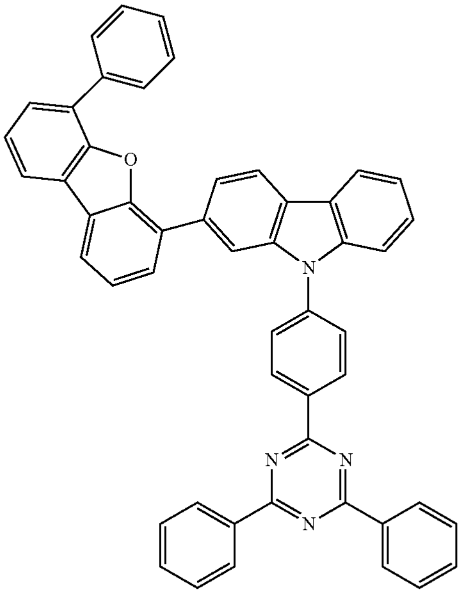
H2-210
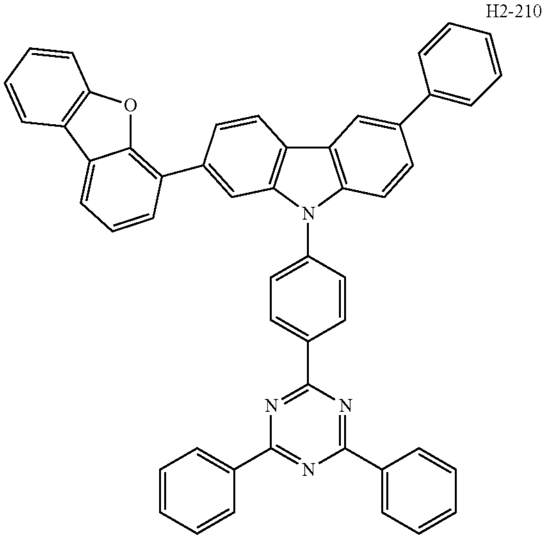
H2-211
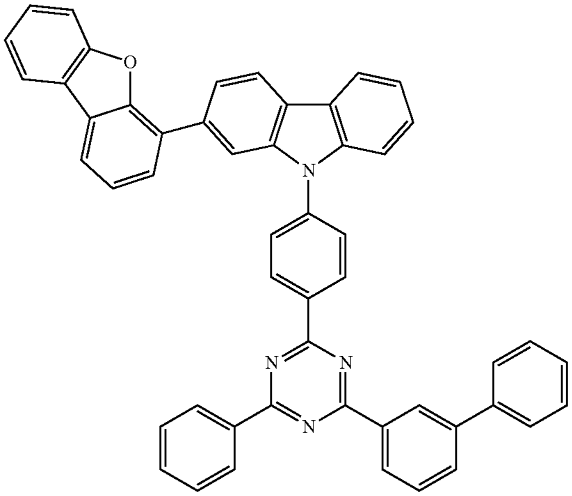
-continued
H2-212
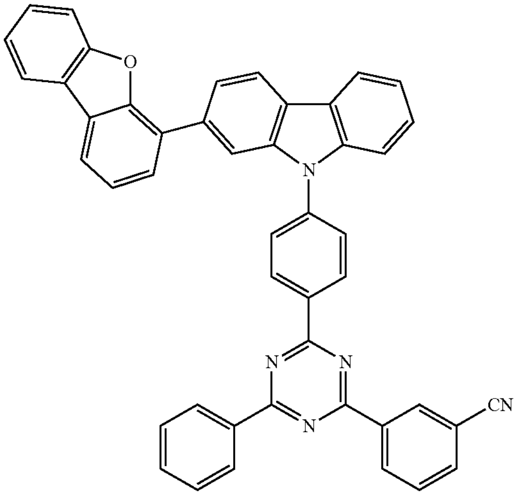
H2-213
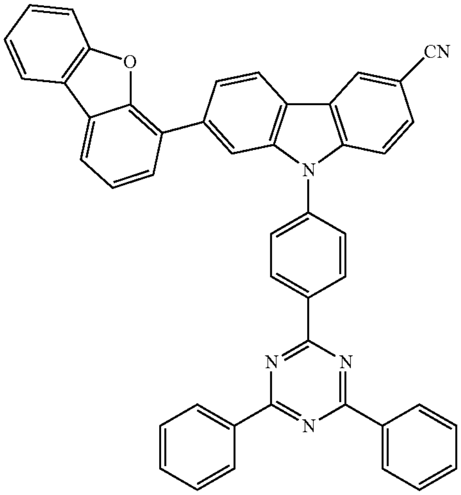
H2-214
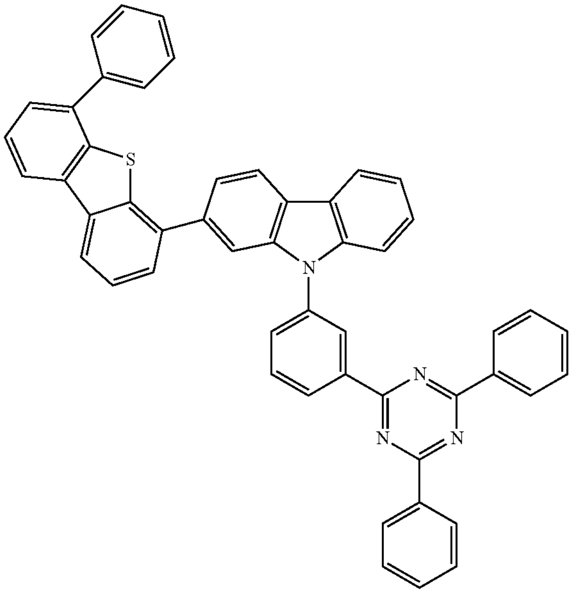

-continued
H2-215
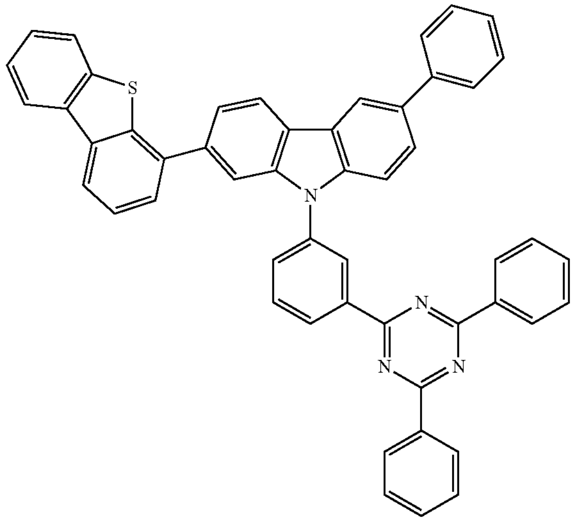
H2-216
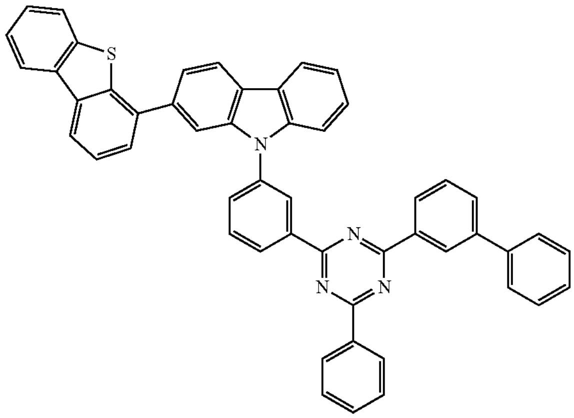
H2-217
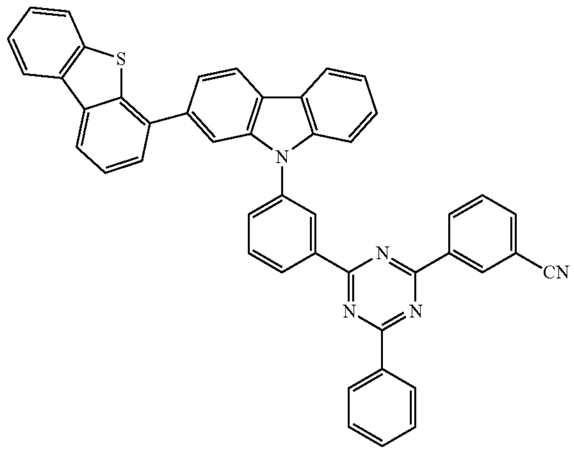
-continued
H2-218
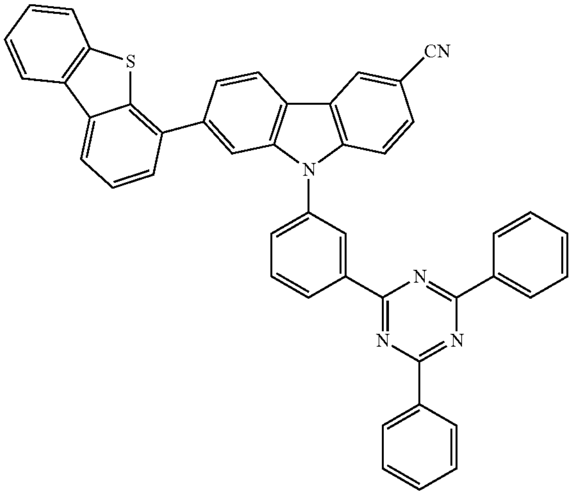
H2-219
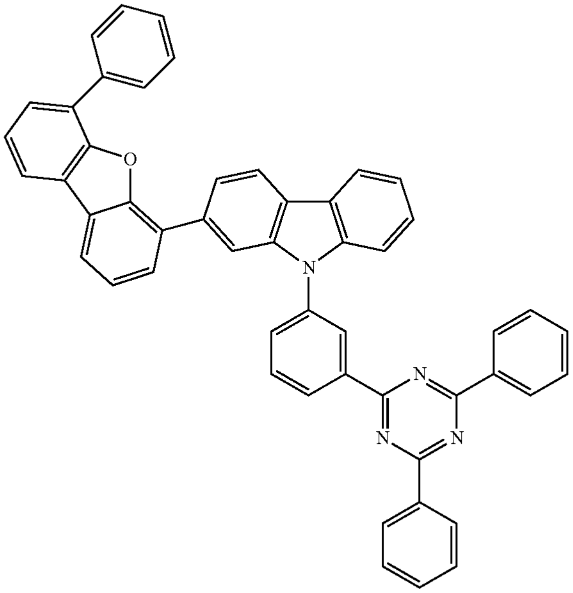
H2-220
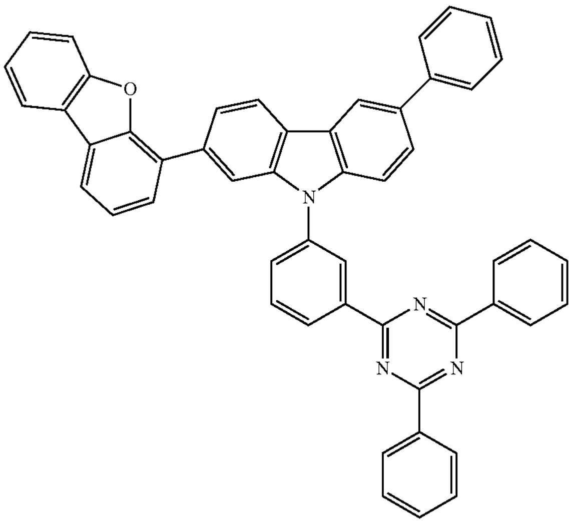

-continued
H2-221
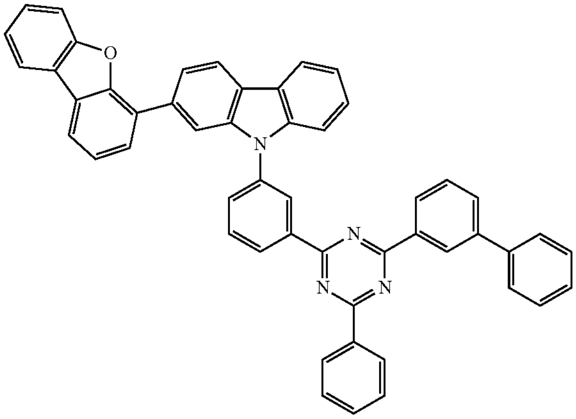
H2-222
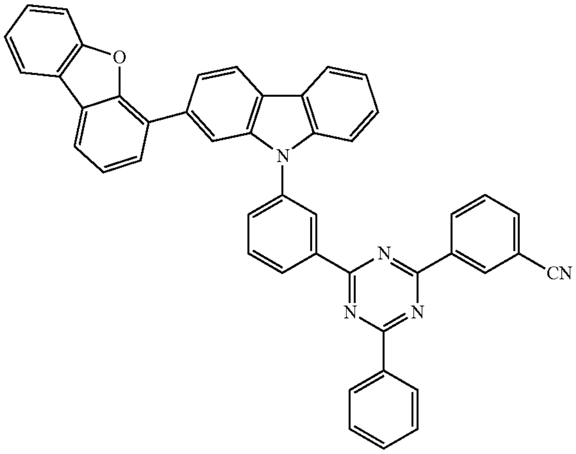
H2-223
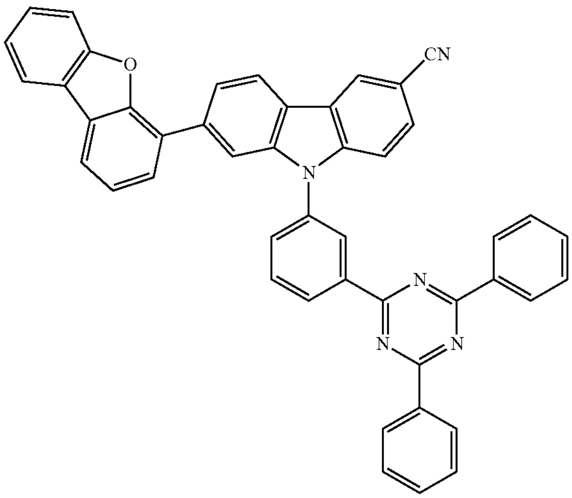
-continued
H2-224
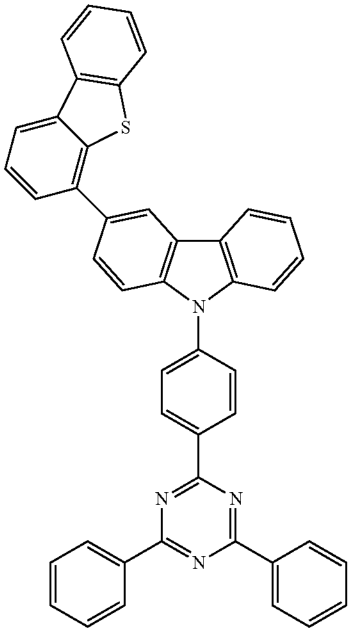
H2-225
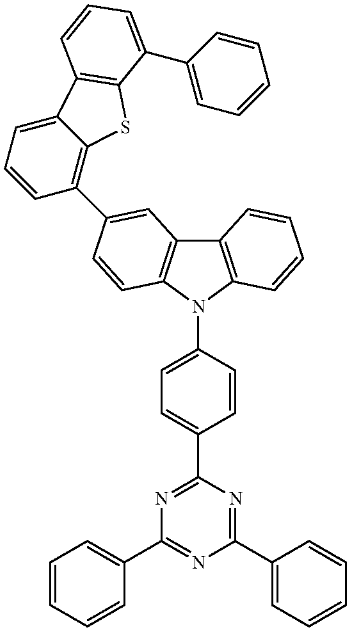

-continued
H2-226
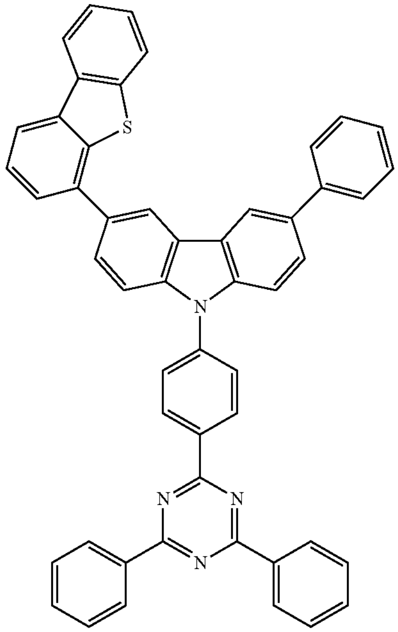
H2-227
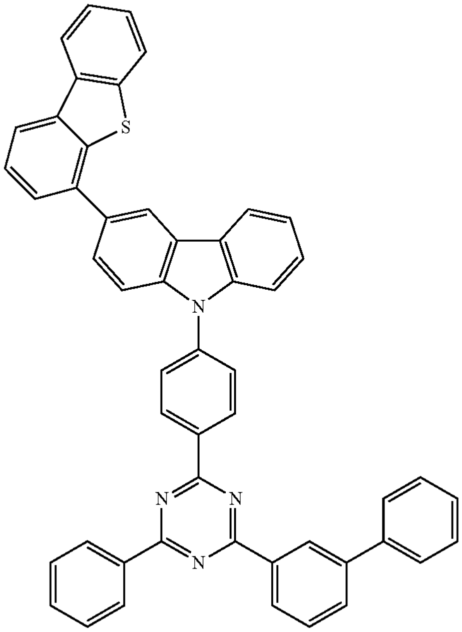
-continued
H2-228
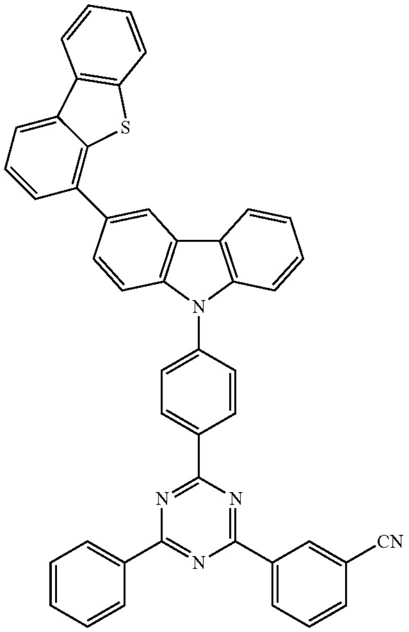
H2-229
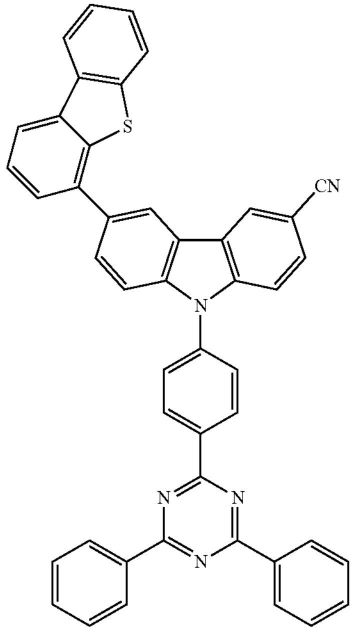

-continued
H2-230
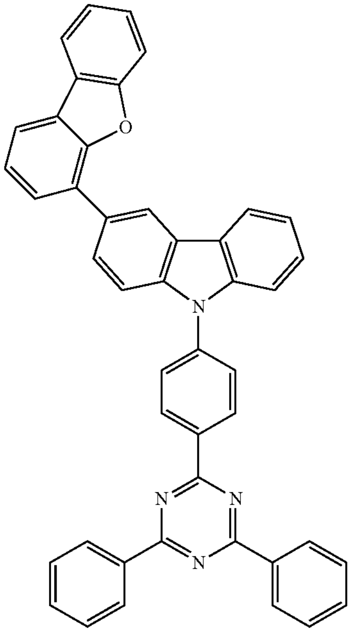
H2-231
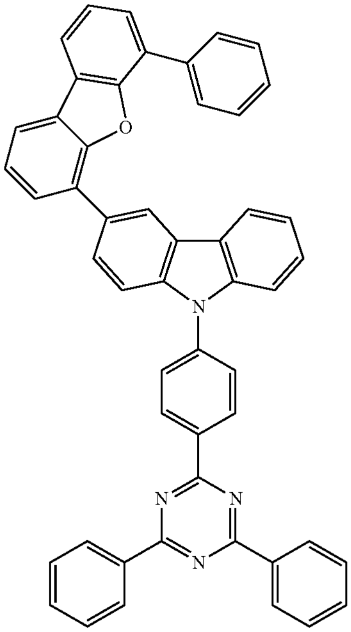
-continued
H2-232
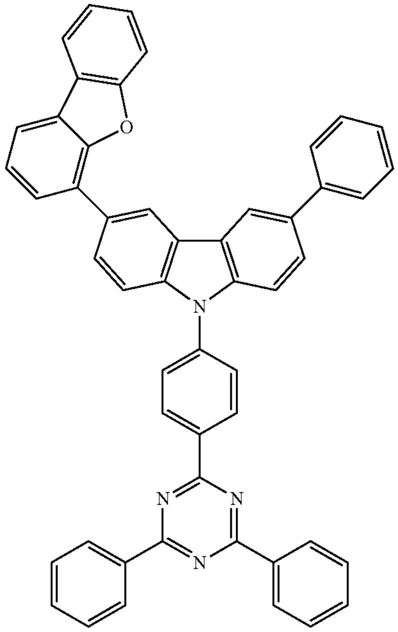
H2-233
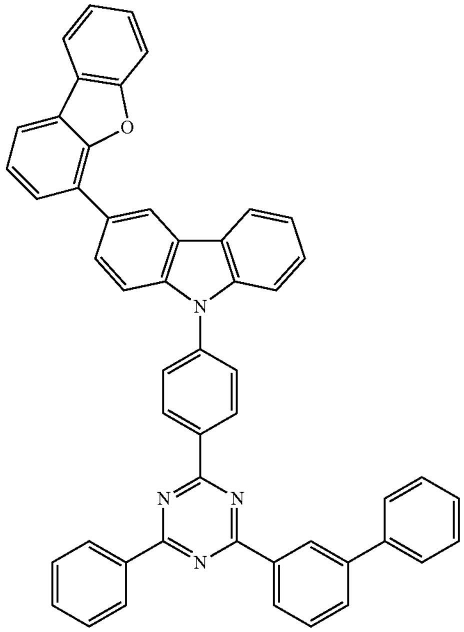

-continued
H2-234
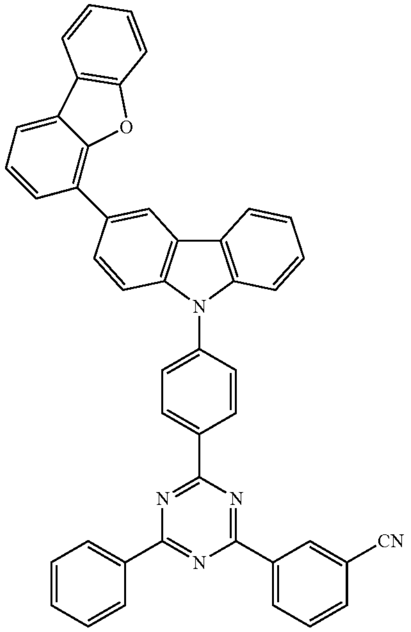
H2-235
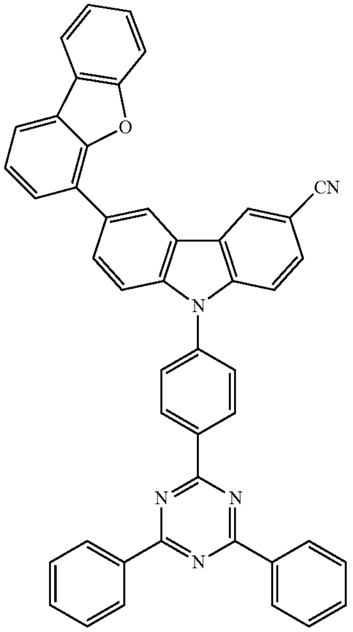
-continued
H2-236
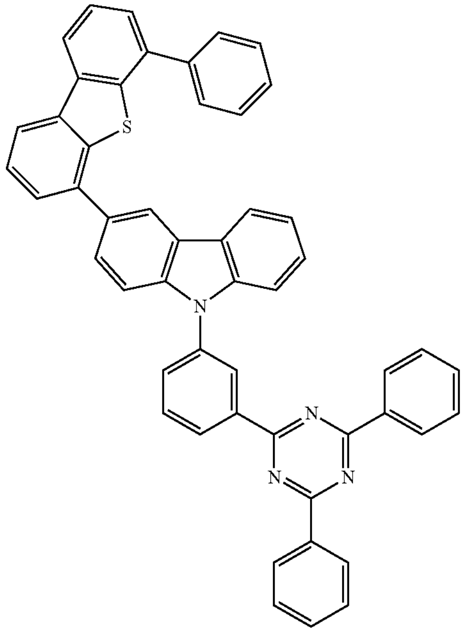
H2-237
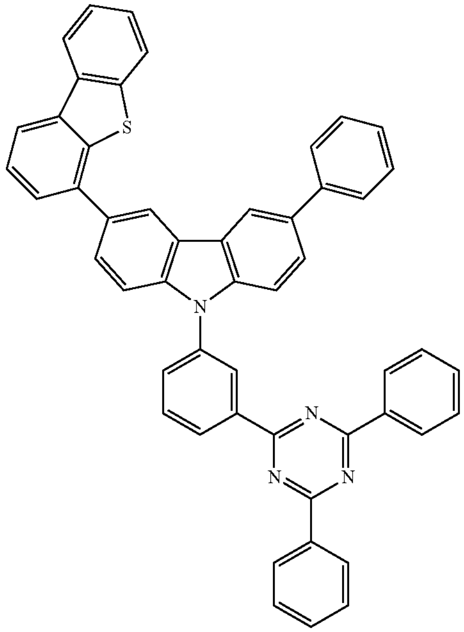

-continued
H2-238
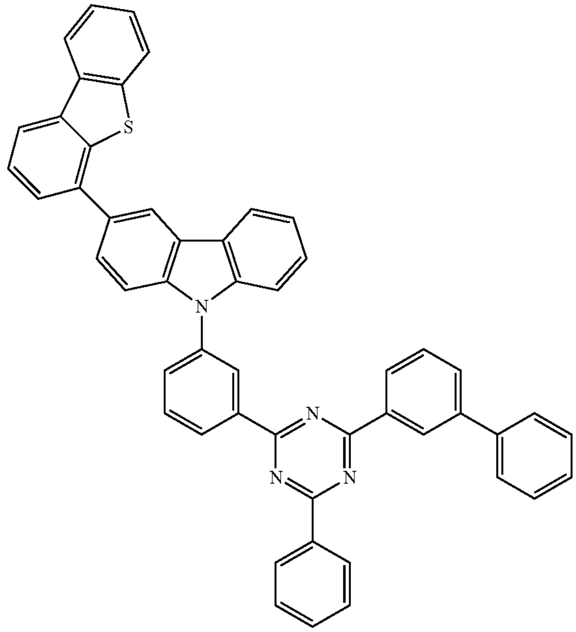
H2-239
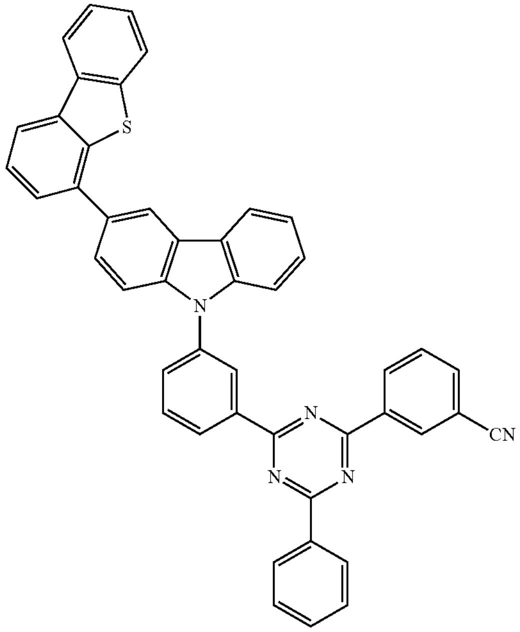
-continued
H2-240
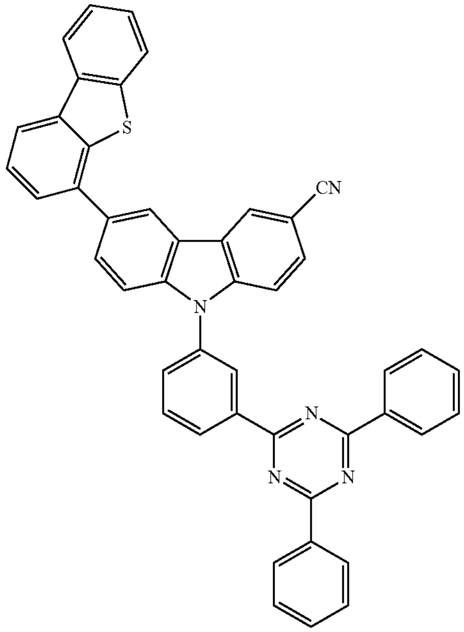
H2-241
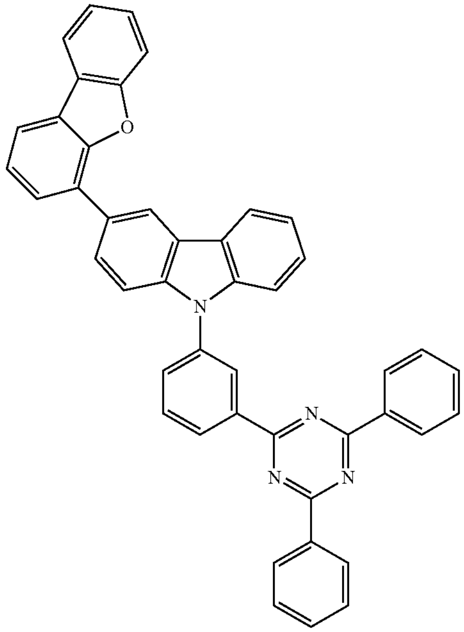

-continued
H2-242
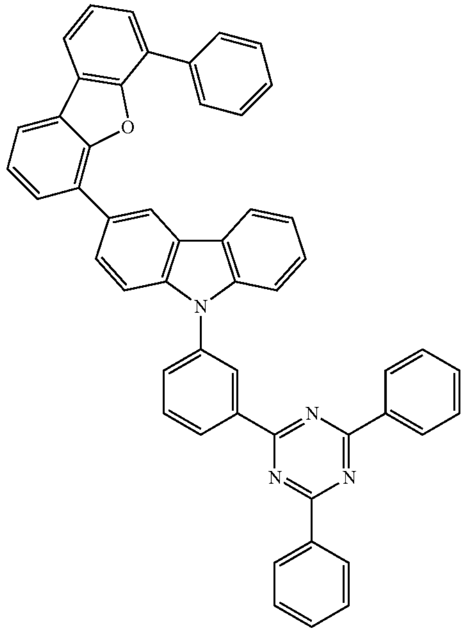
H2-243
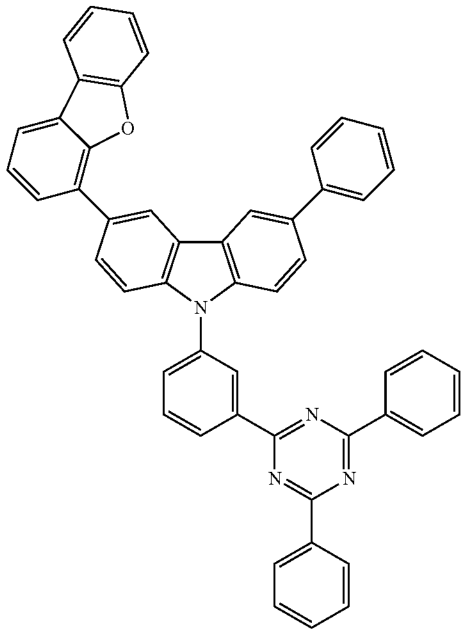
-continued
H2-244
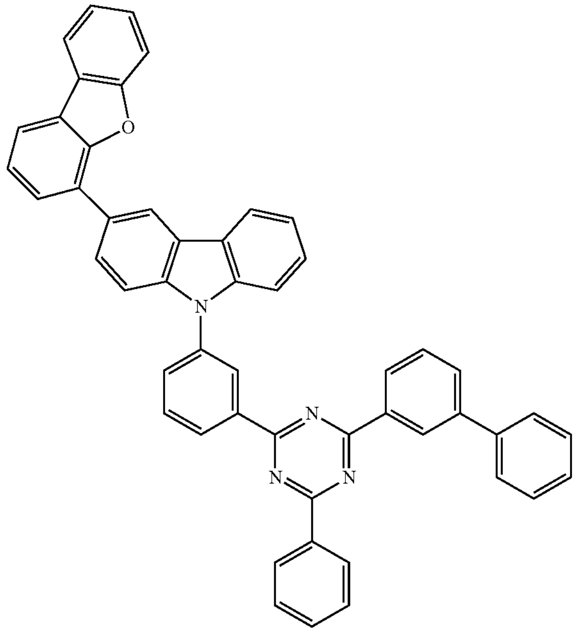
H2-245
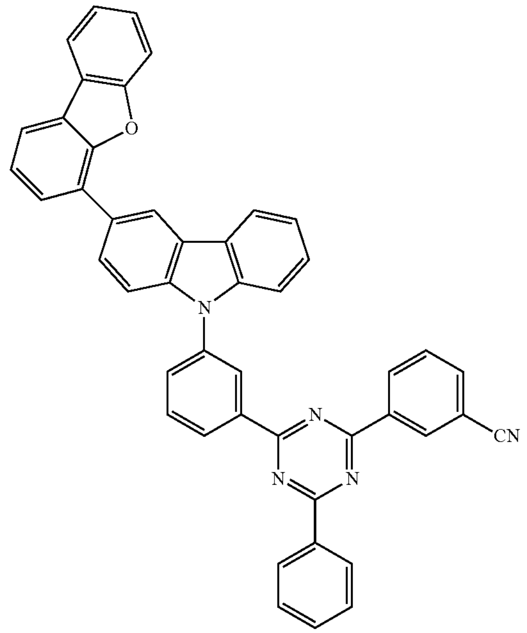

-continued
H2-246
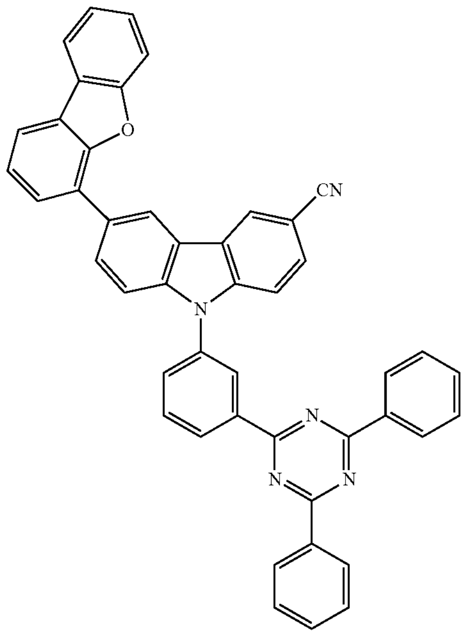
H2-472
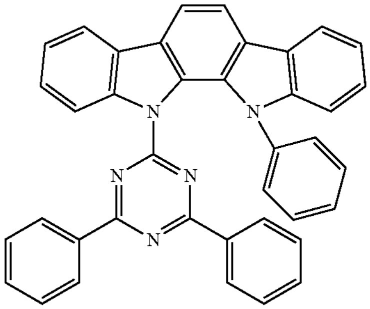
-continued
H2-474
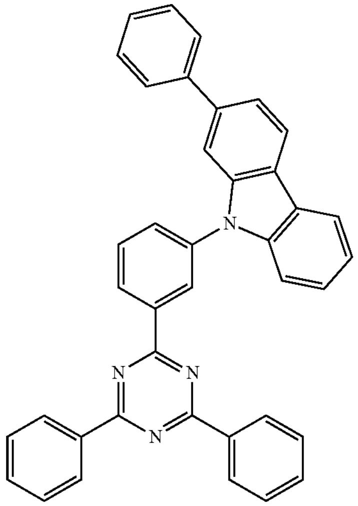
H-475
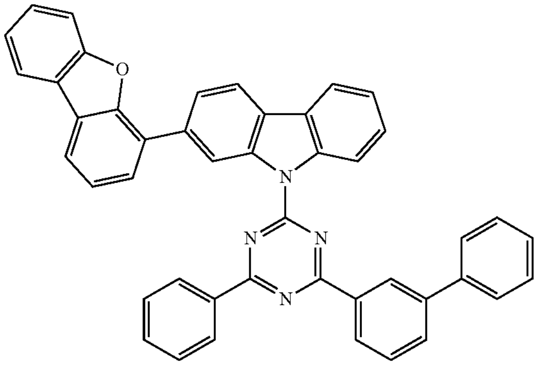
and
H2-477
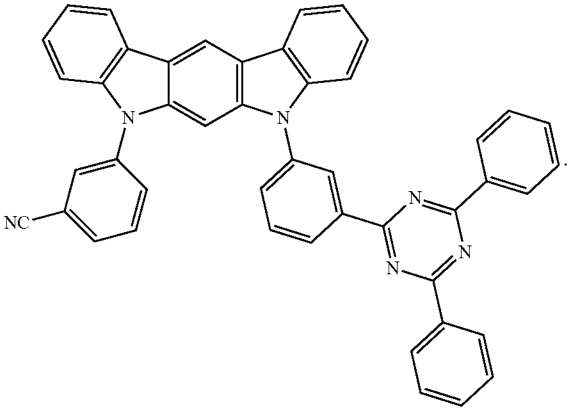
.
* * * * *